(12) United States Patent
Moysey et al.

(10) Patent No.: US 9,758,823 B2
(45) Date of Patent: Sep. 12, 2017

(54) ENZYME METHOD

(71) Applicant: Oxford Nanopore Technologies Limited, Oxford (GB)

(72) Inventors: Ruth Moysey, Oxford (GB); Andrew John Heron, Oxford (GB)

(73) Assignee: Oxford Nanopore Technologies Limited, Oxford (GB)

( * ) Notice: Subject to any disclaimer, the term of this patent is extended or adjusted under 35 U.S.C. 154(b) by 0 days.

(21) Appl. No.: 14/351,038

(22) PCT Filed: Oct. 18, 2012

(86) PCT No.: PCT/GB2012/052579
§ 371 (c)(1),
(2) Date: Apr. 10, 2014

(87) PCT Pub. No.: WO2013/057495
PCT Pub. Date: Apr. 25, 2013

(65) Prior Publication Data
US 2014/0255921 A1  Sep. 11, 2014

Related U.S. Application Data

(60) Provisional application No. 61/599,244, filed on Feb. 15, 2012, provisional application No. 61/549,998, filed on Oct. 21, 2011.

(51) Int. Cl.
*C12Q 1/68* (2006.01)
*C12M 1/34* (2006.01)

(52) U.S. Cl.
CPC .................... *C12Q 1/6869* (2013.01)

(58) Field of Classification Search
CPC ....... C12Q 1/68; C12Q 1/6869; C12Q 1/6874
USPC .................. 435/6.1, 287.2; 977/727, 729
See application file for complete search history.

(56) References Cited

U.S. PATENT DOCUMENTS

| | | | |
|---|---|---|---|
| 7,338,807 B2 | 3/2008 | Harris et al. | |
| 7,745,116 B2 | 6/2010 | Williams | |
| 8,105,846 B2 | 1/2012 | Bayley et al. | |
| 8,785,211 B2 | 7/2014 | Bayley et al. | |
| 8,828,208 B2 | 9/2014 | Canas et al. | |
| 2006/0063171 A1 | 3/2006 | Akeson et al. | |
| 2010/0092960 A1 | 4/2010 | Fehr | |
| 2010/0120098 A1 | 5/2010 | Grunenwald et al. | |
| 2011/0177498 A1 | 7/2011 | Clarke et al. | |
| 2011/0229877 A1 | 9/2011 | Jayasinghe et al. | |
| 2012/0058468 A1 | 3/2012 | Mckeown | |
| 2012/0107802 A1 | 5/2012 | Stoddart et al. | |
| 2013/0149769 A1 | 6/2013 | Kizaki et al. | |
| 2014/0051069 A1 | 2/2014 | Jayasinghe et al. | |
| 2014/0186823 A1 | 7/2014 | Clarke et al. | |
| 2014/0262784 A1 | 9/2014 | Clarke et al. | |
| 2014/0335512 A1 | 11/2014 | Moysey et al. | |
| 2015/0008126 A1 | 1/2015 | Maglia et al. | |
| 2015/0031020 A1 | 1/2015 | Jayasinghe et al. | |
| 2015/0065354 A1 | 3/2015 | Moysey et al. | |
| 2015/0152492 A1 | 6/2015 | Brown et al. | |
| 2015/0191709 A1 | 7/2015 | Heron et al. | |
| 2015/0197796 A1 | 7/2015 | White et al. | |
| 2015/0218629 A1 | 8/2015 | Heron et al. | |
| 2016/0257942 A1 | 9/2016 | Bruce et al. | |

FOREIGN PATENT DOCUMENTS

| | | |
|---|---|---|
| WO | 00/28312 A1 | 5/2000 |
| WO | WO 00/28312 | 5/2000 |
| WO | 2005/124888 A1 | 12/2005 |
| WO | 2006/028508 A2 | 3/2006 |
| WO | 2006/100484 A2 | 9/2006 |
| WO | 2007/057668 A1 | 5/2007 |
| WO | 2008/102120 A1 | 8/2008 |
| WO | 2008/102121 A1 | 8/2008 |
| WO | 2009/035647 A1 | 3/2009 |
| WO | WO 2009/044170 A1 | 4/2009 |
| WO | 2009/077734 A2 | 6/2009 |
| WO | 2010/004265 A1 | 1/2010 |
| WO | 2010/004273 A1 | 1/2010 |
| WO | WO 2010/034018 * | 3/2010 |
| WO | 2010/086603 A1 | 8/2010 |
| WO | 2010/086622 A1 | 8/2010 |
| WO | WO 2010/086602 A1 | 8/2010 |
| WO | 2010/109197 A2 | 9/2010 |
| WO | 2010/122293 A1 | 10/2010 |
| WO | 2011/067559 A1 | 6/2011 |
| WO | WO 2012/033524 A2 | 3/2012 |
| WO | WO 2012/164270 A1 | 12/2012 |
| WO | WO 2013/014451 A1 | 1/2013 |
| WO | WO 2013/041878 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/153359 | 10/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/158665 A1 | 10/2014 |

OTHER PUBLICATIONS

SEQ ID No. 2 search results, printed on Sep. 16, 2015, pp. 1-69.*
Data sheet 1, [Down loaded from the internet http://www.ncbi.nlm.nih.gov/nuccore/AM778123], pp. 1 and 2, printed om Sep. 18, 2015.*
Data sheet 2, [Down loaded from the internet http://blast.ncbi.nlm.nih.gov/Blast.cgi], pp. 1 and 2, printed om Sep. 18, 2015.*
Data sheet 3, [Down loaded from the internet http://blast.ncbi.nlm.nih.gov/Blast.cgi], pp. 1 and 2, printed om Sep. 18, 2015.*
Sathiyamoorthy et al, The Crystal Structure of *Escherichia coli* Group 4 Capsule Protein GfcC Reveals a Domain Organization Resembling That of Wza, 2011, Biochemistry, 50, 5465-5476.*

(Continued)

*Primary Examiner* — Narayan Bhat
(74) *Attorney, Agent, or Firm* — Wolf, Greenfield & Sacks, P.C.

(57) ABSTRACT

The invention relates to a new method of characterizing a target polynucleotide. The method uses a pore and a Hel308 helicase or amolecular motor which is capable of binding to the target polynucleotide at an internal nucleotide. The helicase or molecular motor controls the movement of the target polynucleotide through the pore.

11 Claims, 25 Drawing Sheets

(56) References Cited

OTHER PUBLICATIONS

Altschul, Stephen F., "A Protein Alignment Scoring System Sensitive at All Evolutionary Distances," J. Mol. Evol., vol. 36:290-300 (1993).
Altschul, Stephen F. et al., "Basic Local Alignment Search Tool," J. Mol. Biol., vol. 215:403-410 (1990).
Astier, Yann et al., "Toward Single Molecule DNA Sequencing: Direct Identification of Ribonucleoside and Deoxyribonucleoside 5'-Monophosphates by Using an Engineered Protein Nanopore Equipped with a Molecular Adapter," J. Am. Chem. Soc., vol. 128:1705-1710 (2006).
Braha, Orit et al., "Designed protein pores as components for biosensors," Chemistry & Biology, vol. 4:497-505 (1997).
Butler, Tom Z. et al., "Single-molecule DNA detection wtih an engineered MspA protein nanopore," PNAS, vol. 105 (52):20647-20652 (2008).
Comer, Jeffrey et al., "Microscopic Mechanics of Hairpin DNA Translocation through Synthetic Nanopores," Biophysical Journal, vol. 96:593-608 (2009).
Derrington, Ian M. et al., "Nanopore DNA sequencing with MspA," PNAS, vol. 107(37):16060-16065 (2010).
Devereux, John et al., "A comprehensive set of sequence analysis programs for the VAX," Nucleic Acids Research, vol. 12(1):387-395 (1984).
Grant, Gian Paola G. et al., "A facile method for attaching nitroxide spin labels at the 5' terminus of nucleic acids," Nucleic Acids Research, vol. 35(10):e77, doi:10.1093/nar/gkm240, 8 pages (2007).
Holden, Matthew A. et al., "Direct Introduction of Single Protein Channels and Pores into Lipid Bilayers," J. Am. Chem. Soc., vol. 127:6502-6503 (2005).
Holden, Matthew A. et al., "Functional Bionetworks from Nanoliter Water Droplets," J. Am. Chem. Soc., vol. 129:8650-8655 (2007).
Hopfner, K.P. et al., "Mechanisms of nucleic acid translocases: lessons from structural biology and single-molecule biophysics," Curr. Opin. Struct. Biol., vol. 17(1):87-95 (2007).
Howorka, Stefan et al., "Nanopore analytics: sensing of single molecules," Chem. Soc. Rev., vol. 38:2360-2384 (2009).
Ivanov, Aleksandar P. et al., "DNA Tunneling Detector Embedded in a Nanopore," Nano Letters, vol. 11:279-285 (2011).
Kumar, Abhay et al., "Nonradioactive Labeling of Synthetic Oligonucleotide Probes with Terminal Deoxynucleotidyl Transferase," Analytical Biochemistry, vol. 169:376-382 (1988).
Lieberman, Kate R. et al., "Processive Replication of Single DNA Molecules in a Nanopore Catalyzed by phi29 DNA Polymerase," J. Am. Chem. Soc., vol. 132:17961-17972 (2010).
Marini, Federica et al., "A Human DNA Helicase Homologous to the DNA Cross-link Sensitivity Protein Mus308," The Journal of Biological Chemistry, vol. 277(10):8716-8723 (2002).
Montal, M. et al., "Formation of Biomolecular Membranes from Lipid Monolayers and a Study of Their Electrical Properties," Proc. Natl. Acad. Sci. USA, vol. 69(12):3561-3566 (1972).
Nikolov, Vesselin et al., "Behavior of Giant Vesicles with Anchored DNA Molecules," Biophysical Journal, vol. 92:4356-4368 (2007).
Pfeiffer, Indriati et al., "Bivalent Cholesterol-Binding Coupling of Oligonucleotides to Lipid Membrane Assemblies," J. Am. Chem. Soc., vol. 126:10224-10225 (2004).
Richards, Jodi et al., "Structure of the DNA Repair Helicase HEL308 Reveals DNA Binding and Autoinhibitory Domains," J. Biol. Chem., vol. 283(8):5118-5126 (2008).
Soni, Gautam V. et al., "Synchronous optical and electrical detection of biomolecules traversing through solid-state nanopores," Review of Scientific Instruments, vol. 81:014301-1-014301-7 (2010).
Stoddart, David et al., "Single-nucleotide discrimination in immobilized DNA oligonucleotides with a biological nanopore," PNAS, vol. 106(19):7702-7707 (2009).
Troutt, Anthony B. et al., "Ligation-anchored PCR: a simple amplification technique with single-sided specificity," Proc. Natl. Acad. Sci. USA, vol. 89:9823-9825 (1992).

Van Lengerich, Bettina et al., "Covalent attachment of lipid vesicles to a fluid supported bilayer allows observation of DNA-mediated vesicle interactions," Langmuir, vol. 26(11):8666-8672 (2010).
Yoshina-Ishii, Chiaki et al., "Arrays of Mobile Tethered Vesicles on Supported Lipid Bilayers," J. Am. Chem. Soc., vol. 125:3696-3697 (2003).
Morris, P. et al., "Evidence for a Functional Monomeric Form of the Bacteriophage T4 Dda Helicase," The Journal of Biological Chemistry, vol. 276, No. 23, Issue of Jun. 8, 2001, pp. 19691-19698.
U.S. Appl. No. 13/338,794, filed Dec. 28, 2011, Hagan Bayley.
U.S. Appl. No. 13/968,778, filed Aug. 16, 2013, Lakmal Jayasinghe.
U.S. Appl. No. 14/455,394, filed Aug. 8, 2014, Lakmal Jayasinghe.
U.S. Appl. No. 14/858,138, filed Sep. 18, 2015, Lakmal Jayasinghe.
U.S. Appl. No. 13/338,794, Mar. 13, 2014.
U.S. Appl. No. 13/338,794, Mar. 5, 2013.
U.S. Appl. No. 13/338,794, Sep. 24, 2012.
U.S. Appl. No. 13/338,794, Jul. 19, 2012.
U.S. Appl. No. 13/968,778, Mar. 20, 2015.
U.S. Appl. No. 13/968,778, Jul. 9, 2014.
U.S. Appl. No. 14/455,394, Oct. 2, 2015.
U.S. Appl. No. 14/455,394, May 8, 2015.
U.S. Appl. No. 13/002,717, Jul. 21, 2015.
U.S. Appl. No. 13/147,159, Oct. 20, 2015.
U.S. Appl. No. 13/147,159, Mar. 20, 2015.
U.S. Appl. No. 13/260,178, Aug. 18, 2015.
UniProt Database accession No. b4kac8 sequence. Sep. 23, 2008.
UniProt Database accession No. Q7Y5C3 sequence. Oct. 1, 2003.
UniProt Database accession No. a4slel sequence. May 15, 2007.
UniProt Database accession No. elqus6 sequence. Nov. 30, 2010.
GenPept Accession No. XP 003728286. Jun. 7, 2012.
UniProt Database accession No. i3d0e7 sequence. Jul. 11, 2012.
UniProt Database accession No. I7J3V8 sequence. Oct. 3, 2012.
UniProt Database accession No. k0im99 sequence. Nov. 28, 2012.
UniProt Database accession No. k7nri8 sequence. Feb. 6, 2013.
UniProt Database accession No. D0KN27. Dec. 15, 2009.
Press release: Oxford Nanopore introduces DNA 'strand sequencing' on the high-throughput GridION platform and presents MinION, a sequencer the size of a USB; memory stick, Feb. 2012.
[No Author Listed] Antibodies bind specific molecules through their hypervariable loops. 33.3 Antibody Binding. 6th edition. 2007;953-954.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Byrd et al., A parallel quadruplex DNA is bound tightly but unfolded slowly by pifl helicase. J Biol Chem. Mar. 6, 2015;290(10):6482-94. doi:10.1074/jbc.M114.630749. Epub Jan. 14, 2015.
Cheng et al., Functional characterization of the multidomain F plasmid TraI relaxase-helicase. J Biol Chem. Apr. 8, 2011;286(14):12670-82. doi: 10.1074/jbc.M110.207563. Epub Feb. 2, 2011.
Deamer, Nanopore analysis of nucleic acids bound to exonucleases and polymerases. Annu Rev Biophys. 2010;39:79-90. doi:10.1146/annurev.biophys.093008.131250.
Dostál et al., Tracking F plasmid TraI relaxase processing reactions provides insight into F plasmid transfer. Nucleic Acids Res. Apr. 2011;39(7):2658-70. doi: 10.1093/nar/gkq1137. Epub Nov. 24, 2010.
Dou et al., The DNA binding properties of the *Escherichia coli* RecQ helicase. J Biol Chem. Feb. 20, 2004;279(8):6354-63. Epub Dec. 9, 2003.
Fairman-Williams et al., SF1 and SF2 helicases: family matters. Curr Opin Struct Biol. Jun. 2010;20(3):313-24. doi:10.1016/j.sbi.2010.03.011. Epub Apr. 22, 2010.
Garcillán-Barcia et al., The diversity of conjugative relaxases and its application in plasmid classification. FEMS Microbiol Rev. May 2009;33(3):657-87.
Gonzalez-Perez et al., Biomimetic triblock copolymer membrane arrays: a stable template for functional membrane proteins. Langmuir. Sep. 15, 2009;25(18):10447-50. doi: 10.1021/la902417m.

(56) References Cited

OTHER PUBLICATIONS

Graham et al., Sequence-specific assembly of FtsK hexamers establishes directional translocation on DNA. Proc Natl Acad Sci U S A. Nov. 23, 2010;107(47):20263-8. doi: 10.1073/pnas.1007518107. Epub Nov. 3, 2010.

Green et al., Quantitative evaluation of the lengths of homobifunctional protein cross-linking reagents used as molecular rulers. Protein Sci. Jul. 2001;10(7):1293-304.

Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.

He et al, The T4 phage SF1B helicase Dda is structurally optimized to perform DNA strand separation. Structure. Jul. 3, 2012;20(7):1189-200. doi:10.1016/j.str.2012.04.013. Epub May 31, 2012.

Holden et al., Functional bionetworks from nanoliter water droplets. J Am Chem Soc. Jul. 11, 2007;129(27):8650-5. Epub Jun. 16, 2007.

Hornblower et al., Single-molecule analysis of DNA-protein complexes using nanopores. Nat Methods. Apr. 2007;4(4):315-7. Epub Mar. 4, 2007.

James, Aptamers. Encyclopedia of Analytical Chemistry. R.A. Meyers (Ed.). 4848-4871. John Wiley & Sons Ltd, Chichester, 2000.

Jezewska et al., Interactions of *Escherichia coli* replicative helicase PriA protein with single-stranded DNA. Biochemistry. Aug. 29, 2000;39(34):10454-67. Abstract only.

Kafri et al., Dynamics of molecular motors and polymer translocation with sequence heterogeneity. Biophys J. Jun. 2004;86(6):3373-91.

Kar et al., Defining the structure-function relationships of bluetongue virus helicase protein VP6. J Virol. Nov. 2003;77(21):11347-56.

Keyser, Controlling molecular transport through nanopores. J R Soc Interface. Oct. 7, 2011;8(63):1369-78. doi: 10.1098/rsif.2011.0222. Epub Jun. 29, 2011.

Khafizov, Single Molecule Force Spectroscopy of Single Stranded Dna Binding Protein and Rep Helicase. University of Illinois at Urbana-Champaign Dissertation. 2012.

Korolev et al., Major domain swiveling revealed by the crystal structures of complexes of *E. coli* Rep helicase bound to single-stranded DNA and ADP. Cell. Aug. 22, 1997;90(4):635-47.

Lee et al., Direct imaging of single UvrD helicase dynamics on long single-stranded DNA. Nat Commun 2013;4:1878. doi:10.1038/ncomms2882.

Liu et al., Adding new chemistries to the genetic code. Annu Rev Biochem. 2010;79:413-44. doi: 10.1146/annurev.biochem.052308.105824.

Liu et al., Structure of the DNA repair helicase XPD. Cell. May 30, 2008;133(5):801-12. doi: 10.1016/j.cell.2008.04.029.

Lohman et al., Non-hexameric DNA helicases and translocases:mechanisms and regulation. Nat Rev Mol Cell Biol. May 2008;9(5):391-401. doi:10.1038/nrm2394.

Lohman et al., Mechanisms of helicase-catalyzed DNA unwinding. Annu Rev Biochem. 1996;65:169-214.

Ma et al., Bright functional rotaxanes. Chem Soc Rev. Jan. 2010;39(1):70-80. doi: 10.1039/b901710k. Epub Jul. 21, 2009.

O'Shea et al., X-ray structure of the GCN4 leucine zipper, a two-stranded, parallel coiled coil. Science. Oct. 25, 1991;254(5031):539-44.

Pinero-Fernandez et al., Indole transport across *Escherichia coli* membranes. J Bacteriol. Apr. 2011;193(8):1793-8. doi:10.1128/JB.01477-10. Epub Feb. 4, 2011.

Raney et al., Structure and Mechanisms of SF1 DNA Helicases. Adv Exp Med Biol. 2013;767:17-46. doi: 10.1007/978-1-4614-5037-5_2.

Remaut et al., Protein-protein interaction through beta-strand addition. Trends Biochem Sci. Aug. 2006;31(8):436-44. Epub Jul. 7, 2006.

Saariaho et al., Characteristics of MuA transposase-catalyzed processing of model transposon end DNA hairpin substrates. Nucleic Acids Res. Jun. 6, 2006;34(10):3139-49. Print 2006.

Satapathy et al., ATPase activity of RecD is essential for growth of the Antarctic Pseudomonas syringae Lz4W at low temperature. FEBS J. Apr. 2008;275(8):1835-51. doi:10.1111/j.1742-4658.2008.06342.x. Epub Mar. 9, 2008.

Schneider et al., DNA sequencing with nanopores. Nat Biotechnol. Apr. 10, 2012;30(4):326-8. doi: 10.1038/nbt.2181.

Singleton et al., Structure and mechanism of helicases and nucleic acid translocases. Annu Rev Biochem. 2007;76:23-50.

Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.

Van Heel et al., Single-particle electron cryo-microscopy:towards atomic resolution. Q Rev Biophys. Nov. 2000;33(4):307-69.

Venkatesan et al., Nanopore sensors for nucleic acid analysis. Nat Nanotechnol. Sep. 18, 2011;6(10):615-24. doi: 10.1038/nnano.2011.129.

Vinson, Proteins in motion. Introduction. Science. Apr. 10, 2009;324(5924):197. doi: 10.1126/science.324.5924.197.

Woodman et al., Archaeal HeI308 domain V couples DNA binding to ATP hydrolysis and positions DNA for unwinding over the helicase ratchet. J Mol Biol. Dec. 14, 2007;374(5):1139-44. Epub Oct. 10, 2007.

Allen et al., The genome sequence of the psychrophilic archaeon, Methanococcoides burtonii: the role of genome evolution in cold adaptation. ISME J. 2009 Sep;3(9):1012-35. doi: 10.1038/ismej.2009.45.

Buttner et al., Structural basis for DNA duplex separation by a superfamily-2 helicase. Nat Struct Mol Biol. 2007 Jul;14(7):647-52.

Colas et al., Microscopical investigations of nisin-loaded nanoliposomes prepared by Mozafari method and their bacterial targeting. Micron. 2007;38(8):841-7.

Eliseev et al., Molecular Recognition of Nucleotides, Nucleosides, and Sugars by Aminocyclodextrins. J. Am. Chem. Soc., vol. 116:6081-6088 (1994).

Garalde et al., Highly parallel direct RNA sequencing on an array of nanopores. bioRxiv. 2016. doi: http://dx.doi.org/10.1101/068809.

Kuper et al., Functional and structural studies of the nucleotide excision repair helicase XPD suggest a polarity for DNA translocation. EMBO J. Jan. 2012 18;31(2):494-502. doi: 10.1038/emboj.2011.374.

Langecker et al., Synthetic lipid membrane channels formed by designed DNA nanostructures. Science. Nov. 2012 16;338(6109):932-6. doi: 10.1126/science.1225624.

Maddox et al., Elevated serum levels in human pregnancy of a molecule immunochemically similar to eosinophil granule major basic protein. J Exp Med. Oct. 1, 1983;158(4):1211-26.

Portakal et al., Construction of recB-recD genetic fusion and functional analysis of RecBDC fusion enzyme in *Escherichia coli*. BMC Biochem. Oct. 10, 2008;9:27. doi: 10.1186/1471-2091-927.

Rudolf et al., The DNA repair helicases XPD and FancJ have essential iron-sulfur domains. Mol Cell. Sep. 15, 2006;23(6):801-8.

Rudolf et al., The helicase XPD unwinds bubble structures and is not stalled by DNA lesions removed by the nucleotide excision repair pathway. Nucleic Acids Res. Jan. 2010;38(3):931-41. doi:10.1093/nar/gkp1058.

Wang et al., DNA helicase activity of the RecD protein from Deinococcus radiodurans. J Biol Chem. Dec. 10, 2004;279(50):52024-32.

White, Structure, function and evolution of the XPD family of iron—sulfur-containing 5'—>3' DNA helicases. Biochem Soc Trans. 2009;37:547-551.

Woodman et al., Molecular biology of He1308 helicase in archaea. Biochem Soc Trans. Feb. 2009;37(Pt 1):74-8. doi: 10.1042/BST0370074.

Woodman et al., Winged helix domains with unknown function in He1308 and related helicases. Biochem Soc Trans. Jan. 2011;39(1):140-4. doi:10.1042/BST0390140.

(56) References Cited

OTHER PUBLICATIONS

Zhang et al., Structural evidence for consecutive He1308-like modules in the spliceosomal ATPase Brr2. Nat Struct Mol Biol. Jul. 2009;16(7):731-9. doi: 10.1038/nsmb.1625.

* cited by examiner

ENZYME METHOD

RELATED APPLICATIONS

This application is a 35 U.S.C. 371 national stage filing of International Application PCT/GB2012/052579, filed Oct. 18, 2012, which claims priority to U.S. Provisional Patent Application 61/549,998 filed Oct. 21, 2011 and U.S. Provisional Patent Application 61/599,244 filed on Feb. 15, 2012 in the United States. The contents of the aforementioned applications are hereby incorporated by reference in their entirety.

FIELD OF THE INVENTION

The invention relates to a new method of characterising a target polynucleotide. The method uses a pore and a Hel308 helicase or a molecular motor which is capable of binding to the target polynucleotide at an internal nucleotide. The helicase or molecular motor controls the movement of the target polynucleotide through the pore.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the "Strand Sequencing" method, a single polynucleotide strand is passed through the pore and the identity of the nucleotides are derived. Strand Sequencing can involve the use of a nucleotide handling protein to control the movement of the polynucleotide through the pore.

SUMMARY OF THE INVENTION

The inventors have demonstrated that a Hel308 helicase can control the movement of a polynucleotide through a pore especially when a potential, such as a voltage, is applied. The helicase is capable of moving a target polynucleotide in a controlled and stepwise fashion against or with the field resulting from the applied voltage. Surprisingly, the helicase is capable of functioning at a high salt concentration which is advantageous for characterising the polynucleotide and, in particular, for determining its sequence using Strand Sequencing. This is discussed in more detail below.

Accordingly, the invention provides a method of characterising a target polynucleotide, comprising:

(a) contacting the target polynucleotide with a transmembrane pore and a Hel308 helicase such that the helicase controls the movement of the target polynucleotide through the pore and nucleotides in the target polynucleotide interact with the pore; and (b) measuring one or more characteristics of the target polynucleotide during one or more interactions and thereby characterising the target polynucleotide.

The invention also provides:

a method of forming a sensor for characterising a target polynucleotide, comprising forming a complex between a pore and a Hel308 helicase and thereby forming a sensor for characterising the target polynucleotide;

use of a Hel308 helicase to control the movement of a target polynucleotide through a pore;

a kit for characterising a target polynucleotide comprising (a) a pore and (b) a Hel308 helicase; and an analysis apparatus for characterising target polynucleotides in a sample, comprising a plurality of pores and a plurality of a Hel308 helicase.

The inventors have also demonstrated that a molecular motor which is capable of binding to a target polynucleotide at an internal nucleotide can control the movement of the polynucleotide through a pore especially when a potential, such as a voltage, is applied. The motor is capable of moving the target polynucleotide in a controlled and stepwise fashion against or with the field resulting from the applied voltage. Surprisingly, when the motor is used in the method of the invention it is possible to control the movement of an entire strand of target polynucleotide through a nanopore. This is advantageous for characterising the polynucleotide and, in particular, for determining its sequence using Strand Sequencing.

Hence, the invention also provides a method of characterising a target polynucleotide, comprising:

(a) contacting the target polynucleotide with a transmembrane pore and a molecular motor which is capable of binding to the target polynucleotide at an internal nucleotide such that the molecular motor controls the movement of the target polynucleotide through the pore and nucleotides in the target polynucleotide interact with the pore; and (b) measuring one or more characteristics of the target polynucleotide during one or more interactions and thereby characterising the target polynucleotide.

DESCRIPTION OF THE FIGURES

FIG. 5. The helicase (a) can control the movement of DNA (b) in at least two modes of operation. The helicase moves along the DNA in the 3'-5' direction, but the orientation of the DNA in the nanopore (c) (dependent on which end of the DNA is captured) means that the enzyme can be used to either move the DNA out of the nanopore against the applied field (FIG. 5b), or move the DNA into the nanopore with the applied field (FIG. 5a).

DESCRIPTION OF THE SEQUENCE LISTING

Figure 1A:
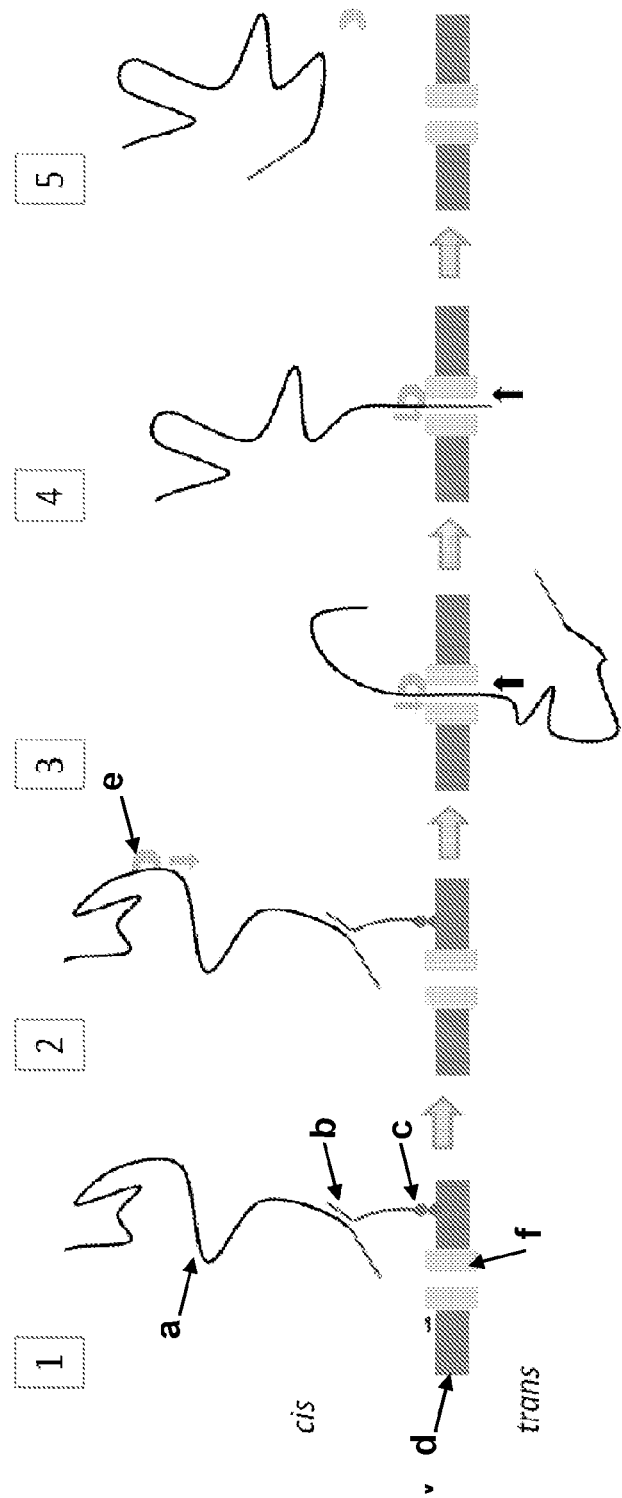
FIG. 1. a) Example schematic of use of a helicase to control DNA movement through a nanopore. 1) A ssDNA substrate (a) with an annealed primer (b) containing a cholesterol-tag (c) is added to the cis side of the bilayer (d). The cholesterol tag binds to the bilayer, enriching the substrate at the bilayer surface. 2) Helicase (e) added to the cis compartment binds to the DNA. In the presence of divalent metal ions and NTP substrate, the helicase moves along the DNA. 3) Under an applied voltage, the DNA substrate is captured by the nanopore (f) via the leader section on the DNA. The DNA is pulled through the pore under the force of the applied potential until a helicase, bound to the DNA, contacts the top of the pore, preventing further uncontrolled DNA translocation. During this process dsDNA sections (such as the primer) are removed. The helicase movement along the DNA in a 3' to 5' direction pulls the threaded DNA out of the pore against the applied field. 4) The helicase pulls the DNA out of the nanopore, feeding it back to the cis compartment. The last section of DNA to pass through the nanopore is the 5'-leader. 5) When the helicase moves the DNA out of the nanopore it is lost back to the cis compartment. b) The DNA substrate design used in the Example (a=400 mer strand of DNA with a 50T leader (b), c=primer, d=cholesterol-tag).

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one subunit of α-hemolysin-E111N/K147N (α-HL-NN; Stoddart et al., PNAS, 2009; 106(19): 7702-7707).

SEQ ID NO: 4 shows the amino acid sequence of one subunit of α-HL-NN.

SEQ ID NOs: 5 to 7 shows the amino acid sequences of MspB, C and D.

SEQ ID NO: 8 shows the amino acid sequence of the Hel308 motif

SEQ ID NO: 9 shows the amino acid sequence of the extended Hel308 motif

SEQ ID NOs: 10 to 58 show the amino acid sequences of the Hel308 helicases and motifs in Table 5.

SEQ ID NOs: 59 to 74 show the sequences used in the Examples.

SEQ ID NO: 75 shows the sequence of Hel308 Dth in the alignmenton on page 57 onwards.

SEQ ID NO: 76 shows the sequence of Hel308 Mmar in the alignment on on page 57 onwards.

SEQ ID NO: 77 shows the sequence of Hel308 Nth in the alignment on page 57 onwards.

SEQ ID NO: 78 shows the consensus sequence in the alignment on page 57 onwards.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a pore" includes two or more such pores, reference to "a helicase" includes two or more such helicases, reference to "a polynucleotide" includes two or more such polynucleotides, and the like.

All publications, patents and patent applications cited herein, whether supra or infra, are hereby incorporated by reference in their entirety.
Hel308 Methods of the Invention The invention provides a method of characterising a target polynucleotide. The method comprises contacting the target polynucleotide with a transmembrane pore and a Hel308 helicase such that the helicase controls the movement of the target polynucleotide through the pore and nucleotides in the target polynucleotide interact with the pore. One or more characteristics of the target polynucleotide are then measured using standard methods known in the art. Steps (a) and (b) are preferably carried out with a potential applied across the pore. As discussed in more detail below, the applied potential typically results in the formation of a complex between the pore and the helicase. The applied potential may be a voltage potential. Alternatively, the applied potential may be a chemical potential. An example of this is using a salt gradient across the lipid membrane. A salt gradient is disclosed in Holden et al., J Am Chem. Soc. 2007 Jul. 11; 129(27):8650-5.

In some instances, the current passing through the pore during one or more interactions is used to determine the sequence of the target polynucleotide. This is Strand Sequencing.

The method has several advantages. First, the inventors have surprisingly shown that Hel308 helicases have a surprisingly high salt tolerance and so the method of the invention may be carried out at high salt concentrations. In the context of Strand Sequencing, a charge carrier, such as a salt, is necessary to create a conductive solution for applying a voltage offset to capture and translocate the target polynucleotide and to measure the resulting sequence-dependent current changes as the polynucleotide passes through the pore. Since the measurement signal is dependent on the concentration of the salt, it is advantageous to use high salt concentrations to increase the magnitude of the acquired signal. High salt concentrations provide a high signal to noise ratio and allow for currents indicative of the presence of a nucleotide to be identified against the background of normal current fluctuations. For Strand Sequencing, salt concentrations in excess of 100 mM are ideal and salt concentrations of 1 M and above are preferred. The inventors have surprisingly shown that Hel308 helicases will function effectively at salt concentrations as high as, for example, 2 M.

Second, when a voltage is applied, Hel308 helicases can surprisingly move the target polynucleotide in two directions, namely with or against the field resulting from the applied voltage. Hence, the method of the invention may be carried out in one of two preferred modes. Different signals are obtained depending on the direction the target polynucleotide moves through the pore, ie in the direction of or against the field. This is discussed in more detail below.

Third, Hel308 helicases typically move the target polynucleotide through the pore one nucleotide at a time. Hel308 helicases can therefore function like a single-base ratchet. This is of course advantageous when sequencing a target polynucleotide because substantially all, if not all, of the nucleotides in the target polynucleotide may be identified using the pore.

Fourth, Hel308 helicases are capable of controlling the movement of single stranded polynucleotides and double stranded polynucleotides. This means that a variety of different target polynucleotides can be characterised in accordance with the invention.

Fifth, Hel308 helicases appear very resistant to the field resulting from applied voltages. The inventors have seen very little movement of the polynucleotide under an "unzipping" condition. This is important because it means that there are no complications from unwanted "backwards" movements when moving polynucleotides against the field resulting from an applied voltage.

Sixth, Hel308 helicases are easy to produce and easy to handle. Their use therefore contributed to a straightforward and less expensive method of sequencing.

The method of the invention is for characterising a target polynucleotide. A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. One or more nucleotides in the target polynucleotide may be modified, for instance with a label or a tag. The target polynucleotide may comprise one or more spacers.

A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), guanosine monophosphate (GMP), thymidine monophosphate (TMP), uridine monophosphate (UMP), cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP or dCMP.

A nucleotide may be abasic (i.e. lack a nucleobase).

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

The whole or only part of the target polynucleotide may be characterised using this method. The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target polynucleotide is present in any suitable sample. The invention is typically carried out on a sample that is known to contain or suspected to contain the target polynucleotide. Alternatively, the invention may be carried out on a sample to confirm the identity of one or more target polynucleotides whose presence in the sample is known or expected.

The sample may be a biological sample. The invention may be carried out in vitro on a sample obtained from or extracted from any organism or microorganism. The organism or microorganism is typically archaean, prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

A transmembrane pore is a structure that permits hydrated ions driven by an applied potential to flow from one side of the membrane to the other side of the membrane.

Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic layer may be a monolayer or a bilayer.

The membrane is preferably a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as bio sensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000,563 (published as WO 2008/102121), International Application No. PCT/GB08/004,127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004,127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial bilayer comprising a pore, (ii) an isolated, naturally-occurring lipid bilayer comprising a pore, or (iii) a cell having a pore inserted therein. The method is preferably carried out using an artificial lipid bilayer. The bilayer may comprise other transmembrane and/or intramembrane proteins as well as other molecules in addition to the pore. Suitable apparatus and conditions are discussed below. The method of the invention is typically carried out in vitro.

The polynucleotide may be coupled to the membrane. This may be done using any known method. If the membrane is an amphiphilic layer, such as a lipid bilayer (as discussed in detail above), the polynucleotide is preferably coupled to the membrane via a polypeptide present in the membrane or a hydrophobic anchor present in the membrane. The hydrophobic anchor is preferably a lipid, fatty acid, sterol, carbon nanotube or amino acid.

The polynucleotide may be coupled directly to the membrane. The polynucleotide is preferably coupled to the membrane via a linker. Preferred linkers include, but are not limited to, polymers, such as polynucleotides, polyethylene glycols (PEGs) and polypeptides. If a polynucleotide is coupled directly to the membrane, then some data will be lost as the characterising run cannot continue to the end of the polynucleotide due to the distance between the membrane and the helicase. If a linker is used, then the polynucleotide can be processed to completion. If a linker is used, the linker may be attached to the polynucleotide at any position. The linker is preferably attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the bilayer and the helicase's active site. If the coupling is transient, then when the coupled end randomly becomes free of the bilayer, then the polynucleotide can be processed to completion. Chemical groups that form stable or transient links with the membrane are discussed in more detail below. The polynucleotide may be transiently coupled to an amphiphilic layer or lipid bilayer using cholesterol or a fatty acyl chain. Any fatty acyl chain having a length of from 6 to 30 carbon atoms, such as hexadecanoic acid, may be used.

In preferred embodiments, polynucleotide is coupled to a lipid bilayer. Coupling of polynucleotides to synthetic lipid bilayers has been carried out previously with various different tethering strategies. These are summarised in Table 1 below.

TABLE 1

| Attachment group | Type of coupling | Reference |
| --- | --- | --- |
| Thiol | Stable | Yoshina-Ishii, C. and S. G. Boxer (2003). "Arrays of mobile tethered vesicles on supported lipid bilayers." J Am Chem Soc 125(13): 3696-7. |
| Biotin | Stable | Nikolov, V., R. Lipowsky, et al. (2007). "Behavior of giant vesicles with anchored DNA molecules." Biophys J 92(12): 4356-68 |
| Cholestrol | Transient | Pfeiffer, I. and F. Hook (2004). "Bivalent cholesterol-based coupling of oligonucletides to lipid membrane assemblies." J Am Chem Soc 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." Langmuir 26(11): 8666-72 |

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the bilayer. The advantages of transient coupling are discussed above.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." Nucleic Acids Res 35(10): e77). A more diverse selection of chemical groups, such as biotin, thiols and fluorophores, can be added using terminal transferase to incorporate modified oligonucletides to the 3' of ssDNA (Kumar, A., P. Tchen, et al. (1988). "Nonradioactive labeling of synthetic oligonucleotide probes with terminal deoxynucleotidyl transferase." Anal Biochem 169(2): 376-82).

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer a reactive group attached to it.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the target DNA amplified will contain a reactive group for coupling.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide, such as DNA or RNA, to be moved through the pore.

The transmembrane protein pore may be a monomer or an oligomer. The pore is preferably made up of several repeating subunits, such as 6, 7 or 8 subunits. The pore is more preferably a heptameric or octameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp comprises the sequence shown in SEQ ID NO: 2 or a variant thereof. SEQ ID NO: 2 is the MS-(B1)$_8$ mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into a lipid bilayer along with other appropriate subunits and its ability to oligomerise to form a pore may be determined. Methods are known in the art for inserting subunits into membranes, such as lipid bilayers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et at (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et at (1990) J Mol Biol 215:403-10. Software for performing BLAST analyses is publicly available through the National Center for Biotechnology Information (http://www.ncbi.nlm.nih.gov/).

SEQ ID NO: 2 is the MS-(B1)$_8$ mutant of the MspA monomer. The variant may comprise any of the mutations in the MspB, C or D monomers compared with MspA. The mature forms of MspB, C and D are shown in SEQ ID NOs:

5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, $K_{47}T$, 149H, 168V, D91G, A96Q, N102D, S103T, V104I, S136K and G141A. The variant may comprise combinations of one or more of the mutations and substitutions from Msp B, C and D. The variant preferably comprises the mutation L88N. The variant of SEQ ID NO: 2 has the mutation L88N in addition to all the mutations of MS-B1 and is called MS-B2. The pore used in the invention is preferably MS-(B2)$_8$.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

Chemical properties of amino acids

| Ala | aliphatic, hydrophobic, neutral | Met | hydrophobic, neutral |
| --- | --- | --- | --- |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

TABLE 3

Hydropathy scale

| Side Chain | Hydropathy |
| --- | --- |
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |

TABLE 3-continued

Hydropathy scale

| Side Chain | Hydropathy |
| --- | --- |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels include, but are not limited to fluorescent molecules, radio-isotopes, e.g. $^{125}$I, $^{35}$S, enzymes, antibodies, antigens, polynucleotides and ligands such as biotin.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with NaBH$_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001,690 (published as WO 2010/004273), PCT/GB09/001,679 (published as WO 2010/004265) or PCT/GB10/000,133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homoheptamer) or different (heteroheptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into a lipid bilayer along with other appropriate subunits and its ability to oligomerise to form a pore may be determined. Methods are known in the art for inserting subunits into membranes, such as lipid bilayers. Suitable methods are discussed above.

The variant may include modifications that facilitate covalent attachment to or interaction with the helicase. The variant preferably comprises one or more reactive cysteine residues that facilitate attachment to the helicase. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001,690 (published as WO 2010/004273), PCT/GB09/001,679 (published as WO 2010/004265) or PCT/GB10/000,133 (published as WO 2010/086603).

The variant may also include modifications that facilitate any interaction with nucleotides.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135. 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive S⁻ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001,690 (published as WO 2010/004273), PCT/GB09/001,679 (published as WO 2010/004265) or PCT/GB10/000,133 (published as WO 2010/086603).

Any Hel308 helicase may be used in accordance with the invention. Hel308 helicases are also known as ski2-like helicases and the two terms can be used interchangeably.

The Hel308 helicase typically comprises the amino acid motif Q-X1-X2-G-R-A-G-R (hereinafter called the Hel308 motif; SEQ ID NO: 8). The Hel308 motif is typically part of the helicase motif VI (Tuteja and Tuteja, air. J. Biochem 271, 1849-1863 (2004)). X1 may be C, M or L. X1 is preferably C. X2 may be any amino acid residue. X2 is typically a hydrophobic or neutral residue. X2 may be A. M, C, V, S, T, P or R. X2 is preferably A, F, M, C, V, L, I, S, T or P. X2 is more preferably A, M or L. X2 is most preferably A or M.

The Hel308 helicase preferably comprises the motif Q-X1-X2-G-R-A-G-R-P (hereinafter called the extended Hel308 motif; SEQ ID NO: 9) wherein X1 and X2 are as described above.

The most preferred Hel308 motifs and extended Hel308 motifs are shown in Table 5 below. The Hel308 helicase may comprise any of these preferred motifs.

The Hel308 helicase is preferably one of the helicases shown in Table 4 below or a variant thereof.

TABLE 4

Preferred Hel308 helicases

| Accession | Description |
| --- | --- |
| NP_578406.1 | ski2-like helicase [*Pyrococcus furiosus* DSM 3638] >sp|O73946.1|HELS_PYRFU RecName: Full = Putative ski2-type helicase >pdb|2ZJ2|A Chain A, Archaeal Dna Helicase Hjm Apo State In Form 1 >pdb|2ZJ5|A Chain A, Archaeal Dna Helicase Hjm Complexed With Adp In Form 1 >pdb|2ZJ8|A Chain A, Archaeal Dna Helicase Hjm Apo State In Form 2 >pdb|2ZJA|A Chain A, Archaeal Dna Helicase Hjm Complexed With Amppcp In Form 2 >dbj|BAA32016.1| helicase [*Pyrococcus furiosus*] >gb|AAL80801.1| helicase [*Pyrococcus furiosus* DSM 3638] |
| NP_126564.1 | ski2-like helicase [*Pyrococcus abyssi* GE5] >sp|Q9V0A9.1|HELS_PYRAB RecName: Full = Putative ski2-type helicase >emb|CAB49795.1| DNA helicase [*Pyrococcus abyssi* GE5] |
| NP_143168.1 | ski2-like helicase [*Pyrococcus horikoshii* OT3] >sp|O59025.1|HELS_PYRHO RecName: Full = Putative ski2-type helicase >dbj|BAA30383.1| 715aa long hypothetical protein [*Pyrococcus horikoshii* OT3] |
| YP_004424773.1 | ski2-like helicase [*Pyrococcus sp.NA2*] >gb|AEC52769.1| ski2-like helicase [*Pyrococcus sp. NA2*] |
| YP_004623750.1 | ski2-like helicase [*Pyrococcus yayanosii* CH1] >gb|AEH24478.1| ski2-like helicase [*Pyrococcus yayanosii* CH1] |
| YP_002307730.1 | ski2-like helicase [*Thermococcus onnurineus* NA1] >gb|ACJ16833.1| DNA helicase [*Thermococcus onnurineus* NA1] |
| YP_004763427.1 | ski2-like helicase [*Thermococcus sp. 4557*] >gb|AEK73750.1| ski2-like helicase [*Thermococcus sp. 4557*] |
| YP_002959236.1 | ski2-like helicase [*Thermococcus gammatolerans* EJ3] >gb|ACS33372.1| ski2-type helicase, putative [*Thermococcus gammatolerans* EJ3] |
| YP_004071709.1 | ski2-type helicase [*Thermococcus barophilus* MP] >gb|ADT84486.1| putative ski2-type helicase [*Thermococcus barophilus* MP] |
| YP_002994328.1 | Putative ski2-type helicase [*Thermococcus sibiricus* MM 739] >gb|ACS89979.1| Putative ski2-type helicase [*Thermococcus sibiricus* MM 739] |
| ZP_04875329.1 | Type III restriction enzyme, res subunit family [*Aciduliprofundum boonei* T469] >gb|EDY35111.1| Type III restriction enzyme, res subunit family [*Aciduliprofundum boonei* T469] |
| YP_003436565.1 | DEAD/DEAH box helicase [*Ferroglobus placidus* DSM 10642] >gb|ADC66290.1| DEAD/DEAH box helicase domain protein [*Ferroglobus placidus* DSM 10642] |
| YP_004485304.1 | ski2-type helicase [*Methanotorris igneus* Kol 5] >gb|AEF97239.1| ski2-type helicase [*Methanotorris igneus* Kol 5] |
| YP_004616424.1 | DEAD/DEAH box helicase domain-containing protein [*Methanosalsum zhilinae* DSM 4017] >gb|AEH61205.1| DEAD/DEAH box helicase domain protein [*Methanosalsum zhilinae* DSM 4017] |

TABLE 4-continued

Preferred Hel308 helicases

| Accession | Description |
|---|---|
| ZP_04873370.1 | Type III restriction enzyme, res subunit family [*Aciduliprofundum boonei* T469] >ref|YP_003482774.1| DEAD/DEAH box helicase domain protein [*Aciduliprofundum boonei* T469] >gb|EDY36687.1| Type III restriction enzyme, res subunit family [*Aciduliprofundum boonei* T469] >gb|ADD08212.1| DEAD/DEAH box helicase domain protein [*Aciduliprofundum boonei* T469] |
| YP_004342552.1 | ski2-type helicase [*Archaeoglobus veneficus* SNP6] >gb|AEA47837.1| ski2-type helicase [*Archaeoglobus veneficus* SNP6] |
| NP_071282.1 | SKI2-family helicase [*Archaeoglobus fulgidus* DSM 4304] |
| 2P6R_A | Chain A, Crystal Structure Of Superfamily 2 Helicase Hel308 In Complex With Unwound Dna >pdb|2P6U|A Chain A, Apo Structure Of The Hel308 Superfamily 2 Helicase |
| YP_685308.1 | ski2-like helicase [uncultured methanogenic archaeon RC-I] >sp|Q0W6L1.1|HELS_UNCMA RecName: Full = Putative ski2-type helicase >emb|CAJ35982.1| putative ski2-type helicase [uncultured methanogenic archaeon RC-I] |
| YP_001048404.1 | ski2-like helicase [*Methanoculleus marisnigri* JR1] >gb|ABN58422.1| DEAD/DEAH box helicase domain protein [*Methanoculleus marisnigri* JR1] |
| YP_919908.1 | DEAD/DEAH box helicase domain-containing protein [*Thermofilum pendens* Hrk 5] >gb|ABL77905.1| DEAD/DEAH box helicase domain protein [*Thermofilum pendens* Hrk 5] |
| YP_843229.1 | ski2-like helicase [*Methanosaeta thermophila* PT] >gb|ABK14589.1| DEAD/DEAH box helicase domain protein [*Methanosaeta thermophila* PT] |
| ZP_08045937.1 | ski2-like helicase [*Haladaptatus paucihalophilus* DX253] >gb|EFW90585.1| ski2-like helicase [*Haladaptatus paucihalophilus* DX253] |
| NP_280985.1 | ski2-like helicase [*Halobacterium sp.NRC*-1] >ref|YP_001690117.1| ski2-like helicase [*Halobacterium salinarum* R1] >sp|Q9HMV6.1|HELS_HALSA RecName: Full = Putative ski2-type helicase >sp|B0R7Q2.1|HELS_HALS3 RecName: Full = Putative ski2-type helicase >gb|AAG20465.1| DNA repair protein [*Halobacterium sp. NRC*-1] >emb|CAP14771.1| putative DNA helicase [*Halobacterium salinarum* R1] |
| YP_003357840.1 | Holliday junction migration helicase [*Methanocella paludicola* SANAE] >dbj|BAI62857.1| Holliday junction migration helicase [*Methanocella paludicola* SANAE] |
| YP_003457479.1 | DEAD/DEAH box helicase domain protein [*Methanocaldococcus* sp. FS406-22] >gb|ADC68743.1| DEAD/DEAH box helicase domain protein [*Methanocaldococcus* sp. FS406-22] |
| YP_003127632.1 | DEAD/DEAH box helicase domain protein [*Methanocaldococcus fervens* AG86] >gb|ACV24132.1| DEAD/DEAH box helicase domain protein [*Methanocaldococcus fervens* AG86] |
| YP_003735335.1 | ski2-like helicase [*Halalkalicoccus jeotgali* B3] >gb|ADJ13543.1| ski2-like helicase [*Halalkalicoccus jeotgali* B3] |
| YP_503885.1 | ski2-1ike helicase [*Methanospirillum hungatei* JF-1] >gb|ABD42166.1| DEAD/DEAH box helicase-like protein [*Methanospirillum hungatei* JF-1] |
| BAJ48115.1 | helicase [*Candidatus Caldiarchaeum subterraneum*] >dbj|BAJ48144.1| helicase [*Candidatus Caldiarchaeum subterraneum*] >dbj|BAJ50919.1| helicase [*Candidatus Caldiarchaeum subterraneum*] |
| YP_001405615.1 | ski2-like helicase [*Candidatus Methanoregula boonei* 6A8] >sp|A7IB61.1|HELS_METB6 RecName: Full = Putative ski2-type helicase >gb|ABS56972.1| DEAD/DEAH box helicase domain protein [*Methanoregula boonei* 6A8] |
| YP_306959.1 | ski2-like helicase [*Methanosarcina barkeri* str. Fusaro] >sp|Q465R3.1|HELS_METBF RecName: Full = Putative ski2-type helicase >gb|AAZ72379.1| helicase [*Methanosarcina barkeri* str. Fusaro] |
| YP_001031179.1 | ski2-like helicase [*Methanocorpusculum labreanum* Z] >gb|ABN07912.1| DEAD/DEAH box helicase domain protein [*Methanocorpusculum labreanum* Z] |
| YP_003541733.1 | DEAD/DEAH box helicase [*Methanohalophilus mahii* DSM 5219] >gb|ADE36088.1| DEAD/DEAH box helicase domain protein [*Methanohalophilus mahii* DSM 5219] |
| YP_004384692.1 | putative Ski2-type helicase [*Methanosaeta concilii* GP6] >gb|AEB68874.1| putative Ski2-type helicase [*Methanosaeta concilii* GP6] |
| YP_003725904.1 | DEAD/DEAH box helicase domain-containing protein [*Methanohalobium evestigatum* Z-7303] >gb|ADI73108.1| DEAD/DEAH box helicase domain protein [*Methanohalobium evestigatum* Z-7303] |
| YP_003405271.1 | DEAD/DEAH box helicase [*Haloterrigena tarkmenica* DSM 5511] >gb|ADB62598.1| DEAD/DEAH box helicase domain protein [*Haloterrigena turkmenica* DSM 5511] |
| YP_004244914.1 | DEAD/DEAH box helicase [*Vulcanisaeta moutnovskia* 768-28] >gb|ADY01412.1| DEAD/DEAH box helicase domain protein [*Vulcanisaeta moutnovskia* 768-28] |
| YP_001540156.1 | DEAD/DEAH box helicase domain-containing protein [*Caldivirga maquilingensis* IC-167] >sp|A8MB76.1|HELS_CALMQ RecName: Full = Putative ski2-type helicase >gb|ABW01166.1| DEAD/DEAH box helicase domain protein [*Caldivirga maquilingensis* IC-167] |
| NP_618094.1 | ski2-like helicase [*Methanosarcina acetivorans* C2A] >sp|Q8TL39.1|HELS_METAC RecName: Full = Putative ski2-type helicase >gb|AAM06574.1| helicase [*Methanosarcina acetivorans* C2A] |

TABLE 4-continued

Preferred Hel308 helicases

| Accession | Description |
|---|---|
| YP_003900980.1 | DEAD/DEAH box helicase domain-containing protein [*Vulcanisaeta distributa* DSM 14429] >gb|ADN49929.1| DEAD/DEAH box helicase domain protein [*Vulcanisaeta distributa* DSM 14429] |
| YP_003896003.1 | DEAD/DEAH box helicase domain-containing protein [*Methanoplanus petrolearius* DSM 11571] >gb|ADN37565.1| DEAD/DEAH box helicase domain protein [*Methanoplanus petrolearius* DSM 11571] |
| YP_003615773.1 | DEAD/DEAH box helicase domain protein [*Methanocaldococcus infernus* ME] >gb|ADG12809.1| DEAD/DEAH box helicase domain protein [*Methanocaldococcus infernus* ME] |
| YP_183745.1 | RNA helicase Ski2-like protein [*Thermococcus kodakarensis* KOD1] >sp|Q5JGV6.1|HELS_PYRKO RecName: Full = Putative ski2-type helicase; Contains: RecName: Full = Endonuclease PI-PkoHel; AltName: Full = Pko Hel intein >dbj|BAD85521.1| RNA helicase Ski2 homolog [*Thermococcus kodakarensis* KOD1] |
| YP_001322557.1 | DEAD/DEAH box helicase domain-containing protein [*Methanococcus vannielii* SB] >sp|A6UN73.1|HELS_METVS RecName: Full = Putative ski2-type helicase >gb|ABR53945.1| DEAD/DEAH box helicase domain protein [*Methanococcus vannielii* SB] |
| YP_002467772.1 | ski2-like helicase [*Methanosphaerula palustris* E1-9c] >gb|ACL18049.1| DEAD/DEAH box helicase domain protein [*Methanosphaerula palustris* E1-9c] |
| YP_003480097.1 | DEAD/DEAH box helicase [*Natrialba magadii* ATCC 43099] >gb|ADD05535.1| DEAD/DEAH box helicase domain protein [*Natrialba magadii* ATCC 43099] |
| YP_004577043.1 | ski2-type helicase [*Methanothermococcus okinawensis* IH1] >gb|AEH07265.1| ski2-type helicase [*Methanothermococcus okinawensis* IH1] |
| YP_004742641.1 | superfamily II helicase [*Methanococcus maripaludis* XI] >gb|AEK19898.1| superfamily II helicase [*Methanococcus maripaludis* X1] |
| NP_632449.1 | ski2-like helicase [*Methanosarcina mazei* Go1] >sp|Q8PZR7.1|HELS_METMA RecName: Full = Putative ski2-type helicase >gb|AAM30121.1| helicase [*Methanosarcina mazei* Go1] |
| YP_001097223.1 | DEAD/DEAH box helicase domain-containing protein [*Methanococcus maripaludis* C5] >gb|ABO35008.1| DEAD/DEAH box helicase domain protein [*Methanococcus maripaludis* C5] |
| YP_004742247.1 | DEAD/DEAH box helicase domain-containing protein [*Methanococcus maripaludis* XI] >gb|AEK19504.1| DEAD/DEAH box helicase domain-containing protein [*Methanococcus maripaludis* X1] |
| YP_004794766.1 | ski2-like helicase [*Haloarcula hispanica* ATCC 33960] >gb|AEM55778.1| ski2-like helicase [*Haloarcula hispanica* ATCC 33960] |
| NP_988010.1 | superfamily II helicase [*Methanococcus maripaludis* S2] >emb|CAF30446.1| superfamily II helicase [*Methanococcus maripaludis* S2] |
| YP_565780.1 | ski2-like helicase [*Methanococcoides burtonii* DSM 6242] >sp|Q12WZ6.1|HELS_METBU RecName: Full = Putative ski2-type helicase >gb|ABE52030.1| DEAD/DEAH box helicase-like protein [*Methanococcoides burtonii* DSM 6242] |
| YP_001549808.1 | DEAD/DEAH box helicase domain-containing protein [*Methanococcus maripaludis* C6] >gb|ABX02576.1| DEAD/DEAH box helicase domain protein [*Methanococcus maripaludis* C6] |
| YP_001548609.1 | DEAD/DEAH box helicase domain-containing protein [*Methanococcus maripaludis* C6] >gb|ABX01377.1| DEAD/DEAH box helicase domain protein [*Methanococcus maripaludis* C6] |
| YP_001329359.1 | DEAD/DEAH box helicase domain-containing protein [*Methanococcus maripaludis* C7] >gb|ABR65208.1| DEAD/DEAH box helicase domain protein [*Methanococcus maripaludis* C7] |
| YP_004595982.1 | ski2-type helicase [*Halopiger xanaduensis* SH-6] >gb|AEH36103.1| ski2-type helicase [*Halopiger xanaduensis* SH-6] |
| YP_656795.1 | ski2-like helicase [*Haloquadratum walsbyi* DSM 16790] >emb|CAJ51138.1| ATP-dependent DNA helicase [*Haloquadratum walsbyi* DSM 16790] |
| CCC38992.1 | ATP-dependent DNA helicase Hel308 [*Haloquadratum walsbyi* C23] |
| YP_004035272.1 | superfamily ii helicase [*Halogeometricum borinquense* DSM 11551] >gb|ADQ65833.1| superfamily II helicase [*Halogeometricum borinquense* DSM 11551] |
| YP_137330.1 | ski2-like helicase [*Haloarcula marismortui* ATCC 43049] >sp|Q5UYM9.1|HELS_HALMA RecName: Full = Putative ski2-type helicase >gb|AAV47624.1| putative ski2-type helicase [*Haloarcula marismortui* ATCC 43049] |
| YP_001581577.1 | DEAD/DEAH box helicase domain-containing protein [*Nitrosopumilus maritimus* SCM1] >gb|ABX12139.1| DEAD/DEAH box helicase domain protein [*Nitrosopumilus maritimus* SCM1] |
| EET90255.1 | DEAD/DEAH box helicase domain protein [*Candidatus Micrarchaeum acidiphilum* ARMAN-2] |
| NP_376477.1 | helicase [*Sulfolobus tokodaii* str. 7] >sp|Q974S1.1|HELS_SULTO RecName: Full = Putative ski2-type helicase >dbj|BAK54341.1| Holliday junction migration helicase [*Sulfolobus tokodaii* str. 7] |
| YP_001097792.1 | DEAD/DEAH box helicase domain-containing protein [*Methanococcus maripaludis* C5] >gb|ABO35578.1| DEAD/DEAH box helicase domain protein [*Methanococcus maripaludis* C5] |

TABLE 4-continued

Preferred Hel308 helicases

| Accession | Description |
|---|---|
| ZP_08667240.1 | DEAD/DEAH box helicase domain protein [*Nitrosopumilus* sp. *MY*1] >gb|EGP92972.1| DEAD/DEAH box helicase domain protein [*Nitrosopumilus* sp. *MY*1] |
| YP_254972.1 | DNA helicase [*Sulfolobus acidocaldarius* DSM 639] >sp|Q4JC00.1|HELS_SULAC RecName: Full = Putative ski2-type helicase >gb|AAY79679.1| DNA helicase [*Sulfolobus acidocaldarius* DSM 639] |
| EFD92533.1 | DEAD/DEAH box helicase domain protein [*Candidatus Parvarchaeum acidophilus* ARMAN-5] |
| YP_003176527.1 | ski2-like helicase [*Halomicrobium mukohataei* DSM 12286] >gb|ACV46820.1| DEAD/DEAH box helicase domain protein [*Halomicrobium mukohataei* DSM12286] |
| EGD71904.1 | DEAD/DEAH box helicase domain protein [*Candidatus Parvarchaeum acidophilus* ARMAN-5_'5-way FS'] |
| YP_001040230.1 | DEAD/DEAH box helicase domain-containing protein [*Staphylothermus marinus* F1] >gb|ABN69322.1| DEAD/DEAH box helicase domain protein [*Staphylothermus marinus* F1] |
| ABZ07376.1 | putative DEAD/DEAH box helicase [uncultured marine crenarchaeote HF4000_ANIW133M9] |
| YP_001097458.1 | DEAD/DEAH box helicase domain-containing protein [*Methanococcus maripaludis* C5] >gb|ABO35243.1| DEAD/DEAH box helicase domain protein [*Methanococcus maripaludis* C5] |
| ABZ08606.1 | putative DEAD/DEAH box helicase [uncultured marine crenarchaeote HF4000_APKG3H9] |
| YP_325906.1 | ski2-like helicase [*Natronomonas pharaonis* DSM 2160] >sp|Q31U46.1|HELS_NATPD RecName: Full = Putative ski2-type helicase >emb|CAI48337.1| ATP-dependent DNA helicase 1 [*Natronomonas pharaonis* DSM 2160] |
| YP_930665.1 | DEAD/DEAH box helicase domain-containing protein [*Pyrobaculum islandicum* DSM 4184] >gb|ABL88322.1| DEAD/DEAH box helicase domain protein [*Pyrobaculum islandicum* DSM 4184] |
| YP_001435870.1 | DEAD/DEAH box helicase [*Ignicoccus hospitalis* KIN4/1] >gb|ABU82463.1| DEAD/DEAH box helicase domain, protein [*Ignicoccus hospitalis* KIN4/I] |
| YP_003668634.1 | DEAD/DEAH box helicase domain-containing protein [*Staphylothermus hellenicus* DSM 12710] >gb|ADI31735.1| DEAD/DEAH box helicase domain protein [*Staphylothermus hellenicus* DSM 12710] |
| ZP_08558598.1 | ski2-like helicase [*Halorhabdus tiamatea* SARL4B] >gb|EGM36528.1| ski2-like helicase [*Halorhabdus tiamatea* SARL4B] |
| YP_002428409.1 | DEAD/DEAH box helicase domain-containing protein [*Desulfurococcus kamchatkensis* 1221n] >gb|ACL11042.1| DEAD/DEAH box helicase domain protein [*Desulfurococcus kamchatkensis* 1221n] |
| YP_004336918.1 | ATP-dependent, DNA binding helicase [*Thermoproteus uzoniensis* 768-20] >gb|AEA11606.1| ATP-dependent, DNA binding helicase [*Thermoproteus uzoniensis* 768-20] |
| ZP_08257442.1 | DEAD/DEAH box helicase domain-containing protein [*Candidatus Nitrosoarchaeum limnia* SFB1] >gb|EGG41989.1| DEAD/DEAH box helicase domain-containing protein [*Candidatus Nitrosoarchaeum limnia* SFB1] |
| YP_004459284.1 | DEAD/DEAH box helicase domain-containing protein [*Acidianus hospitalis* W1] >gb|AEE94986.1| DEAD/DEAH box helicase domain protein [*Acidianus hospitalis* W1] |
| NP_558924.1 | ATP-dependent, DNA binding helicase [*Pyrobaculum aerophilum* str. IM2] >gb|AAL63106.1| ATP-dependent, DNA binding helicase [*Pyrobaculum aerophilum* str. IM2] |
| YP_004409449.1 | DEAD/DEAH box helicase domain-containing protein [*Metallosphaera cuprina* Ar-4] >gb|AEB94965.1| DEAD/DEAH box helicase domain-containing protein [*Metallosphaera cuprina* Ar-4] |
| YP_003649556.1 | DEAD/DEAH box helicase domain-containing protein [*Thermosphaera aggregans* DSM 11486] >gb|ADG90604.1| DEAD/DEAH box helicase domain protein [*Thermosphaera aggregans* DSM 11486] |
| ZP_06387115.1 | DEAD/DEAH box helicase domain protein [*Sulfolobus solfataricus* 98/2] >gb|ACX90562.1| DEAD/DEAH box helicase domain protein [*Sulfolobus solfataricus* 98/2] |
| 2VA8_A | Chain A, Dna Repair Helicase Hel308 >pdb|2VA8|B Chain B, Dna Repair Helicase Hel308 >emb|CAO85626.1| DNA helicase [*Sulfolobus solfataricus*] |
| YP_004809267.1 | ski2-type helicase [halophilic archaeon DL31] >gb|AEN06894.1| ski2-type helicase [halophilic archaeon DL31] |
| ADX84345.1 | DEAD/DEAH box helicase domain protein [*Sulfolobus islandicus* REY15A] >gb|ADX81629.1| DEAD/DEAH box helicase domain protein [*Sulfolobus islandicus* HVE10/4] |
| YP_002828439.1 | DEAD/DEAH box helicase [*Sulfolobus islandicus* M.14.25] >ref|YP_002842325.1| DEAD/DEAH box helicase domain protein [*Sulfolobus islandicus* M.16.27] >gb|ACP37141.1| DEAD/DEAH box helicase domain protein [*Sulfolobus islandicus* M.14.25] >gb|ACP54280.1| DEAD/DEAH box helicase domain protein [*Sulfolobus islandicus* M.16.27] |
| YP_002913571.1 | DEAD/DEAH box helicase domain protein [*Sulfolobus islandicus* M.16.41 >gb|ACR40903.1| DEAD/DEAH box helicase domain protein [*Sulfolobus islandicus* M.16.4] |

TABLE 4-continued

Preferred Hel308 helicases

| Accession | Description |
|---|---|
| Q97VY9.1 | RecName: Full = Putative ski2-type helicase |
| YP_002841682.1 | DEAD/DEAH box helicase domain protein [*Sulfolobus islandicus* Y.N.15.51] >gb|ACP49760.1| DEAD/DEAH box helicase domain protein [*Sulfolobus islandicus* Y.N.15.51] |
| YP_002831080.1 | DEAD/DEAH box helicase domain protein [*Sulfolobus islandicus* L.S.2.15] >ref|YP_003418425.1| DEAD/DEAH box helicase domain protein [*Sulfolobus islandicus* L.D.8.5] >gb|ACP34435.1| DEAD/DEAH box helicase domain protein [*Sulfolobus islandicus* L.S.2.15] >gb|ADB86055.1| DEAD/DEAH box helicase domain protein [*Sulfolobus islandicus* L.D.8.5] |
| YP_001054984.1 | DEAD/DEAH box helicase domain-containing protein [*Pyrobaculum calidifontis* JCM 11548] >sp|A3MSA1.1|HELS_PYRCJ RecName: Full = Putative ski2-type helicase >gb|ABO07518.1| DEAD/DEAH box helicase domain protein [*Pyrobaculum calidifontis* JCM 11548] |
| NP_343811.1 | DNA helicase related protein [*Sulfolobus solfataricus* P2] >ref|YP_002836469.1| DEAD/DEAH box helicase [*Sulfolobus islandicus* Y.G.57.14] >gb|AAK42601.1| DNA helicase related protein [*Sulfolobus solfataricus* P2] >gb|ACP44547.1| DEAD/DEAH box helicase domain protein [*Sulfolobus islandicus* Y.G.57.14] |
| YP_001152379.1 | DEAD/DEAH box helicase domain-containing protein [*Pyrobaculum arsenaticum* DSM 135141 >gb|ABP49727.1| DEAD/DEAH box helicase domain protein [*Pyrobaculum arsenaticum* DSM 13514] |
| YP_001191456.1 | DEAD/DEAH box helicase domain-containing protein [*Metallosphaera sedula* DSM 5348] >gb|ABP95532.1| DEAD/DEAH box helicase domain protein [*Metallosphaera sedula* DSM 5348] |
| NP_147034.2 | holliday junction migration helicase [*Aeropyrum pernix* K1] >sp|Q9YFQ8.2|HELS_AERPE RecName: Full = Putative ski2-type helicase >dbj|BAA79103.2| holliday junction migration helicase [*Aeropyrum pernix* K1] |
| YP_024158.1 | ski2-like helicase [*Picrophilus torridus* DSM 9790] >gb|AAT43965.1| helicase involved in UV-protection [*Picrophilus torridus* DSM 9790] |
| YP_003816358.1 | Putative ski2-type helicase [*Acidilobus saccharovorans* 345-15] >gb|ADL19327.1| Putative ski2-type helicase [*Acidilobus saccharovorans* 345-15] |
| YP_003860265.1 | DEAD/DEAH box helicase domain protein [*Ignisphaera aggregans* DSM 17230] >gb|ADM28385.1| DEAD/DEAH box helicase domain protein [*Ignisphaera aggregans* DSM 17230] |
| NP_394295.1 | ski2-like helicase [*Thermoplasma acidophilum* DSM 1728] >sp|Q9HJX7.1|HELS_THEAC RecName: Full = Putative ski2-type helicase >emb|CAC11964.1| DNA helicase related protein [*Thermoplasma acidophilum*] |
| YP_876638.1 | superfamily II helicase [*Cenarchaeum symbiosum* A] >gb|ABK78334.1| superfamily II helicase [*Cenarchaeum symbiosum* A] |
| ZP_05571398.1 | ski2-like helicase [*Ferroplasma acidarmanus* fer1] |
| YP_004176252.1 | DEAD/DEAH box helicase domain-containing protein [*Desulfurococcus mucosus* DSM 2162] >gb|ADV64770.1| DEAD/DEAH box helicase domain protein [*Desulfurococcus mucosus* DSM 2162] |
| YP_001737782.1 | DEAD/DEAH box helicase domain-containing protein [*Candidatus Korarchaeum cryptofilum* OPF8] >gb|ACB08099.1| DEAD/DEAH box helicase domain protein [*Candidatus Korarchaeum cryptofilum* OPF8] |
| EGQ40435.1 | superfamily II helicase [*Candidatus Nanosalinarum* sp. J07AB56] |
| YP_002567343.1 | ski2-like helicase [*Halorubrum lacusprofundi* ATCC 49239] >gb|ACM58273.1| DEAD/DEAH box helicase domain protein [*Halorubrum lacusprofundi* ATCC 49239] |
| YP_001793507.1 | DEAD/DEAH box helicase domain-containing protein [*Thermoproteus neutrophilus* V24Sta] >gb|ACB39061.1| DEAD/DEAH box helicase domain protein [*Thermoproteus neutrophilus* V24Sta] |
| YP_003534088.1 | ATP-dependent DNA helicase Hel308a [*Haloferax volcanii* DS2] >gb|ADE04048.1| ATP-dependent DNA helicase Hel308a [*Haloferax volcanii* DS2] |
| YP_004037165.1 | superfamily ii helicase [*Halogeometricum borinquense* DSM 11551] >gb|ADQ67720.1| superfamily II helicase [*Halogeometricum borinquense* DSM 11551] |
| NP_111333.1 | ski2-like helicase [*Thermoplasma volcanium* GSS1] >sp|Q97AI2.1|HELS_THEVO RecName: Full = Putative ski2-type helicase >dbj|BAB59970.1| DNA helicase [*Thermoplasma volcanium* GSS1] |
| YP_002565871.1 | DEAD/DEAH box helicase [*Halorubrum lacusprofundi* ATCC 49239] >gb|ACM56801.1| DEAD/DEAH box helicase domain protein. [*Halorubrum lacusprofundi* ATCC 49239] |
| CCC39675.1 | ATP-dependent DNA helicase Hel308 [*Haloquadratum walsbyi* C23] |
| YP_657401.1 | ATP-dependent DNA helicase [*Haloquadratum walsbyi* DSM 16790] >emb|CAJ51759.1| ATP-dependent DNA helicase [*Haloquadratum walsbyi* DSM 16790] |
| YP_003535028.1 | ATP-dependent DNA helicase Hel308b [*Haloferax volcanii* DS2] >gb|ADE02398.1| ATP-dependent DNA helicase Hel308b [*Haloferax volcanii* DS2] |
| YP_003706863.1 | DEAD/DEAH box helicase domain-containing protein [*Methanococcus voltae* A3] >gb|ADI35890.1| DEAD/DEAH box helicase domain protein [*Methanococcus voltae* A3] |

TABLE 4-continued

Preferred Hel308 helicases

| Accession | Description |
|---|---|
| ABD17736.1 | helicase [*Methanococcus voltae* PS] |
| NP_613398.1 | superfamily II helicase [*Methanopyrus kandleri* AV19] >gb|AAM01328.1| Predicted Superfamily II helicase [*Methanopyrus kandleri* AV19] |
| CBH38575.1 | putative ski2-type helicase [uncultured archaeon] |
| EEZ93258.1 | DEAD/DEAH box helicase domain protein [*Candidatus Parvarchaeum acidiphilum* ARMAN-4] |
| EGQ40350.1 | superfamily II helicase [*Candidatus Nanosalinarum* sp.J07AB56] |
| YP_004004246.1 | dead/deah box helicase domain protein [*Methanothermus fervidus* DSM 2088] >gb|ADP77484.1| DEAD/DEAH box helicase domain protein [*Methanothermus fervidus* DSM 2088] |
| YP_003850109.1 | helicase [*Methanothermobacter marburgensis* str. Marburg] >gb|ADL58796.1| predicted helicase [*Methanothermobacter marburgensis* str. Marburg] |
| YP_003424423.1 | DEAD/DEAH box helicase domain-containing protein [*Methanobrevibacter ruminantium* M1] >gb|ADC47531.1| DEAD/DEAH box helicase domain-containing protein [*Methanobrevibacter ruminantium* M1] |
| YP_004291107.1 | DEAD/DEAH box helicase domain-containing protein [*Methanobacterium* sp. AL-21] >gb|ADZ10135.1| DEAD/DEAH box helicase domain protein [*Methanobacterium* sp.AL-21] |
| YP_447162.1 | helicase [*Methanosphaera stadtmanae* DSM 3091] >gb|ABC56519.1| predicted helicase [*Methanosphaera stadtmanae* DSM 3091] |
| YP_004519549.1 | DEAD/DEAH box helicase domain-containing protein [*Methanobacterium* sp. SWAN-1] >gb|AEG17748.1| DEAD/DEAH box helicase domain protein [*Methanobacterium* sp. SWAN-1] |
| NP_275949.1 | DNA helicase related protein [*Methanothermobacter thermautotrophicus* str. Delta H] >sp|O26901.1|HELS_METTH RecName: Full = Putative ski2-type helicase >gb|AAB85310.1| DNA helicase related protein [*Methanothermobacter thermautotrophicus* str. Delta H] |
| ZP_05975717.2 | putative Ski2-type helicase [*Methanobrevibacter smithii* DSM 2374] >gb|EFC93382.1| putative Ski2-type helicase [*Methanobrevibacter smithii* DSM 2374] |
| ZP_03607647.1 | hypothetical protein METSMIALI_00751 [*Methanobrevibacter smithii* DSM 2375] >gb|EEE41862.1| hypothetical protein METSMIALI_00751 [*Methanobrevibacter smithii* DSM 2375] |
| YP_001273412.1 | ATP-dependent helicase [*Methanobrevibacter smithii* ATCC 35061] >gb|ABQ87044.1| ATP-dependent helicase [*Methanobrevibacter smithii* ATCC 35061] |
| YP_003247505.1 | DEAD/DEAH box helicase domain protein [*Methanocaldococcus vulcanius* M7] >gb|ACX73023.1| DEAD/DEAH box helicase domain protein [*Methanocaldococcus vulcanius* M7] |
| NP_248116.1 | SKI2 family helicase [*Methanocaldococcus jannaschii* DSM 2661] >sp|Q58524.1| HELS_METJA RecName: Full = Putative ski2-type helicase; Contains: RecName: Full = Endonuclease PI-MjaHel; AltName: Full = Mja Hel intein; AltName: Full = Mja Pep3 intein >gb|AAB99126.1| putative SKI2-family helicase [*Methanocaldococcus jannaschii* DSM 2661] |
| YP_001324295.1 | DEAD/DEAH box helicase domain-containing protein [*Methanococcus aeolicus* Nankai-3] >gb|ABR55683.1| DEAD/DEAH box helicase domain protein [*Methanococcus aeolicus* Nankai-3] |
| YP_003536960.1 | Pre-mRNA splicing helicase [*Haloferax volcanii* DS2] >gb|ADE02332.1| Pre-mRNA splicing helicase [*Haloferax volcanii* DS2] |
| YP_003131029.1 | DEAD/DEAH box helicase domain protein [*Halorhabdus utahensis* DSM 12940] >gb|ACV12296.1| DEAD/DEAH box helicase domain protein [*Halorhabdus utahensis* DSM 12940] |
| YP_002567151.1 | DEAD/DEAH box helicase [*Halorubrum lacusprofundi* ATCC 49239] >gb|ACM58081.1| DEAD/DEAH box helicase domain protein [*Halorubrum lacusprofundi* ATCC 49239] |
| YP_004035351.1 | superfamily ii helicase [*Halogeometricum borinquense* DSM 11551] >gb|ADQ65912.1| superfamily II helicase [*Halogeometricum borinquense* DSM11551] |
| YP_004808851.1 | DEAD/DEAH box helicase domain-containing protein [halophilic archaeon DL31] >gb|AEN06478.1| DEAD/DEAH box helicase domain protein [halophilic archaeon DL31] |
| XP_002716686.1 | PREDICTED: DNA polymerase theta isoform 1 [*Oryctolagus cuniculus*] |
| YP_656834.1 | ATP-dependent DNA helicase [*Haloquadratum walsbyi* DSM 16790] >emb|CAJ51176.1| ATP-dependent DNA helicase [*Haloquadratum walsbyi* DSM 16790] |
| XP_003248103.1 | PREDICTED: DNA polymerase theta-like isoform 1 [*Acyrthosiphon pisum*] |
| ABC72356.1 | ATP-dependent DNA helicase [*Haloquadratum walsbyi*] |
| CCC39031.1 | DEAD/DEAH box helicase [*Haloquadratum walsbyi* C23] |
| XP_001165150.2 | PREDICTED: DNA polymerase theta isoform 1 [*Pan troglodytes*] |
| XP_003225852.1 | PREDICTED: DNA polymerase theta-like [*Anolis carolinensis*] |
| XP_615375.3 | PREDICTED: DNA polymerase theta [*Bos taurus*] >ref|XP_002684835.1| PREDICTED: polymerase (DNA directed), theta-like [*Bos taurus*] >gb|DAA33456.1| polymerase (DNA directed), theta-like [*Bos taurus*] |
| XP_002813286.1 | PREDICTED: LOW QUALITY PROTEIN: DNA polymerase theta-like [*Pongo abelii*] |

TABLE 4-continued

Preferred Hel308 helicases

| Accession | Description |
| --- | --- |
| AAR08421.2 | DNA polymerase theta [*Homo sapiens*] |
| EAW79510.1 | polymerase (DNA directed), theta, isoform CRA_a [*Homo sapiens*] |
| NP_955452.3 | DNA polymerase theta [*Homo sapiens*] >sp|O75417.2|DPOLQ_HUMAN RecName: Full = DNA polymerase theta; AltName: Full = DNA polymerase eta >gb|AAI72289.1| Polymerase (DNA directed), theta [synthetic polynucleotide] |
| NP_001099348.1 | DNA polymerase theta [*Rattus norvegicus*] >gb|EDM11249.1| polymerase (DNA directed), theta (predicted), isoform CRA_a [*Rattus norvegicus*] |
| XP_003341262.1 | PREDICTED: LOW QUALITY PROTEIN: DNA polymerase theta-like [*Monodelphis domestica*] |
| XP_001502374.3 | PREDICTED: DNA polymerase theta [*Equus caballus*] |
| XP_545125.3 | PREDICTED: LOW QUALITY PROTEIN: DNA polymerase theta [*Canis lupus familiaris*] |
| XP_002928855.1 | PREDICTED: LOW QUALITY PROTEIN: DNA polymerase theta-like [*Ailuropoda melanoleuca*] |
| NP_084253.1 | DNA polymerase theta isoform 1 [*Mus musculus*] >gb|AAL77225.1| DNA polymerase theta [*Mus musculus*] >gb|EDK97951.1| polymerase (DNA directed), theta, isoform CRA_a [*Mus musculus*] >gb|AAI38361.1| Polymerase (DNA directed), theta [*Mus musculus*] >gb|AAI57901.1| Polymerase (DNA directed), theta [*Mus musculus*] |
| AAK39635.1 | DNA polymerase theta [*Homo sapiens*] |
| AAN39838.1 | DNA polymerase Q [*Mus musculus*] |
| XP_003412882.1 | PREDICTED: DNA polymerase theta [*Loxodonta africana*] |
| YP_003735206.1 | DEAD/DEAH box helicase domain-containing protein [*Halalkalicoccus jeotgali* B3] >gb|ADJ13414.1| DEAD/DEAH box helicase domain protein [*Halalkalicoccus jeotgali* B3] |
| YP_004794841.1 | pre-mRNA splicing helicase [*Haloarcula hispanica* ATCC 33960] >gb|AEM55853.1| pre-mRNA splicing helicase [*Haloarcula hispanica* ATCC 33960] |
| XP_416549.2 | PREDICTED: similar to DNA polymerase theta [*Gallus gallus*] |
| XP_003427319.1 | PREDICTED: helicase POLQ-like isoform 2 [*Nasonia vitripennis*] |
| XP_003202748.1 | PREDICTED: DNA polymerase theta-like [*Meleagris gallopavo*] |
| XP_969311.1 | PREDICTED: similar to DNA polymerase theta [*Tribolium castaneum*] >gb|EEZ97532.1| hypothetical protein TcasGA2_TC011380 [*Tribolium castaneum*] |
| ZP_08046037.1 | DEAD/DEAH box helicase domain protein [*Haladaptatus paucihalophilus* DX253] >gb|EFW90685.1| DEAD/DEAH box helicase domain protein [*Haladaptatus paucihalophilus* DX253] |
| YP 461714.1 | helicase [*Syntrophus aciditrophicus* SB] >gb|ABC77546.1| helicase [*Syntrophus aciditrophicus* SB] |
| YP 003176510.1 | DEAD/DEAH box helicase [*Halomicrobium mukohataei* DSM 12286] >gb|ACV46803.1] DEAD/DEAH box helicase domain protein [*Halomicrobium mukohataei* DSM 12286] |
| YP_137400.1 | Pre-mRNA splicing helicase [*Haloarcula marismortui* ATCC 43049] >gb|AAV47694.1| Pre-mRNA splicing helicase [*Haloarcula marismortui* ATCC 43049] |
| NP_001184156.1 | polymerase (DNA directed), theta [*Xenopus (Silurana) tropicalis*] |
| NP_280861.1 | pre-mRNA splicing helicase [*Halobacterium* sp. NRC-1] >ref|YP_001689987.1| ATP-dependent DNA helicase [*Halobacterium salinarum* R1] >gb|AAG20341.1| pre-mRNA splicing helicase [*Halobacterium sp.NRC-1*] >emb|CAP14641.1| ATP-dependent DNA helicase [*Halobacterium salinarum* R1] |
| YP_004595640.1 | DEAD/DEAH box helicase domain-containing protein [*Halopiger xanaduensis* SH-6] >gb|AEH35761.1| DEAD/DEAH box helicase domain protein [*Halopiger xanaduensis* SH-6] |
| XP_001521144.2 | PREDICTED: DNA polymerase theta, partial [*Ornithorhynchus anatinus*] |
| XP_003261953.1 | PREDICTED: DNA polymerase theta, partial [*Nomascus leucogenys*] |
| XP_001358456.2 | GA19301 [*Drosophila pseudoobscura pseudoobscura*] >gb|EAL27595.2| GA19301 [*Drosophila pseudoobscura pseudoobscura*] |
| ZP_08560003.1 | DEAD/DEAH box helicase domain protein [*Halorhabdus tiamatea* SARL4B] >gb|EGM34502.1| DEAD/DEAH box helicase domain protein [*Halorhabdus tiamatea* SARL4B] |
| XP_002187783.1 | PREDICTED: similar to polymerase (DNA directed), theta [*Taeniopygia guttata*] |
| XP_002112587.1 | hypothetical protein TRIADDRAFT_25163 [*Trichoplax adhaerens*] >gb|EDV24697.1| hypothetical protein TRIADDRAFT_25163 [*Trichoplax adhaerens*] |
| YP_003405139.1 | DEAD/DEAH box helicase [*Haloterrigena turkmenica* DSM 5511] >gb|ADB62466.1| DEAD/DEAH box helicase domain protein [*Haloterrigena turkmenica* DSM 5511] |
| EGV92665.1 | DNA polymerase theta [*Cricetulus griseus*] |
| CBY24305.1 | unnamed protein product [*Oikopleura dioica*] |
| YP_003130565.1 | DEAD/DEAH box helicase domain protein [*Halorhabdus utahensis* DSM 12940] >gb|ACV11832.1| DEAD/DEAH box helicase domain protein. [*Halorhabdus utahensis* DSM 12940] |
| YP_003479811.1 | DEAD/DEAH box helicase [*Natrialba magadii* ATCC 43099] >gb|ADD05249.1| DEAD/DEAH box helicase domain protein [*Natrialba magadii* ATCC 43099] |
| EFB22383.1 | hypothetical protein PANDA_000253 [*Ailuropoda melanoleuca*] |

TABLE 4-continued

Preferred Hel308 helicases

| Accession | Description |
|---|---|
| YP_003357334.1 | putative ATP-dependent helicase [*Methanocella paludicola* SANAE] >dbj|BAI62351.1| putative ATP-dependent helicase [*Methanocella paludicola* SANAE] |
| YP_325942.1 | ATP-dependent DNA helicase 2 [*Natronomonas pharaonis* DSM 2160] >emb|CA148373.2| ATP-dependent DNA. helicase 2 [*Natronomonas pharaonis* DSM 2160] |
| XP_002912509.1 | PREDICTED: LOW QUALITY PROTEIN: helicase POLQ-like [*Ailuropoda melanoleuca*] |
| XP_002704678.1 | PREDICTED: helicase, POLQ-like [*Bos taurus*] |
| CAE47762.2 | novel protein similar to humna, DNA-directed polymerase theta (POLQ) [*Danio rerio*] |
| XP_003205636.1 | PREDICTED: helicase POLQ-like [*Meleagris gallopavo*] |
| XP_544959.2 | PREDICTED: helicase, POLQ-like [*Canis lupus familiaris*] |
| EFX86757.1 | hypothetical protein DAPPUDRAFT_312857 [*Daphnia pulex*] |
| YP_003389641.1 | DEAD/DEAH box helicase [*Spirosoma linguale* DSM 74] >gb|ADB40842.1| DEAD/DEAH box helicase domain protein [*Spirosoma linguale* DSM 74] |
| XP_002602932.1 | hypothetical protein BRAFLDRAFT_251779 [*Branchiostoma floridae*] >gb|EEN58944.1| hypothetical protein BRAFLDRAFT_251779 [*Branchiostoma floridae*] |
| YP_004144962.1 | peptidase C14 caspase catalytic subunit p20 [*Mesorhizobium ciceri biovar biserrulae* WSM1271] >rel|YP_004614892.1| DEAD/DEAH box helicase domain-containing protein [*Mesorhizobium opportunistum* WSM2075] >gb|ADV14912.1| peptidase C14 caspase catalytic subunit p20 [*Mesorhizobium ciceri biovar biserrulae* WSM1271] >gb|AEH90798.1| DEAD/DEAH box helicase domain protein [*Mesorhizobium opportunistum* WSM2075] |
| XP_002124758.1 | PREDICTED: similar to DNA polymerase theta [*Ciona intestinalis*] |
| XP_694437.5 | PREDICTED: DNA polymerase theta [*Danio rerio*] |
| XP_420565.1 | PREDICTED: similar to DNA helicase HEL308 [*Gallus gallus*] |
| XP_003129397.1 | PREDICTED: helicase POLQ-like [*Sus scrofa*] |
| EDL20278.1 | mCG128467, isoform CRA_b [*Mus musculus*] |
| XP_001517710.2 | PREDICTED: helicase POLQ, partial [*Ornithorhynchus anatinus*] |
| AAH82601.1 | Helicase, mus308-like (*Drosophila*) [*Mus musculus*] |
| XP_003384429.1 | PREDICTED: DNA polymerase theta-like [*Amphimedon queenslandica*] |
| XP_003221282.1 | PREDICTED: helicase POLQ-like [*Anolis carolinensis*] |
| NP_524333.1 | mutagen-sensitive 308 [*Drosophila melanogaster*] >gb|AAB67306.1| Mus308 [*Drosophila melanogaster*] >gb|AAF54S58.1| mutagen-sensitive 308 [*Drosophila melanogaster*] >gb|ACH92234.1| FI03732p [*Drosophila melanogaster*] |
| AAX33507.1 | LP14642p [*Drosophila melanogaster*] |
| NP_001074576.1 | helicase POLQ-like [*Mus musculus*] >sp|Q2VPA6.2|HELQ_MOUSE RecName: Full = Helicase POLQ-like; AltName: Full = Mus308-like helicase: AltName: Full = POLQ-like helicase >gb|AAI09171.2| Helicase, mus308-like (*Drosophila*) [*Mus musculus*] |
| YP_003523727.1 | DEAD/DEAH box helicase domain protein [*Sideroxydans lithotrophicus* ES-1] >gb|ADE11340.1| DEAD/DEAH box helicase domain protein [*Sideroxydans lithotrophicus*ES-1] |
| XP_002120889.1 | PREDICTED: similar to DNA helicase HEL308 [*Ciona intestinalis*] |
| XP_001892566.1 | Type III restriction enzyme, res subunit family protein [*Brugia malayi*] >gb|EDP38603.1| Type III restriction enzyme, res subunit family protein [*Brugia malayi*] |
| ABZ09232.1 | putative helicase conserved C-terminal domain protein [uncultured marine crenarchaeote HF4000_APKG7F11] |
| XP_002814981.1 | PREDICTED: LOW QUALITY PROTEIN: helicase POLQ-like [*Pongo abelii*] |
| XP_002717082.1 | PREDICTED: DNA helicase HEL308 [*Oryctolagus cuniculus*| |
| XP_001104832.1 | PREDICTED: helicase, POLQ-like [*Macaca mulatta*] |
| AAL85274.1 | DNA helicase HEL308 [*Homo sapiens*] |
| NP_598375.2 | helicase POLQ-like [*Homo sapiens*] >gb|EAX05934.1| DNA helicase HEL308, isoform CRA_a [*Homo sapiens*] >gb|AAI41525.1| Helicase, POLQ-like [synthetic polynucleotide] |
| Q8TDG4.2 | RecName: Full = Helicase POLQ-like; AltName: Full = Mus308-like helicase: AltName: Full = POLQ-like helicase |
| XP_003265889.1 | PREDICTED: helicase POLQ [*Nomascus leucogenys*] |
| XP_002745688.1 | PREDICTED: helicase POLQ-like [*Callithrix jacchus*] |
| XP_003310356.1 | PREDICTED: LOW QUALITY PROTEIN: helicase POLQ-like [*Pan troglodytes*] |
| NP_001014156.2 | helicase, POLQ-like [*Rattus norvegicus*] >rf|XP_001060858.1 PREDICTED: helicase, POLQ-like [*Rattus norvegicus*] >gb|EDL99554.1| rCG37823, isoform CRA_c [*Rattus norvegicus*] |
| XP_001850567.1 | ATP-dependent DNA helicase MER3 [*Culex quinquefasciatus*] >gb|EDS32308.1| ATP-dependent DNA helicase MER3 [*Culex quinquefasciatus*] |
| XP_003427318.1 | PREDICTED: helicase POLQ-like isoform 1 [*Nasonia vitripennis*] |
| XP_003143912.1 | hypothetical protein LOAG_08332 [*Loa loa*; >gb|EFO20157.1| hypothetical protein LOAG_08332 [*Loa loa*] |
| CAG11187.1 | unnamed protein product [*Tetraodon nigroviridis*] |
| XP 001111254.2 | PREDICTED: DNA polymerase theta isoform 2 [*Macaca mulatta*] |
| XP 003414242.1 | PREDICTED: helicase POLQ [*Loxodonta africana*] |

TABLE 4-continued

Preferred Hel308 helicases

| Accession | Description |
|---|---|
| XP_002681870.1 | predicted protein [*Naegleria gruberi*] >gb|EFC49126.1| predicted protein [*Naegleria gruberi*] |
| EAX05935.1 | DNA helicase HEL308, isoform CRA_b [*Homo sapiens*] |
| AAH59917.1 | Ascc3 protein [*Mus musculus*] |
| ZP_07082808.1 | DEAD/DEAH box helicase domain protein [*Sphingobacterium spiritivorum* ATCC 33861] >gb|EFK55937.1| DEAD/DEAH box helicase domain protein [*Sphingobacterium spiritivorum* ATCC 33861] |
| XP_001494572.3 | PREDICTED: LOW QUALITY PROTEIN: helicase POLQ-like [*Equus Caballus*] |
| XP_002714920.1 | PREDICTED: activating signal cointegrator 1 complex subunit 3 [*Oryctolagus cuniculus*] |
| XP_002598278.1 | hypothetical protein BRAFLDRAFT_204526 [*Branchiostoma floridae*] >gb|EEN54290.1| hypothetical protein BRAFLDRAFT_204526 [*Branchiostoma floridae*] |
| XP_001943294.1 | PREDICTED: helicase POLQ-like isoform 1 [*Acyrthosiphon pisum*] >ref|XP_003240510.1 PREDICTED: helicase POLQ-like isoform 2 [*Acyrthosiphon pisum*] |
| XP_002803889.1 | PREDICTED: activating signal cointegrator 1 complex subunit 3-like [*Macaca mulatta*] |
| XP_001651546.1 | DNA polymerase theta [*Aedes aegypti*] >gb|EAT42599.1| DNA polymerase theta [*Aedes aegypti*] |
| CAA11679.1 | RNA helicase [*Homo sapiens*] |
| XP_002837795.1 | hypothetical protein [*Tuber melanosporum* Mel28] >emb|CAZ81986.1| unnamed protein product [*Tuber melanosporum*] |
| EGT47882.1 | hypothetical protein CAEBREN_02542 [*Caenorhabditis brenneri*] |
| EDL99655.1 | activating signal cointegrator 1 complex subunit 3 (predicted), isoform CRA_b [*Rattus norvegicus*] |
| NP_932124.2 | activating signal cointegrator I complex subunit 3 [*Mus musculus*] |
| EDL05054.1 | mCG119534 [*Mus musculus*] |
| gi|352115865 | DEAD/DEAH box helicase domain protein |
| ZP_08963952.1 | [*Natrinema pellirubrum* DSM 15624] |

The Hel308 helicase is more preferably one of the helicases shown in Table 5 below or a variant thereof. The Hel308 helicase more preferably comprises the sequence of one of the helicases shown in Table 5, i.e. one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58, or a variant thereof.

TABLE 5

More preferred Hel308 helicases and most preferred Hel308 motifs and extended Hel308 motifs

| SEQ ID NO: | Helicase | Names | % Identity Hel308 Pfu | % Identity Hel308 Mbu | Hel308 motif | Extended Hel308 motif |
|---|---|---|---|---|---|---|
| 10 | Hel308 Mbu | *Methanococcoides burtonii* | 37% | — | QMAGRAGR (SEQ ID NO: 11) | QMAGRAGRP (SEQ ID NO: 12) |
| 13 | Hel308 Pfu | *Pyrococcus furiosus* DSM 3638 | — | 37% | QMLGRAGR (SEQ ID NO: 14) | QMLGRAGRP (SEQ ID NO: 15) |
| 16 | Hel308 Hvo | *Haloferax volcanii* | 34% | 41% | QMMGRAGR (SEQ ID NO: 17) | QMMGRAGRP (SEQ ID NO: 18) |
| 19 | Hel308 Hla | *Halorubrum lacusprofundi* | 35% | 42% | QMCGRAGR (SEQ ID NO: 20) | QMCGRAGRP (SEQ ID NO: 21) |
| 22 | Hel308 Csy | *Cenarchaeum symbiosum* | 34% | 34% | QLCGRAGR (SEQ ID NO: 23) | QLCGRAGRP (SEQ ID NO: 24) |
| 25 | Hel308 Sso | *Sulfolobus solfataricus* | 35% | 33% | QMSGRAGR (SEQ ID NO: 26) | QMSGRAGRP (SEQ ID NO: 27) |
| 28 | Hel308 Mfr | *Methanogenium frigidum* | 37% | 44% | QMAGRAGR (SEQ ID NO: 11) | QMAGRAGRP (SEQ ID NO: 12) |
| 29 | Hel308 Mok | *Methanothermococcus okinawensis* | 37% | 34% | QCIGRAGR (SEQ ID NO: 30) | QCIGRAGRP (SEQ ID NO: 31) |
| 32 | Hel308 Mig | *Methanotorris igneus* Kol 5 | 40% | 35% | QCIGRAGR (SEQ ID NO: 30) | QCIGRAGRP (SEQ ID NO: 31) |
| 33 | Hel308 Tga | *Thermococcus gammatolerans* EJ3 | 60% | 38% | QMMGRAGR (SEQ ID NO: 17) | QMMGRAGRP (SEQ ID NO: 18) |

TABLE 5-continued

More preferred Hel308 helicases and most preferred Hel308 motifs and extended Hel308 motifs

| SEQ ID NO: | Helicase | Names | % Identity Hel308 Pfu | % Identity Hel308 Mbu | Hel308 motif | Extended Hel308 motif |
|---|---|---|---|---|---|---|
| 34 | Hel308 Tba | *Thermococcus barophilus* MP | 57% | 35% | QMIGRAGR (SEQ ID NO: 35) | QMIGRAGRP (SEQ ID NO: 36) |
| 37 | Hel308 Tsi | *Thermococcus sibiricus* MM 739 | 56% | 35% | QMMGRAGR (SEQ ID NO: 17) | QMMGRAGRP (SEQ ID NO: 18) |
| 38 | Hel308 Mba | *Methanosarcina barkeri* str. *Fusaro* | 39% | 60% | QMAGRAGR (SEQ ID NO: 11) | QMAGRAGRP (SEQ ID NO: 12) |
| 39 | Hel308 Mac | *Methanosarcina acetivorans* | 38% | 60% | QMAGRAGR (SEQ ID NO: 11) | QMAGRAGRP (SEQ ID NO: 12) |
| 40 | Hel308 Mmah | *Methanohalophilus mahii* DSM 5219 | 38% | 60% | QMAGRAGR (SEQ ID NO: 11) | QMAGRAGRP (SEQ ID NO: 12) |
| 41 | Hel308 Mmaz | *Methanosarcina mazei* | 38% | 60% | QMAGRAGR (SEQ ID NO: 11) | QMAGRAGRP (SEQ ID NO: 12) |
| 42 | Hel308 Mth | *Methanosaeta thermophila* PT | 39% | 46% | QMAGRAGR (SEQ ID NO: 11) | QMAGRAGRP (SEQ ID NO: 12) |
| 43 | Hel308 Mzh | *Methanosalsum zhilinae* DSM 4017 | 39% | 57% | QMAGRAGR (SEQ ID NO: 11) | QMAGRAGRP (SEQ ID NO: 12) |
| 44 | Hel308 Mev | *Methanohalobium evestigatum* Z-7303 | 38% | 61% | QMAGRAGR (SEQ ID NO: 11) | QMAGRAGRP (SEQ ID NO: 12) |
| 45 | Hel308 Mma | *Methanococcus maripaludis* | 36% | 32% | QCIGRAGR (SEQ ID NO: 30) | QCIGRAGRP (SEQ ID NO: 31) |
| 46 | Hel308 Nma | *Natrialba magadii* | 37% | 43% | QMMGRAGR (SEQ ID NO: 17) | QMMGRAGRP (SEQ ID NO: 18) |
| 47 | Hel308 Mbo | *Methanoregula boonei* 6A8 | 38% | 45% | QMAGRAGR (SEQ ID NO: 11) | QMAGRAGRP (SEQ ID NO: 12) |
| 48 | Hel308 Fac | *Ferroplasma acidarmanus* | 34% | 32% | QMIGRAGR (SEQ ID NO: 35) | QMIGRAGRP (SEQ ID NO: 36) |
| 49 | Hel308 Mfe | *Methanocaldococcus fervens* AG86 | 40% | 35% | QCIGRAGR (SEQ ID NO: 30) | QCIGRAGRP (SEQ ID NO: 31) |
| 50 | Hel308 Mja | *Methanocaldococcus jannaschii* | 24% | 22% | QCIGRAGR (SEQ ID NO: 30) | QCIGRAGRP (SEQ ID NO: 31) |
| 51 | Hel308 Min | *Methanocaldococcus infernus* | 41% | 33% | QCIGRAGR (SEQ ID NO: 30) | QCIGRAGRP (SEQ ID NO: 31) |
| 52 | Hel308 Mhu | *Methanospirillum hungatei* JF-1 | 36% | 40% | QMAGRAGR (SEQ ID NO: 11) | QMAGRAGRP (SEQ ID NO: 12) |
| 53 | Hel308 Afu | *Archaeoglobus fulgidus* DSM 4304 | 40% | 40% | QMAGRAGR (SEQ ID NO: 11) | QMAGRAGRP (SEQ ID NO: 12) |
| 54 | Hel308 Htu | *Haloterrigena turkmenica* | 35% | 43% | QMAGRAGR (SEQ ID NO: 11) | QMAGRAGRP (SEQ ID NO: 12) |
| 55 | Hel308 Hpa | *Haladaptatus paucihalophilus* DX253 | 38% | 45% | QMFGRAGR (SEQ ID NO: 56) | QMFGRAGRP (SEQ ID NO: 57) |
| 58 | ski2-like helicase | *Halobacterium* sp. NRC-1 | 36.8% | 42.0% | QMFGRAGR (SEQ ID NO: 56) | QMFGRAGRP (SEQ ID NO: 57) |

The Hel308 helicase more preferably comprises (a) the sequence of Hel308 Mbu (i.e. SEQ ID NO: 10) or a variant thereof, (b) the sequence of Hel308 Pfu (i.e. SEQ ID NO: 13) or a variant thereof, (c) the sequence of Hel308 Mok (i.e. SEQ ID NO: 29) or a variant thereof, (d) the sequence of Hel308 Mma (i.e. SEQ ID NO: 45) or a variant thereof, (e) the sequence of Hel308 Fac (i.e. SEQ ID NO: 48) or a variant thereof or (f) the sequence of Hel308 Mhu (i.e. SEQ ID NO: 52) or a variant thereof. The Hel308 helicase more preferably comprises the sequence shown in SEQ ID NO: 10 or a variant thereof.

The Hel308 helicase more preferably comprises (a) the sequence of Hel308 Tga (i.e. SEQ ID NO: 33) or a variant thereof, (b) the sequence of Hel308 Csy (i.e. SEQ ID NO: 22) or a variant thereof or (c) the sequence of Hel308 Mhu (i.e. SEQ ID NO: 52) or a variant thereof. The Hel308 helicase most preferably comprises the sequence shown in SEQ ID NO: 33 or a variant thereof.

A variant of a Hel308 helicase is an enzyme that has an amino acid sequence which varies from that of the wild-type helicase and which retains polynucleotide binding activity. In particular, a variant of any one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 is an enzyme that has an amino acid sequence which varies from that of any one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 and which retains polynucleotide binding activity. A variant of SEQ ID NO: 10 or 33 is an enzyme that has an amino acid sequence which varies from that of SEQ ID NO: 10 or 33 and which retains polynucleotide binding activity. The variant retains helicase activity. The variant must work in at least one of the two modes discussed below. Preferably, the variant works in both modes. The variant may include modifications that facilitate handling of the polynucleotide encoding the helicase and/or facilitate its activity at high salt concentrations and/or room temperature. Variants typically differ from the wild-type helicase in regions outside of the Hel308 motif or extended Hel308 motif discussed above. However, variants may include modifications within these motif(s).

Over the entire length of the amino acid sequence of any one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58, such as SEQ ID NO: 10 or 33, a variant will preferably be at least 30% homologous to that sequence based on amino acid identity. More preferably, the variant polypeptide may be at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of any one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58, such as SEQ ID NO: 10 or 33, over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NOs: 2 and 4.

A variant of any one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 preferably comprises the Hel308 motif or extended Hel308 motif of the relevant wild-type sequence. For instance, a variant of SEQ ID NO: 10 preferably comprises the Hel308 motif of SEQ ID NO: 10 (QMAGRAGR; SEQ ID NO: 11) or extended Hel308 motif of SEQ ID NO: 10 (QMAGRAGRP; SEQ ID NO: 12). The Hel308 motif and extended Hel308 motif of each of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 are shown in Table 5. However, a variant of any one SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 may comprise the Hel308 motif or extended Hel308 motif from a different wild-type sequence. For instance, a variant of SEQ ID NO: 10 may comprise the Hel308 motif of SEQ ID NO: 13 (QMLGRAGR; SEQ ID NO: 14) or extended Hel308 motif of SEQ ID NO: 13 (QMLGRAGRP; SEQ ID NO: 15). A variant of any one SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 may comprise any one of the preferred motifs shown in Table 5. Variants of any one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 may also include modifications within the Hel308 motif or extended Hel308 motif of the relevant wild-type sequence. Suitable modifications at X1 and X2 are discussed above when defining the two motifs.

A variant of SEQ ID NO: 10 may lack the first 19 amino acids of SEQ ID NO: 10 and/or lack the last 33 amino acids of SEQ ID NO: 10. A variant of SEQ ID NO: 10 preferably comprises a sequence which is at least 70%, at least 75%, at least 80%, at least 85%, at least 90% or more preferably at least 95%, at least 97% or at least 99% homologous based on amino acid identity with amino acids 20 to 211 or 20 to 727 of SEQ ID NO: 10.

The helicase may be covalently attached to the pore. The helicase is preferably not covalently attached to the pore. The application of a voltage to the pore and helicase typically results in the formation of a sensor that is capable of sequencing target polynucleotides. This is discussed in more detail below.

Any of the proteins described herein, i.e. the transmembrane protein pores or Hel308 helicases, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or helicase. An example of this would be to react a gel-shift reagent to a cysteine engineered on the outside of the pore. This has been demonstrated as a method for separating hemolysin hetero-oligomers (Chem. Biol. 1997 July; 4(7): 497-505).

The pore and/or helicase may be labelled with a revealing label. The revealing label may be any suitable label which allows the pore to be detected. Suitable labels include, but are not limited to fluorescent molecules, radioisotopes, e.g. $^{125}$I, $^{35}$S, enzymes, antibodies, antigens, polynucleotides and ligands such as biotin.

Proteins may be made synthetically or by recombinant means. For example, the pore and/or helicase may be synthesized by in vitro translation and transcription (IVTT). The amino acid sequence of the pore and/or helicase may be modified to include non-naturally occurring amino acids or to increase the stability of the protein. When a protein is produced by synthetic means, such amino acids may be introduced during production. The pore and/or helicase may also be altered following either synthetic or recombinant production.

The pore and/or helicase may also be produced using D-amino acids. For instance, the pore or helicase may comprise a mixture of L-amino acids and D-amino acids. This is conventional in the art for producing such proteins or peptides.

The pore and/or helicase may also contain other non-specific modifications as long as they do not interfere with pore formation or helicase function. A number of non-specific side chain modifications are known in the art and may be made to the side chains of the protein(s). Such modifications include, for example, reductive alkylation of amino acids by reaction with an aldehyde followed by reduction with NaBH$_4$, amidination with methylacetimidate or acylation with acetic anhydride.

The pore and helicase can be produced using standard methods known in the art. Polynucleotide sequences encoding a pore or helicase may be derived and replicated using standard methods in the art. Polynucleotide sequences encoding a pore or helicase may be expressed in a bacterial host cell using standard techniques in the art. The pore and/or helicase may be produced in a cell by in situ expression of the polypeptide from a recombinant expression vector. The expression vector optionally carries an inducible promoter to control the expression of the polypeptide. These methods are described in described in Sambrook, J. and Russell, D. (2001). Molecular Cloning: A Laboratory Manual, 3rd Edition. Cold Spring Harbor Laboratory Press, Cold Spring Harbor, N.Y.

The pore and/or helicase may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

The method of the invention involves measuring one or more characteristics of the target polynucleotide. The method may involve measuring two, three, four or five or more characteristics of the target polynucleotide. The one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be measured in accordance with the invention.

For (i), the length of the polynucleotide may be measured using the number of interactions between the target polynucleotide and the pore.

For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem. Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interation with each nucleotide.

A variety of different types of measurements may be made. This includes without limitation: electrical measurements and optical measurements. Possible electrical measurements include: current measurements, impedance measurements, tunneling measurements (Ivanov A P et al., Nano Lett. 2011 Jan. 12; 11(1):279-85), and FET measurements (International Application WO 2005/124888). Optical measurements may be combined 10 with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem. Soc. 2010; 132(50):17961-72, and International Application WO-2000/28312. Alternatively, electrical measurements may be made using a multi-channel system, for example as described in International Application WO-2009/077734 and International Application WO-2011/067559.

In a preferred embodiment, the method comprises:

(a) contacting the target polynucleotide with a transmembrane pore and a Hel308 helicase such that the helicase controls the movement of the target polynucleotide through the pore and nucleotides in the target polynucleotide interact with the pore; and (b) measuring the current passing through the pore during one or more interactions to measure one or more characteristics of the target polynucleotide and thereby characterising the target polynucleotide.

The methods may be carried out using any apparatus that is suitable for investigating a membrane/pore system in which a pore is inserted into a membrane. The method may be carried out using any apparatus that is suitable for transmembrane pore sensing. For example, the apparatus comprises a chamber comprising an aqueous solution and a barrier that separates the chamber into two sections. The barrier has an aperture in which the membrane containing the pore is formed.

The methods may be carried out using the apparatus described in International Application No. PCT/GB08/000, 562 (WO 2008/102120).

The methods may involve measuring the current passing through the pore during one or more interactions with the nucleotide(s). Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore during one or more interactions with the nucleotide. Suitable conditions for measuring ionic currents through transmembrane protein pores are known in the art and disclosed in the Example. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. As discussed above, Hel308 helicases surprisingly work under high salt concentrations. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method is typically carried out in the presence of free nucleotides or free nucleotide analogues and an enzyme cofactor that facilitate the action of the helicase. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the helicase to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The target polynucleotide may be contacted with the Hel308 helicase and the pore in any order. In is preferred that, when the target polynucleotide is contacted with the Hel308 helicase and the pore, the target polynucleotide firstly forms a complex with the helicase. When the voltage is applied across the pore, the target polynucleotide/helicase complex then forms a complex with the pore and controls the movement of the polynucleotide through the pore.

As discussed above, Hel308 helicases may work in two modes with respect to the nanopore. First, the method is preferably carried out using the Hel308 helicase such that it moves the target sequence through the pore with the field resulting from the applied voltage. In this mode the 3' end of the DNA is first captured in the nanopore, and the enzyme moves the DNA into the nanopore such that the target sequence is passed through the nanopore with the field until it finally translocates through to the trans side of the bilayer. Alternatively, the method is preferably carried out such that the enzyme moves the target sequence through the pore against the field resulting from the applied voltage. In this mode the 5' end of the DNA is first captured in the nanopore, and the enzyme moves the DNA through the nanopore such that the target sequence is pulled out of the nanopore against the applied field until finally ejected back to the cis side of the bilayer.

The method of the invention most preferably involves a pore derived from MspA and a helicase comprising the sequence shown in SEQ ID NO: 8 or 10 or a variant thereof. Any of the embodiments discussed above with reference to MspA and SEQ ID NO: 8 and 10 may be used in combination.

Other Methods

The invention also provides a method of forming a sensor for characterising a target polynucleotide. The method comprises forming a complex between a pore and a Hel308 helicase. The complex may be formed by contacting the pore and the helicase in the presence of the target polynucleotide and then applying a potential across the pore. The applied potential may be a chemical potential or a voltage potential as described above. Alternatively, the complex may be formed by covalently attaching the pore to the helicase. Methods for covalent attachment are known in the art and disclosed, for example, in International Application Nos. PCT/GB09/001,679 (published as WO 2010/004265) and PCT/GB10/000,133 (published as WO 2010/086603). The complex is a sensor for characterising the target polynucleotide. The method preferably comprises forming a complex between a pore derived from Msp and a Hel308 helicase. Any of the embodiments discussed above with reference to the method of the invention equally apply to this method.

Kits

The present invention also provides kits for characterising a target polynucleotide. The kits comprise (a) a pore and (b) a Hel308 helicase. Any of the embodiments discussed above with reference to the method of the invention equally apply to the kits.

The kit may further comprise the components of a membrane, such as the phospholipids needed to form a lipid bilayer.

The kits of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an apparatus for characterising a target polynucleotide. The apparatus comprises a plurality of pores and a plurality of a Hel308 helicase. The apparatus preferably further comprises instructions for carrying out the method of the invention. The apparatus may be any conventional apparatus for polynucleotide analysis, such as an array or a chip. Any of the embodiments discussed above with reference to the methods of the invention are equally applicable to the apparatus of the invention.

The apparatus is preferably set up to carry out the method of the invention.

The apparatus preferably comprises:
a sensor device that is capable of supporting the membrane and plurality of pores and being operable to perform polynucleotide characterising using the pores and helicases;
at least one reservoir for holding material for performing the characterising;
a fluidics system configured to controllably supply material from the at least one reservoir to the sensor device; and
a plurality of containers for receiving respective samples, the fluidics system being configured to supply the samples selectively from the containers to the sensor device. The apparatus may be any of those described in International Application No. PCT/GB08/004,127 (published as WO 2009/077734), PCT/GB10/000,789 (published as WO 2010/122293), International Application No. PCT/GB10/002,206 (not yet published) or International Application No. PCT/US99/25679 (published as WO 00/28312).

Internally Binding Molecular Motors

Molecular motors are commonly used as a means for controlling the translocation of a polymer, particularly a polynucleotide, through a nanopore. Surprisingly, the inventors have found that molecular motors which are capable of binding to a target polynucleotide at an internal nucleotide, i.e. a position other than a 5' or 3' terminal nucleotide, can provide increased read lengths of the polynucleotide as the molecular motor controls the translocation of the polynucleotide through a nanopore. The ability to translocate an entire polynucleotide through a nanopore under the control of a molecular motor allows various characteristics of the polynucleotide, such as its sequence, to be estimated with improved accuracy and speed over known methods. This becomes more important as strand lengths increase and molecular motors are required with improved processivity. The molecular motor used in the invention is particularly effective in controlling the translocation of target polynucleotides of 500 nucleotides or more, for example 1000 nucleotides, 5000, 10000 or 20000 or more.

The invention thus provides a method of characterising a target polynucleotide, comprising:

(a) contacting the target polynucleotide with a transmembrane pore and a molecular motor which is capable of binding to the target polynucleotide at an internal nucleotide such that the molecular motor controls the movement of the target polynucleotide through the pore and nucleotides in the target polynucleotide interact with the pore; and (b) measuring one or more characteristics of the target polynucleotide during one or more interactions and thereby characterising the target polynucleotide.

Any of the embodiments discussed above in relation to the Hel308 methods of the invention equally apply to this method of the invention.

A problem which occurs in sequencing polynucleotides, particularly those of 500 nucleotides or more, is that the molecular motor which is controlling translocation of the polynucleotide may disengage from the polynucleotide. This allows the polynucleotide to be pulled through the pore rapidly and in an uncontrolled manner in the direction of the applied field. Multiple instances of the molecular motor used in the invention bind to the polynucleotide at relatively short distances apart and thus the length of polynucleotide which can be pulled through the pore before a further molecular motor engages with the pore is relatively short.

An internal nucleotide is a nucleotide which is not a terminal nucleotide in the target polynucleotide. For example, it is not a 3' terminal nucleotide or a 5' terminal nucleotide. All nucleotides in a circular polynucleotide are internal nucleotides.

Generally, a molecular motor which is capable of binding at an internal nucleotide is also capable of binding at a terminal nucleotide, but the tendency for some molecular motors to bind at an internal nucleotide will be greater than others. For a molecular motor suitable for use in the invention, typically at least 10% of its binding to a polynucleotide will be at an internal nucleotide. Typically, at least 20%, at least 30%, at least 40% or at least 50% of its binding will be at an internal nucleotide. Binding at a terminal nucleotide may involve binding to both a terminal nucleotide and adjacent internal nucleotides at the same time. For the purposes of the invention, this is not binding to the target polynucleotide at an internal nucleotide. In other words, the molecular motor used in the invention is not only capable of binding to a terminal nucleotide in combination with one or more adjacent internal nucleotides. The molecular motor must be capable of binding to an internal nucleotide without concurrent binding to a terminal nucleotide.

A molecular motor which is capable of binding at an internal nucleotide may bind to more than one internal nucleotide. Typically, the molecular motor binds to at least 2 internal nucleotides, for example at least 3, at least 4, at least 5, at least 10 or at least 15 internal nucleotides. Typically the molecular motor binds to at least 2 adjacent internal nucleotides, for example at least 3, at least 4, at least 5, at least 10 or at least 15 adjacent internal nucleotides. The at least 2 internal nucleotides may be adjacent or non-adjacent.

The ability of a molecular motor to bind to a polynucleotide at an internal nucleotide may be determined by carrying out a comparative assay. The ability of a motor to bind to a control polynucleotide A is compared to the ability to bind to the same polynucleotide but with a blocking group attached at the terminal nucleotide (polynucleotide B). The blocking group prevents any binding at the terminal nucleotide of strand B, and thus allows only internal binding of a molecular motor. An example of this type of assay is disclosed in Example 4.

Suitable molecular motors are well known in the art and typically include, but are not limited to, single and double strand translocases, such as polymerases, helicases, topoisomerases, ligases and nucleases, such as exonucleases. Preferably the molecular motor is a helicase, for example a Hel308 helicase. Examples of Hel308 helicases which are capable of binding at an internal nucleotide include, but are not limited to, Hel308 Tga, Hel308 Mhu and Hel308 Csy. Hence, the molecular motor preferably comprises (a) the sequence of Hel308 Tga (i.e. SEQ ID NO: 33) or a variant thereof or (b) the sequence of Hel308 Csy (i.e. SEQ ID NO: 22) or a variant thereof or (c) the sequence of Hel308 Mhu (i.e. SEQ ID NO: 52) or a variant thereof. The variant typically has at least 40% homology to SEQ ID NO: 33, 22 or 52 based on amino acid identity over the entire sequence and retains helicase activity. Further possible variants are discussed above.

The molecular motor used in the invention may be made by any of the methods discussed above and may be modified or labelled as discussed above. The molecular motor may be used in the methods described herein or as part of the apparatus described herein. The invention further provides a method of forming a sensor for characterising a target polynucleotide, comprising forming a complex between a pore and a molecular motor which is capable of binding to the target polynucleotide at an internal nucleotide and thereby forming a sensor for characterising the target polynucleotide. The invention also provides use of a molecular motor which is capable of binding to the target polynucleotide at an internal nucleotide to control the movement of a target polynucleotide through a pore. The invention also provides a kit for characterising a target polynucleotide comprising (a) a pore and (b) a molecular motor which is capable of binding to the target polynucleotide at an internal nucleotide. The invention also provides an analysis apparatus for characterising target polynucleotides in a sample, comprising a plurality of pores and a plurality of a molecular motor which is capable of binding to the target polynucleotide at an internal nucleotide.

The following Examples illustrate the invention.

Example 1

Figure 1B:
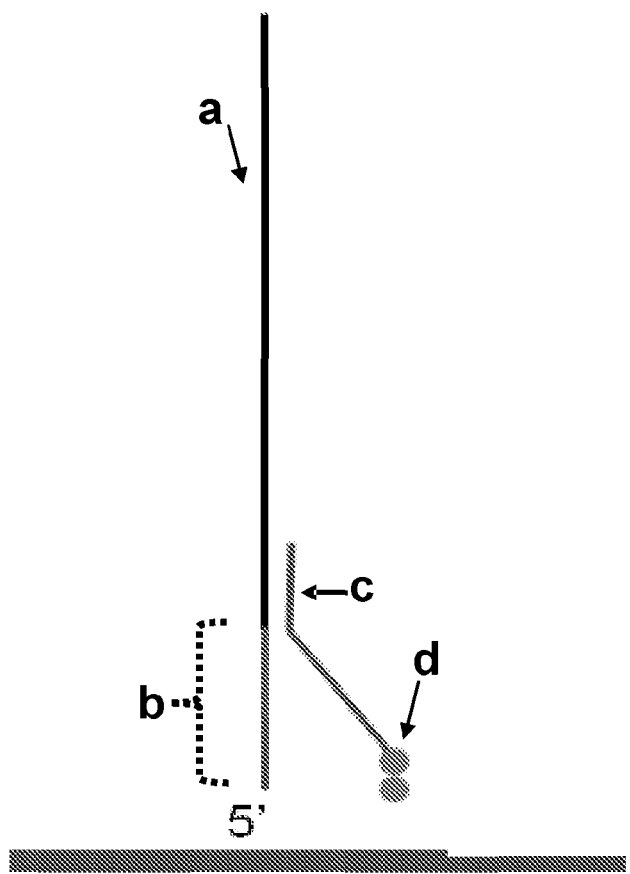

This Example illustrates the use of a Hel308 helicase (Hel308 MBu) to control the movement of intact DNA strands through a nanopore. The general method and substrate employed throughout this example is shown in FIG. 1 and described in the figure caption.

Materials and Methods

Primers were designed to amplify a ~400 bp fragment of PhiX174. Each of the 5'-ends of these primers included a 50 nucleotide non-complimentary region, either a homopolymeric stretch or repeating units of 10 nucleotide homopolymeric sections. These serve as identifiers for controlled translocation of the strand through a nanopore, as well as determining the directionality of translocation. In addition, the 5'-end of the forward primer was "capped" to include four 2'-O-Methyl-Uracil (mU) nucleotides and the 5'-end of the reverse primer was chemically phosphorylated. These primer modifications then allow for the controlled digestion of predominantly only the antisense strand, using lambda exonuclease. The mU capping protects the sense strand from nuclease digestion whilst the PO4 at the 5' of the antisense strand promotes it. Therefore after incubation with lambda exonuclease only the sense strand of the duplex remains intact, now as single stranded DNA (ssDNA). The generated ssDNA was then PAGE purified as previously described.

Figure 6A:
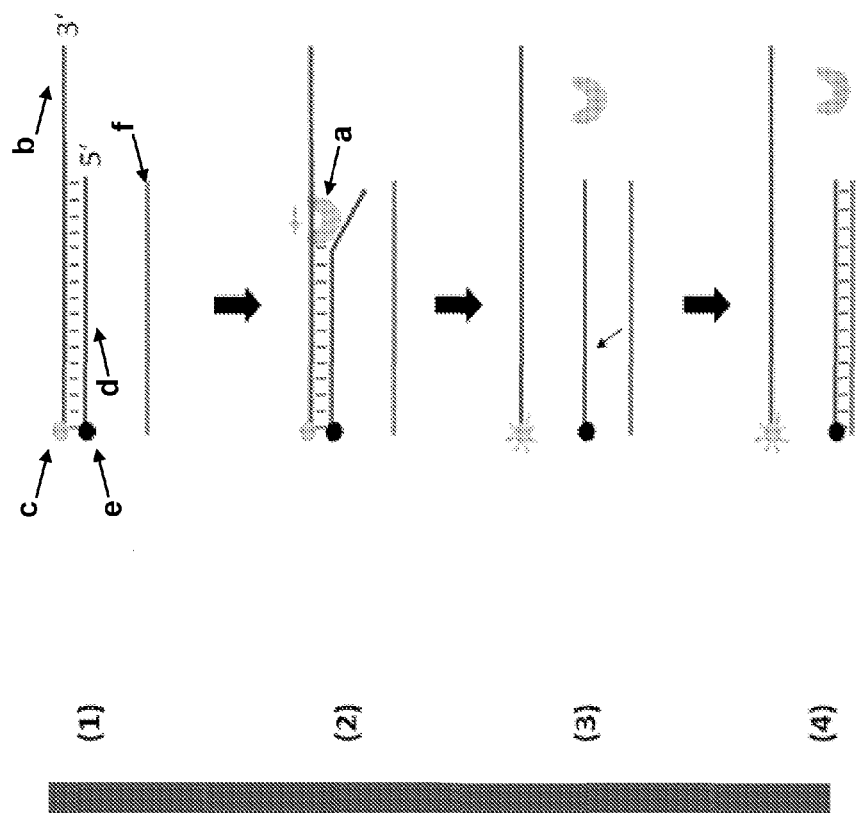
FIG. 6. Fluorescence assay for testing enzyme activity. a) A custom fluorescent substrate was used to assay the ability of the helicase (a) to displace hybridised dsDNA. 1) The fluorescent substrate strand (100 nM final) has a 3' ssDNA overhang, and a 40 base section of hybridised dsDNA. The major upper strand (b) has a carboxyfluorescein base (c) at the 5' end, and the hybridised complement (d) has a black-hole quencher (BHQ-1) base (e) at the 3' end. When hybridised the fluorescence from the fluorescein is quenched by the local BHQ-1, and the substrate is essentially non-fluorescent. 1 µM of a capture strand (f) that is complementary to the shorter strand of the fluorescent substrate (d) is included in the assay. 2) In the presence of ATP (1 mM) and $MgCl_2$ (5 mM), helicase (100 nM) added to the substrate binds to the 3' tail of the fluorescent substrate, moves along the major strand, and displaces the complementary strand as shown. 3) Once the complementary strand with BHQ-1 is fully displaced the fluorescein on the major strand fluoresces. 4) Excess of capture strand preferentially anneals to the complementary DNA to prevent re-annealing of initial substrate and loss of fluorescence. b) Graph of the initial rate of activity (y-axis, relative activity) in buffer solutions (10 mM Hepes pH 8.0, 1 mM ATP, 5 mM $MgCl_2$, 100 nM fluorescent substrate DNA, 1 µM capture DNA) containing different concentrations of KCl (x-axis, mM) from 400 mM to 2 M.
Figure 6B:
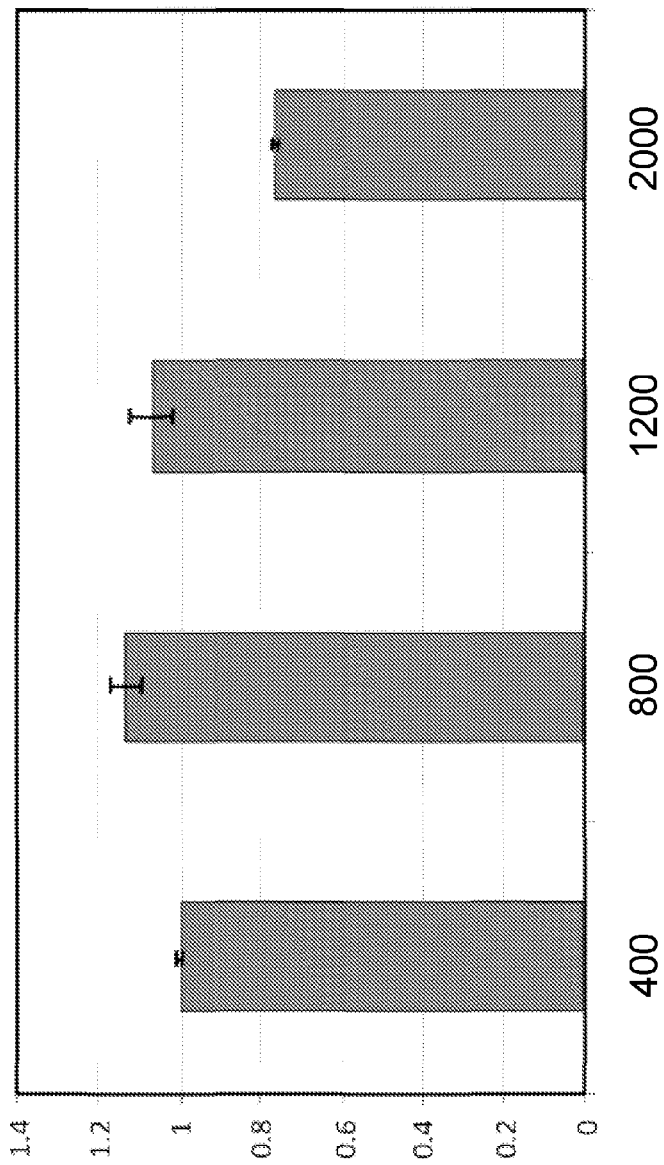

The DNA substrate design used in all the experiments described here is shown in FIG. 6. The DNA substrate consists of a 400 base section of ssDNA from PhiX, with a 50T 5'-leader to aid capture by the nanopore (SEQ ID NO: 59) Annealed to this strand just after the 50T leader is a primer (SEQ ID NO: 60) containing a 3' cholesterol tag to enrich the DNA on the surface of the bilayer, and thus improve capture efficiency.

Buffered solution: 400 mM-2 M KCl, 10 mM Hepes pH 8.0, 1 mM ATP, 1 mM MgCl$_2$, 1 mM DTT Nanopore: E. coli MS (B2)8 MspA ONLP3271 MS-(L88N/D90N/D91N/D93N/D118R/D134R/E139K)8

Enzyme: Hel308 Mbu (ONLP3302, ~7.7 µM) 12.5 µl→100 nM final.

Electrical measurements were acquired from single MspA nanopores inserted in 1,2-diphytanoyl-glycero-3-phosphocholine lipid (Avanti Polar Lipids) bilayers. Bilayers were formed across ~100 µm diameter apertures in 20 µm thick PTFE films (in custom Delrin chambers) via the Montal-Mueller technique, separating two 1 mL buffered solutions. All experiments were carried out in the stated buffered solution. Single-channel currents were measured on Axopatch 200B amplifiers (Molecular Devices) equipped with 1440A digitizers. Ag/AgCl electrodes were connected to the buffered solutions so that the cis compartment (to which both nanopore and enzyme/DNA are added) is connected to the ground of the Axopatch headstage, and the trans compartment is connected to the active electrode of the headstage. After achieving a single pore in the bilayer, DNA polynucleotide and helicase were added to 100 µL of buffer and pre-incubated for 5 mins (DNA=1.5 nM, Enzyme=1 µM). This pre-incubation mix was added to 900 µL of buffer in the cis compartment of the electrophysiology chamber to initiate capture of the helicase-DNA complexes in the MspA nanopore (to give final concentrations of DNA=0.15 nM, Enzyme=0.1 µM). Helicase ATPase activity was initiated as required by the addition of divalent metal (1 mM MgCl$_2$) and NTP (1 mM ATP) to the cis compartment. Experiments were carried out at a constant potential of +180 mV.

Results and Discussion

Figure 2:
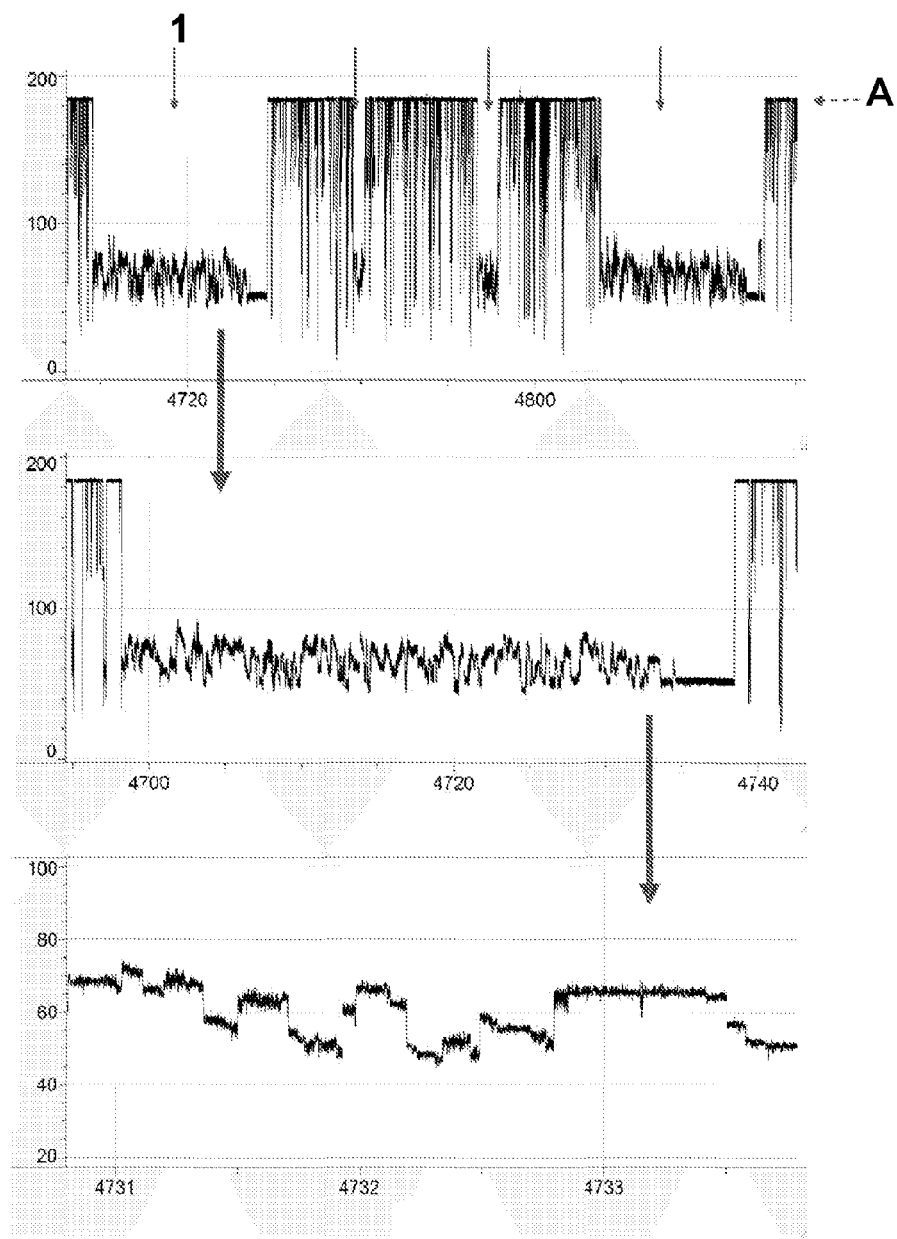
FIG. 2. Helicase is able to move DNA through a nanopore in a controlled fashion, producing stepwise changes in current as the DNA moves through the nanopore. Example helicase-DNA events (indicated by small arrows in the top section) (180 mV. 400 mM KCl, Hepes pH 8.0, 0.15 nM 400 mer DNA, 100 nM Hel308 Mbu, 1 mM DTT, 1 mM ATP, 1 mM $MgCl_2$). Top) Section of current (y-axis, pA) vs. time α-axis, s) acquisition of Hel308 400 mer DNA events. The open-pore current is ~180 pA (labelled A). DNA is captured by the nanopore under the force of the applied potential (+180 mV). DNA with enzyme attached results in a long block (at ~60 pA in this condition) that shows stepwise changes in current as the enzyme moves the DNA through the pore. Middle) The middle section is an enlargement of one of the DNA events (1), showing DNA-enzyme capture, stepwise current changes as the DNA is pulled through the pore, and ending in a characteristic long polyT level before exiting the nanopore. Bottom) enlargement of the stepwise changes in current as DNA is moved through the nanopore.

The addition of Helicase-DNA substrate to MspA nanopores as shown in FIG. 1 produces characteristic current blocks as shown in FIG. 2. DNA without helicase bound interacts transiently with the nanopore producing short-lived blocks in current (<<1 second). DNA with helicase bound and active (ie. moving along the DNA strand under ATPase action) produces long characteristic blocks levels with stepwise changes in current as shown in FIG. 2. Different DNA motifs in the nanopore give rise to unique current block levels.

Figure 3A:
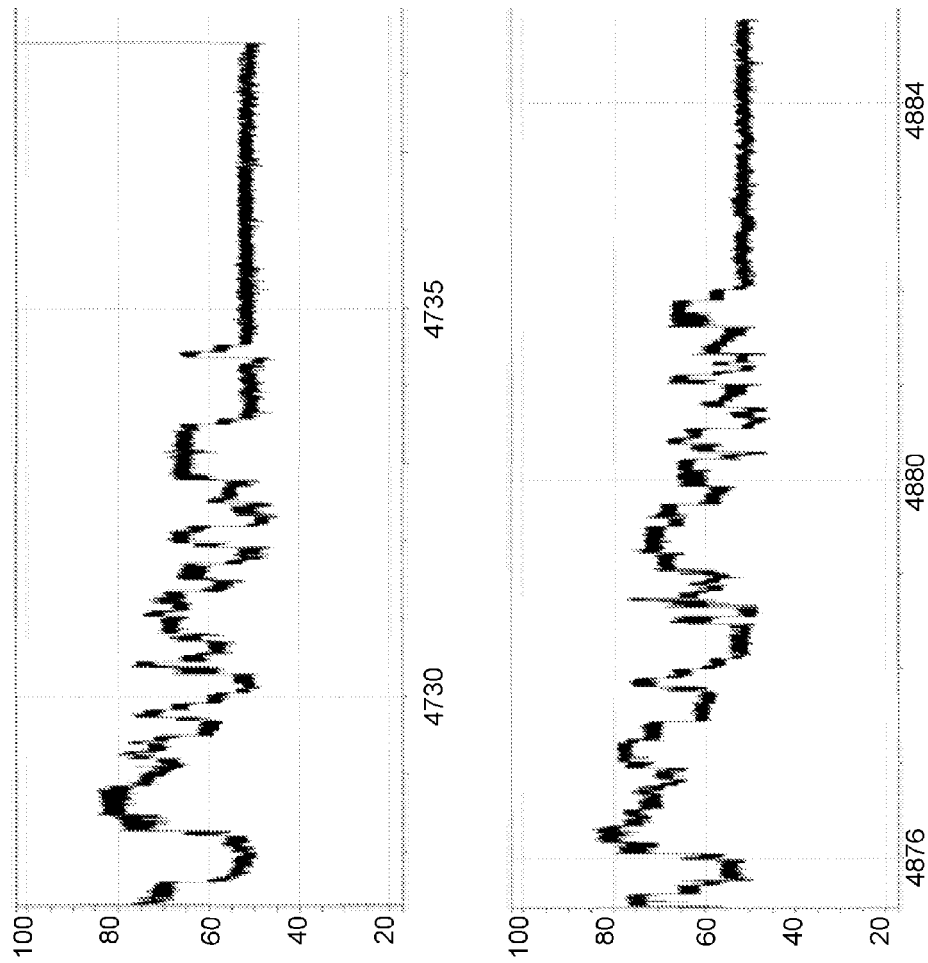
FIG. 3. Helicase controlled DNA movement resulting in a consistent pattern of current transitions as DNA is passed through the nanopore (y-axis=current (pA), x-axis=time (s) for FIGS. 3a and 3b). Examples of the last ~80 current transitions from four typical DNA events that end in the polyT level. The four examples (two in 3a and two in 3b) illustrate that a consistent pattern of current transitions are observed.
Figure 3B:
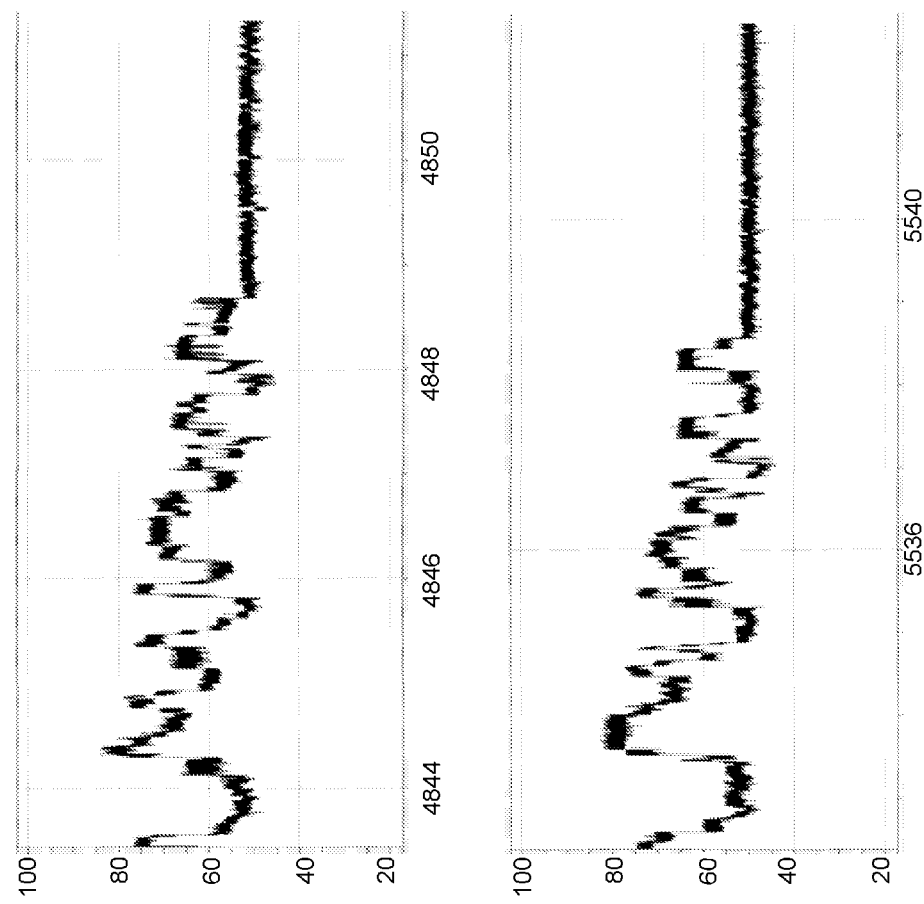
Figure 4A:
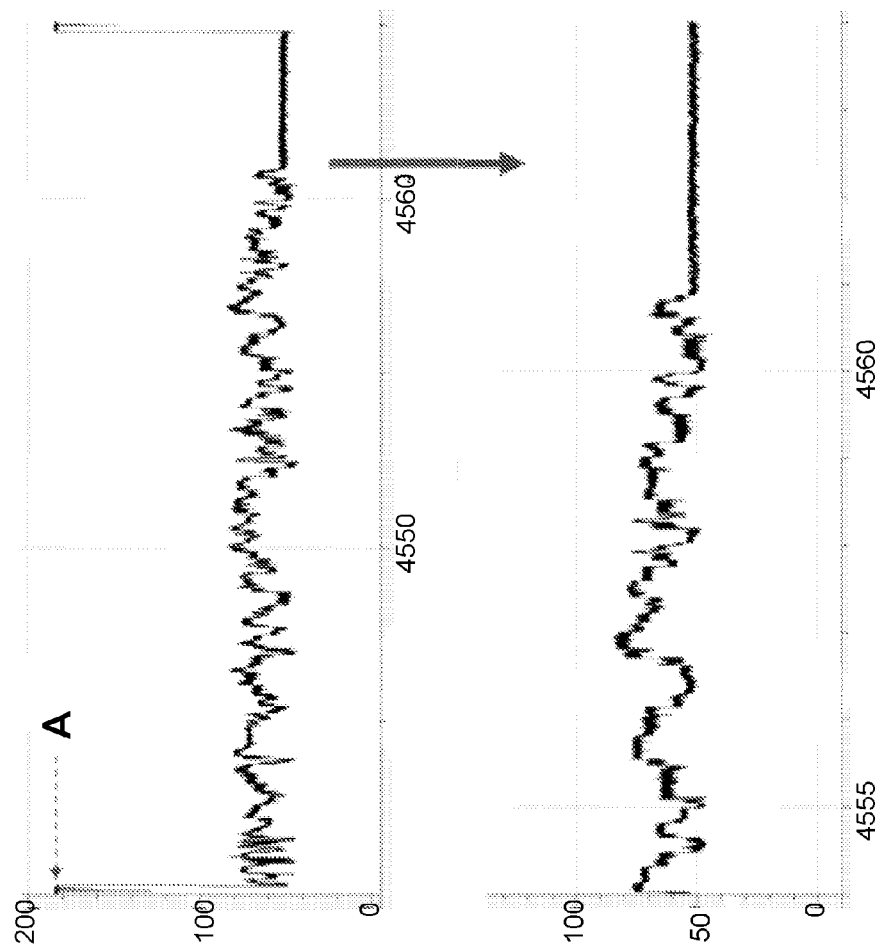
FIG. 4. Increased salt concentration increases pore current and gives a larger DNA discrimination range (range=minimum current to maximum current across the DNA current transitions). Example helicase-DNA events (y-axis=current (pA), x-axis=time (s) for FIGS. 4a-c, 180 mV, Hepes pH 8.0, 0.15 nM 400 mer DNA SEQ ID NOs: 59 and 60, 100 nM Hel308 Mbu, 1 mM DTT, 1 mM ATP, 1 mM $MgCl_2$) at 400 mM, 1 M, and 2 M KCl are shown in FIGS. 4 and 4c. Top traces show a full event that ends in the polyT level (with I-open indicated by A), and lower traces show a zoom section of the last 10 seconds of each event with a constant y-axis current scale of 150 pA. Increasing the salt concentration from 400 mM KCl to 2M KCl leads to a ~350% increase in the open-pore current (1-open from ~180 pA to ~850 pA), and a ~200% increase in discrimination range (~25 pA to ~75 pA).
FIG. 4d is a plot of DNA discrimination range as a function of salt concentration (y-axis=range (pA), x-axis=salt (mM)).
Figure 4B:
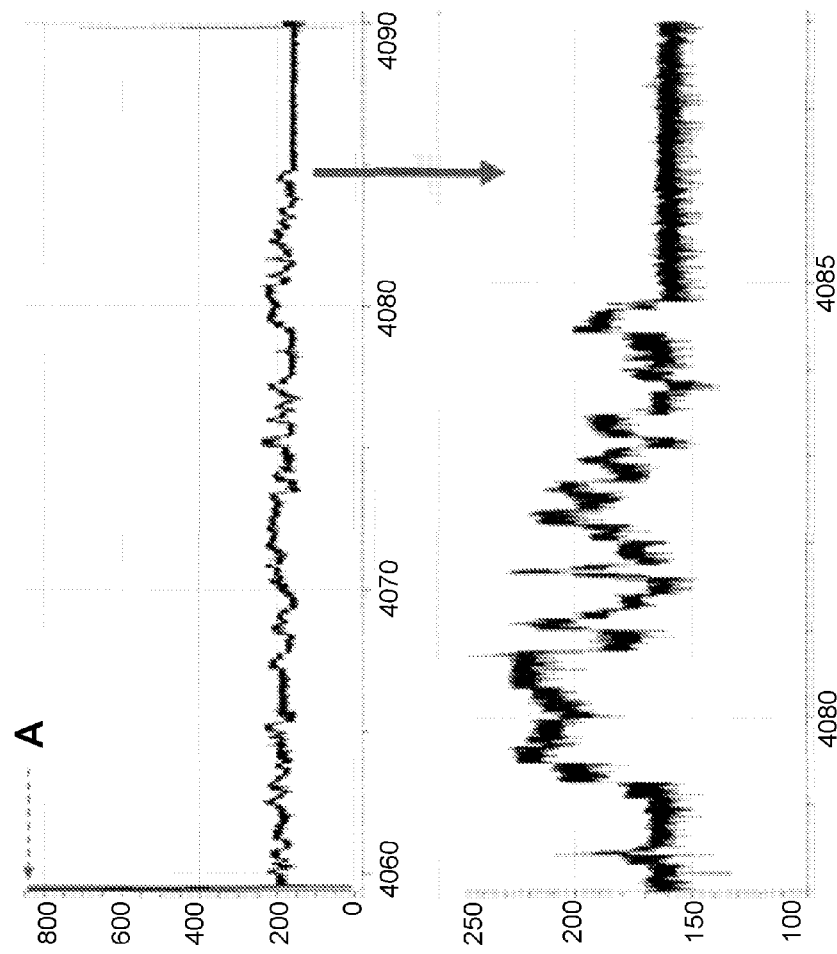
Figure 4C:
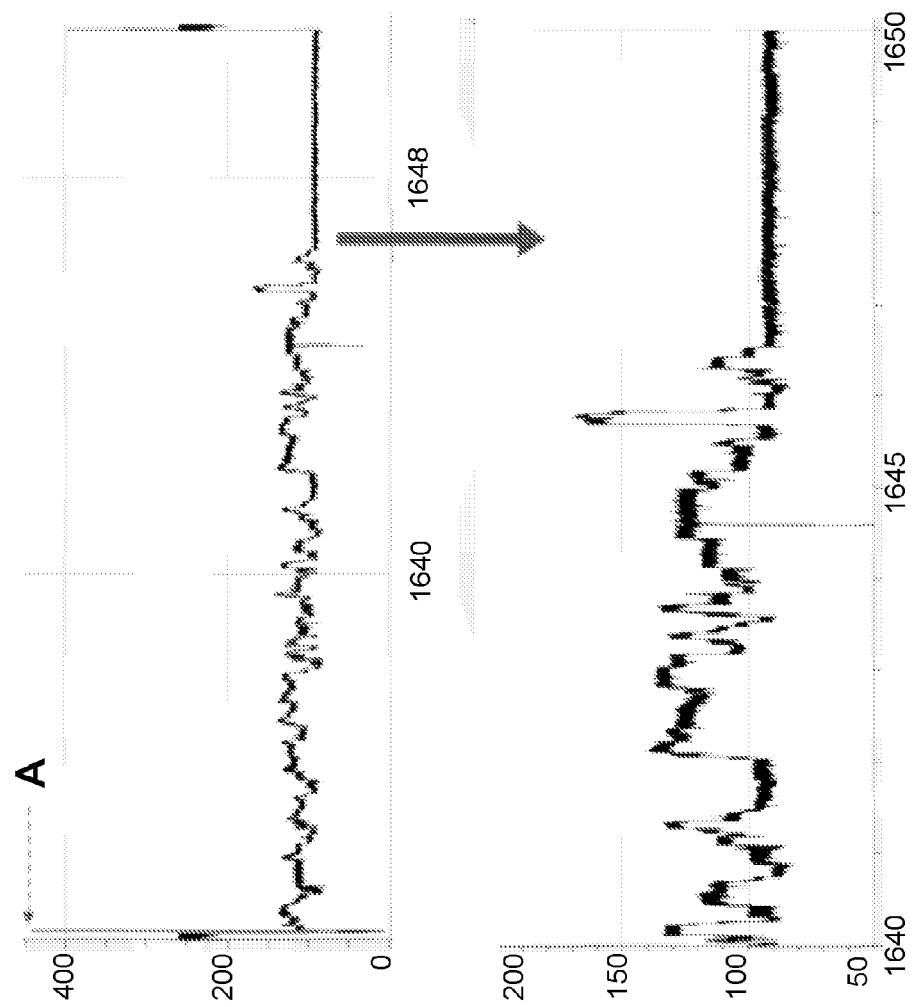
Figure 4D:
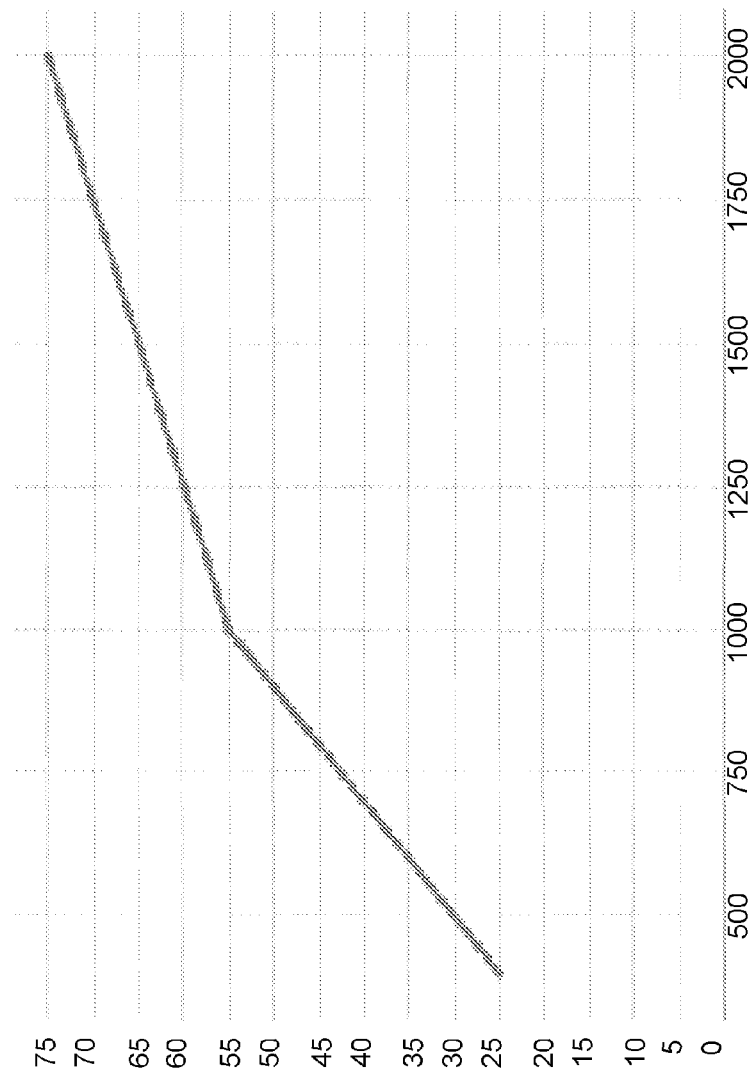

For a given substrate, we observe a characteristic pattern of current transitions that reflects the DNA sequence (examples in FIG. 3).

In the implementation shown in FIG. 1, the DNA strand is sequenced from a random starting point as the DNA is captured with a helicase at a random position along the strand. However, as long as the enzyme does not dissociate, the strands will all end in the same way at the 50T leader (FIG. 1). As FIG. 2 shows, we observe the same characteristic ending to most strands, with the current transitions ending in a long dwell time polyT level (FIG. 3).

Salt Tolerance

Nanopore strand sequencing experiments of this type require ionic salts. The ionic salts are necessary to create a conductive solution for applying a voltage offset to capture and translocate DNA, and to measure the resulting sequence dependent current changes as the DNA passes through the nanopore. Since the measurement signal is dependent in the concentration of the ions, it is advantageous to use high concentration ionic salts to increase the magnitude of the acquired signal. For nanopore sequencing salt concentrations in excess of 100 mM KCl are ideal, and salt concentrations of 1 M KCl and above are preferred.

However, many enzymes (including some helicases and DNA motor proteins) do not tolerate high salt conditions. Under high salt conditions the enzymes either unfold or lose structural integrity, or fail to function properly. The current literature for known and studied helicases shows that almost all helicases fail to function above salt concentrations of approximately 100 mM KCl/NaCl, and there are no reported helicases that show correct activity in conditions of 400 mM KCl and above. While potentially halophilic variants of similar enzymes from halotolerant species exist, they are extremely difficult to express and purify in standard expression systems (e.g. *E. coli*).

We surprisingly show in this Example that Hel308 from Mbu displays salt tolerance up to very high levels of KCl. We find that the enzyme retains functionality in salt concentrations of 400 mM KCl through to 2 M KCl, either in fluorescence experiments or in nanopore experiments (FIG. 4). FIG. 4 shows the Hel308 Mbu DNA events at 400 mM KCl, 1 M KCl, and 2 M KCl salt conditions carried out using the same system described in FIG. 1. We observe similar movement across the range of salt concentrations. As the salt concentration is increased we observe an increase in the current through the nanopore (1-open) at a fixed voltage. This reflects the increase in the conductivity of the solution and the increased number of ions flowing through the nanopore under the applied field. In addition we also observe an increase in the minimum to maximum range of discrimination in the current levels of the DNA events (see FIG. 4 enlargements and bottom right plot). We observe a ~200% increase in DNA discrimination range as the salt concentration is increased from 400 mM KCl to 2M KCl (Table 6 below).

TABLE 6

Effect of increasing salt concentration on pore current and DNA range

| Salt (KCl) (M) | Open-pore current (pA) | DNA range (pA) |
| --- | --- | --- |
| 0.4 | 180 | 25 |
| 1.0 | 440 | 55 |
| 2.0 | 840 | 75 |

Forward and Reverse Modes of Operation

Figure 5A:
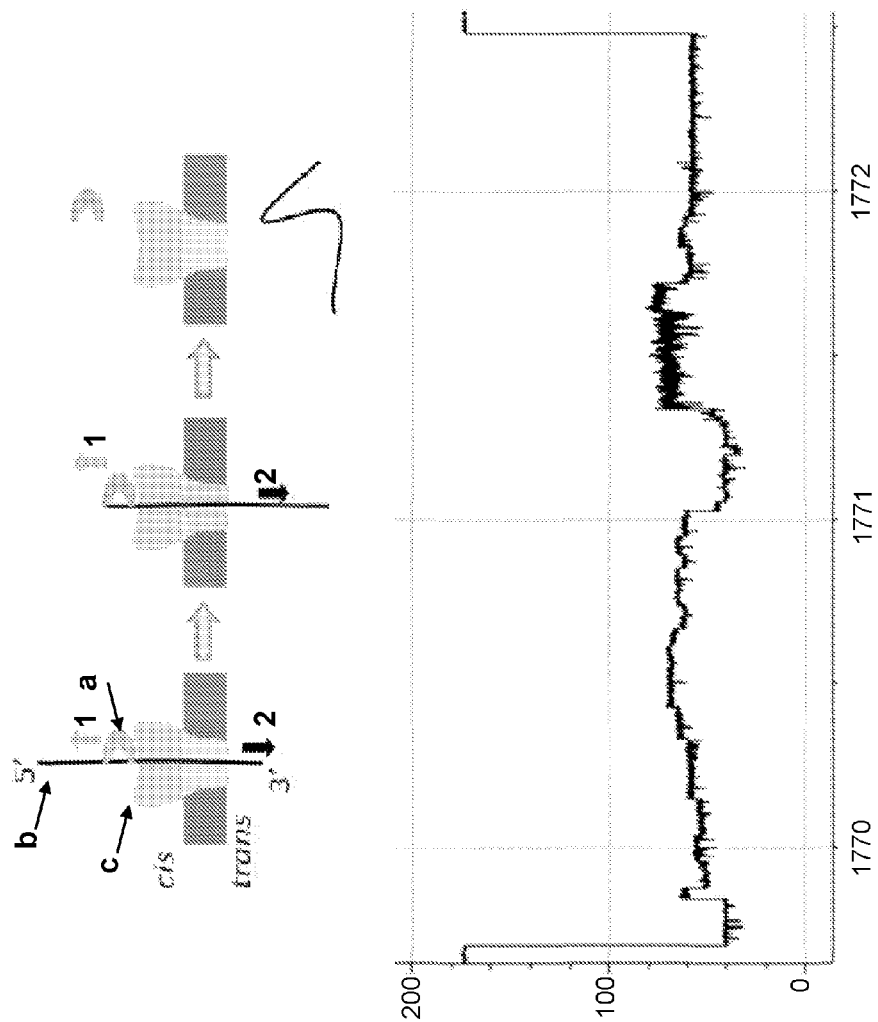
FIG. 5a) When the DNA is captured 3'-down in the nanopore, the enzyme moves the DNA into the nanopore in the direction of the field until it is fully translocated through the pore and lost on the trans side of the bilayer. On the right is an example DNA-helicase event from Hel308 running 3'-down with the applied field (y-axis=current (pA), x-axis=time (s)). Current traces vary between the 5' down and 3' down orientations of DNA.
Figure 5B:
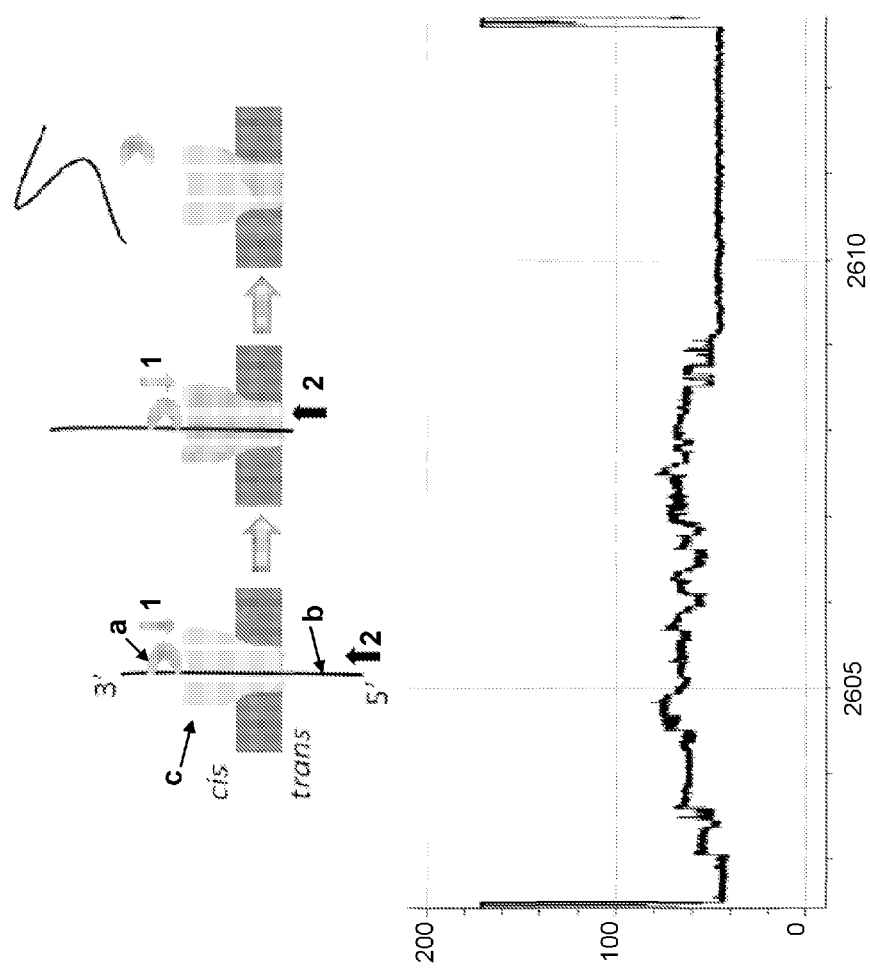
FIG. 5b) When the 5' end of the DNA is captured the helicase works against the direction of the field applied by the voltage, pulling the threaded DNA out of the nanopore until the DNA is ejected back to the cis chamber. On the right is an example DNA-helicase event from Hel308 running 5' down against the applied field (y-axis=current (pA), x-axis=time (s)).

Most helicases move along single-stranded polynucleotide substrates in uni-directional manner, moving a specific number of bases for each NTPase turned over. Although FIG. 1 illustrates the use of this movement to pull threaded DNA out of the nanopore, helicase movement could be exploited in other manners to feed DNA through the nanopore in a controlled fashion. FIG. 5 illustrates the basic 'forward' and 'reverse' modes of operation. In the forward mode, the DNA is fed into the pore by the helicase in the same direction as the DNA would move under the force of the applied field. For Hel308 Mbu, which is a 3'-5' helicase, this requires capturing the 3' end of the DNA in the nanopore until a helicase contacts the top of the nanopore, and the DNA is then fed into the nanopore under the control of the helicase with the field from the applied potential, finally exiting on the trans side of the bilayer. The reverse mode requires capturing the 5' end of the DNA, after which the helicase proceeds to pull the threaded DNA back out of the nanopore against the field from the applied potential, finally ejecting it on this cis side of the bilayer. FIG. 5 shows these two modes of operation using Hel308 Mbu, and typical example DNA events.

Example 2

This Example illustrates the salt tolerance of a Hel308 helicase (Hel308 MBu) using a fluorescence assay for testing enzyme activity.

A custom fluorescent substrate was used to assay the ability of the helicase to displace hybridised dsDNA (FIG. 6A). As shown in 1) of FIG. 6A, the fluorescent substrate strand (100 nM final) has a 3' ssDNA overhang, and a 40 base section of hybridised dsDNA. The major upper strand has a carboxyfluorescein base at the 5' end, and the hybrised complement has a black-hole quencher (BHQ-1) base at the 3' end. When hybrised the fluorescence from the fluorescein is quenched by the local BHQ-1, and the substrate is essentially non-fluorescent. 1 µM of a capture strand that is complementary to the shorter strand of the fluorescent substrate is included in the assay. As shown in 2), in the presence of ATP (1 mM) and $MgCl_2$ (5 mM), helicase (100 nM) added to the substrate binds to the 3' tail of the fluorescent substrate, moves along the major strand, and displaces the complementary strand as shown. As shown in 3), once the complementary strand with BHQ-1 is fully displaced the fluorescein on the major strand fluoresces. As shown in 4), an excess of capture strand preferentially anneals to the complementary DNA to prevent re-annealing of initial substrate and loss of fluorescence.

Substrate DNA: 5'FAM-SEQ ID NO: 61 and SEQ ID NO: 62-BHQ1-3'. FAM=carboxyfluorescein and BHQ1=Black Hole Quencher-1

Capture DNA: SEQ ID NO: 62.

The graph in FIG. 6 shows the initial rate of activity in buffer solutions (10 mM Hepes pH 8.0, 1 mM ATP, 5 mM $MgCl_2$, 100 nM fluorescent substrate DNA, 1 µM capture DNA) containing different concentrations of KCl from 400 mM to 2 M. The helicase works at 2 M.

Example 3

Figure 7A:
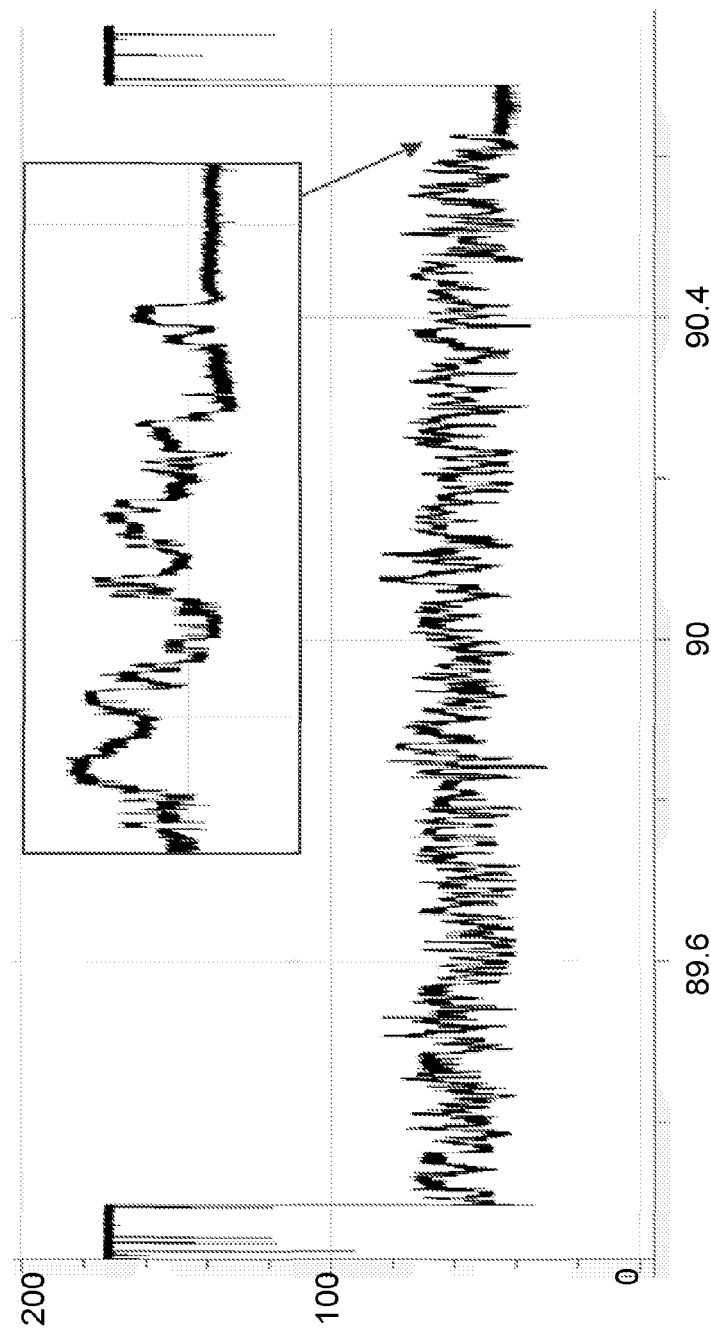
FIG. 7 shows examples of helicase controlled DNA events using different Hel308 helicases (y-axis=current (pA), x-axis=time (min) for FIGS. 7a-c, 180 mV, Hepes pH 8.0, 0.15 nM 400 mer DNA SEQ ID NOs: 59 and 60, 100 nM Hel308, 1 mM DTT, 1 mM ATP, 1 mM $MgCl_2$): Hel308 Mhu (a), Hel308 Mok (b) and Hel308 Mma (c). These represent typical examples of DNA controlled movement through MspA nanopores that ended at the polyT level.
Figure 7B:
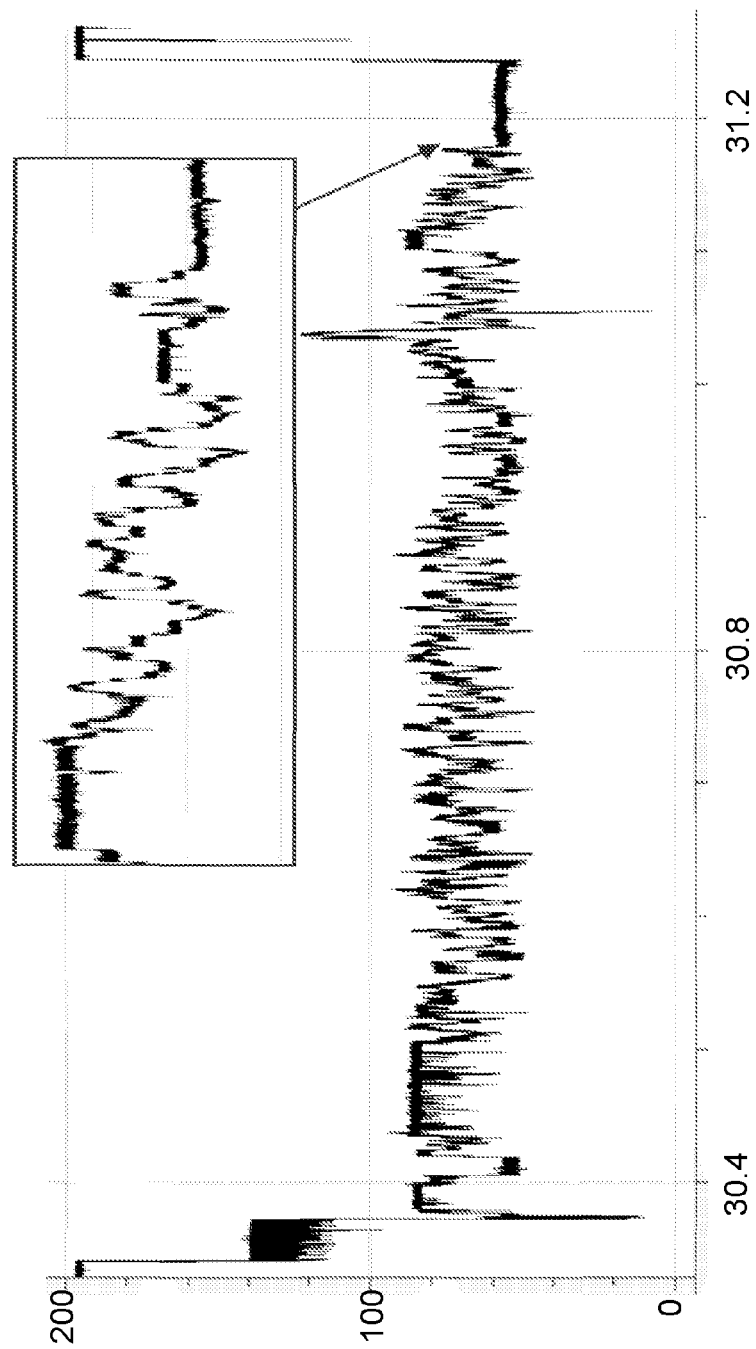
Figure 7C:
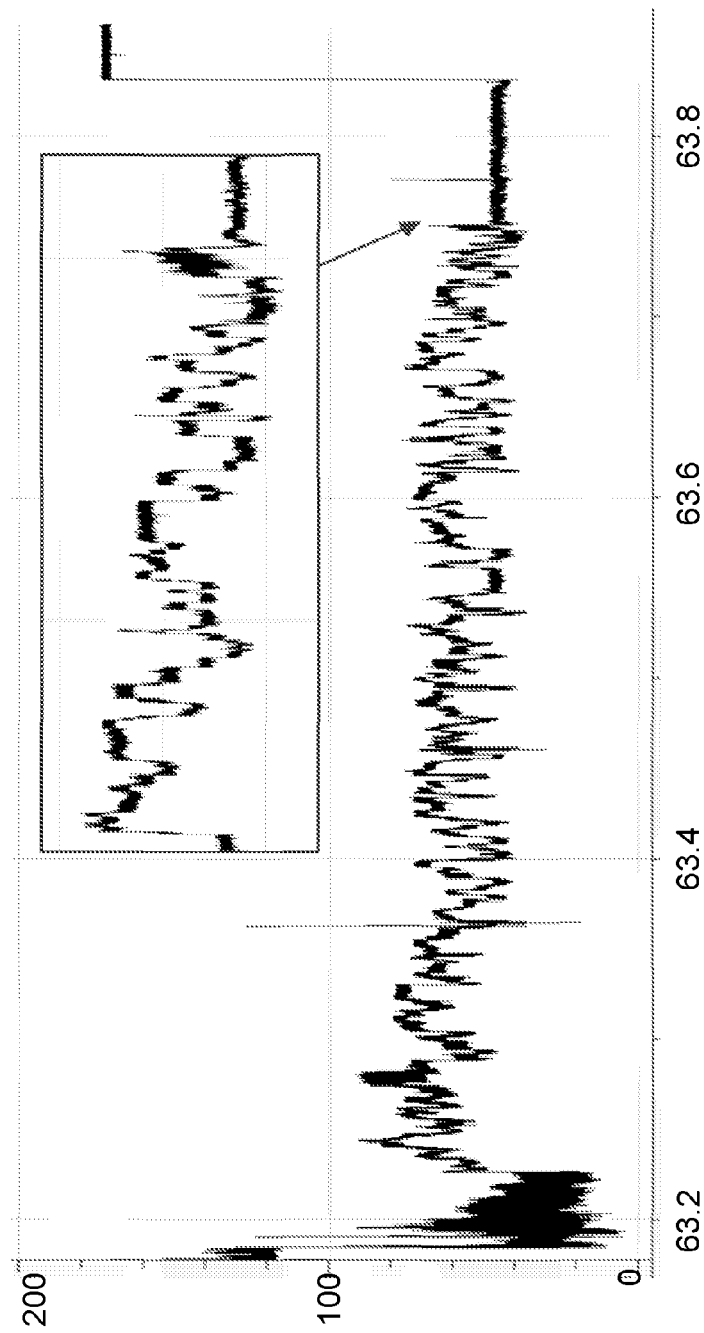

In this Example, three different Hel308 helicases were used, namely Hel308 Mhu (SEQ ID NO: 52), Hel308 Mok (SEQ ID NO: 29) and Hel308 Mma (SEQ ID NO: 45). All experiments were carried out as previously described in Example 1 under the same experimental conditions (pore=MspA B2, DNA=400 mer SEQ ID NO: 59 and 60, buffer=400 mM KCl, 10 mM Hepes pH 8.0, 1 mM dtt, 1 mM ATP, 0.1 mM $MgCl_2$). The results are shown in FIG. 7.

Example 4

This Example measures the internal binding capabilities of a number of Hel308 helicases using a fluorescence assay.

Figure 8:
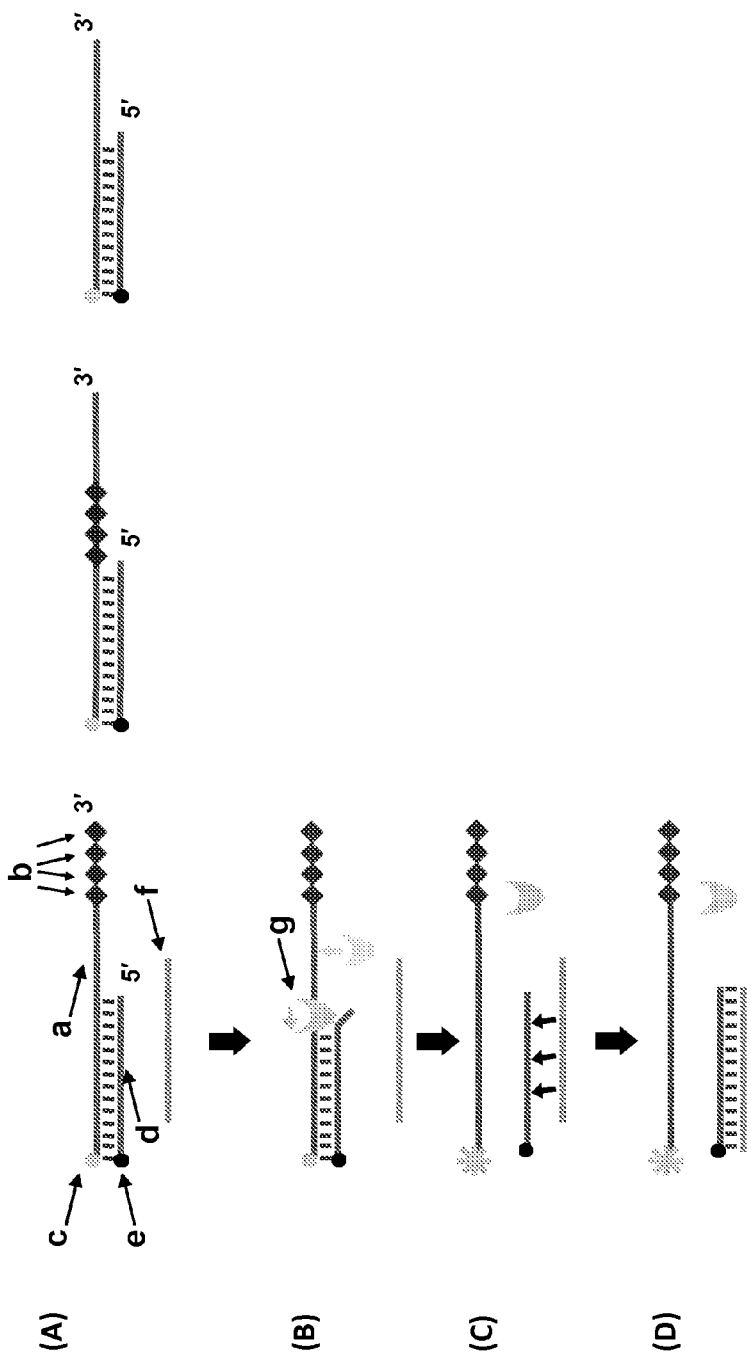
FIG. 8. Fluorescence assay for testing helicase internal binding activity. A) Custom fluorescent substrates were used to assay the ability of the helicases to bind to DNA lacking native 3' ends, allowing them to subsequently displace hybridised dsDNA. The fluorescent substrate strand (50 nM final) has a 3' ssDNA overhang, and a 40 base section of hybridised dsDNA. The major upper strands (a) are modified with four consecutive non-DNA-derived triethylene glycol spacers (referred to as "spacer 9" groups, labelled b), either at the 3' end, or internally, at the junction between the overhang and the dsDNA (as a negative control). Furthermore, the major upper strand has a carboxyfluorescein base (c) at the 5' end, and the hybridised complement (d) has a black-hole quencher (BHQ-1) base (e) at the 3' end. When hybridised, the fluorescence from the fluorescein is quenched by the local BHQ-1, and the substrate is essentially non-fluorescent. A capture strand (1 f), that is complementary to the shorter strand (d) of the fluorescent substrate, is included in the assay. B) In the presence of ATP (1 mM) and $MgCl_2$ (1 mM), a Hel308 helicase homologue (20 nM, g), added to the substrate containing 3'-terminal "spacer 9" groups, can bind to the ssDNA overhang of the fluorescent substrate, move along the major strand, and displace the complementary strand. C) Once the complementary strand with BHQ-1 is fully displaced the fluorescein on the major strand fluoresces. D) An excess of capture strand preferentially anneals to the complementary DNA to prevent re-annealing of initial substrate and loss of fluorescence.

Custom fluorescent substrates were used to assay the ability of the helicases to initiate on DNA lacking native 3' ends, allowing them to subsequently displace hybrised dsDNA (FIG. 8). As shown in section A of FIG. 8, the fluorescent substrate strand (50 nM final) has a 3' ssDNA overhang, and a 40 base section of hybridised dsDNA. The major upper strands are modified with four consecutive "spacer 9" groups, either at the 3' end, or internally, at the junction between the overhang and the dsDNA (as a negative control). Furthermore, the major upper strand has a carboxyfluorescein base at the 5' end, and the hybridised complement has a black-hole quencher (BHQ-1) base at the 3' end. When hybridised, the fluorescence from the fluorescein is quenched by the local BHQ-1, and the substrate is essentially non-fluorescent. A capture strand (1 µM), that is complementary to the shorter strand of the fluorescent substrate, is included in the assay. In the presence of ATP (1 mM) and $MgCl_2$ (1 mM), a Hel308 helicase homologue (20 nM), added to the substrate containing 3'-terminal "spacer 9" groups, can bind to the ssDNA overhang of the fluorescent substrate, move along the major strand, and displace the complementary strand as shown in section B. Once the complementary strand with BHQ-1 is fully displaced (section C) the fluorescein on the major strand fluoresces. An excess of capture strand preferentially anneals to the complementary DNA to prevent re-annealing of initial substrate and loss of fluorescence (section D).

Substrate DNA: SEQ ID NO: 63 with a 5' FAM; SEQ ID NO: 63 with a 5' FAM and 3' spacer ((spacer 9)$_4$); SEQ ID NOs: 64 (with a 5' FAM) and 65 separated by a spacer ((spacer 9)$_4$); and SEQ ID NO: 62 with a 3' BHQ1.

Capture DNA: SEQ ID NO: 66.

Figure 9:
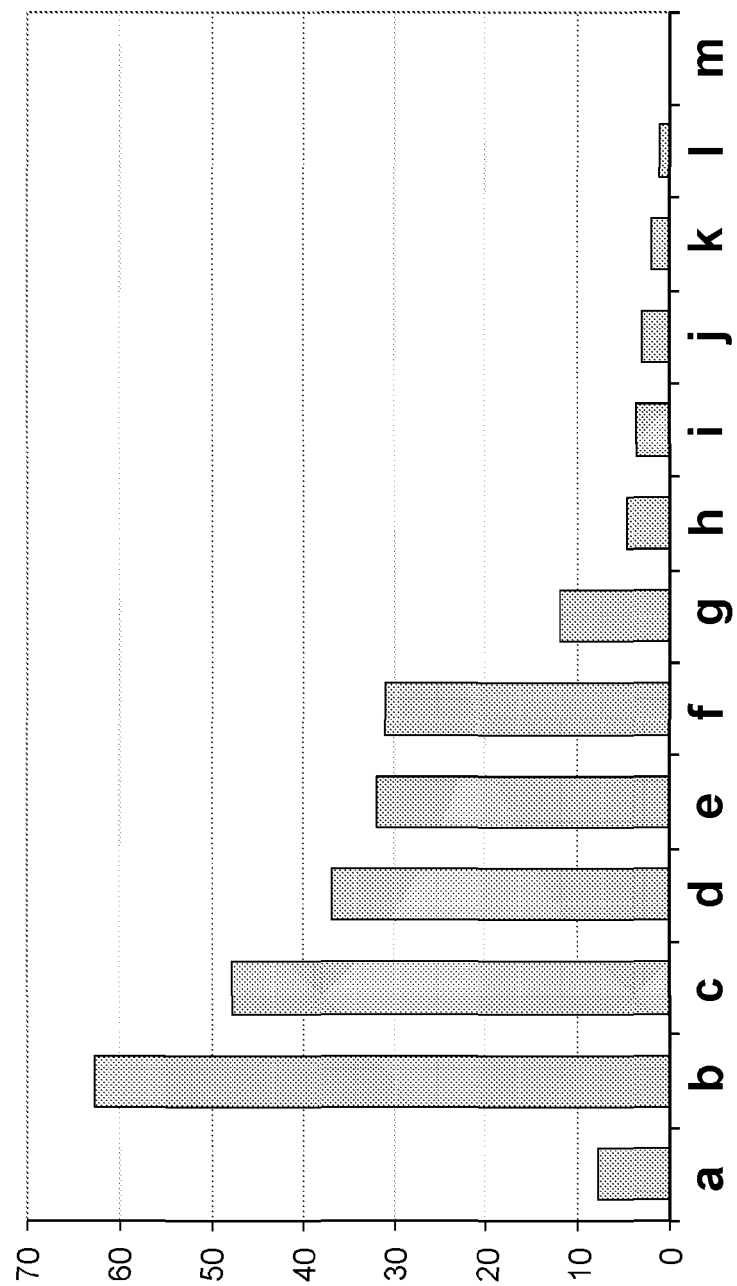
FIG. 9 shows the relative rates of Hel308-mediated dsDNA turnover comparing 3'-unmodified DNA and 3'-"spacer 9" DNA in 400 mM NaCl, 10 mM Hepes, pH 8.0, 1 mM ATP, 1 mM $MgCl_2$, 50 nM fluorescent substrate DNA, 1 µM capture DNA (y-axis=relative "3'-Sp9" activity (% wrt native 3'), x-axis=a (Mbu), b (Csy), c (Tga), d (Mma), e (Mhu), f (Min), g (Mig), h (Mmaz), i (Mac), j (Mok), k (Mth), l (Mba), m (Mzh)).

A number of different Hel308 helicase homologues were investigated for their mid-binding abilities, these included Hel308 Mbu, Hel308 Csy, Hel308 Tga, Hel308 Mma, Hel308 Mhu, Hel308 Min, Hel308 Mig, Hel308 Mmaz, Hel308 Mac, Hel308 Mok, Hel308 Mth, Hel308 Mba and Hel308 Mzh. The graph in FIG. 9 shows the relative rates of Hel308-mediated dsDNA turnover, comparing 3'-unmodified DNA and 3'-"spacer 9" DNA in 400 mM NaCl, 10 mM Hepes, pH 8.0, 1 mM ATP, 1 mM $MgCl_2$, 50 nM fluorescent substrate DNA, 1 µM capture DNA. Several Hel308 homologues were observed to have greater than 20% relative rates of Hel308-mediated dsDNA turnover including, Hel308 Csy, Hel308 Tga, Hel308 Mma, Hel308 Mhu and Hel308 Min.

Example 5

Figure 10:
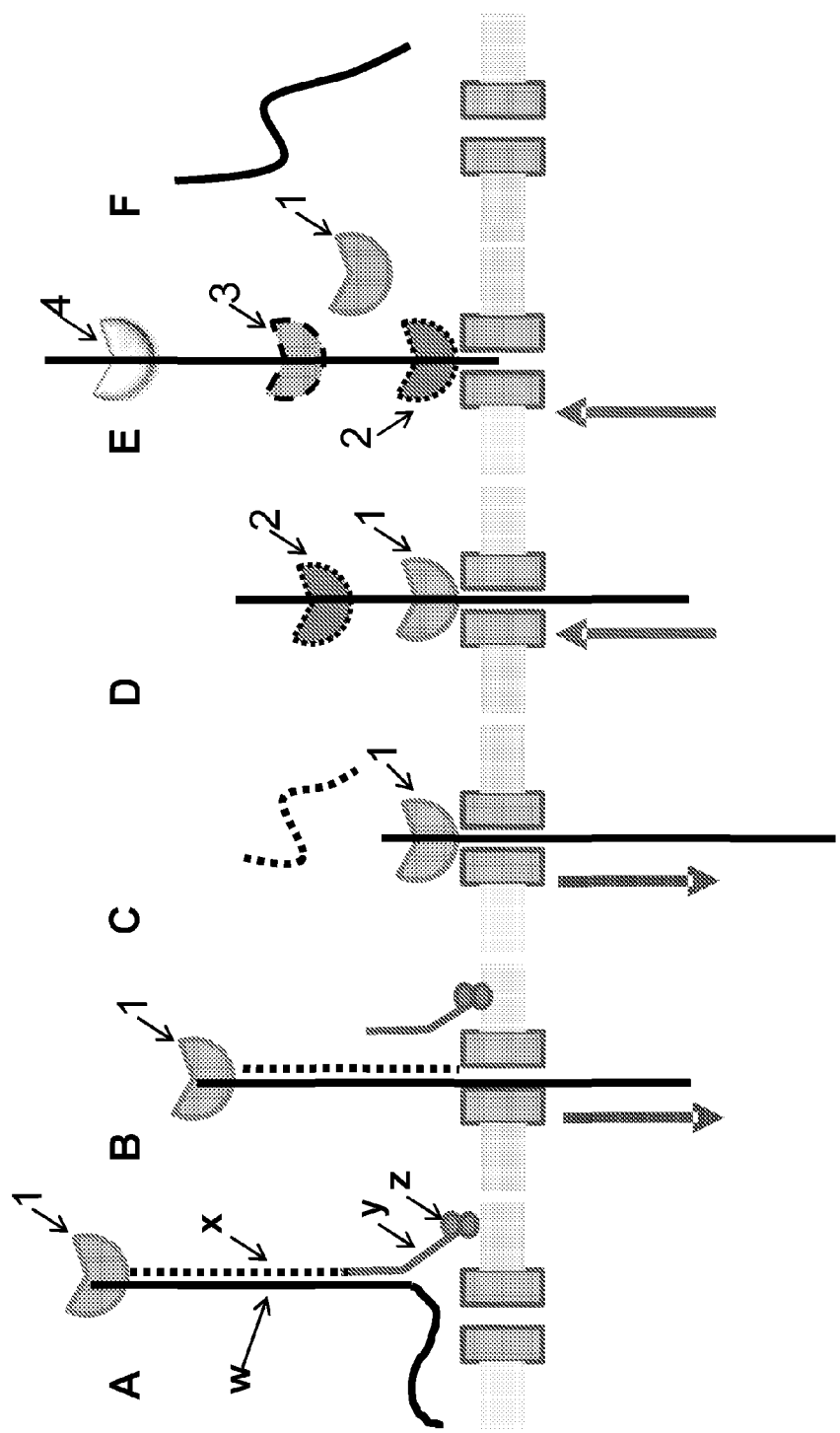
FIG. 10. Schematic of the use of a helicase to control DNA movement through a nanopore which is employed in example 5. A) A DNA substrate (SEQ ID NOs 67 (labelled w) and 68 (labelled x)) with an annealed primer (SEQ ID NO 69 (labelled y)) with an attached cholesterol-tag (labelled z) is added to the cis side of the bilayer. The cholesterol tag binds to the bilayer, enriching the substrate at the bilayer surface. Helicase (labelled l) added to the cis compartment binds to the 4 bp leader of SEQ ID NO 67. B) Under an applied voltage, the DNA substrate is captured by the nanopore via the 5' leader section on the DNA, which strips off SEQ ID NO 69. C) Under the force of the applied field the DNA is pulled into the pore until the bound helicase (l) contacts the top of the pore and prevents further uncontrolled translocation. In this process the antisense strand SEQ ID NO 68 is stripped from the DNA strand. D) In the presence of divalent metal ions and NTP substrate, the helicase (l) on top of the pore moves along the DNA and controls the translocation of the DNA through the pore. The helicase movement along the DNA in a 3' to 5' direction pulls the threaded DNA out of the pore against the applied field. The exposed single stranded DNA on the cis side (3' in this case) is available for further helicases (2-4) to bind either at the terminal nucleotide or at an internal nucleotide. E) If the helicase at the pore (1) disengages from the DNA, the DNA is pulled into the pore by the field until the next helicase (2) on the DNA reaches the pore. The helicase at the pore pulls the DNA out of the nanopore, feeding it back to the cis compartment. The last section of DNA to pass through the nanopore is the 5'-leader. F) When the helicase moves the DNA out of the nanopore it is lost back to the cis compartment. Arrows indicate the direction of DNA movement.

This Example compares the use of two Hel308 helicases, Hel308 MBu and Hel 308 Tga, and their ability to control the movement of intact long DNA strands (900 mer) through a nanopore. The general method and substrate employed throughout this Example are shown in FIG. 10 and described in the description of the Figure above.
Materials and Methods
The DNA was formed by ligating a 50-polyT 5' leader to a ~900 base fragment of PhiX dsDNA. The leader also contains a complementary section to which SEQ ID NO: 69 with a Chol-tag was hybridized to allow the DNA to be tethered to the bilayer. Finally the 3' end of the PhiX dsDNA was digested with AatII digestion enzyme to yield a 4 nt 3'-overhang of ACGT.

Sequences used: SEQ ID NO: 67-900 mer sense strand including 5' leader and tether; SEQ ID NO: 68—anti-sense minus 4 base-pair leader 5'; and SEQ ID NO: 69 with several spacers and a Chol-tag at the 3' end.
Buffered solution: 400 mM-2 NaCl, 10 mM potassium ferrocyanide, 10 mM potassium ferricyanide, 100 mM Hepes, pH 8.0, 1 mM ATP, 1 mM MgCl2, Nanopore: MS-(B1-G75S-G77S-L88N-Q126R)8 (ONT Ref B2C)
Enzyme: Hel308 Mbu 1000 nM or Hel308 Tga 400 nM final.

Figure 11:
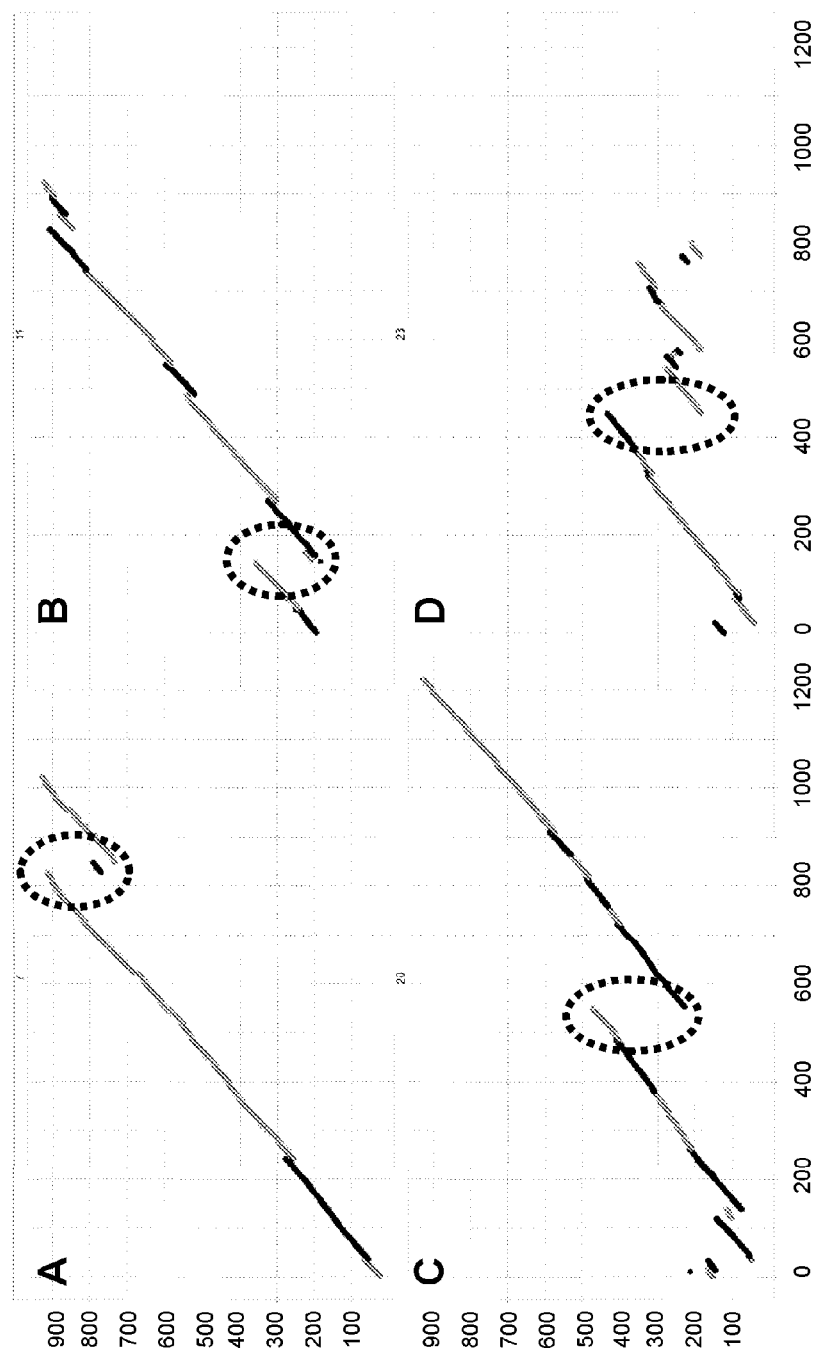
FIG. 11 shows data plots (y-axis=position in the 900 mer, x-axis=index) which indicate how the position of the region of DNA in the nanopore of the 900 mer (y-axis) varied as the Hel308 helicase homologue Mbu controlled the translocation of the DNA strand through the MspA pore (x-axis) during each helicase event. A-C show examples of typical translocation events of the entire DNA strand from approximately the beginning of the strand through to the end of the strand (exiting via polyT leader), whereas event D shows an example of incomplete DNA translocation, where enzyme detachment means the DNA never makes it to the end of the strand. The slips (eg. such as the large slips highlighted by dotted circles) indicate the sequence falling back to a previous point in the strand, and are the result of enzyme detachment. When an enzyme detaches the DNA will be pulled back under the force of the field into the nanopore until another enzyme further along the strand contacts the pore, then continuing helicase movement.
Figure 12:
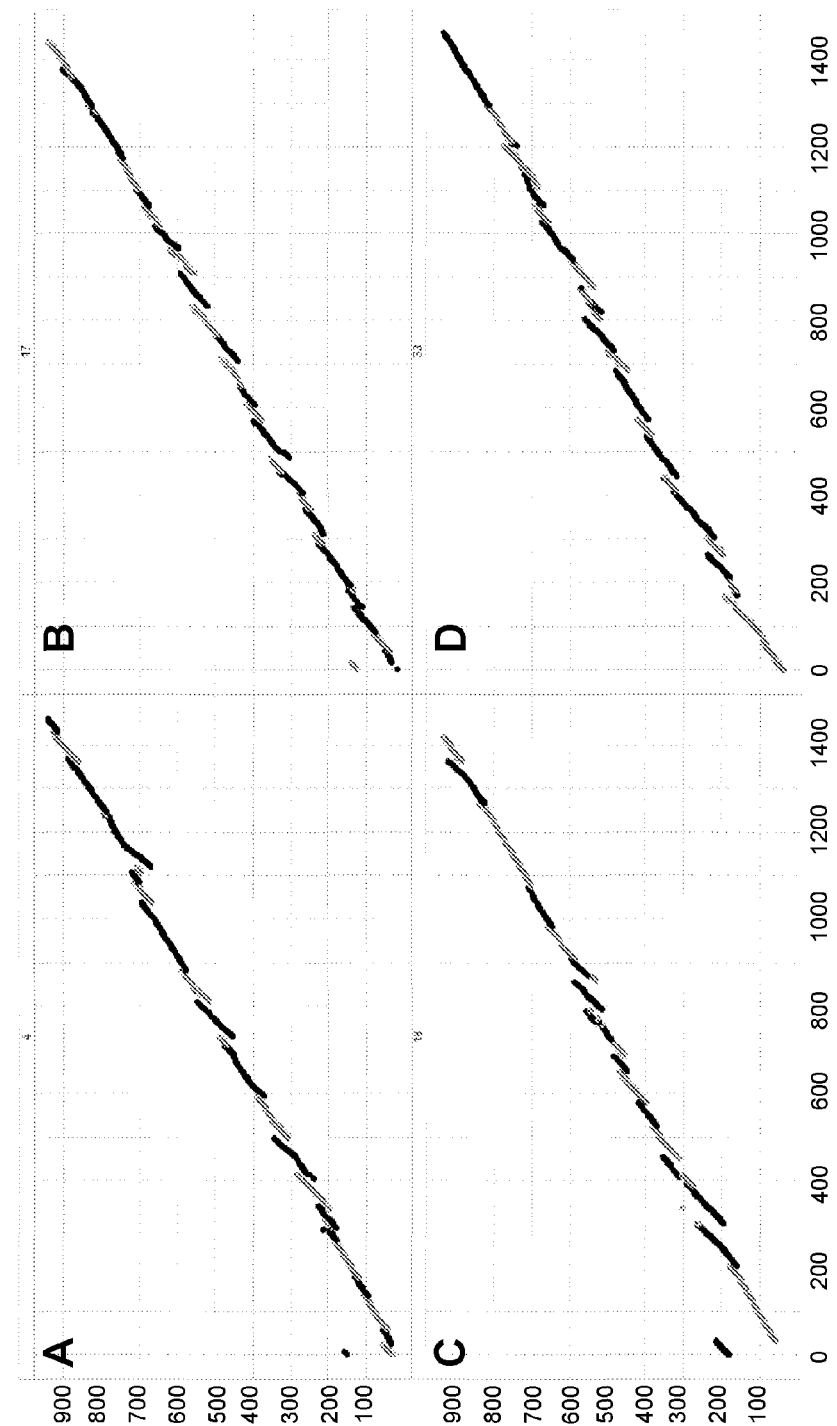
FIG. 12 shows data plots (y-axis=position in the 900 mer, x-axis=index) which indicate how the position of the 900 mer varied as the Hel308 helicase homologue Tga controlled the translocation of the DNA strand through the MspA pore. Events A-D show translocation of the entire DNA strand.

Electrical experiments were set up as described in Example 1 in order to achieve a single pore inserted into a lipid bilayer. After achieving a single pore in the bilayer, ATP (1 mM) and $MgCl_2$ (1 mM) were added to the chamber. A control recording at +140 mV was run for 2 minutes. DNA polynucleotide SEQ ID NOs: 67, 68 and 69 (DNA=0.15 nM) were then added and DNA events observed. Finally, Hel308 helicase (Mbu 1000 nM or Tga, 400 nM) was added to the cis compartment of the electrophysiology chamber to initiate capture of the helicase-DNA complexes in the MspA nanopore. Experiments were carried out at a constant potential of +140 mV.
Results and Discussion The addition of Helicase-DNA substrate to MspA nanopores as shown in FIG. 10 produces characteristic current blocks as the helicase controls the translocation of the DNA through the pore. FIG. 11 shows example event traces which indicate how the position of the 900 mer varied as the Hel308 helicase homologue Mbu controlled the translocation of the DNA strand through the MspA pore. This helicase was found to mediate control of DNA translocation, however, when the helicase detached from the DNA, the strand was observed to move back through the pore, owing to the force exerted by the externally applied potential. In the case of the Hel308 helicase homologue Mbu, the 900 mer strand slipped back a large number of positions (approximately 100-200 bases) each time a helicase disengaged. These rapid changes in position are indicated in FIG. 11 by dotted circles. For this experiment, where Hel308 helicase homologue Mbu was used as the molecular motor, 32% of all of the events detected were found to have read the entire length of the 900 mer strand sequence. FIG. 12 shows similar example event traces indicating how the position of the 900 mer varied as the Hel308 helicase homologue Tga controlled the translocation of the DNA strand through the MspA pore. This enzyme exhibited an greater tendency to bind internally, than the Mbu homologue, because when the Tga helicase disengages (indicated by a change in colour black to grey in FIG. 12), the DNA strand moves back through the pore by a relatively small distance (<50 bases). For this experiment, where Hel308 helicase homologue Tga was used as the molecular motor, 74% of all of the events detected were found to have read the entire length of the 900 mer strand sequence. This means that the Tga helicase homologue can provide increased read lengths of single-stranded DNA in comparison to the Mbu helicase homologue owing to its increased tendency to bind internally.

Example 6

This Example illustrates that by employing the Hel308 helicase homologue Tga it is possible to control the translocation of a 5 kb strand of DNA.

A similar experimental procedure was followed to that described in Example 5. It was observed that by employing the Hel308 Tga it was possible to detect the controlled translocation of an entire 5 kb strand of DNA through MS-(B1-G75S-G77S-L88N-Q126R)8. In an identical experiment using Hel308 Mbu, it was not possible to detect translocation of an entire 5 kB strand.

Example 7

This example compares the enzyme processivity of Hel308 Mbu helicase (SEQ ID NO: 10) with Hel308 Mok (SEQ ID NO: 29) using a fluorescence based assay.

Figure 13:
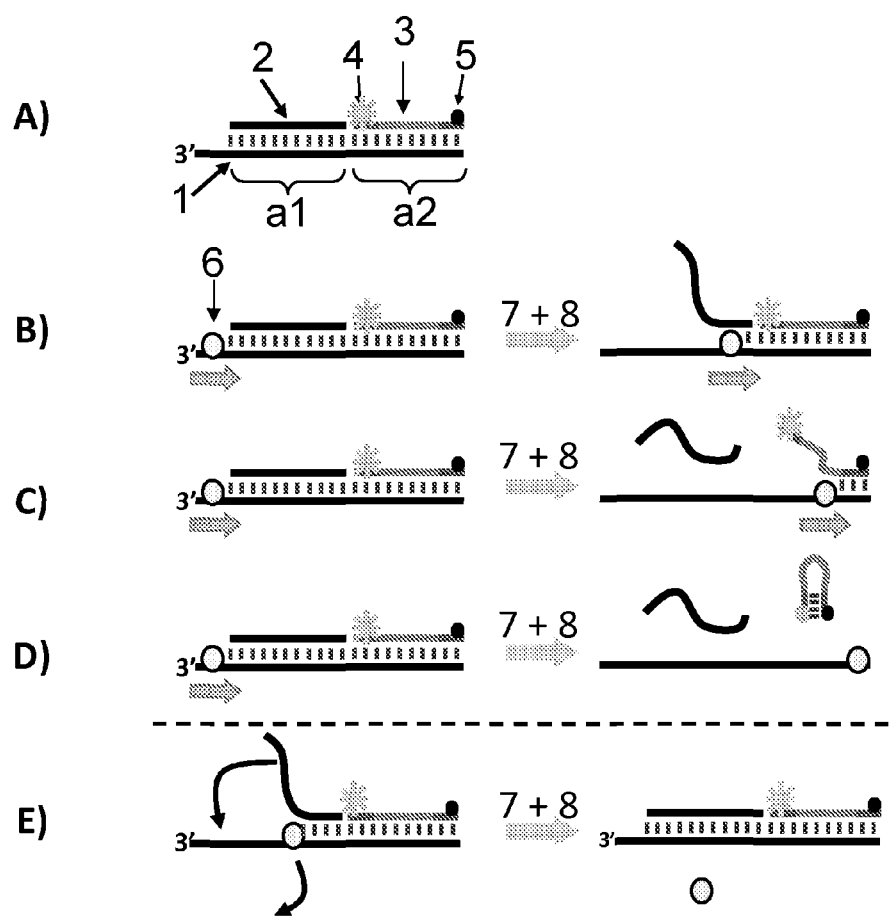
FIG. 13 shows a fluorescence assay used to compare the enzyme processivity of Hel308 Mbu helicase (SEQ ID NO: 10) to that of Hel 308 Mok helicase (SEQ ID NO: 29). A custom fluorescent substrate was used to assay the ability of the helicase to displace hybridised dsDNA. The fluorescent substrate (50 nM final) has a 3' ssDNA overhang, and 80 (a1) and 33 base-pair (a2) sections of hybridised dsDNA (section A, SEQ ID NO: 70). The major bottom "template" strand (1) is hybridised to an 80 nt "blocker" strand (2, SEQ ID NO: 71), adjacent to its 3' overhang, and a 33 nt fluorescent probe (3, SEQ ID NO: 72), labelled at its 5' and 3' ends with carboxyfluorescein (FAM) (4) and black-hole quencher (BHQ-1) (5) bases, respectively. When hybridised, the FAM is distant from the BHQ-1 and the substrate is essentially fluorescent. In the presence of ATP (1 mM) and $MgCl_2$ (10 mM) (addition of ATP and MgCl2 is indicated by 7 and 8 respectively), the helicase (6, nM) binds to the substrate's 3' overhang (SEQ ID NO: 70), moves along the lower strand, and begins to displace the 80 nt blocker strand (SEQ ID NO: 71), as shown in section B. If processive, the helicase displaces the fluorescent probe too (section C, SEQ ID NO: 72, labeled with a carboxyfluorescein (FAM) at its 5' end a black-hole quencher (BHQ-1) at its 3' end). The fluorescent probe is designed in such a way that its 5' and 3' ends are self-complementary and thus form a kinetically-stable hairpin once displaced, preventing the probe from re-annealing to the template strand (section D). Upon formation of the hairpin product, the FAM is brought into the vicinity of the BHQ-1 and its fluorescence is quenched. A processive enzyme, capable of displacing the 80 mer "blocker" (SEQ ID NO: 71) and fluorescent (SEQ ID NO: 72, labeled with a carboxyfluorescein (FAM) at its 5' end a black-hole quencher (BHQ-1) at its 3' end) strands will therefore lead to a decrease in fluorescence over time. However, if the enzyme has a processivity of less than 80 nt it would be unable to displace the fluorescent strand (SEQ ID NO: 72, labeled with a carboxyfluorescein (FAM) at its 5' end a black-hole quencher (BHQ-1) at its 3' end) and, therefore, the "blocker" strand (SEQ ID NO: 71) would reanneal to the major bottom strand (section E).

A custom fluorescent substrate was used to assay the ability of the helicase to displace hybridised dsDNA (FIG. 3). The fluorescent substrate (50 nM final) has a 3' ssDNA overhang, and 80 and 33 base-pair sections of hybridised dsDNA (FIG. 13 section A, SEQ ID NO: 70). The major lower "template" strand is hybridised to an 80 nt "blocker" strand (SEQ ID NO: 71), adjacent to its 3' overhang, and a 33 nt fluorescent probe, labelled at its 5' and 3' ends with carboxyfluorescein (FAM) and black-hole quencher (BHQ-1) bases, respectively (SEQ ID NO: 72). When hybridised, the FAM is distant from the BHQ-1 and the substrate is essentially fluorescent. In the presence of ATP (1 mM) and $MgCl_2$ (10 mM), the helicase (20 nM) binds to the substrate's 3' overhang (SEQ ID NO: 70), moves along the lower strand, and begins to displace the 80 nt blocker strand (SEQ ID NO: 71), as shown in FIG. 13 section B. If processive, the helicase displaces the fluorescent probe (SEQ ID NO: 72, labeled with a carboxyfluorescein (FAM) at its 5' end a black-hole quencher (BHQ-1) at its 3' end) too (FIG. 13 section C). The fluorescent probe is designed in such a way that its 5' and 3' ends are self-complementary and thus form a kinetically-stable hairpin once displaced, preventing the probe from re-annealing to the template strand (FIG. 13 section D). Upon formation of the hairpin product, the FAM is brought into the vicinity of the BHQ-1 and its fluorescence is quenched. A processive enzyme, capable of displacing the 80 mer "blocker" (SEQ ID NO: 71) and fluorescent (SEQ ID NO: 72, labeled with a carboxyfluorescein (FAM) at its 5' end a black-hole quencher (BHQ-1) at its 3' end) strands will therefore lead to a decrease in fluorescence over time. However, if the enzyme has a processivity of less than 80 nt it would be unable to displace the fluorescent strand (SEQ ID NO: 72, labeled with a carboxyfluorescein (FAM) at its 5' end a black-hole quencher (BHQ-1) at its 3' end) and, therefore, the "blocker" strand (SEQ ID NO: 71) would reanneal to the major bottom strand (FIG. 13 section E, SEQ ID NO: 70).

Figure 14:
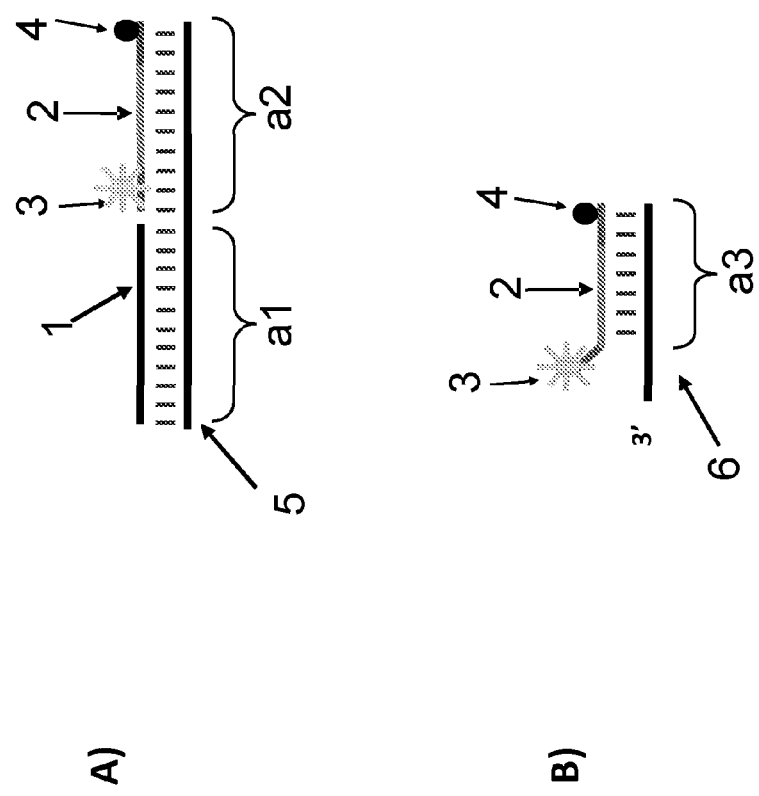
FIG. 14 shows additional custom fluorescent substrates which were also used for control purposes. The substrate used as a negative control was identical to that of the one described in FIG. 3 but lacking the 3' overhang (section A, (SEQ ID NOs: 71 (labelled 1), 72 (labelled 2) (labeled with a carboxyfluorescein (FAM) (3) at its 5' end a black-hole quencher (BHQ-1) (4) at its 3' end) and 73 (labelled 5, consisting of an 80 bp section (a1) and a 33 bp section (a2)))). A similar substrate to that described in FIG. 3 but lacking the 80 base pair section (SEQ ID NOs: 72 (labelled 2) (labeled with a carboxyfluorescein (FAM) (3) at its 5' end a black-hole quencher (BHQ-1) (4) at its 3' end) and 74 (labelled 6, consisting of a 28 bp section (a3))), was used as a positive control for active, but not necessarily processive, helicases (section B).

Additional custom fluorescent substrates were also used for control purposes. The substrate used as a negative control was identical to that of the one described in FIG. 13 but lacking the 3' overhang (FIG. 14 section A, (SEQ ID NOs: 71, 72 (labeled with a carboxyfluorescein (FAM) at its 5' end a black-hole quencher (BHQ-1) at its 3' end) and 73)). A similar substrate to that described in FIG. 13 but lacking the 80 base pair section, used as a positive control for active, but not necessarily processive, helicases (FIG. 14 section B, (SEQ ID NOs: 72 (labeled with a carboxyfluorescein (FAM) at its 5' end a black-hole quencher (BHQ-1) at its 3' end) and 74)).

Figure 15:
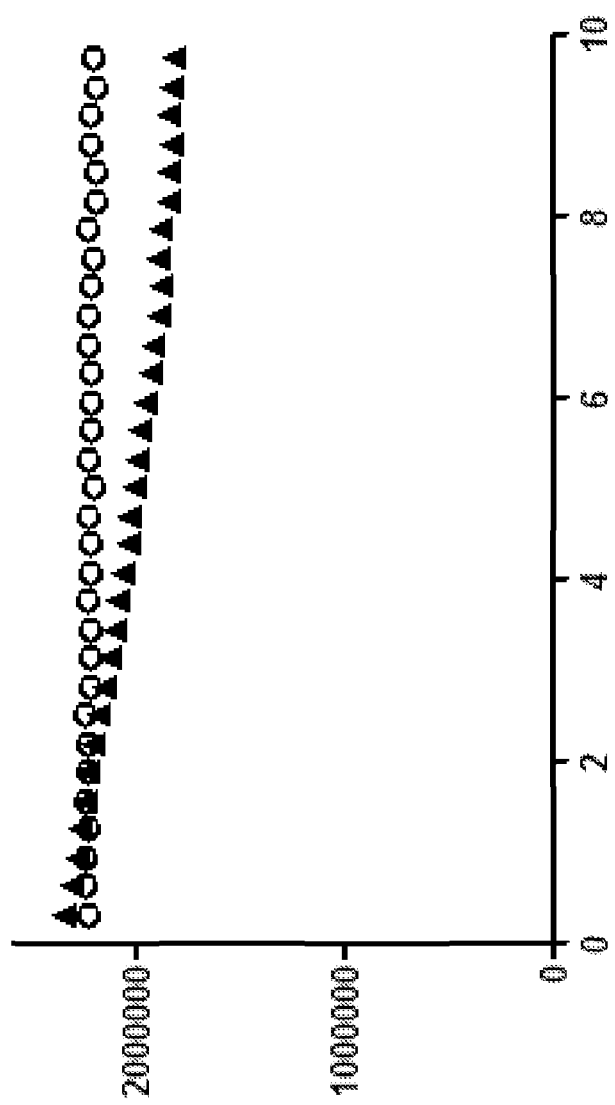
FIG. 15 shows a graph (y-axis=fluorescence (arbitrary units), x-axis=time (min)) of the time-dependent fluorescence changes upon testing Hel308 Mbu helicase (SEQ ID NO: 10, empty circles) and Hel 308 Mok helicase (SEQ ID NO: 29, black triangles) against the processivity substrate shown in FIG. 13 in buffered solution (400 mM NaCl, 10 mM Hepes pH 8.0, 1 mM ATP, 10 mM $MgCl_2$, 50 nM fluorescent substrate DNA (SEQ ID NOs: 70, 71 and 72 (labeled with a carboxyfluorescein (FAM) at its 5' end a black-hole quencher (BHQ-1) at its 3' end). The decrease in fluorescence exhibited by Hel308 Mok denotes the increased processivity of these complexes as compared to Hel308 Mbu (SEQ ID NO: 10).
Figure 16:
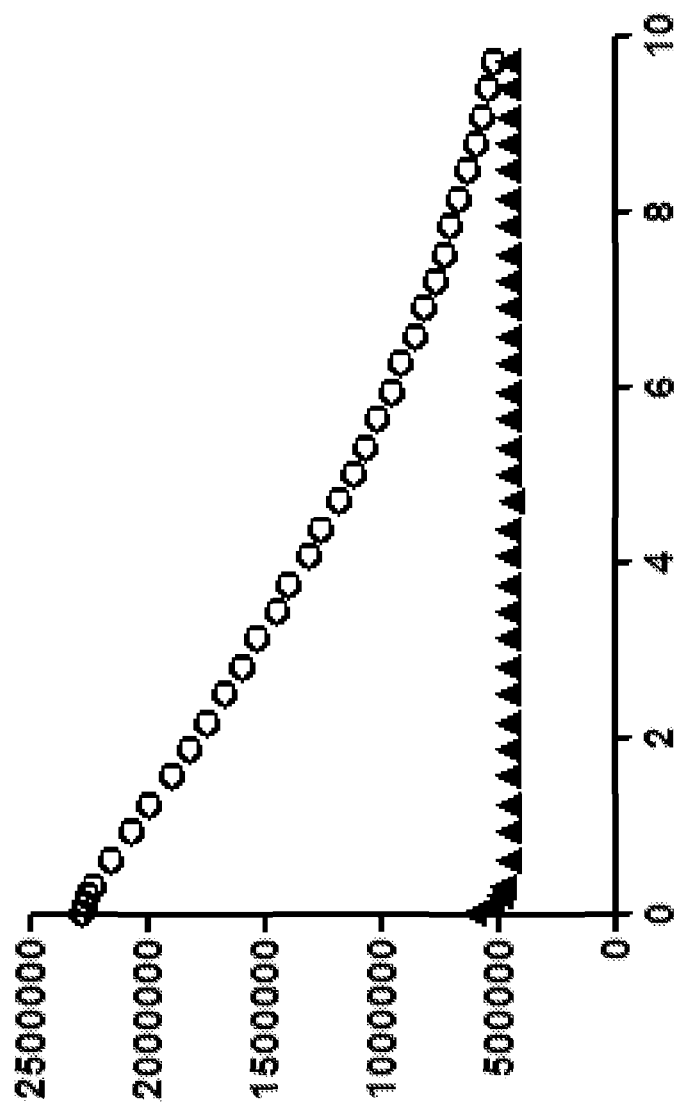
FIG. 16 shows a graph (y-axis=fluorescence (arbitrary units), x-axis=time (min)) of the time-dependent fluorescence changes upon testing Hel308 Mbu helicase (SEQ ID NO: 10, empty circles) and Hel 308 Mok helicase (SEQ ID NO: 29, black triangles) against the positive control processivity substrate (shown in FIG. 14 section B, SEQ ID NOs: 72 (labeled with a carboxyfluorescein (FAM) at its 5' end a black-hole quencher (BHQ-1) at its 3' end) and 74) in buffered solution (400 mM NaCl, 10 mM Hepes pH 8.0, 1 mM ATP, 10 mM MgCl$_2$, 50 nM fluorescent substrate DNA (SEQ ID NOs: 72 (labeled with a carboxyfluorescein (FAM) at its 5' end a black-hole quencher (BHQ-1) at its 3' end) and 74)). This positive control demonstrated that both helicases were indeed active, as denoted by a fluorescence decrease for both samples.

FIG. 15 shows a graph of the time-dependent fluorescence changes upon testing Hel308 Mbu helicase (SEQ ID NO: 10) and Hel 308 Mok helicase (SEQ ID NO: 29) against the processivity substrate shown in FIG. 13 in buffered solution (400 mM NaCl, 10 mM Hepes pH 8.0, 1 mM ATP, 10 mM $MgCl_2$, 50 nM fluorescent substrate DNA (SEQ ID NOs: 70, 71 and 72 (labeled with a carboxyfluorescein (FAM) at its 5' end a black-hole quencher (BHQ-1) at its 3' end). The decrease in fluorescence exhibited by Hel308 Mok denotes the increased processivity of these complexes as compared to Hel308 Mbu (SEQ ID NO: 10). FIG. 16 shows positive controls demonstrating that all helicases were indeed active, as denoted by a fluorescence decrease for all samples.

```
SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54 and 55 (Table 4) are
aligned below The number below the * indicates the SEQ ID NO. The "-" are shown for alignment purposes only and do not form part of the sequences.

*                                    1                                                                                               95
10    Hel308 Mbu        (1)  ---------------MMIRELDIPRDIIGFYEDSGIKELYPPQAEAIEMGLLE-KKNLLAAIPTASGKILLAELAMIK
53    Hel308 Afu        (1)  ---------------MKVEELAESISSYAVGILKEEGIEELYPPQAEAVEKVFS--GKNLLLAMPTAAGKILLAEMAMVR
22    Hel308 Csy        (1)  ---------------MRISELDIPRPAIEFLEGEGYKKLYPPQAAAAKAGLID-GKSVLVSAPTASGKILLAAIAMIS
75    Hel308 Dth        (1)  MPGVDELLQQMGQGDLQGLSTVAVKEIPAREAEFSGIEGLPPPLKQALTESGIENFYTHQARAVNLVRK--GRSVTATPTASGKSLIYNIPVLE
48    Hel308 Fac        (1)  ---------------MKLSEITPSEFLKVTDNNDFTLYEHQEEAVAKLREN--KNVISVPTASGKTLLIGYISIYD
19    Hel308 Hla        (1)  ---------------MQPSSLSGLPAGVGEALEAEGVAELYPPQAEAVEAGTE-GESLVAAVPTASGKILLAELAMLS
55    Hel308 Hpa        (1)  ---------------MNVADLTGLPDGVPEHHPAQGIEELYPPQAEAVEAGITE-GESVVASIPTASGKTFIAELAMLS
54    Hel308 Htu        (1)  ---------------MNLEELTGLPPGATDHERGEGIEELYPPQADAVEAGATD-GENLVAAVPTASGKIMIAALSMLS
16    Hel308 Hvo        (1)  ---------------MRTADLTGLPTGIPEALRDEGIEELYPPQAERAVEAGLID-GESLVAAVPTASGKILLAELAMLS
39    Hel308 Mac        (1)  ---------------MKIESLDLPDEVKREYENSGIPELYPPQAERAVEKGLLE-GKNLLAAIPTASGKILLAELAMLK
38    Hel308 Mba        (1)  ---------------MKIESLDLPDEVKQFYLNSGIEELYPPQAERAVEKGLLE-GRNLLAAIPTASGKILLAELAMLK
47    Hel308 Mbo        (1)  ---------------MQIQDLAIEPLRQQYIGLGIRELYPPQAERAVEKGLLD--NKNLLAAIPTASGKILIAEMAMHR
44    Hel308 Mev        (1)  ---------------METGKLELPEYVIQFYLDTGIEKLYPPQAERAVEKGLLD-GKNLLVAIPTASGKTLSELAMLK
49    Hel308 Mfe        (1)  ---------------MPTNKILEILKDFGIEELRPPQKKALEKGLLDKNKNFLISIPTGAGKTLIGEMALIN
28    Hel308 Mfr        (1)  ---------------DLSLPKAFIQYYKDKGIESLYPPQSECIENGLLQ--GADLLVAIPTASGKILIAEMAMHA
52    Hel308 Mhu        (1)  ---------------MEIASLPLPDSFIRACHAKGIRSLYPPQAECIEKGLLE--GKNLLISIPTASGKILIAEMAMWS
32    Hel308 Mig        (1)  ---------------MQKYSHVFEVLKENGIKELRPPQKKVIEKGLLNKEKNFLICIPTASGKILIGEMALIN
51    Hel308 Min        (1)  ---------------MDEILKFLGLIKELRPPQKKALELGILDEGLFDKTKNFLICIPTASGKTLIGEMALIN
45    Hel308 Mma        (1)  ---------------MHVLDLLKENKITELRPPQKKIGIEEELYPPQADAVEKGLLQ--GENLLAAIPTASGKILLAEMAMLS
40    Hel308 Mmah       (1)  ---------------MKIEELDLPSEAIEVVLQAGIEELYPPQAERAVEAGVIE-GENLVASIPTASGKILLAELAMLK
76    Hel308 Mmar       (1)  ---------------MDVADLPGVPEWLPDHLRDDGIEELYPPQAERAVEAGVIE-GENLLAAIPTASGKILLAEMAFIN
41    Hel308 Mmaz       (1)  ---------------MKIESLDLPDEIKREYENSGLLELYPPQKKVEGGLLNKNKNFLICIPTASGKILIGEMAFIN
29    Hel308 Mok        (1)  ---------------MLMLMEVLKENGIAELRPPQKKVEGGLLNKNKNFLICIPTASGKILLAELAMLK
42    Hel308 Mth        (1)  ---------------MLTIRDLIRWLPESVIELYEALGIDELYPPQAERAVEAGIDELGRNMIISVPTAAGKILLAELAMLK
43    Hel308 Mzh        (1)  ---------------MKVKKYYTDIGIVDLYPPQREAVDKGLLD--GENIVAAIPTASGKILLAELCMLK
46    Hel308 Nma        (1)  ---------------MNINNLNLPEKVKKYYTDIGIVDLYPPQREAVDKGLLD-GENIVAAIPTASGKIMAALSMLS
77    Hel308 Nth        (1)  ---------------MNVEELSGLPPGARSHFQEQGIEELYPPQAEAVEAGATE-GENLVAAVPTASGKIMAALSMLS
13    Hel308 Pfu        (1)  ---------------MSETFYLLSERMQKKIWEMGGWDEFTPVQDKTIPIVMNT--NKDVVSSGIASGKTEAVFLPILS
25    Hel308 Sso        (1)  ---------------MRVDELR---VDERIKSTLEKGLLE-VDERLKAVILKERGIEELYPPQAEALKSGIELE-GKNALISIPTASGKILIAEMGIIS
34    Hel308 Tba        (1)  ---------------MSLELEWMPIEDLIKLPSNVIEIIRRKIEERGISEFYPPQAEALRSGVLN--GENLLAIPTASGKILVAEIVMLH
37    Hel308 Tga        (1)  ---------------MLSTKPKAYKRESPIG--YAMQYDELSKFGVDERIIRKIERGISEFYPPQAEALKSGALE-GRNLVLAIPTASGKIIVSEIVMVN
50    Hel308 Tsi        (1)  ---------------MKVDELP---VDERIKAVILKERGIEELYPPQAEAALKTEVLK-GKNALISIPTASGKILVAEIVMIN
78    Hel308 Mja        (1)  ---------------MKLNKLKSYINAFLLGMVMSMKVDELKSLGVDERILRLLRERGIEELYPPQADALKTEVLK--GKNLLAIPTASGKILVAEIVMIN
                             ---------------MDKILEIIKDFGIVELRPPQKKALERGLLDKNKNFLISIPTASGKTLIGEMALIN
Consensus                                   LP  V   L E  GI  ELYPPQAEAVE  GLLD  GKNLLIAIPTASGKTLIAELAML 96                                                                                              190
10    Hel308 Mbu       (63)  AIREGG-----------KALYIVPLRALASEKFPERFK-ELAP---FGIKVGISTGDLDSRADWLGVNDIIVATSEKTDSLLRNGTSWMD------EIT
53    Hel308 Afu       (64)  EAIKGG-----------KSLYVVPLRALAAGEKYESFK-KWEK---IGLRIGISTGDYESRDEHLGDCDIIVTTSEKADSLIRNRASWIK------AVS
22    Hel308 Csy       (63)  HLSRNR-----------GKAVLSPLRALAAEKFAEFGKIGGIPL--GRPVRVGVSTGDFEKAGRSLGNNDILVLTNERMDSLIRRRPDWMD-----EVG
75    Hel308 Dth       (94)  SIINDP-----------ASRALYLPPLKALTRDQLTSLEEFARLLAGKVHVDSAVYDGDTDPQARARIRSKPPNILLTNPDMIHRSFLPYHRSWQKFFSALK
48    Hel308 Fac       (60)  TYLKGK-----------KSMYIVPLRSLAMEKFSELL-SLRN----LGVKVTMSIGDYDVPPSFVKNYDVIIATSERADSMLHRDPDILN------YFG
19    Hel308 Hla       (64)  SIERGG-----------KALYIVPLRALASEKKTEFE-RWEE----FGVTVGVSTGNYESDGEWLATRDIIVATSEKVDSLIRNGAPWID------DLT
55    Hel308 Hpa       (64)  SVARGG-----------KALYIVPLRALASEKKEEFE-RFEQ----YGVSIGVSTGNYESDGDWLASRDIIVATSEKVDSLVRNGAKWID------DLS
54    Hel308 Htu       (64)  AVQRGG-----------KALYIVPLRALASEKKEEFE-AYEE----FGVTGVTTGNYESTDDWLATRDIIVATSEKVDSLVRNGADWLS------ELT
16    Hel308 Hvo       (63)  SVARGG-----------KALYIVPLRALASEKKAEFE-RWEE----YGIDVGVSTGNYESDGEWLSSRDIIVATSEKVDSLVRNNAAWMD------QLT
39    Hel308 Mac       (63)  SVLAGG-----------KALYIVPLRALASEKFRRFQ-DFSE----LGIRVGISTGDYDRDEGLGINDIIVATSEKTDSLLRNETAWMQ------EIS
38    Hel308 Mba       (63)  SILAGG-----------KALYIVPLRALASEKFRRFR-EFSE----LGIRVGISTGDYDLRDEGLGVNDILRDEGLVNDIIVATSEKTDSLRNETVWMQ------EIS
```

```
SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54 and 55 (Table 4) are
aligned below The number below the * indicates the SEQ ID NO. The "-" are shown for alignment purposes only and do not form part of the sequences.

Hel308  Mbo   (63)   HIANGG------KCLYIVPLKALASEKYEEFG-NK------GVKVGLSTGDLDRRDDALGKNDIIVATSEKVDSLLRNGARWIP------DIT
Hel308  Mev   (63)   SISNGG------KCLYIVPLRALASEKPERFK-QFSS----IGVNIGISTGDFDSTDEWLGSNDIIVATSEKADSLLRNETSWMK------DIT
Hel308  Mfe   (58)   HLLDENKNPTNKKGIFIVPLKALASEKYEEFKNKYER----YGLRVALSIGDYD-EDEDLSRYHLITTAEKLDSLWRHKIDWID------DVS
Hel308  Mfr   (59)   AIARGG------MCLYIVPLKALATEKAQEFK-GK------GAEIGVATGDYDQKEKRLGSNDIVIATSEKTDSLLRNGVPWLS------QVT
Hel308  Mhu   (63)   RIAAGG------VIRVGIATGDSIGDYD-EKEDLSSYNIIITTAEKLDSLMRHEIDWLN------QIT
Hel308  Mig   (59)   HLLDENKTPTNKKGLFIVPLKALASEKYEEFRRKYEK----YGLKVALSIGDYD-EKEDLENDLIITTAEKFPDSLWRHGIKLS------YVS
Hel308  Min   (53)   GKKGVYIVPLKALASEKYEEFKKKYEK----FGVRVALSIGDYD-EDEDLENLIITTSEKLDSLMRHVEWIN------DIS
Hel308  Mma   (55)   HLLDENKNLTGKKGLFIVPLKALANEKFDEFREKYEK----YGIKTAISTGDPD-TKENLSKFPHIIITTSEKLDSLLRNSTPWMK------DIT
Hel308  Mmah  (63)   AIKKGG------KALYIVPLRALASEKFRDFK-RFES----YGLDIGVSTGNYESEGGWLADKDIIVATSEKTDSLLRNETAWMQ------DLT
Hel308  Mmar  (64)   SVARGG------KALYIVPLRALASEKQADFE-EFEQ----LGMRVGLSTGDYDRDEGLGINDIIVATSEKTDSLIRHKVEWIK------DIS
Hel308  Mmaz  (63)   SVLNGG------KALYIVPLRALASEKPRRFQ-EFSV----LGLRVGLSTGDFEKDRLGRNDIIATSEKADSLIRNGASWVR------RIG
Hel308  Mok   (56)   HLLDNNKTPTNKKGLFIVPLKALANEKYEEFKGKYEK----LGIKVGIATGDLDSREEWLGKNDIIIATSEKTDSLLRNESSWMK------EIN
Hel308  Mth   (66)   GALSGK------RSLYIVPLRALASEKPESFS-RFSK----FGVTTGVATGNYESTSEWLATKDIVATSEKVDSLVRNGADWLS------DLT
Hel308  Mzh   (63)   SIGMGG------KCLYIVPLRALASEKYSRFR-EFES----IPIHRWHGDVNQNKKKQLTKNPAGILQITPESIESLFINRTNELNYIL----SDIE
Hel308  Nma   (64)   AVQRGG------KALYIVPLRALASEKKAEFD-AYEE----IPIHRWHGDVNQNKKKQLTKNPAGILQITPESIESLFINRTNELNYIL----SDIE
Hel308  Nth   (65)   QIEKDAT-----KDLKLIYLISPLKALINDQPERIIKLCEKSY-IPIHRWHGDVNQNKKKQLTKNPAGILQITPESIESLFINRTNELNYIL----SDIE
Hel308  Pfu   (63)   RIITGG------GKAVYIVPLRALASEKFESFS-DWEK----LGIRVAMATGDYDSDEWLGKYDIIIATAEKPDSLLRHGSSWIK------DVK
Hel308  Sso   (70)   FLLKNG------GKAIYVTPLRALTNEKYLTFK-DWEL----IGFKVAMTSGDYDTDDAWLKNVDIIITTYEKLDSLWRHPEWLN------EVN
Hel308  Tba   (84)   KLFTGG------GKAVYLVPLKALAEEKYREFK-TWED----LGVRVAVTTGDYDYDSSEWLGKYDIIIATSEKPDSLLRHKSRWIR------DVT
Hel308  Tga   (63)   KLIQEG------GKTVYLVPLKALAEEKYREFK-FWEK----LGIRIAMTTGDYDSTEWLGKYDIIATSEKPDSLLRHGARWIN------DVK
Hel308  Tsi   (86)   KILREG------GKTVYLVPLKALAEEKYREFK-FWEK----LGIRIAMTTGDYDSTEWLGKYDIIATSEKPDSLLRHKSPWIK------DIN
Hel308  Mja   (56)   HLLDGNKNPTNKKGIFIVPLKALASEKYSKYER----YGLRIALSIGDYD-EDEDLSKYHLIITTAEKLDSLWRHKIDWIN------DVS
          Consensus  (96)   IL GG        KALYIVPLRALASEKY  EFK  FE       GVRVGISTGDYD   DEWLG  DIIVATSEKVDSLLRN    WI        DIT 191                                                                                                     285
Hel308  Mbu   (140)  TVVVDEIHLLDSKNRGPTLEVITKLMRLNPD----VQVVALSATVGNAREMADWLG---AALVLSEWRPTDLHEGVLFGDAINFPG-SQKKIDR
Hel308  Afu   (141)  CLVVDEIHLLDSEKRGATLEILVTKMRRMNKA---LRVIGLSATAPNVKELFD-----ADYYVSDWRPVPLVSEGVLCEGTLELFD---GAFS
Hel308  Csy   (145)  LVIADEIHLIGDRSRGPLEMVLTKLRHLRSS----POVVALSATISNADEIAGWLD---CTLVHSTWRPVDLPSEGVYQDGEVAMGDGSRHEVAA
Hel308  Dth   (185)  YIVVDEVHTYRG-VMGSMAWVPRRLRRICAQYGREPVFIFSSATIANGQLCSALTGHEPEVIQKGGAPAGKKHFLLLDPEMQGAAQS----
Hel308  Pac   (137)  LVIIDEIHMISDDPSRGPRLETVISSLLYLNPE--ILLLGLSATVSNIQEIAEWMN---AETVVSNFRAVPLETGIIFKGNLITDG---
Hel308  Hla   (141)  CVVSDEVHLVDDPNRGPTLEVTLAKLRKVNPG---LQTVALSATVGNADVIAEWLD---AELVESDWRPIDLRMGVHFGNAIDFADGSKREVPV
Hel308  Hpa   (141)  CVVSDEVHLIVNDAHRGPTLEVTLAKLRRVNPD---LQTVALSATVGNADVIAEWLD---AELVESDWRPIDLRKGVLYGQALHFDDGTQQELAR
Hel308  Htu   (141)  CVVSDEVHLIDDRNRGPTLEVTLAKLRLNPG----MOVVALSATVGNADEIADWLD---ASLVDTDWRPIDLQMGVHYGNALNFDDGSTREVPV
Hel308  Hvo   (141)  CVVADEVHLVDDRHRGPTLEVTLAKLRRLNTN---LQVVALSATVGNAGVVSDWLD---AELVKSDWRPIDLKMGVHYGNAVSFADGSQREVPV
Hel308  Mac   (140)  VVVVDEVHLIDSADRGPTLEVTLAKLRKMNPF---CQILALSATVGNADELAAWLD---AELVLSEWRPTDLMEGVFFDGTFFCKD-KEKLIEQ
Hel308  Mba   (140)  VVVADEVHLIDSPDRGPTLEVTLAKLRKMNPS---CQILALSATVGNADELAVWLE---AELVLSEWRPTELLEGVFFNGTFYCKD-REKTVEQ
Hel308  Mbo   (137)  LVVIDEIHLIDSPDRGPTLEMVIAKMRSKNPG---MOLIGLSATIGNPKVLAGWLD---AELVTSSWRPVDLRQGVFYDNRIQFAE-RMRPVKQ
Hel308  Mev   (140)  TIVVDEVHLIDSADRGPTLEVTLAKLRLNPN----SQIIGLSATIGNAEEIAGWLD---AELVQSQWRPIELYEGVPLEDNINFKQ-SQKPIKN
Hel308  Mfe   (141)  VVVVDEIHLIDSESRGPTLEMVITKLRHASPD---IQIIGLSATIGNPEELANWLN---AELIVDDWRPVELKKGIYKNGIIEFINGE----N
Hel308  Mfr   (133)  CLVLDEVHLIGSENRGATLEMVITKLRYTNPV---MOVIGLSATIGNPAQLAEWLD---ATLITSWRPVDLRQGVYYNGKIRFSD-SERPIQG
Hel308  Mhu   (138)  CIVLDEVHLIGSENRGATLEMVITKLRYTNPV---MOVIGLSATIGNPAQLAEWLD---ATLITSWRPVDLRQGVYYNGKIRFSD-SERPIQG
Hel308  Mig   (142)  VAIVDEIHMINDEKRGGTLEVLTKLKNLD-----VQIIGLSATIGNPEELAEWLN---AELIIDNWRPVKLKRGIFPQNKIMYLNGA----C
Hel308  Min   (131)  VVVVDEIHVIGDSERGGTLEVLTKLKLED------LQTIGLSATIGNPEELSEWLN---AELLLDNWRPVELRKGIYREGVIEYLDGE---
Hel308  Mma   (138)  LAVIDEIHLIGDNERGGTLEVLITKLNLN------AQVVGLSATIGNPEELSNWLN---AKLIVDGWRPVELKKGIYFENELEFLKNP----A
Hel308  Mmah  (140)  AVIVDEVHLLDSANRGPTLEVTLAKLRLNPG---WLE--AKLVLSEWRPTYLHEGIFYGDAINFDE-DQTFIER
Hel308  Mmar  (141)  CVVTDEVHLIDSPDRGPTLEVTLAKLRRLNPD---LQTVALSATIGNAEALATWLD---AGLVDSDWRPIDLQKGVHYGQALHLEDGSQQRLSV
Hel308  Mmaz  (140)  VVVADEVHLIDSPDRGPTLEVTLAKLRRMNPS---CQVLALSATVGNADELAAWLD---AELVLSEWRPTDLMEGVFYNGLIFYCKD-KEKPVGQ
Hel308  Mok   (139)  VVVIDEIHLIGDESRGGTLEVLLTKLTKKT-----IQIIGLSATIGNPEELAKWLN---AELIVDEWRPVKLKKGIGYGNKIMFIDDNGNTINE
Hel308  Mth   (143)  VLVVDEIHLLDSANRGPTLEMTKLMHLNPE-----MOVIGLSATIANGREIADWIK---GEIVSSDMRPVRLREGVLLEDRLVFPD-GEIQLEN
```

```
SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54 and 55 (Table 4) are
aligned below The number below the * indicates the SEQ ID NO. The "-" are shown for alignment purposes only and do not form part of the sequences.

Hel308    Mzh   (140)  TVVADEVHLLNSVNRGPTLEITLAKLIHLNPG---SQIIALSATIGNPEDIAGWLG---ARIVVSEWRPTDLYEGILLDGLLIHIGN-IKKDIQD
Hel308    Nma   (141)  CVVSDEVHLIDDRNRGPTLEVTLAKLRRLNPQ---LQVVALSATVGNADELADWLD---AELVDTDWRPIDLQMGVHYGNALNFDDGETREVPV
Hel308    Nth   (152)  FIIIDELHAFLDNERGVHLRSLLSRLENYIKEK---PRYFALSATLNNFKLIKEWIN---YNDIKNVEIIDSNEDDKDLLLSLMHFDKGKDYKKP
Hel308    Pfu   (141)  ILVADEIHLIGSRDRGATLEVILAHMLGKA-----QIIGLSATIGNPEELAEWLN---AELIVSDWRPVKLRRGVFYQGFVTWEDGSIDRFSS
Hel308    Sso   (141)  YFVLDELHYLNDPERGPVVESVTIRAKKRN-----LLALSATISNYKQIAKWLG---AEPVATNWRPVPLIEGVIYPERKKEYNVIFKDNT
Hel308    Tba   (162)  LIVADEIHLLGSYDRGATLEMILSHMLGKA-----QIILALSATVGNAEELAEWLN---AKLVVSDWRPVKLRKGVFAHGQLIWEDGKVDKFPP
Hel308    Tga   (141)  LVIADEVHLIGSYDRGATLEMILTHMLGRA-----QIILALSATVGNAEELAEWLD---ADLVVSDWRPVQLRRGVFHLGTLIWEDGKVESYPE
Hel308    Tsi   (164)  LVIADEIHLLGSYDRGATLEMILAHLDDKA-----QIIGLSATVGNAEEVAEWLN---ADLVMSEWRPVALRKGVFYHGELFWEDGSIERFPT
Hel308    Mja   (139)  VVVVDEIHLINDETRGGTLEILLTKLKEFN-----QIIGLSATIGNPDELAEWLN---AELIVDDWRPVELKKGIYKNEAIEFINGEIREIKA
          (191)  VVVVDEIHLI D RGPTLEVLLAKLR LNP      LQIIALSATIGNAEELAEWL     AELVVSDWRPVDLR GVFY   L F D     I
Consensus                                        *

380
Hel308    Mbu   (227)  LEK-----DDAVNILVLDTIKAEGQ-----CLVFESSRRNCAGFAKTASS---KVAKILDNDIMIKLAGIAEEVES---TGEETDTAIVLANCIRKGV
Hel308    Afu   (225)  TSRR----VKFEELVEECVAENGG-----VLVFESTRRGAEKTAVKLSA---ITAKYVEN-----EGLEKAILE---ENEGEMSRKLAECVRKGA
Hel308    Csy   (233)  TGGG----PAVDLAAESVAEGGQ------SLIFADTRARSASLAAKASA---VIPEAKGADAAKLAAAAKKIISS--GGETKLAKTLAELVEKGA
Hel308    Dth   (273)  --------AIRVLQKALELGLR-------TIVYTQSRKMTELIAMWASQRAGRLKKYISAYRAGFLPEQRREIEQKLASGELLAVVSTSALELGI
Hel308    Fac   (217)  -EKKHLGRDDEVSLIKESIESGQ-------ALVFRNSRRNAEKYAQSMVN---------------FFDFQNDFEKLEIPPDLFNEAQANMVAHGV
Hel308    Hla   (229)  ERGE----DQTARLIVADALDTEEDGQGGSSLVFVNSRRNAESSARKLTD---VTGPRLTDDERDQLRELADEIRS---GSDTDTASDLADAVEQGS
Hel308    Hpa   (229)  -GNE----KETAALVRDTLEDGGS------SLVFVNSRRNAEAAAKRLAD---VTKTHLTDDERRDLLDIADQIRD---VSDTETSDDLATATEKGA
Hel308    Htu   (229)  EGSE----KQEAALVRDILREGGS------SLVFVNSRRNAEGAAKRLGQ---VSSREITEDDERAELAELADDIRD---DSDTETSADLADCVERGA
Hel308    Hvo   (229)  GRGE----RQTPAIVADALEGDEGDGQSSLVFVNSRRNAESAARRMAD---VTERYVTGDERSDLAELAAEIRD---VSDTETSDDLANAVAKGA
Hel308    Mac   (227)  PTK-----DEAVNILVLDTLREGGQ-----CLVFESSRKNCMGFAKKATS---AVKKTLSAEDKEKLAGIADEILE---NSETDTASVLASCVRAGT
Hel308    Mba   (227)  STK-----YDDLNLCLDTIAEGGQ-----CLVFESSRRNAEAFAKRAAG---AIKSEDA-----ALAACAERLLE---GTPTEMVKTLAACVAKGA
Hel308    Mbo   (224)  VSKN----VIPEAKGADAAKLAAAAKKIISS-----AIKSEDA-----AIKSEDA-----
Hel308    Mev   (227)  IVK-----DTAVNILVLDTIDENGQ-----CLVFCNTKRGAVNEAKKLN---KVGKSLDKGLLAELNNIABEVLE---NSETDTSTNLAVCIRSGT
Hel308    Mfe   (222)  REIKAINNNDIYNLVVDCVKDGGC-----CLVFVSSRRNAEGYAKRAAT---ALKCSHA----ALDSIAEKLEA---AAETDMGRVLATCVKKGA
Hel308    Mfr   (220)  PAK-----TEDINLLLDCVADGGQ-----CLVFVSSRRNAEGYAKRAAG---ALKAGSP----DSKALAQELRR---LRDRDEGNVLADCVERGA
Hel308    Mhu   (225)  KTK-----HDDLNLCLDTIEEGGQ-----CLVFCNSRRNCEGGC------CLVFCNSKNGAVSEAKKLN---LKKYLSNSEKYELQLKEEILSILDPPTETCKTLAECLEKGV
Hel308    Mig   (223)  KELPNFSNNPMLNLVLDCVKEGGC-----CLVFCNSKNGAVSEAKKLN---LKKYLSNSEKYELQLKEEILSILDPPTETCKTLAECLEKGV
Hel308    Min   (211)  --------VKECQDIVKEVVKDNGS-----VIIFCPTKCKAENRALSLD---LSDLLKKSEKRKLEISEELLSFLFDPPTELCKKLASCVRKGI
Hel308    Mma   (219)  KKIKQVSRNNLTDLIVDSVEEKGS------CLIFCNSKRNAVGEAKKHN---LAKYLTRTEQHELNKLSEEILSILDRPVETCKALSCKCIQNGV
Hel308    Mmah  (229)  RHK-----EDSVNLIVIDTVIQGGQ-----CLVFDSSRRNCVGFAKKCAP---AVGELLDRQNRNELREVAKEVLE---NGETKLTETLAYCIKKGV
Hel308    Mmar  (229)  QNNE----KQTAAIVRDTLEDGGS------TLVFRNSRRNAEAAGRLAN---TVRPHLSTEERDQLADIAEEIRD---VSDTETSDDLADAVADGA
Hel308    Mmaz  (227)  PTK-----DEAVNILVLDTIKEGGQ-----CLVFESSRKNCMGFAKKAVS---AVKKTLSNEDRETLAGIADEIIE---NSETDVSSVLATCVRSGT
Hel308    Mok   (226)  VIVDEISKNNMFNLVVDSILKDGS-----CIIFCNSKRGAVGEAKKLN---LKKYLSPDEISELRHLKEEVSVLDNPTKTCKDLAECIEKGV
Hel308    Mth   (230)  RNR-----DPVLNIVLDTVDQGGQ-----MLIFESTRRNAESMAKKVSG---ALQESGE-----TIELAERLS---GEGKTAKKLAMCLRHGA
Hel308    Mzh   (227)  ESR-----ESDVNLIVRDILREGGS------CLVFESSRRNCMGFAKKLS---WVSKILDEHDTIQLKSLSQEIGE---AGETEIADVLSRCVRQGV
Hel308    Nma   (229)  EAGE----KQEAALVRDILQEGGS------SLVFVNSRRNAEAAARRLGQ---VSSRELTAGHEQNDLAALATEIRE---DSDTETSQDLADCVERGA
Hel308    Nth   (241)  --------ID-LYQDLRELTKN-------VHSLIFCNSRAEVEETTLYLNR---LANREVNTELYLAHHSSIDKKER-EYVEKTMANSKSPKSVVTT
Hel308    Pfu   (226)  --------WEELIVYDAIRKKKG-------ALIFVNMRRKAERVALELSK---KVKSLLTKPEIRALNELADSLE---ENPTNEKLAKAIRGGV
Hel308    Sso   (232)  --------VLVFRNSRRNAMESTALKIAN--YMNFVSLDEN-ALSEILKQLDDIEGGSDEKELLKSLISKGV
Hel308    Tba   (247)  TKKVHG--DDAIIAYTLDSLSKNGQ-----ALVFVNTRRSAEKEAGMLGK---KVRRLLTKPEARRLKELAESLE---SNPTNDKLKEVLVNGA
Hel308    Tga   (226)  Q-------WDSLVIDAVKKGKG-------ALVFVNTRRSAEKEALLLAG---LVSSHLTKPEKRALESLASQLE---DNPTSEKLRALQNKG
Hel308    Tsi   (249)  N-------WYSLVVDAVKRGKG-------ALVFVNTRRSAEKEALLLAG---KIQRFLTKPEERKLQLADGLD---TTPTNQKLKEALTKGV
Hel308    Mja   (225)  Q-------WDSLVIDALKKGKQ-------ALVFVNTRRSAEKEALLLAG---KIQRFLTKPEERKLQLADGLD---TTPTNQKLKEALTKGV
Hel308          (286)  VDN-----NDIYNLVVDCVKEGG-----CLVFCNTKRNAVNEAKKLN---LQRFLTEEEKIRLKEIAEEILSLLPPTEMCKTLAECILNGS
                      LVLDTV EGGQ           LVF NSRRNAE AKKLA              V K LT  E   L   LAEEI    ETETS  LA CV KG
Consensus                                                             *
```

SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54 and 55 (Table 4) are aligned below The number below the * indicates the SEQ ID NO. The "-" are shown for alignment purposes only and do not form part of the sequences.

```
                  381                                                                                            475
Hel308 Mbu   (307) AFHHAGLNSNH-------RKLVENGFRQNLIKVISSTPTLAA--------------------------------------------------
Hel308 Afu   (300) AFHHAGLLNGQ-------RRVVEDAFRRGNIKVVATPTLAA--------------------------------------------------
Hel308 Csy   (313) AFHHAGLNQDC-------RSVVEEEFRSGRIRLLASTPTLAA-------------------------------------------------
Hel308 Dth   (353) DIGHLDLCLLVGYPGSVMATMQRGGRVGRSGRDSAIMLIGHEDALDQYLLRNPREFFSLEPESAVINPDNPSIMRRHLVCAAAEKPIALQEMMLD
Hel308 Fac   (290) MFHHAGLSNDQ-------RTMIEKLFKQGYIKLTATPTLAA--------------------------------------------------
Hel308 Hla   (315) AFHHAGLRSED-------RARVEDAFRDRLIKCISATPTLAA-------------------------------------------------
Hel308 Hpa   (309) AFHHAGLASDH-------RSLVEDAFRDKLIKVISATPTLAA-------------------------------------------------
Hel308 Htu   (310) AFHHAGLSSTQ-------RSLVEDAFRDRLLKVISATPTLAA-------------------------------------------------
Hel308 Hvo   (315) AFHHAGLAAEH-------RTLVEDAFRDRLIKCICATPTLAA-------------------------------------------------
Hel308 Mac   (307) AFHHAGLTSPL-------RELVETGFREGYVKLISSTPTLAA-------------------------------------------------
Hel308 Mba   (300) AFHHAGLTTPL-------RELVEDGFRAGRIKLISSTPTLAA-------------------------------------------------
Hel308 Mbo   (307) AFHHAGLSRKE-------RSIVEAFRKNLLKCISSTPTLAA--------------------------------------------------
Hel308 Mev   (307) AFHHAGLNSAQ-------RKIVEDNFRNNKIKVISSTPTLAA-------------------------------------------------
Hel308 Mfe   (307) AFHHAGLTYQH-------RKIVEDAFRNLLIKVICCTPTLSV-------------------------------------------------
Hel308 Mfr   (295) AFHHAGMNRMQ-------RKIVEGGFRDGFIKSISSTPTLAA-------------------------------------------------
Hel308 Mhu   (300) AFHHAGLIRQE-------RTIIBEGFRNGYIEVIAATPTLAA-------------------------------------------------
Hel308 Mig   (308) AFHHAGLTYEH-------RKIVEEGFRNKLIKVICCTPTLSA-------------------------------------------------
Hel308 Min   (289) AFHHSGLTYEH-------RKIIEKAFRERILKVICSTTTLAF-------------------------------------------------
Hel308 Mma   (304) AFHHAGLTYKH-------RKIVEDGFRNRLIKVICCTPTLSA-------------------------------------------------
Hel308 Mmah  (307) AFHHAGLNSAH-------RRIVEDAFRNNLIKMICSTPTLAA-------------------------------------------------
Hel308 Mmar  (310) AFHHAGLSRGH-------RELVENGFREGRIKLISSTPTLAA-------------------------------------------------
Hel308 Mmaz  (307) AFHHAGLTTPL-------RELVEGFRQNVVKVIACTPTLAA--------------------------------------------------
Hel308 Mok   (311) AFHHAGLLPEQ-------RRLIELGFRQNVVKVIACTPTLAA-------------------------------------------------
Hel308 Mth   (302) AFHHAGLGRTE-------RRMVEEGFRRKNLIKMISSTPTLAA------------------------------------------------
Hel308 Mzh   (307) AFHHAGLNSEH-------RSLVEDAFRDRLLKVISAPTLAA--------------------------------------------------
Hel308 Nma   (310) AFHHAGLSSTQ-------IDYVVQIDDTHTVSSLKQRLGRSG-------------------------------------------------
Hel308 Nth   (318) SSLELGIDIGA-------RVLVEENFRKGIIKAVVATPTLSA-------------------------------------------------
Hel308 Pfu   (298) AFHHAGLGRDE-------RDLIBEGFRQRKIKVIVATPTLAA-------------------------------------------------
Hel308 Sso   (316) AYHHAGLSKAL-------RTLIEDAFREGLIKVLTAPTLAM--------------------------------------------------
Hel308 Tba   (320) AFHHAGLGRAE-------RSTIEDAFREGLIKVITAIPTLSA-------------------------------------------------
Hel308 Tga   (299) AFHHAGLSRVE-------RSIIEDAFREGLIKVITATPTLSA-------------------------------------------------
Hel308 Tsi   (322) AFHHAGLGRTE-------RSIIEDAFRRFDP-SAGG--------------------------------------------------------
Hel308 Mja   (305) AFHHAGLTYQH-------RKIVEDAFRKRLIKVICCTPTLSA-------------------------------------------------
Consensus    (381) AFHHAGL            R LVEDAFR LIKVI ATPTLAA 476                                                                                570
Hel308 Mbu   (342) -------------------------------GLNLPARRVIIRSYRRFDS-NFG-------MQPIPVLE
Hel308 Afu   (335) -------------------------------GVNLPARRVIVRSLYRFDG-YSK-------RIKVSE
Hel308 Csy   (348) -------------------------------GVNLPARRVVISSVMRYNS-SSGM------SEPISILE
Hel308 Dth   (448) NEAGKCIKSLEKDGELLASRDRSFYYTRARYPHKDVDLRGIGQTYNIPEHSTGEYLGEVDGVRAFKETHPGAVYLHMGETYVVQDLLETFAVYA
Hel308 Fac   (325) -------------------------------GVNLPARTVIIRDITRFSD--GY-------SKPISGIE
Hel308 Hla   (350) -------------------------------GVNTPARRVIVRDWRRYDG-EFGG------MKPLDVLE
Hel308 Hpa   (344) -------------------------------GVNTPSRRVIVRDWRRYDG-DIGG------MQPLDVLE
Hel308 Htu   (345) -------------------------------GVNTPARRVIVRDWRRFDP-SAGG------MAPLDVLE
Hel308 Hvo   (350) -------------------------------GVNTPSRRVVVRDMWQRYDG-DYGG------MKPLDVLE
Hel308 Mac   (342) -------------------------------GLNLPARRVIIRSYRRYSS-DSG-------MQPIPVLE
Hel308 Mba   (335) -------------------------------GLNLPARRVIIRNYRRYSS-EDG-------MQPIPVLE
Hel308 Mbo   (335) -------------------------------GLNLPARRVIIRDYLRFSA-GEG-------MQPIPVSE
```

```
SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54 and 55 (Table 4) are
aligned below The number below the * indicates the SEQ ID NO. The "-" are shown for alignment purposes only and do not form part of the sequences.

Hel308   Mev    (342)  ----------------------------GLNLPARRVIVRNYKRYDP-NFG----MQPIPVLD
Hel308   Mfe    (342)  ----------------------------GLNLPCRRAIVKDLTRYT-NRG----MRYIPIME
Hel308   Mfr    (330)  ----------------------------GLNLPARRVIIRDYLRYSG-GEG----MRPIPVRE
Hel308   Mhu    (335)  ----------------------------GLNLPARRVIIRDYNRFAS-GLG----MVPIPVGE
Hel308   Mig    (343)  ----------------------------GININPCRRAIVRDLMRFS-NGR----MKPIPIME
Hel308   Min    (324)  ----------------------------GLNLPCRRVIISELKRYT-RRG----LTYIPIME
Hel308   Mma    (339)  ----------------------------GLNLPCRRAIVRDIKRYS-QNG----LVDIPRME
Hel308   Mmah   (342)  ----------------------------GLNLPARRVIIRSYKRYDP-NAG----MQPIPVLD
Hel308   Mmar   (345)  ----------------------------GVNTPSRRVVVRDRMRYDG-SAGG---MAPLSVLE
Hel308   Mmaz   (342)  ----------------------------GLNLPARRVIIRSYRRYSS-DSG----MQPIPVLE
Hel308   Mok    (346)  ----------------------------GINMPCRRAIIRDLKRFS-SRG----YIPIPKME
Hel308   Mth    (337)  ----------------------------GLNLPARRVLIRSYKRYEA-GLG----TRPIPVME
Hel308   Mzh    (342)  ----------------------------GLNLPARRVIIRSYKRYDP-NFG----MKPIPVLE
Hel308   Nma    (345)  ----------------------------GVNTPARRVIVRDWRRFDP-SAGG---MAPLDVLE
Hel308   Nth    (353)  ----------------------------RKLGTNQVLQVYSTNDSLVQSLA----VIDLLLEK
Hel308   Pfu    (333)  ----------------------------GINTPAFRVIIGDIYRDIWRYS--DFG----MERIPIIE
Hel308   Sso    (351)  ----------------------------GVNLPARTVIIGDIYRFNKKIAGY--YDEIPIME
Hel308   Tba    (355)  ----------------------------GVNLPSFRVIIRDTKRYS-TFG----WSDIPVLE
Hel308   Tga    (334)  ----------------------------GVNLPSFRVIIRDTKRYA-GFG----WTDIPVLE
Hel308   Tsi    (357)  ----------------------------GLNLPAYRVIIRDTKRYS-NFG----WVDIPVLE
Hel308   Mja    (340)  ----------------------------GLNLPCRRAIVKDLTRFIN----KG----MRYIPIME
                       (476)                                                          665
Consensus              ----------------------------GLNLPARRVIIRDYKRY       G         M PIPVLE Hel308   Mbu    (372)  YKQMAGRAGRPHLDPYGESVLLAKTYDEF--AQLMENYVEADAEDIWSKLGTENALRTHVLSTIVNGFASTRQELFDFFGATFFAYQQ-DKNMLE
Hel308   Afu    (363)  YKQMAGRAGRPGMDERGEAIIIVGKRDR---EIAVKRYIFGEPERITSKLGVETHLRFPHSLSIICDGYAKTLEELEDFFADTFFFKQN--EISLS
Hel308   Csy    (379)  YKQLCGRAGRPQYDKSGEAIVVGGVNAD---EIFDRYIGGEPEPIRSAMVDDRALRIHVLSIVTTSPGIKEDDVTEFFLGTLGGQQS-GESTVK
Hel308   Dth    (543)  AKSEANYTRPITEKYTEIVEVQATRATAAGELCLGELKVTEHVSAYEKRLVRGQARIGLIPLDLPPLVFETQGMWFTLDSGIATDLKGIQDPYGKTLLAAQN-DIDGYE
Hel308   Fac    (354)  IQQMIGRAGRPKYDKKGYIYIYAASPG---MIRVAEGYLTGELEPYIYSRMDSNSLIRPNVLALISSGIATDLKGIQDPYGKTLLAAQN-DIDGYE
Hel308   Hla    (381)  VHQMCGRAGRPGLDPYGEAVLLANDADTK--EELFERYLWADPEPVRSKLAAEPALRTHVLATVASGFASTRDGLLSFLDNTLYATQTDDEGRLA
Hel308   Hpa    (375)  VHQMFGRAGRPGLDPHGEAVLLAKSHDEL--QELFDQYVWADPEPVHSKLAAEPALRTHIIATVASGFAGTEEELLDDFLERTLYATQFDETGRLE
Hel308   Htu    (376)  VHQMMGRAGRPGLDPYGEAVLLAKSHDES--EELFDRYIWADPEPVRSKLAAEPALRTHVLATIASGFARTRGGLLLEFLEATLYASQSSEAGRLE
Hel308   Hvo    (381)  VHQMMGRAGRPGLDPYGEAVLLAKDADAR--DELFERYIWADAEDVRSKLAAEPALRTHLLATVASGFAHTREGLLEFLDQTLYATQTDDPPERLG
Hel308   Mac    (372)  YKQMAGRAGRPRLDPYGEAVLLAKSYEEL--LFLFEKYIEAGAEDIWSKLGTENALRTHVLSTISNGFARTKEELMDFLEATFFAYQY-SNFGLS
Hel308   Mba    (372)  YKQMAGRAGRPRLDPYGESVLLAKSYKEF--VPLFENYIEANAEDIWSKLGTENALRTHVLSIVASGFAGTRGELTEFMNRSFYVHEHKQGRLIH
Hel308   Mbo    (365)  YRQMAGRAGRPSLDPYGEAVLLAKSYEEF--PELFEVYIEAEAEDVHSRIAEPTALYTHVLSIVASGPAGTRGELTEFMNRSFYVHEHKQGRLIH
Hel308   Mev    (372)  YKQMAGRAGRPLDPYGEAVLLAKSYKEF---TDLLDRYIDAEPDILLSNQAVLRTQLGMIATREIENEFDLISFIKNTFYAHQYGNLGGVL
Hel308   Mfe    (371)  YKQMAGRAGRPRLDPYGEGIIVAKNDR---DYLRSYQVLTQKPEPIYSKLSNQAVLRTQLLGTAHILSLIATGYARSYDELMAFLEKTLYAYOHTGKKALT
Hel308   Mfr    (360)  YKQMAGRAGRPHLDPYGEAILIAKTEYAV--NDLHEBYVEAPDEDVTSRCGEKGVLTAHILSLIATGYARSYDELMAFLEKTLYAYOHTGKKALT
Hel308   Mhu    (365)  VHQMAGRAGRPHLDPYGEAVLLAKDAPSV--BRLFETFIDAEAERVDSQCVDDASLCAHILSLIATGFAHDQEALSSFMERTFYFFQHPKTRSLP
Hel308   Mig    (372)  IHQCIGRAGRPGLDPYGEGIIFVKNER---DLERAEQYLEGKPEYIYSKLSNQAVLRTQLLGMIATREIENEFDLISFIKNTFYAHQYGNLGGVL
Hel308   Min    (353)  VQQCIGRAGRPGLDEYGEGILVAKDER---DYLRALQCLTQKPEPIYSKLSNDSVLRTQILGLIATRVLDEYDLEEFIKNTFYAYOKNLDEIK
Hel308   Mma    (368)  IQQCIGRAGRPGLDPYGEGIIYIKNER---DAEKAYEILTGSVENIYSKLANQKVLRIHILGLISTGEIKDQSQNLVNFMKNTFYAHQFGNIGAVL
Hel308   Mmah   (372)  YKQMAGRAGRPRLDPYGEAVLLAKSYEEF--TDVLERYISASAEDIWSKLGTENALRTHILSTIASGFANCHREILTFLGSTFFAHQQ-QSWNFE
Hel308   Mmar   (376)  VHQMAGRAGRPGLDPYGEAVLLASSHDEV--DELFERYVWADPEPVRSKLAAEPALRTHILATVASGFARSRKGLLLEFLEQTLYASQTDDSQLE
Hel308   Mmaz   (372)  YKQMAGRAGRPRLDPYGEAVLLAKSYEEF--VPLFEKYIEAGAED IWSKLGTENALRTHILSTISNGFARTREELMDFLEATFFAFQY-SNFGLS
Hel308   Mok    (375)  YKQMAGRAGRPNLDPYGEGIIYINNTENPELIENAKNYLIGNVEEIYSKLSNQKVLRTHMLGLITTGDIKNKNDLEEFIKNTFYAYOYQNTKKIL
Hel308   Mth    (367)  YRQMAGRAGRPSLDPYGEGIIVARSRESEL--QKLMDHYVMGEPEDIWSKLASERALRTHVLATIASRFADSVDSLSRLMASTFYARQQ-DPSYLG
Hel308   Mzh    (372)  YKQMAGRAGRPHLDPYGEAVLLAKSYDEF--MDIMENYVNADPEDIWSKLGTENALRTHVLSTIVNGFAYTYRGLMDFVKMTFFAYQK-EASDLH
```

-continued

```
SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54 and 55 (Table 4) are
aligned below The number below the * indicates the SEQ ID NO. The "-" are shown for alignment purposes only and do not form part of the sequences.

Hel308 Nma   (376) VHQMMGRAGRPGLDPYGEAVLLAKSHDES--QELFDRYVWADPEPVRSKLAAEPALRTHVLATIASGFARTREGLLEFLEATLYASQSSEGGRLE
Hel308 Nth   (385) WIEPATEYPLPLDILFHQIISICHEANGVRLDPLIDNIKANAAFYKLKEEDINHVINYMIENDFLQLIRNSAELIVGLEGERLLRGKEFYAVFMT
Hel308 Pfu   (362) VHQMIGRAGRPKYDEVGEGIIVSTSDD---PREVMNHYIFGKPEKLFSQLSNESNLRSQVLALIATFGYSTVEEILKFISNTFYAYQRKDTYSLE
Hel308 Sso   (383) YKQMSGRAGRPGPDQIGESIVVVRDKEDV--DRVFKKYVLSDVEPIRSKLGSERAFYTFLLGILSAEGNLSEKQLENFAYESLLAKQL-----VD
Hel308 Dth   (384) IQQMIGRAGRPKYDKEGEAIIVAKTEK----PEELMEKYIFGKPEKLFSMISNDAAFRSQVLALITNFGVESFRELIGFLEKTFYYHQRKDLEILE
Hel308 Tba   (363) IQQMMGRAGRPRYDKYGEAIIVARTDE---PGKLMERYIRGKPEKLFSMLANEQAFRSQVLALITNFGIRSFPELVRFLERTFYAHQRKDLSSLE
Hel308 Tga   (386) IQQMMGRAGRPKYDIEQGAIIIAKTEK---PEDLMKRYVLGKPEKLFSMISNEASFRSQVLALITNFGVGNPKELVNFLERIFYYHQRKNLEALE
Hel308 Tsi   (369) IQQCIGRAGRPGLDPYGEGIIVAKNDRDY--LRAYQALTQKPEPIYSKLSNQAVLRTQLLGLIATGEIRDEYDLEWFIRNTFYAHQYGNLREVA
Hel308 Mja   (571) I QM GRAGRP LDPYGRAVLIAKS D    EL E YI ADPE IWSKLA E ALRTHVLALIASGFA T ELLDFL TFYAYQ        L
Consensus 666                                                                                     760
Hel308 Mbu   (464) EVINDCLEFLIDKAMVSET-E----------------------------------DIEDASKLFLRGTRLGSLVSMLYIDPLSGSKIVDGF
Hel308 Afu   (453) YELERVVRQLENWGMVVEAAH----------------------------------------LAPTKLGSLVSRLYIDPLTGFIFHDVL
Hel308 Csy   (469) FSVAVALRFLQEEGMLGRR------------------------------------GGRLAATKMGRLVSRLYMDPMTAVTLRDAV
Hel308 Dth   (638) GGLHALEHGLIGCMPLIILTDRNDLGGIASPVHEQLHKG----------------AVFIYDGTPGGIGLCRQAFELGDRLVARAMGILSSCTCENGC
Hel308 Fac   (474) LAFESALYFLKDNDFITEEN-----------------------------------DIYSAKTKFGRLTSDLYIDPVVSSLIIKKCL
Hel308 Hla   (445) AVTDTVLDYLAVNDFIERDRD----------------------------------GGSESLTATGIGHTVSRLYLDPMSAAEMIDGL
Hel308 Hpa   (468) TVTQHVLDYLDRNGFLERDD----------------------------------RLRATGLGHRVSQLYLDPMSAAEIIDGL
Hel308 Htu   (469) SVTDDVLDYLERNDFIERSR---DDEAEDSGEDDGPFTSAADLAEQ---------REETLEATSLGHTVSRLYLDPMSAAEIVHGL
Hel308 Hvo   (474) QVTDRVLDYLEVNGFVEPEG----------------------------QAAK---ETIQATPVGHTVSRLYLDPMSAAEIIDGL
Hel308 Mac   (474) VVVDECLNFLRQEGMLEQDS-----------------------------------DALISTMFGKLVSRLYIDPLSAALIAKGL
Hel308 Mba   (464) TVVNECLNFLREGMLEKD------------------------------------DALIPTSFGKLVSRLYIDPLSAARIAKGL
Hel308 Mbo   (464) RAIDEALQFLITAEMVEV-------------------------------------GEHIGATELGTLVSRMYIDPRSAFAIVTTL
Hel308 Mev   (464) DVVDDCIEFLQDNEMIKD-------------------------DG--ER------LYATRLGQVISTLYIDPLSGAIIDKL
Hel308 Mfe   (463) KNINEVIRFLEEK---------------------------------EFMIDFIPTELGKRVAELYIDPHSAEIITTAL
Hel308 Mfr   (453) RTLDDALGFLTRAEMVTDL----------------------------SGMLHATEYGDLTSRLYIDPHSAEIITTAL
Hel308 Mhu   (458) RLVADAIRFLTTAGMVEER---------------------------ENTLSATRLGSLVSRLYLNPCTARLIIDSL
Hel308 Mig   (464) RNIKEVINFLEEN---------------------------------DFIADYFPTKLGKRVSELYIDPLSAKIIDGL
Hel308 Min   (445) KKIKEIIRFLEDCN----------------------------------FIKNFEVTPELGKKVSNLYLDPLSAKIMIDNI
Hel308 Mma   (460) LNVSEVVEFLEKNKFLETTIHKKTENKVRELSFDS--------S-NN--LVLDSKETSFDLTNPNSNIEFRSTKLGKRISELYIDPMSSEIIIEEL
Hel308 Mmah  (464) ELLEDCLIFLKNEGMLEQD-N--------------------------ET-----IRATELGKMISSLYIDPLSASKIIRGL
Hel308 Mmar  (464) RVVDDVLTYLQRNDFLEIEAG---------------------------------ELDATSLGHTVSRLYLDPMSAAEIVDGL
Hel308 Mmaz  (464) AVVDECLDFLRREGMLEKDP----------------------------------DALVSTVFGKLVSRLYIDPLSAALIAKGL
Hel308 Mok   (470) ENIYEITNFLEKNGFIELNYRDENKDKSNNSHNNKNISNTNNSIKMLVLDNNNSLTIKSRHEEDVYYNITPLGKKVSELYIDPLSAEYIIDGL
Hel308 Mth   (459) ETIASVLEFLVRSDMIKD--------------------------------------LTPTPLGALVSRLYIDPLSAMVMQEI
Hel308 Mzh   (464) DVIEECVRFLIDNEMIISD-S---------------------------NDILPES-AFRSTATGKLISMLYIDPLSGSLIMDGI
Hel308 Nma   (469) RVTDDVLSYLERNDFIERSGGPEDTLNSEADAASAFTSAADLADS----DGGDSGGTGQEEDLEATSLGHTVSRLYLDPMSAAEIVHGL
Hel308 Nth   (480) QEEFEVREGIRKIGSIDKS-----------------------------------LMVSEGDNIILAGQLWTIKNIDIERDIIYVAKA
Hel308 Pfu   (454) EKIRNILYFLLEN-----------------------------------EFIEISLEDKIRPLSLGIRTAKLYIDPYTAKMFKDKM
Hel308 Sso   (471) VYPDRAIRWLLEHSFIKEE------------------------------------GNTFALTNFGKRVADLYINPFTADIIRKGL
Hel308 Tba   (476) GKAKSIVFLLEN------------------------------------EFIDLNDSFIALPFGIRTSQLYIDPLTAKKFDAL
Hel308 Tga   (455) YKAKEVVVFLIEN------------------------------------EFIDLEDRFIPLPFGKRTSQLYIDPLTAKKFDAL
Hel308 Tsi   (478) GKAKSIVYFLEN-----------------------------------EFIDLNDQFMPLPLGIRTSQLYIDPVTAKKFKDAF
Hel308 Mja   (461) KNINEVIRFLEENEFI-------------------------------------IDFMPTELGKRVSELYIDPLSAKFIIDGL
Consensus    (666)   I EVL FL   N I                                                              L AT LG  VS LYIDPLSA  IIDGL
```

```
SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54 and 55 (Table 4) are
aligned below The number below the * indicates the SEQ ID NO. The "-" are shown for alignment purposes only and do not form part of the sequences.

761                                                                                     855
Hel308 Mbu    (520) KDIGKSTGGNMGSLEDDKG-----------------------------------------DDITVTDMTLLHLVCSTPDMRQLY
Hel308 Afu    (501) SRMELS-------------------------------------------------------DIGALHLICRTPDMERLT
Hel308 Csy    (518) GEASPGR------------------------------------------------------MHTLGFLHLVSECSEFMPRF
Hel308 Dth    (719) PGCIHSPKCCGSGNR----------------------------------------------PLDKEAAMHMLAVLAGERCGE
Hel308 Fac    (494) DLEFS--------------------------------------------------------EELYLYYISKTPDMLTFN
Hel308 Hla    (527) RSVARDAADTGASAEADNG-EFVRTGDADDASGGDEPGFGTYYTRAGDDESGER-------ETENEETDEEETEASEVTPLGLYHLISRTPDMELY
Hel308 Hpa    (516) RDADG--------------------------------------------------------KPTALGLYHLVSRTPDMYQLY
Hel308 Htu    (547) ERADER-------------------------------------------------------PTALGLYQLVSRTPDMYELY
Hel308 Hvo    (523) EWAADHRTEKLRALAGETPEKPTRDRSESDESGGFQRASEMVADDGDGGGEDGVGANGDGDSDDADGVETDRTYPTPLGLYHLVCRTPDMYQLY
Hel308 Mac    (513) REAGT--------------------------------------------------------LTELTLLHLVCSTPDMRLMY
Hel308 Mba    (512) KGAKS--------------------------------------------------------LSELTLLHLVCSTPDMRLLY
Hel308 Mbo    (507) REQEK--------------------------------------------------------YADLGLIQLICTTPDMPTLY
Hel308 Mev    (513) KKADK--------------------------------------------------------VTDMTMLHIICSTPDMRQLY
Hel308 Mfe    (508) NEMENED------------------------------------------------------DIYYLYLISKTLEMMPNL
Hel308 Mfr    (502) REEGE--------------------------------------------------------LTDLALLQLLCMTPDMFTLY
Hel308 Mhu    (507) KSCKT--------------------------------------------------------PTLIGLLHVICVSPDMQRLY
Hel308 Mig    (509) KEMGNVDNE----------------------------------------------------ELYYLYLISKTLEMMPLL
Hel308 Min    (490) EVKDDLH------------------------------------------------------LLYILCKCIEMKPLL
Hel308 Mma    (545) HELKKKCDQLDR-------------------------------------------------SKIDQYLPYLISKTNEMRPLL
Hel308 Mmah   (513) EKTTH--------------------------------------------------------VTDMTLLQLICSTPDMRLLY
Hel308 Mmar   (518) RDWERGASDSTSASGSPAD------AQAEP-PANSGFTTASELAEDADESDADRD------PDDISALGLYHLVSRTPDMYQLY
Hel308 Mmaz   (513) REAGT--------------------------------------------------------LTELTLLHLICSTPDMRIMY
Hel308 Mok    (565) KNLHKKTLSNPKNM-----------------------------------------------ECYILHILYIISKTTEMQPVL
Hel308 Mth    (505) RGIRR--------------------------------------------------------PTVLTLLHVITMTPDMELLF
Hel308 Mzh    (519) RKADY--------------------------------------------------------FEDITMMHLICSTPDMKNLY
Hel308 Nma    (555) EDADER-------------------------------------------------------PTALGLYQLVSRTPDMYELY
Hel308 Nth    (532) VDGKPPK------------------------------------------------------YSGGGFILNPKIPERMHKIL
Hel308 Pfu    (504) EEVVKDPN-----------------------------------------------------PIGIFHLISLTPDITPFN
Hel308 Sso    (520) EGHKAS-------------------------------------------------------CELAYLHLLAFTPDGPLVS
Hel308 Tba    (526) PQIEENPN-----------------------------------------------------PLGIFQLLASTPDMGTLS
Hel308 Tga    (505) PAIERNPN-----------------------------------------------------PFGIFQLIASTPDNATLT
Hel308 Tsi    (528) EKLEKNPN-----------------------------------------------------PLGIFQLLASTPDMSSLR
Hel308 Mja    (506) EEMENEE------------------------------------------------------EIYYLYLISKTLEMMPNL
Consensus     (761)                                                              LGLLHLIS TPDM  LY 856                                                                                     950
Hel308 Mbu    (563) LRNTDYITVNEYIVAHSDEFH-------EIPDKLKETDYEWFMGEVKTAMLLEEW------VTEVSAEDITRHFNVGEGDIHALADTSEW
Hel308 Afu    (525) VRKTDSWVEEEAFRLRKELSY-------YPSDFS-VEYDWFLSEVKTALCCLKDW------IEEKDEDEICAKYGIAPGDLRRIVETAEW
Hel308 Csy    (545) ALRQKDHEVAEMMIEAGRGELLR----P--VISYECRGRLLALHRW---------------IGESPEAKLAEDLKFBSGDVHRMVESSGW
Hel308 Dth    (754) AKRKDVSCRIETDEGSMEIDSG-YTKSDQAELPYAVLDIETRYSAQEVGGWGNCHRMGVSFAVVFDSRNQEFVTFDQEQAADLGSFLEDFSLVVG
Hel308 Fac    (517) YRASDYEYLEEFLDRHNISDFS-------EESMGAAKTAIIINEW----------------INEVPINTIAETFGIGPGDIQAKASSADW
Hel308 Hla    (615) LKSGDRETYTELCYERETEFLG------DVPSEYEDVRFEDWLASLKTARLLEDW------VNEVDEDRITERYGVGPGDIRGKVDTAEW
Hel308 Hpa    (542) LRSGDRERYTEIAYEREPEFLG------HMPSEFEDNAFEDWLSALKTARLLEDW-------ASELDEDRITERYAIGPGDIRGKVETAQW
Hel308 Htu    (573) LRSGEDKFGELFYERETELLG-------DAPSEYEDREFEDWLAALKTGKLLEDW-------ADETDEETITDRYKIGPGDLRGKVDTAEW
Hel308 Hvo    (618) LKSGDRETYTELCYEREPEFLG------RVPSEYEDVAFEDWLSALKTAKLLEDW-------VGEVDEDRITERYGVGPGDIRGKVETSEW
Hel308 Mac    (538) MRSQDYQDINDFVMAHAEEFS-------KVPSPFNIVEYEWFLSEVKTSLLLLMDW------IHEKPENEICLKFGTGEGDIHTTADIAEW
Hel308 Mba    (537) MRSHDYQDINDYVMAHASEFV-------KVPSPFDTTEYEWFLGEVKTSLLLLDW-------IHEKSENEICLKFGTGEGDIHSIADIAEW
Hel308 Mbo    (532) AKNADLPALSRMIEVRGADIW-------LPP-PLDDDAAETYRAVKTAMLLSDW--------TDELSEEKICERYGVGPGDVFGMVENINW
```

-continued

```
SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54 and 55 (Table 4) are
aligned below The number below the * indicates the SEQ ID NO. The "-" are shown for alignment purposes only and do not form part of the sequences.

Hel308 Mev       (538) LRSKEYEKINEYVMTHSDEFV---EVPNPFKSIEYEWFLGEVKTALLINEW------------------------IDEKTLDDITAEFGVGEGDINALSDISEW
Hel308 Mfe       (533) RVYKSEE--LNLIDEMENLG-----IKSFE----IEDLEAFKTAKMLYDW------------------------ISEVPDEILKKYKIEPGILRYKVENAVW
Hel308 Mfr       (527) VKKNDLGTLEKFPFEHEEEFR----T---EFSYDEMEDFFRSLKTAMLLSDW------------------------TDEIGDDTICTRFGVGPGDIFNAVQGISW
Hel308 Mhu       (532) LKAADTQLLRTFLFKHKDDLI---LPL-PFEQEEEELWLSGLKTALVLTDW------------------------ADEFSEGMIEERYGIGAGDLYNIVDSGKW
Hel308 Mig       (536) RVNSFEE--LDLILEMEEAG-----IYDRT---YDDLAAFKNAKMLYDW------------------------INEVPEDEILKKYKIEPGILRYKVEQAKW
Hel308 Min       (512) RVVRKEE--EELAEEELLNYE-----F-IS----YENLEEFKTAKMLYDW------------------------INEVPEDEILKTYKVEPGILRYKVEVAKW
Hel308 Mma       (578) RIRPNEE--LDLILEMDKMG-----LKDYS---IENIEAFKNSKMFCDW------------------------VSEIPBEIILEKYGVEPGILRYKVEQAKW
Hel308 Mmah      (589) LRNRDYEIINDYVMNHTEEFI---EVPSPFKQIEYEWFLSEVKTALLLLEW------------------------INEKSLEKIVENYQVGEGDIYASSDIAEW
Hel308 Mmar      (538) LRSGDREYEMELFEREELLG---PTPSEFEEGRFEDWLSALKTARLLEDW------------------------ATEVDEATITDRYGVGPGDIRGKVETAQM
Hel308 Mmaz      (538) MRSQDYQEVNDYVMAHAGEFS---KVPNPFNIAEYEWFLGEVKTSLLLMDW------------------------IHEKPENEICLKFGIGEGDIHATADIAEW
Hel308 Mok       (600) RVRRKEE--NDLINDMIKLDIDVDDVIYGIS---SENLEYFKNAKLFYDW------------------------INEIPEEELLGYNIEPGILRYNVEQAKW
Hel308 Mth       (530) VQQS-DNWLEDFISEHSSELG----NEKN-----FDWLLREVKTASMLMDW------------------------INEVHEDRIEDRYSISPGDLVRIAETAEW
Hel308 Mzh       (544) MRSSDYENVNMYVLQNKDKFI---SMPSPFKMIEYEWFLGEVKTALLLLDW------------------------INEVPADDICKKYGIGEGDIRMFSETAEW
Hel308 Nma       (581) LRSGEDEKFGELYYERERELLG---DAPSEFEEERFEDWLAALKTGKLLEDW------------------------ATEDDEEQITERYKIGPGDLRGKVDTAEW
Hel308 Nth       (559) CERKNFEFIDNMAQNHLEEQR-----------KPFELYNIK------------------------PNERVIWNNGDEILFTYTGTKIFQTLAW
Hel308 Pfu       (530) YSKREFERLEEEYYEFKDRLYFDDPYISGYDPYLERKFFRAFKTALVLLAW-----------------------INEVPEGEIVEKYSVEPGDIYRIVETAEW
Hel308 Sso       (545) VGRNEENEILELLEDLDCELL----IEEPYEDEYSLYINALKVALIKNDW------------------------MDEVDEDTILSKYNIGSGDLRNMVETMDW
Hel308 Tba       (552) IKRKEQESYLDYAYEMEDYLYRSIPYWEDYE---FQKFLSEVKTAKLLLDW------------------------INEVSEAKLIEAYGIDTGDLYRIIELADW
Hel308 Tga       (531) ARRREMEDYLDLAYELEDKLYASIPYYEDSR---FQGFLGQVKTAKVLLDW------------------------INEVPEARIYETYSIDPGDLYRLLELADW
Hel308 Tsi       (554) VKRKEQDLLDYAYEMEEYLYQNIPYWEDYK---FEKFLGETKTAKLLLDW------------------------INEVNDVKILETYEIDTGDLYRILELVDW
Hel308 Mja       (856) RVYNSEE--LNLIDEMDSLGIK-------SFEIEDLEAFKTAKMLYDW------------------------INEVPEDEILKRYKIEPGILRYKVENAVW Consensus              LR  D E L E I E   E         F     F E FL  VKTA LL DW                         I EV ED I ERYGIGPGDL    VE AEW
                                                                                                                         1045

Hel308 Mbu       (640) LMHAAAKLAELLGVEYSS-------HAYSLEKRIRYGSGLDIMELVGIRGVRGVRARKLLYNAGFVS---------VAKLKGADISVLSKLVGP-
Hel308 Afu       (600) LSNAMNRIAEEVG-N--T-------SVSGLTERIKHGVKEELLELVELRIRHIGRVRARKLYNAGIRN--------AEDIVRHREKVASLIGRG-
Hel308 Csy       (614) LLRCIWEISKHQERPDLLG------ELDVLRSRVAYGIKAELVPLVSIKGIGRVRSRRLFRGGIKG---------PGDLAAVPVERLSRVEGIG
Hel308 Dth       (848) FNLLKPDYRVIQGLSDYDFSSLPILDMVREIEARLGHRLSLDHLARTLGINKSANGLMALKWWKEGELDKIVEYCRQDVSVIRDLYLFGRDKGY
Hel308 Fac       (584) ISYSLYRIGSMFDKENEN-------NLLHLNRIKEGVKEIRRIIEIPQVGRVRGRRLYNNGFKS---------IDDIANARVEDISRIFGFS
Hel308 Hla       (693) LLRAAETLARDVEGVDGDVVV----AVREARKRIEYGVREELLDLAGVRNVGRVRNVGRKRARRLYEAGIES---------RADLREADKAVVLGALRGR
Hel308 Hpa       (620) LLNAAERILAAELIQRDDAEGIPSATTTAVREARKRVEYGVREBELLDLAGVRNVGRVRNVGRKRARRLYDAGIEE---------RADLRSADKGIVLSVLKG-
Hel308 Htu       (651) LLGAAESLAAEIIDSEWTV------AVREAKRVEYGVREELLDLAGVRVGRKRARRLFEAGVET---------RADLREADKPRVLAALRGR
Hel308 Hvo       (696) LLGAAERLATELD---LDSVY----AVREAKRVEYGVREELLDLAGVRVGRKRARRLFEAGVET---------RADLREADKPRVLAALRGR
Hel308 Mac       (615) IMHVATQLARLLDLKGAK-------EAAELEKRIHYGAGPELMDLLDIRGIGRVRARKLYGAGFKS---------TADLAGATPEKVAALVGP-
Hel308 Mba       (614) IMHVTSQLAGLLDLKGAR-------QIADCEICMKNGIRREILPVLRLRGIGRVRARKLYEAGFKS---------SAELAEVDPEKVAALLGP-
Hel308 Mbo       (608) LLHATSQLARMFVPKFYG-------KAQELEKRIHHGVRGLLAGKEDIELLNVKYIGRVRARKLYNAGIRN--------PEELSRHKKEDIVKILGS-
Hel308 Mev       (615) LMHSAVNLANLITDLDAD-------SEIPEKLEIRLEYGAKEDIELLNVKYIGRVRARKLYNAGIRN--------VSDIKNTKLHILSNYLGR-
Hel308 Mfe       (601) LMHALKEMAKIIGKN----------SEIPEKLEIRLEYGAKEDIELLNVKYIGRVRARKLYNAGIRN--------VEDIINNPSK---VASIIG
Hel308 Mfr       (601) LLHASGRLARLVAPEHRD-------AVEETLRVRHGIRNGIIRRELIPLVRVKGIGRVRARRLYNNGITG---------PELLAADPSVVGHIVGG-
Hel308 Mhu       (608) LLHGTERLIVSVEMPEMSQ------VVKTLSVRVHHGVKSELLPVALRNIGRVRARARTLYNAGYPD--------PEAVARAGLSTIARIGE-
Hel308 Mig       (604) MIYSTKEIAKLLNRN----------IDTLSKLEIRLEYGAKEDIIELLIKYVGRARARKLYDAGIRS---------VEDIINNPK----VASLLG
Hel308 Min       (579) LSYSLKEIAKILNKEVP--------NLELRLEYGAKEELELLKIKYIGRVRARKLYSAGIRN---------REDIIKNPKK---VANILG
Hel308 Mma       (646) MIYSTKEIAKLIHLDNSE-------IYKSLLKMEVRIEYGAKEELIELLNVKNVGRIRSRKLYDAGIRS---------KIEINKNPEK--ILELFG
Hel308 Mmah      (615) LMHATQRIASRINPQLET-------BCAKLEKRIHYGAGSELIELVEIPNVGRARARKLFKKGYRS---------REDLATADEKQLAGIVGP-
Hel308 Mmar      (667) LLGAAESLASEVDLDAAR-------AISEARIRVEHGVREELVDLAGVRVGRKRARRLFQAGITD---------RAQLRDADKAVVLAALRGR
Hel308 Mmaz      (615) IMHVTAQLAGLLDLKGAK-------EASELEKRIRYGAAPELMDLLDIRSGVRVRARKLYEAGFKS---------TAELAAASPEHIAVLVGP-
Hel308 Mok       (674) MIHSAKEIFNLLNIDNKV-------IKDCLNDLEIRMEYGAKQDIIELLKIKHIGRARARILYNAGIKN--------ANDIINNQKN---IINLLG
Hel308 Mth       (600) LMSALHRISKHMDLGVTY-------LAERLALRIHYGAGDELLQLLELKGIGRVRARKLYQAGYRS---------LEDLKAADKSTLSEIIGP-
Hel308 Mzh       (621) LMHATSRLSGLLKVSEASE------KSKELERKLSYGINSELVNIVALKGIGRVRARKIYENGYRS---------IDDLKKADPLKLSKIVGS-
```

-continued

SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54 and 55 (Table 4) are aligned below The number below the * indicates the SEQ ID NO. The "-" are shown for alignment purposes only and do not form part of the sequences.

```
Hel308    Nma    (659)  LLGAAESLASEIDSEWAV-------AVREARARVEHGVGEELLELVSVSGIGRKRARRLYAAGIEE------PAALRSADKGVILHVLKG-
Hel308    Nth    (618)  ILRSYNVNIKEIDGIGRIN------IEEGIDLPGVLQDIKETDMRPEYLLDFTLEQEKFKSKFSPYLP----KDLQDKMHIAHLVDIEGVK
Hel308    Pfu    (610)  LVYSLKEIAKVLG-AYE--------IVDYLETLRVRVKYGIREELIPLMQLPLVGRRRARALYNSGFRS---IEDISQARPEELLKIEBIG
Hel308    Sso    (621)  LITYSAYHLSRELKLNEHAD-----KLRILNLRVRDGIKEELLELVQISGVGRKRARLLYNNGIKE------LGDVVMNPDKVKNLLGQK-
Hel308    Tba    (629)  TKIKYLRRLHLRLKHGVREELLELVELVELPMIGRRARALYNAGFKN------VNDIVKAKPSELLAVEGIG
Hel308    Tga    (608)  LMYSLIELYKLFEPKEE--------ILNVLRDLHLRLHGVREELLELVRLPNIGRKRARALYNAGFRS---VEAIANAKPAELLAVEGIG
Hel308    Tsi    (631)  LMYSLIELYKLFDPKPE--------VLDFLKKLHIRVKHGVREELLELITLPMIGRKRARALYNAGFKG---IDDIVRAKASELLKVEGIG
Hel308    Mja    (599)  IMHALKEIAKLIGKSSDI-------PEKLEIRLEYGAKEDIIELLSIKYIGRVRARKLYNAGIRS-------VASIIG
Consensus        (951)  LMHA  LAKLL           L EL IRI YGVKEELLELV IR IGRVRARKLY AGIRS           DL  A   L  ILG
```

1046                                                                                                                                                                                        1140

```
Hel308    Mbu    (717)  -KVAYNILSGIGVRVNDKHFNSAPISSNTLD--------------------TLLDKNQKTFNDFQ----------------------
Hel308    Afu    (674)  --IAERVVEGISVKSLNPESAAALEHHHHHH------------------------------------------------------
Hel308    Csy    (693)  ATLANNIKSQLRKGG------------------------------------------------------------
Hel308    Dth    (943)  LLFKNKAGKKVRIPVSWQDTAFQV------------------------------------------------------
Hel308    Fac    (662)  TKLAKDIIENAGKLNNRYYR--------------------------------------------------------
Hel308    Hla    (774)  ERTAERILEHAGREDPSMDDVRPDKSASAAATAGS-----------ASDEDGEGQASLGDFR----------------
Hel308    Hpa    (706)  KKTAENLLENVGRQDPSLDDVRADAET---------AA-----TSARATNDGGQQSLGDFE----------------
Hel308    Htu    (728)  EKTAENILENAGREDPSMDGVEPADGPAVGAATNGSSGGSETDETGRADAAERSDDSQSSLGDF----------------
Hel308    Hvo    (774)  RKTAENILEAAGRKDPSMDAVDEDDADPDDAVPDDA--G--------FETAKERADQQASLGDFEGS------------
Hel308    Mac    (692)  -KIAERIFPKQIGRREAVSEISDSERLEKS-------------------SDQGQSTISDF----------------
Hel308    Mba    (691)  -KIADRIFPKQIRGRGTSSGIIASEPPKS--------------------PYSQKTISDY----------------
Hel308    Mbo    (685)  -GIAEQVLEQLHPSKDTGKKEPPSGDKNTN-------------------PG-QSTLPHFG----------------
Hel308    Mev    (691)  -KTAYKVLEQLGVEPEDNQQIDEEPESIKSY-------------------SGNDQQKTFNDF----------------
Hel308    Mfe    (675)  EKITKKILEDLG--IKFGQ---------------------------------QKLIF------------------
Hel308    Mfr    (678)  -KTAESII---------------------------------------------------------------
Hel308    Mhu    (685)  -GIARQVIDEITGVKRSGIHSSDDDYQQKT----------------PE-LLTDIPGIKKMAEKLQNAGIITVSDLLTADEVLLSDV
Hel308    Mig    (678)  EKIAKKILGELG--MKFGQ---------------------------QTLQI---------------------
Hel308    Min    (650)  EKISKKIPEELG--VRYGQ---------------------------QRLI----------------------
Hel308    Mma    (724)  EKIGKKILGEHG--MKYGQ---------------------------QTLLNFN--------------------
Hel308    Mmah   (692)  -KIAQKILSYLGRETDSNGYVEPETLENK-----------------KQ-QKTFQDFI-----------------
Hel308    Mmar   (745)  RKTAENVLENAGHRDPSMEGVEPAPDVSVDLNDGADGD-----------ASAESTANDDQASLGDFI---------
Hel308    Mmaz   (692)  -KITERIFKQIGRREAVEFSDIEPLEKG---------------------SSDGQRTISDY---------------
Hel308    Mok    (752)  EKIARKILSELGVDTKFGQ-----------------------------MRLSI---------------------
Hel308    Mth    (677)  -KIAEGVISQLK-EPGVSA------------------------------------------------------
Hel308    Mzh    (699)  -KISQKILKQLDIDVDISEIKEKDSDTVP-E----------------P-ESSQKTISDFT---------------
Hel308    Nma    (736)  EKTAENILENAGREEPSMDGVEPIPVEGGSGSSNSSGSSNADANATEDDADDNQSSLGDF---------------
Hel308    Nth    (699)  TFLENKKIKEIKL---------------------------------------------------------
Hel308    Pfu    (689)  VKTVEAIPKFLGKNVKISE-------------------------------KPRKSTLDYFLKS-------------
Hel308    Sso    (699)  -LGEKVVQEAARLLNRFH---------------------------------------------------
Hel308    Tba    (709)  VKVLERIYRHFGVELPLLKNIKDPKPKEKP-------------------KPKKGTLDYFLK---------------
Hel308    Tga    (688)  AKILDGIYRHLGIEKRVTE-------EK---------------K------PKRKGTLEDFLR---------------
Hel308    Tsi    (711)  IGVIEKIYQHFGVELPTNE-------KK--------------------KVKKGTLDEFFK---------------
Hel308    Mja    (673)  EKIAKKILDELGVKFGQQKLSFSGGSAWSHPQPEKGGGSGGGSGGGSAWSHPQFEK-----KL------------
Consensus        (1046) KIAEKIL  LG                                              TL  F
```

-continued

SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54 and 55 (Table 4) are aligned below The number below the * indicates the SEQ ID NO. The "-" are shown for alignment purposes only and do not form part of the sequences.

```
                              1141                                                              1186
Hel308  Mbu    (761) ---------------------------------------------
Hel308  Afu    (703) ---------------------------------------------
Hel308  Csy    (708) ---------------------------------------------
Hel308  Dth    (967) ---------------------------------------------
Hel308  Fac    (682) ---------------------------------------------
Hel308  Hla    (825) ---------------------------------------------
Hel308  Hpa    (753) ---------------------------------------------
Hel308  Htu    (792) ---------------------------------------------
Hel308  Hvo    (830) ---------------------------------------------
Hel308  Mac    (731) ---------------------------------------------
Hel308  Mba    (730) ---------------------------------------------
Hel308  Mbo    (724) ---------------------------------------------
Hel308  Mev    (734) ---------------------------------------------
Hel308  Mfe    (697) ---------------------------------------------
Hel308  Mfr    (685) ---------------------------------------------
Hel308  Mhu    (754) LGAARARKVLAFLSNSEKENSSSDKTEEIPDTQKIRGQSSWEDFGC
Hel308  Mig    (700) ---------------------------------------------
Hel308  Min    (671) ---------------------------------------------
Hel308  Mma    (748) ---------------------------------------------
Hel308  Mmah   (730) ---------------------------------------------
Hel308  Mmar   (800) ---------------------------------------------
Hel308  Mmaz   (731) ---------------------------------------------
Hel308  Mok    (776) ---------------------------------------------
Hel308  Mth    (694) ---------------------------------------------
Hel308  Mzh    (740) ---------------------------------------------
Hel308  Nma    (800) ---------------------------------------------
Hel308  Nth    (712) ---------------------------------------------
Hel308  Pfu    (721) ---------------------------------------------
Hel308  Sso    (716) ---------------------------------------------
Hel308  Tba    (756) ---------------------------------------------
Hel308  Tga    (721) ---------------------------------------------
Hel308  Tsi    (745) ---------------------------------------------
Hel308  Mja    (730) ---------------------------------------------
        Consensus (1141)
```

The invention claimed is:

1. A method of characterising a target polynucleotide, comprising:
   (a) providing in an aqueous solution a transmembrane pore and a membrane, wherein the transmembrane pore is present in the membrane, and wherein the aqueous solution comprises a salt at a concentration in a range of 0.3 M to 3 M;
   (b) combining, in the aqueous solution of step (a), the target polynucleotide and a Hel308 helicase, wherein the helicase binds to the target polynucleotide to form a polynucleotide helicase complex, thereby controlling the movement of the target polynucleotide through the transmembrane pore; and
   (c) measuring, during an application of a potential across the transmembrane pore, an ionic current as the target polynucleotide moves through the transmembrane pore, to determine one or more characteristics of the target polynucleotide and thereby characterising the target polynucleotide.

2. A method according to claim 1, wherein the one or more characteristics are selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified.

3. A method according to claim 2, wherein the target polynucleotide is modified by methylation, by oxidation, by damage, with one or more proteins or with one or more labels, tags or spacers.

4. A method according to claim 1, wherein at least a portion of the polynucleotide is double stranded.

5. A method according to claim 1, wherein the transmembrane pore is a protein pore.

6. A method according to claim 5, wherein the transmembrane protein pore is selected from the group consisting of: α-hemolysin, leukocidin, *Mycobacterium smegmatis* porin A (MspA), outer membrane porin F (OmpF), outer membrane porin G (OmpG), outer membrane phospholipase A, *Neisseria* autotransporter lipoprotein (NalP) and WZA.

7. A method according to claim 1, wherein the Hel308 helicase comprises the amino acid motif Q-X1-X2 G R A G R (SEQ ID NO: 8), wherein X1 is C, M or L and X2 is any amino acid residue.

8. A method according to claim 7, wherein X2 is A, F, M, C, V, L, I, S, T or P.

9. A method according to claim 1, wherein the Hel308 helicase is capable of binding to the target polynucleotide at an internal nucleotide.

10. A method according to claim 1, wherein the salt is KCl.

11. A method according to claim 10, wherein the salt concentration is at least 1.0 M.

* * * * *

SEQUENCE LISTING

<160> NUMBER OF SEQ ID NOS: 78

<210> SEQ ID NO 1
<211> LENGTH: 558
<212> TYPE: DNA
<213> ORGANISM: Artificial sequence
<220> FEATURE:
<223> OTHER INFORMATION: Mycobacterium smegmatis porin A mutant
      (D90N/D91N/D93N/D118R/D134R/E139K)

<400> SEQUENCE: 1

```
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                   558
```

<210> SEQ ID NO 2
<211> LENGTH: 184
<212> TYPE: PRT
<213> ORGANISM: Artificial sequence
<220> FEATURE:
<223> OTHER INFORMATION: Mycobacterium smegmatis porin A mutant
      (D90N/D91N/D93N/D118R/D134R/E139K)

<400> SEQUENCE: 2

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 3
<211> LENGTH: 885
<212> TYPE: DNA
<213> ORGANISM: Artificial sequence
<220> FEATURE:
<223> OTHER INFORMATION: alpha-hemolysin mutant E111N/K147N

<400> SEQUENCE: 3

```
atggcagatt ctgatattaa tattaaaacc ggtactacag atattggaag caatactaca      60
gtaaaaacag gtgatttagt cacttatgat aaagaaaatg gcatgcacaa aaaagtattt     120
tatagtttta tcgatgataa aaatcacaat aaaaaactgc tagttattag aacaaaaggt     180
accattgctg gtcaatatag agtttatagc gaagaaggtg ctaacaaaag tggtttagcc     240
tggccttcag cctttaaggt acagttgcaa ctacctgata tgaagtagc tcaaatatct      300
gattactatc caagaaattc gattgataca aaaaactata tgagtacttt aacttatgga     360
ttcaacggta atgttactgg tgatgataca ggaaaaattg gcggccttat tggtgcaaat     420
gtttcgattg gtcatacact gaactatgtt caacctgatt tcaaaacaat tttagagagc     480
ccaactgata aaaagtagg ctggaaagtg atatttaaca atatggtgaa tcaaaattgg     540
ggaccatacg atcgagattc ttggaacccg gtatatggca atcaactttt catgaaaact     600
agaaatggtt ctatgaaagc agcagataac ttccttgatc ctaacaaagc aagttctcta     660
ttatcttcag ggttttcacc agacttcgct acagttatta ctatggatag aaaagcatcc     720
aaacaacaaa caaatataga tgtaatatac gaacgagttc gtgatgatta ccaattgcat     780
tggacttcaa caaattggaa aggtaccaat actaaagata aatggacaga tcgttcttca     840
gaaagatata aaatcgattg ggaaaaagaa gaaatgacaa attaa                     885
```

<210> SEQ ID NO 4
<211> LENGTH: 293
<212> TYPE: PRT
<213> ORGANISM: Artificial sequence
<220> FEATURE:
<223> OTHER INFORMATION: alpha-hemolysin mutant E111N/K147N

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
```

```
                145                 150                 155                 160
        Thr Asp Lys Lys Val Gly Trp Lys Val Ile Phe Asn Asn Met Val Asn
                        165                 170                 175

Gln Asn Trp Gly Pro Tyr Asp Arg Asp Ser Trp Asn Pro Val Tyr Gly
                        180                 185                 190

Asn Gln Leu Phe Met Lys Thr Arg Asn Gly Ser Met Lys Ala Ala Asp
                        195                 200                 205

Asn Phe Leu Asp Pro Asn Lys Ala Ser Ser Leu Leu Ser Ser Gly Phe
                        210                 215                 220

Ser Pro Asp Phe Ala Thr Val Ile Thr Met Asp Arg Lys Ala Ser Lys
        225                 230                 235                 240

Gln Gln Thr Asn Ile Asp Val Ile Tyr Glu Arg Val Arg Asp Asp Tyr
                            245                 250                 255

Gln Leu His Trp Thr Ser Thr Asn Trp Lys Gly Thr Asn Thr Lys Asp
                        260                 265                 270

Lys Trp Thr Asp Arg Ser Ser Glu Arg Tyr Lys Ile Asp Trp Glu Lys
                        275                 280                 285

Glu Glu Met Thr Asn
                    290

<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
        1               5                   10                  15

Thr Val Gln Gln Trp Asp Thr Phe Leu Asn Gly Val Phe Pro Leu Asp
                        20                  25                  30

Arg Asn Arg Leu Thr Arg Glu Trp Phe His Ser Gly Arg Ala Lys Tyr
                    35                  40                  45

Ile Val Ala Gly Pro Gly Ala Asp Glu Phe Glu Gly Thr Leu Glu Leu
            50                  55                  60

Gly Tyr Gln Ile Gly Phe Pro Trp Ser Leu Gly Val Gly Ile Asn Phe
        65                  70                  75                  80

Ser Tyr Thr Thr Pro Asn Ile Leu Ile Asp Asp Gly Asp Ile Thr Ala
                        85                  90                  95

Pro Pro Phe Gly Leu Asn Ser Val Ile Thr Pro Asn Leu Phe Pro Gly
                        100                 105                 110

Val Ser Ile Ser Ala Asp Leu Gly Asn Gly Pro Gly Ile Gln Glu Val
                        115                 120                 125

Ala Thr Phe Ser Val Asp Val Ser Gly Pro Ala Gly Gly Val Ala Val
                        130                 135                 140

Ser Asn Ala His Gly Thr Val Thr Gly Ala Ala Gly Gly Val Leu Leu
        145                 150                 155                 160

Arg Pro Phe Ala Arg Leu Ile Ala Ser Thr Gly Asp Ser Val Thr Thr
                        165                 170                 175

Tyr Gly Glu Pro Trp Asn Met Asn
                    180

<210> SEQ ID NO 6
<211> LENGTH: 184
<212> TYPE: PRT
<213> ORGANISM: Mycobacterium smegmatis
```

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Val Ala Val
    130                 135                 140

Ser Asn Ala His Gly Thr Val Thr Gly Ala Ala Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

```
Gly Glu Pro Trp Asn Met Asn
            180

<210> SEQ ID NO 8
<211> LENGTH: 8
<212> TYPE: PRT
<213> ORGANISM: Artificial sequence
<220> FEATURE:
<223> OTHER INFORMATION: Amino acid sequence of the Hel308 motif
<220> FEATURE:
<221> NAME/KEY: MISC_FEATURE
<222> LOCATION: (2)..(2)
<223> OTHER INFORMATION: Xaa = C, M or L
<220> FEATURE:
<221> NAME/KEY: MISC_FEATURE
<222> LOCATION: (3)..(3)
<223> OTHER INFORMATION: Xaa = any amino acid

<400> SEQUENCE: 8

Gln Xaa Xaa Gly Arg Ala Gly Arg
1               5

<210> SEQ ID NO 9
<211> LENGTH: 9
<212> TYPE: PRT
<213> ORGANISM: Artificial sequence
<220> FEATURE:
<223> OTHER INFORMATION: Amino acid sequence of the extended Hel308 motif
<220> FEATURE:
<221> NAME/KEY: MISC_FEATURE
<222> LOCATION: (2)..(2)
<223> OTHER INFORMATION: Xaa = C, M or L
<220> FEATURE:
<221> NAME/KEY: MISC_FEATURE
<222> LOCATION: (3)..(3)
<223> OTHER INFORMATION: Xaa = any amino acid

<400> SEQUENCE: 9

Gln Xaa Xaa Gly Arg Ala Gly Arg Pro
1               5

<210> SEQ ID NO 10
<211> LENGTH: 760
<212> TYPE: PRT
<213> ORGANISM: Methanococcoides burtonii

<400> SEQUENCE: 10

Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
        115                 120                 125

Arg Asn Gly Thr Ser Trp Met Asp Glu Ile Thr Thr Val Val Val Asp
    130                 135                 140
```

```
Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
            195                 200                 205

Val Leu Phe Gly Asp Ala Ile Asn Phe Pro Gly Ser Gln Lys Lys Ile
210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Val Glu Ser
        275                 280                 285

Thr Gly Glu Thr Asp Thr Ala Ile Val Leu Ala Asn Cys Ile Arg Lys
    290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Arg Arg Phe Asp Ser Asn Phe Gly Met Gln Pro Ile Pro
        355                 360                 365

Val Leu Glu Tyr Lys Gln Met Ala Gly Arg Ala Gly Arg Pro His Leu
    370                 375                 380

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415

Ser Lys Leu Gly Thr Glu Asn Ala Leu Arg Thr His Val Leu Ser Thr
            420                 425                 430

Ile Val Asn Gly Phe Ala Ser Thr Arg Gln Glu Leu Phe Asp Phe Phe
        435                 440                 445

Gly Ala Thr Phe Phe Ala Tyr Gln Gln Asp Lys Trp Met Leu Glu Glu
    450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
            500                 505                 510

Ser Lys Ile Val Asp Gly Phe Lys Asp Ile Gly Lys Ser Thr Gly Gly
        515                 520                 525

Asn Met Gly Ser Leu Glu Asp Lys Gly Asp Asp Ile Thr Val Thr
    530                 535                 540

Asp Met Thr Leu Leu His Leu Val Cys Ser Thr Pro Asp Met Arg Gln
545                 550                 555                 560
```

-continued

```
Leu Tyr Leu Arg Asn Thr Asp Tyr Thr Ile Val Asn Glu Tyr Ile Val
            565                 570                 575

Ala His Ser Asp Glu Phe His Glu Ile Pro Asp Lys Leu Lys Glu Thr
        580                 585                 590

Asp Tyr Glu Trp Phe Met Gly Glu Val Lys Thr Ala Met Leu Leu Glu
    595                 600                 605

Glu Trp Val Thr Glu Val Ser Ala Glu Asp Ile Thr Arg His Phe Asn
610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
            660                 665                 670

Asp Leu Met Glu Leu Val Gly Ile Arg Gly Val Gly Arg Val Arg Ala
        675                 680                 685

Arg Lys Leu Tyr Asn Ala Gly Phe Val Ser Val Ala Lys Leu Lys Gly
    690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
            740                 745                 750

Gln Lys Thr Phe Asn Asp Phe Gln
        755                 760

<210> SEQ ID NO 11
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 11

Gln Met Ala Gly Arg Ala Gly Arg
1               5

<210> SEQ ID NO 12
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 12

Gln Met Ala Gly Arg Ala Gly Arg Pro
1               5

<210> SEQ ID NO 13
<211> LENGTH: 720
<212> TYPE: PRT
<213> ORGANISM: Pyrococcus furiosus

<400> SEQUENCE: 13

Met Arg Val Asp Glu Leu Arg Val Asp Glu Arg Ile Lys Ser Thr Leu
1               5                   10                  15

Lys Glu Arg Gly Ile Glu Ser Phe Tyr Pro Pro Gln Ala Glu Ala Leu
            20                  25                  30
```

-continued

Lys Ser Gly Ile Leu Glu Gly Lys Asn Ala Leu Ile Ser Ile Pro Thr
          35                  40                  45

Ala Ser Gly Lys Thr Leu Ile Ala Glu Ile Ala Met Val His Arg Ile
 50                  55                  60

Leu Thr Gln Gly Gly Lys Ala Val Tyr Ile Val Pro Leu Lys Ala Leu
 65                  70                  75                  80

Ala Glu Glu Lys Phe Gln Glu Phe Gln Asp Trp Glu Lys Ile Gly Leu
                 85                  90                  95

Arg Val Ala Met Ala Thr Gly Asp Tyr Asp Ser Lys Asp Glu Trp Leu
                100                 105                 110

Gly Lys Tyr Asp Ile Ile Ala Thr Ala Glu Lys Phe Asp Ser Leu
                115                 120                 125

Leu Arg His Gly Ser Ser Trp Ile Lys Asp Val Lys Ile Leu Val Ala
    130                 135                 140

Asp Glu Ile His Leu Ile Gly Ser Arg Asp Arg Gly Ala Thr Leu Glu
145                 150                 155                 160

Val Ile Leu Ala His Met Leu Gly Lys Ala Gln Ile Ile Gly Leu Ser
                165                 170                 175

Ala Thr Ile Gly Asn Pro Glu Glu Leu Ala Glu Trp Leu Asn Ala Glu
                180                 185                 190

Leu Ile Val Ser Asp Trp Arg Pro Val Lys Leu Arg Arg Gly Val Phe
        195                 200                 205

Tyr Gln Gly Phe Val Thr Trp Glu Asp Gly Ser Ile Asp Arg Phe Ser
    210                 215                 220

Ser Trp Glu Glu Leu Val Tyr Asp Ala Ile Arg Lys Lys Gly Ala
225                 230                 235                 240

Leu Ile Phe Val Asn Met Arg Arg Lys Ala Glu Arg Val Ala Leu Glu
                245                 250                 255

Leu Ser Lys Lys Val Lys Ser Leu Leu Thr Lys Pro Glu Ile Arg Ala
                260                 265                 270

Leu Asn Glu Leu Ala Asp Ser Leu Glu Glu Asn Pro Thr Asn Glu Lys
                275                 280                 285

Leu Ala Lys Ala Ile Arg Gly Gly Val Ala Phe His His Ala Gly Leu
    290                 295                 300

Gly Arg Asp Glu Arg Val Leu Val Glu Glu Asn Phe Arg Lys Gly Ile
305                 310                 315                 320

Ile Lys Ala Val Val Ala Thr Pro Thr Leu Ser Ala Gly Ile Asn Thr
                325                 330                 335

Pro Ala Phe Arg Val Ile Arg Asp Ile Trp Arg Tyr Ser Asp Phe
                340                 345                 350

Gly Met Glu Arg Ile Pro Ile Ile Glu Val His Gln Met Leu Gly Arg
                355                 360                 365

Ala Gly Arg Pro Lys Tyr Asp Glu Val Gly Glu Gly Ile Ile Val Ser
    370                 375                 380

Thr Ser Asp Asp Pro Arg Glu Val Met Asn His Tyr Ile Phe Gly Lys
385                 390                 395                 400

Pro Glu Lys Leu Phe Ser Gln Leu Ser Asn Glu Ser Asn Leu Arg Ser
                405                 410                 415

Gln Val Leu Ala Leu Ile Ala Thr Phe Gly Tyr Ser Thr Val Glu Glu
                420                 425                 430

Ile Leu Lys Phe Ile Ser Asn Thr Phe Tyr Ala Tyr Gln Arg Lys Asp
                435                 440                 445

Thr Tyr Ser Leu Glu Glu Lys Ile Arg Asn Ile Leu Tyr Phe Leu Leu

```
                450             455             460
Glu Asn Glu Phe Ile Glu Ile Ser Leu Glu Asp Lys Ile Arg Pro Leu
465                 470                 475                 480

Ser Leu Gly Ile Arg Thr Ala Lys Leu Tyr Ile Asp Pro Tyr Thr Ala
                    485                 490                 495

Lys Met Phe Lys Asp Lys Met Glu Glu Val Val Lys Asp Pro Asn Pro
                500                 505                 510

Ile Gly Ile Phe His Leu Ile Ser Leu Thr Pro Asp Ile Thr Pro Phe
            515                 520                 525

Asn Tyr Ser Lys Arg Glu Phe Glu Arg Leu Glu Glu Glu Tyr Tyr Glu
        530                 535                 540

Phe Lys Asp Arg Leu Tyr Phe Asp Asp Pro Tyr Ile Ser Gly Tyr Asp
545                 550                 555                 560

Pro Tyr Leu Glu Arg Lys Phe Phe Arg Ala Phe Lys Thr Ala Leu Val
                565                 570                 575

Leu Leu Ala Trp Ile Asn Glu Val Pro Glu Gly Glu Ile Val Glu Lys
                580                 585                 590

Tyr Ser Val Glu Pro Gly Asp Ile Tyr Arg Ile Val Glu Thr Ala Glu
            595                 600                 605

Trp Leu Val Tyr Ser Leu Lys Glu Ile Ala Lys Val Leu Gly Ala Tyr
        610                 615                 620

Glu Ile Val Asp Tyr Leu Glu Thr Leu Arg Val Arg Val Lys Tyr Gly
625                 630                 635                 640

Ile Arg Glu Glu Leu Ile Pro Leu Met Gln Leu Pro Leu Val Gly Arg
                645                 650                 655

Arg Arg Ala Arg Ala Leu Tyr Asn Ser Gly Phe Arg Ser Ile Glu Asp
                660                 665                 670

Ile Ser Gln Ala Arg Pro Glu Leu Leu Lys Ile Glu Gly Ile Gly Gly
            675                 680                 685

Val Lys Thr Val Glu Ala Ile Phe Lys Phe Leu Gly Lys Asn Val Lys
        690                 695                 700

Ile Ser Glu Lys Pro Arg Lys Ser Thr Leu Asp Tyr Phe Leu Lys Ser
705                 710                 715                 720

<210> SEQ ID NO 14
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 14

Gln Met Leu Gly Arg Ala Gly Arg
1               5

<210> SEQ ID NO 15
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 15

Gln Met Leu Gly Arg Ala Gly Arg Pro
1               5

<210> SEQ ID NO 16
<211> LENGTH: 829
```

<212> TYPE: PRT
<213> ORGANISM: Haloferax volcanii

<400> SEQUENCE: 16

```
Met Arg Thr Ala Asp Leu Thr Gly Leu Pro Thr Gly Ile Pro Glu Ala
1               5                   10                  15
Leu Arg Asp Glu Gly Ile Glu Glu Leu Tyr Pro Pro Gln Ala Glu Ala
                20                  25                  30
Val Glu Ala Gly Leu Thr Asp Gly Glu Ser Leu Val Ala Ala Val Pro
            35                  40                  45
Thr Ala Ser Gly Lys Thr Leu Ile Ala Glu Leu Ala Met Leu Ser Ser
        50                  55                  60
Val Ala Arg Gly Gly Lys Ala Leu Tyr Ile Val Pro Leu Arg Ala Leu
65                  70                  75                  80
Ala Ser Glu Lys Lys Ala Glu Phe Glu Arg Trp Glu Glu Tyr Gly Ile
                85                  90                  95
Asp Val Gly Val Ser Thr Gly Asn Tyr Glu Ser Asp Gly Glu Trp Leu
                100                 105                 110
Ser Ser Arg Asp Ile Ile Val Ala Thr Ser Glu Lys Val Asp Ser Leu
            115                 120                 125
Val Arg Asn Asn Ala Ala Trp Met Asp Gln Leu Thr Cys Val Val Ala
        130                 135                 140
Asp Glu Val His Leu Val Asp Asp Arg His Arg Gly Pro Thr Leu Glu
145                 150                 155                 160
Val Thr Leu Ala Lys Leu Arg Arg Leu Asn Thr Asn Leu Gln Val Val
                165                 170                 175
Ala Leu Ser Ala Thr Val Gly Asn Ala Gly Val Val Ser Asp Trp Leu
                180                 185                 190
Asp Ala Glu Leu Val Lys Ser Asp Trp Arg Pro Ile Asp Leu Lys Met
            195                 200                 205
Gly Val His Tyr Gly Asn Ala Val Ser Phe Ala Asp Gly Ser Gln Arg
        210                 215                 220
Glu Val Pro Val Gly Arg Gly Glu Arg Gln Thr Pro Ala Leu Val Ala
225                 230                 235                 240
Asp Ala Leu Glu Gly Asp Gly Glu Gly Asp Gln Gly Ser Ser Leu Val
                245                 250                 255
Phe Val Asn Ser Arg Arg Asn Ala Glu Ser Ala Ala Arg Met Ala
                260                 265                 270
Asp Val Thr Glu Arg Tyr Val Thr Gly Asp Glu Arg Ser Asp Leu Ala
            275                 280                 285
Glu Leu Ala Ala Glu Ile Arg Asp Val Ser Asp Thr Glu Thr Ser Asp
        290                 295                 300
Asp Leu Ala Asn Ala Val Ala Lys Gly Ala Ala Phe His His Ala Gly
305                 310                 315                 320
Leu Ala Ala Glu His Arg Thr Leu Val Glu Asp Ala Phe Arg Asp Arg
                325                 330                 335
Leu Ile Lys Cys Ile Cys Ala Thr Pro Thr Leu Ala Ala Gly Val Asn
                340                 345                 350
Thr Pro Ser Arg Arg Val Val Arg Asp Trp Gln Arg Tyr Asp Gly
            355                 360                 365
Asp Tyr Gly Gly Met Lys Pro Leu Asp Val Leu Glu Val His Gln Met
        370                 375                 380
Met Gly Arg Ala Gly Arg Pro Gly Leu Asp Pro Tyr Gly Glu Ala Val
385                 390                 395                 400
```

```
Leu Leu Ala Lys Asp Ala Asp Ala Arg Asp Glu Leu Phe Glu Arg Tyr
            405                 410                 415

Ile Trp Ala Asp Ala Glu Asp Val Arg Ser Lys Leu Ala Ala Glu Pro
            420                 425                 430

Ala Leu Arg Thr His Leu Leu Ala Thr Val Ala Ser Gly Phe Ala His
            435                 440                 445

Thr Arg Glu Gly Leu Leu Glu Phe Leu Asp Gln Thr Leu Tyr Ala Thr
            450                 455                 460

Gln Thr Asp Asp Pro Glu Arg Leu Gly Gln Val Thr Asp Arg Val Leu
465                 470                 475                 480

Asp Tyr Leu Glu Val Asn Gly Phe Val Glu Phe Glu Gly Glu Thr Ile
            485                 490                 495

Gln Ala Thr Pro Val Gly His Thr Val Ser Arg Leu Tyr Leu Asp Pro
            500                 505                 510

Met Ser Ala Ala Glu Ile Ile Asp Gly Leu Glu Trp Ala Ala Asp His
            515                 520                 525

Arg Thr Glu Lys Leu Arg Ala Leu Ala Gly Glu Thr Pro Glu Lys Pro
            530                 535                 540

Thr Arg Asp Arg Ser Glu Ser Asp Glu Ser Gly Gly Phe Gln Arg Ala
545                 550                 555                 560

Ser Glu Met Val Ala Asp Asp Gly Asp Gly Gly Glu Asp Gly
            565                 570                 575

Val Gly Ala Asn Gly Asp Gly Asp Ser Asp Asp Ala Asp Gly Val Glu
            580                 585                 590

Thr Asp Arg Thr Tyr Pro Thr Pro Leu Gly Leu Tyr His Leu Val Cys
            595                 600                 605

Arg Thr Pro Asp Met Tyr Gln Leu Tyr Leu Lys Ser Gly Asp Arg Glu
            610                 615                 620

Thr Tyr Thr Glu Leu Cys Tyr Glu Arg Glu Pro Glu Phe Leu Gly Arg
625                 630                 635                 640

Val Pro Ser Glu Tyr Glu Asp Val Ala Phe Glu Asp Trp Leu Ser Ala
            645                 650                 655

Leu Lys Thr Ala Lys Leu Leu Glu Asp Trp Val Gly Glu Val Asp Glu
            660                 665                 670

Asp Arg Ile Thr Glu Arg Tyr Gly Val Gly Pro Gly Asp Ile Arg Gly
            675                 680                 685

Lys Val Glu Thr Ser Glu Trp Leu Leu Gly Ala Ala Glu Arg Leu Ala
            690                 695                 700

Thr Glu Leu Asp Leu Asp Ser Val Tyr Ala Val Arg Glu Ala Lys Lys
705                 710                 715                 720

Arg Val Glu Tyr Gly Val Arg Glu Glu Leu Leu Asp Leu Ala Gly Val
            725                 730                 735

Arg Gly Val Gly Arg Lys Arg Ala Arg Arg Leu Phe Glu Ala Gly Val
            740                 745                 750

Glu Thr Arg Ala Asp Leu Arg Glu Ala Asp Lys Pro Arg Val Leu Ala
            755                 760                 765

Ala Leu Arg Gly Arg Arg Lys Thr Ala Glu Asn Ile Leu Glu Ala Ala
            770                 775                 780

Gly Arg Lys Asp Pro Ser Met Asp Ala Val Asp Glu Asp Ala Pro
785                 790                 795                 800

Asp Asp Ala Val Pro Asp Asp Ala Gly Phe Glu Thr Ala Lys Glu Arg
            805                 810                 815
```

Ala Asp Gln Gln Ala Ser Leu Gly Asp Phe Glu Gly Ser
            820                 825

<210> SEQ ID NO 17
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 17

Gln Met Met Gly Arg Ala Gly Arg
1               5

<210> SEQ ID NO 18
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 18

Gln Met Met Gly Arg Ala Gly Arg Pro
1               5

<210> SEQ ID NO 19
<211> LENGTH: 824
<212> TYPE: PRT
<213> ORGANISM: Halorubrum lacusprofundi

<400> SEQUENCE: 19

Met Gln Pro Ser Ser Leu Ser Gly Leu Pro Ala Gly Val Gly Glu Ala
1               5                   10                  15

Leu Glu Ala Glu Gly Val Ala Glu Leu Tyr Pro Pro Gln Glu Ala Ala
            20                  25                  30

Val Glu Ala Gly Val Ala Asp Gly Glu Ser Leu Val Ala Ala Val Pro
        35                  40                  45

Thr Ala Ser Gly Lys Thr Leu Ile Ala Glu Leu Ala Met Leu Ser Ser
    50                  55                  60

Ile Glu Arg Gly Gly Lys Ala Leu Tyr Ile Val Pro Leu Arg Ala Leu
65                  70                  75                  80

Ala Ser Glu Lys Lys Thr Glu Phe Glu Arg Trp Glu Glu Phe Gly Val
                85                  90                  95

Thr Val Gly Val Ser Thr Gly Asn Tyr Glu Ser Asp Gly Glu Trp Leu
            100                 105                 110

Ala Thr Arg Asp Ile Ile Val Ala Thr Ser Glu Lys Val Asp Ser Leu
        115                 120                 125

Ile Arg Asn Gly Ala Pro Trp Ile Asp Leu Thr Cys Val Val Ser
    130                 135                 140

Asp Glu Val His Leu Val Asp Asp Pro Asn Arg Gly Pro Thr Leu Glu
145                 150                 155                 160

Val Thr Leu Ala Lys Leu Arg Lys Val Asn Pro Gly Leu Gln Thr Val
                165                 170                 175

Ala Leu Ser Ala Thr Val Gly Asn Ala Asp Val Ile Ala Glu Trp Leu
            180                 185                 190

Asp Ala Glu Leu Val Glu Ser Asp Trp Arg Pro Ile Asp Leu Arg Met
        195                 200                 205

Gly Val His Phe Gly Asn Ala Ile Asp Phe Ala Asp Gly Ser Lys Arg
    210                 215                 220

```
Glu Val Pro Val Glu Arg Gly Glu Asp Gln Thr Ala Arg Leu Val Ala
225                 230                 235                 240

Asp Ala Leu Asp Thr Glu Glu Asp Gly Gln Gly Gly Ser Ser Leu Val
                245                 250                 255

Phe Val Asn Ser Arg Arg Asn Ala Glu Ser Ser Ala Arg Lys Leu Thr
            260                 265                 270

Asp Val Thr Gly Pro Arg Leu Thr Asp Asp Glu Arg Asp Gln Leu Arg
        275                 280                 285

Glu Leu Ala Asp Glu Ile Arg Ser Gly Ser Asp Thr Asp Thr Ala Ser
    290                 295                 300

Asp Leu Ala Asp Ala Val Glu Gln Gly Ser Ala Phe His His Ala Gly
305                 310                 315                 320

Leu Arg Ser Glu Asp Arg Ala Arg Val Glu Asp Ala Phe Arg Asp Arg
                325                 330                 335

Leu Ile Lys Cys Ile Ser Ala Thr Pro Thr Leu Ala Ala Gly Val Asn
            340                 345                 350

Thr Pro Ala Arg Arg Val Ile Val Arg Asp Trp Arg Arg Tyr Asp Gly
        355                 360                 365

Glu Phe Gly Gly Met Lys Pro Leu Asp Val Leu Glu Val His Gln Met
    370                 375                 380

Cys Gly Arg Ala Gly Arg Pro Gly Leu Asp Pro Tyr Gly Glu Ala Val
385                 390                 395                 400

Leu Leu Ala Asn Asp Ala Asp Thr Lys Glu Glu Leu Phe Glu Arg Tyr
                405                 410                 415

Leu Trp Ala Asp Pro Glu Pro Val Arg Ser Lys Leu Ala Ala Glu Pro
            420                 425                 430

Ala Leu Arg Thr His Val Leu Ala Thr Val Ala Ser Gly Phe Ala Ser
        435                 440                 445

Thr Arg Asp Gly Leu Leu Ser Phe Leu Asp Asn Thr Leu Tyr Ala Thr
    450                 455                 460

Gln Thr Asp Asp Glu Gly Arg Leu Ala Ala Val Thr Asp Thr Val Leu
465                 470                 475                 480

Asp Tyr Leu Ala Val Asn Asp Phe Ile Glu Arg Asp Arg Asp Gly Gly
                485                 490                 495

Ser Glu Ser Leu Thr Ala Thr Gly Ile Gly His Thr Val Ser Arg Leu
            500                 505                 510

Tyr Leu Asp Pro Met Ser Ala Ala Glu Met Ile Asp Gly Leu Arg Ser
        515                 520                 525

Val Ala Arg Asp Ala Ala Asp Thr Gly Ala Ser Ala Glu Ala Asp Asn
    530                 535                 540

Gly Glu Phe Val Arg Thr Gly Asp Ala Asp Ala Ser Gly Gly Asp
545                 550                 555                 560

Glu Pro Gly Phe Gly Thr Tyr Thr Arg Ala Gly Asp Glu Ser Gly
                565                 570                 575

Glu Arg Glu Thr Glu Asn Glu Gly Thr Asp Glu Glu Thr Glu Ala
            580                 585                 590

Ser Glu Val Thr Pro Leu Gly Leu Tyr His Leu Ile Ser Arg Thr Pro
        595                 600                 605

Asp Met Tyr Glu Leu Tyr Leu Lys Ser Gly Asp Arg Glu Thr Tyr Thr
    610                 615                 620

Glu Leu Cys Tyr Glu Arg Glu Thr Glu Phe Leu Gly Asp Val Pro Ser
625                 630                 635                 640

Glu Tyr Glu Asp Val Arg Phe Glu Asp Trp Leu Ala Ser Leu Lys Thr
```

```
                    645                 650                 655
Ala Arg Leu Leu Glu Asp Trp Val Asn Glu Val Asp Glu Asp Arg Ile
            660                 665                 670

Thr Glu Arg Tyr Gly Val Gly Pro Gly Asp Ile Arg Gly Lys Val Asp
        675                 680                 685

Thr Ala Glu Trp Leu Leu Arg Ala Ala Glu Thr Leu Ala Arg Asp Val
690                 695                 700

Glu Gly Val Asp Gly Asp Val Val Ala Val Arg Glu Ala Arg Lys
705                 710                 715                 720

Arg Ile Glu Tyr Gly Val Arg Glu Leu Leu Asp Leu Ala Gly Val
                725                 730                 735

Arg Asn Val Gly Arg Lys Arg Ala Arg Arg Leu Phe Glu Ala Gly Ile
            740                 745                 750

Glu Thr Arg Ala Asp Leu Arg Glu Ala Asp Lys Ala Val Val Leu Gly
        755                 760                 765

Ala Leu Arg Gly Arg Glu Arg Thr Ala Glu Arg Ile Leu Glu His Ala
    770                 775                 780

Gly Arg Glu Asp Pro Ser Met Asp Asp Val Arg Pro Asp Lys Ser Ala
785                 790                 795                 800

Ser Ala Ala Ala Thr Ala Gly Ser Ala Ser Asp Glu Asp Gly Glu Gly
                805                 810                 815

Gln Ala Ser Leu Gly Asp Phe Arg
            820

<210> SEQ ID NO 20
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 20

Gln Met Cys Gly Arg Ala Gly Arg
1               5

<210> SEQ ID NO 21
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 21

Gln Met Cys Gly Arg Ala Gly Arg Pro
1               5

<210> SEQ ID NO 22
<211> LENGTH: 707
<212> TYPE: PRT
<213> ORGANISM: Cenarchaeum symbiosum

<400> SEQUENCE: 22

Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
                20                  25                  30

Lys Ala Gly Leu Thr Asp Gly Lys Ser Val Leu Val Ser Ala Pro Thr
            35                  40                  45

Ala Ser Gly Lys Thr Leu Ile Ala Ala Ile Ala Met Ile Ser His Leu
```

```
              50                  55                  60
Ser Arg Asn Arg Gly Lys Ala Val Tyr Leu Ser Pro Leu Arg Ala Leu
 65                  70                  75                  80

Ala Ala Glu Lys Phe Ala Glu Phe Gly Lys Ile Gly Ile Pro Leu
                 85                  90                  95

Gly Arg Pro Val Arg Val Gly Val Ser Thr Gly Asp Phe Glu Lys Ala
                    100                 105                 110

Gly Arg Ser Leu Gly Asn Asn Asp Ile Leu Val Leu Thr Asn Glu Arg
                    115                 120                 125

Met Asp Ser Leu Ile Arg Arg Pro Asp Trp Met Asp Glu Val Gly
                130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                    165                 170                 175

Pro Gln Val Val Ala Leu Ser Ala Thr Ile Ser Asn Ala Asp Glu Ile
                180                 185                 190

Ala Gly Trp Leu Asp Cys Thr Leu Val His Ser Thr Trp Arg Pro Val
                195                 200                 205

Pro Leu Ser Glu Gly Val Tyr Gln Asp Gly Glu Val Ala Met Gly Asp
    210                 215                 220

Gly Ser Arg His Glu Val Ala Ala Thr Gly Gly Pro Ala Val Asp
225                 230                 235                 240

Leu Ala Ala Glu Ser Val Ala Glu Gly Gly Gln Ser Leu Ile Phe Ala
                    245                 250                 255

Asp Thr Arg Ala Arg Ser Ala Ser Leu Ala Ala Lys Ala Ser Ala Val
                260                 265                 270

Ile Pro Glu Ala Lys Gly Ala Asp Ala Ala Lys Leu Ala Ala Ala
                275                 280                 285

Lys Lys Ile Ile Ser Ser Gly Gly Glu Thr Lys Leu Ala Lys Thr Leu
                290                 295                 300

Ala Glu Leu Val Glu Lys Gly Ala Ala Phe His His Ala Gly Leu Asn
305                 310                 315                 320

Gln Asp Cys Arg Ser Val Val Glu Glu Glu Phe Arg Ser Gly Arg Ile
                325                 330                 335

Arg Leu Leu Ala Ser Thr Pro Thr Leu Ala Ala Gly Val Asn Leu Pro
                340                 345                 350

Ala Arg Arg Val Val Ile Ser Ser Val Met Arg Tyr Asn Ser Ser Ser
                355                 360                 365

Gly Met Ser Glu Pro Ile Ser Ile Leu Glu Tyr Lys Gln Leu Cys Gly
    370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Glu
                405                 410                 415

Pro Glu Pro Ile Arg Ser Ala Met Val Asp Asp Arg Ala Leu Arg Ile
                420                 425                 430

His Val Leu Ser Leu Val Thr Thr Ser Pro Gly Ile Lys Glu Asp Asp
                435                 440                 445

Val Thr Glu Phe Phe Leu Gly Thr Leu Gly Gly Gln Gln Ser Gly Glu
    450                 455                 460

Ser Thr Val Lys Phe Ser Val Ala Val Ala Leu Arg Phe Leu Gln Glu
465                 470                 475                 480
```

-continued

```
Glu Gly Met Leu Gly Arg Arg Gly Arg Leu Ala Ala Thr Lys Met
            485                 490                 495
Gly Arg Leu Val Ser Arg Leu Tyr Met Asp Pro Met Thr Ala Val Thr
        500                 505                 510
Leu Arg Asp Ala Val Gly Glu Ala Ser Pro Gly Arg Met His Thr Leu
    515                 520                 525
Gly Phe Leu His Leu Val Ser Glu Cys Ser Glu Phe Met Pro Arg Phe
530                 535                 540
Ala Leu Arg Gln Lys Asp His Glu Val Ala Glu Met Met Leu Glu Ala
545                 550                 555                 560
Gly Arg Gly Glu Leu Leu Arg Pro Val Tyr Ser Tyr Glu Cys Gly Arg
                565                 570                 575
Gly Leu Leu Ala Leu His Arg Trp Ile Gly Glu Ser Pro Glu Ala Lys
            580                 585                 590
Leu Ala Glu Asp Leu Lys Phe Glu Ser Gly Asp Val His Arg Met Val
        595                 600                 605
Glu Ser Ser Gly Trp Leu Leu Arg Cys Ile Trp Glu Ile Ser Lys His
    610                 615                 620
Gln Glu Arg Pro Asp Leu Leu Gly Glu Leu Asp Val Leu Arg Ser Arg
625                 630                 635                 640
Val Ala Tyr Gly Ile Lys Ala Glu Leu Val Pro Leu Val Ser Ile Lys
                645                 650                 655
Gly Ile Gly Arg Val Arg Ser Arg Arg Leu Phe Arg Gly Gly Ile Lys
            660                 665                 670
Gly Pro Gly Asp Leu Ala Ala Val Pro Val Glu Arg Leu Ser Arg Val
        675                 680                 685
Glu Gly Ile Gly Ala Thr Leu Ala Asn Asn Ile Lys Ser Gln Leu Arg
    690                 695                 700
Lys Gly Gly
705

<210> SEQ ID NO 23
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 23

Gln Leu Cys Gly Arg Ala Gly Arg
1               5

<210> SEQ ID NO 24
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 24

Gln Leu Cys Gly Arg Ala Gly Arg Pro
1               5

<210> SEQ ID NO 25
<211> LENGTH: 715
<212> TYPE: PRT
<213> ORGANISM: Sulfolobus solfataricus

<400> SEQUENCE: 25
```

```
Met Ser Leu Glu Leu Glu Trp Met Pro Ile Glu Asp Leu Lys Leu Pro
1               5                   10                  15

Ser Asn Val Ile Glu Ile Ile Lys Lys Arg Gly Ile Lys Lys Leu Asn
            20                  25                  30

Pro Pro Gln Thr Glu Ala Val Lys Lys Gly Leu Leu Glu Gly Asn Arg
        35                  40                  45

Leu Leu Leu Thr Ser Pro Thr Gly Ser Gly Lys Thr Leu Ile Ala Glu
    50                  55                  60

Met Gly Ile Ile Ser Phe Leu Leu Lys Asn Gly Gly Lys Ala Ile Tyr
65                  70                  75                  80

Val Thr Pro Leu Arg Ala Leu Thr Asn Glu Lys Tyr Leu Thr Phe Lys
                85                  90                  95

Asp Trp Glu Leu Ile Gly Phe Lys Val Ala Met Thr Ser Gly Asp Tyr
            100                 105                 110

Asp Thr Asp Asp Ala Trp Leu Lys Asn Tyr Asp Ile Ile Thr Thr
        115                 120                 125

Tyr Glu Lys Leu Asp Ser Leu Trp Arg His Arg Pro Glu Trp Leu Asn
    130                 135                 140

Glu Val Asn Tyr Phe Val Leu Asp Glu Leu His Tyr Leu Asn Asp Pro
145                 150                 155                 160

Glu Arg Gly Pro Val Val Glu Ser Val Thr Ile Arg Ala Lys Arg Arg
                165                 170                 175

Asn Leu Leu Ala Leu Ser Ala Thr Ile Ser Asn Tyr Lys Gln Ile Ala
            180                 185                 190

Lys Trp Leu Gly Ala Glu Pro Val Ala Thr Asn Trp Arg Pro Val Pro
        195                 200                 205

Leu Ile Glu Gly Val Ile Tyr Pro Glu Arg Lys Lys Lys Glu Tyr Asn
    210                 215                 220

Val Ile Phe Lys Asp Asn Thr Thr Lys Val His Gly Asp Asp Ala
225                 230                 235                 240

Ile Ile Ala Tyr Thr Leu Asp Ser Leu Ser Lys Asn Gly Gln Val Leu
                245                 250                 255

Val Phe Arg Asn Ser Arg Lys Met Ala Glu Ser Thr Ala Leu Lys Ile
            260                 265                 270

Ala Asn Tyr Met Asn Phe Val Ser Leu Asp Glu Asn Ala Leu Ser Glu
        275                 280                 285

Ile Leu Lys Gln Leu Asp Asp Ile Glu Glu Gly Gly Ser Asp Glu Lys
    290                 295                 300

Glu Leu Leu Lys Ser Leu Ile Ser Lys Gly Val Ala Tyr His His Ala
305                 310                 315                 320

Gly Leu Ser Lys Ala Leu Arg Asp Leu Ile Glu Glu Gly Phe Arg Gln
                325                 330                 335

Arg Lys Ile Lys Val Ile Val Ala Thr Pro Thr Leu Ala Ala Gly Val
            340                 345                 350

Asn Leu Pro Ala Arg Thr Val Ile Gly Asp Ile Tyr Arg Phe Asn
        355                 360                 365

Lys Lys Ile Ala Gly Tyr Tyr Asp Glu Ile Pro Ile Met Glu Tyr Lys
    370                 375                 380

Gln Met Ser Gly Arg Ala Gly Arg Pro Gly Phe Asp Gln Ile Gly Glu
385                 390                 395                 400

Ser Ile Val Val Val Arg Asp Lys Glu Asp Val Asp Arg Val Phe Lys
                405                 410                 415
```

```
Lys Tyr Val Leu Ser Asp Val Glu Pro Ile Glu Ser Lys Leu Gly Ser
                420                 425                 430

Glu Arg Ala Phe Tyr Thr Phe Leu Leu Gly Ile Leu Ser Ala Glu Gly
            435                 440                 445

Asn Leu Ser Glu Lys Gln Leu Glu Asn Phe Ala Tyr Glu Ser Leu Leu
        450                 455                 460

Ala Lys Gln Leu Val Asp Val Tyr Phe Asp Arg Ala Ile Arg Trp Leu
465                 470                 475                 480

Leu Glu His Ser Phe Ile Lys Glu Gly Asn Thr Phe Ala Leu Thr
                485                 490                 495

Asn Phe Gly Lys Arg Val Ala Asp Leu Tyr Ile Asn Pro Phe Thr Ala
                500                 505                 510

Asp Ile Ile Arg Lys Gly Leu Glu Gly His Lys Ala Ser Cys Glu Leu
                515                 520                 525

Ala Tyr Leu His Leu Leu Ala Phe Thr Pro Asp Gly Pro Leu Val Ser
                530                 535                 540

Val Gly Arg Asn Glu Glu Glu Leu Ile Glu Leu Leu Glu Asp Leu
545                 550                 555                 560

Asp Cys Glu Leu Leu Ile Glu Glu Pro Tyr Glu Glu Asp Glu Tyr Ser
                565                 570                 575

Leu Tyr Ile Asn Ala Leu Lys Val Ala Leu Ile Met Lys Asp Trp Met
                580                 585                 590

Asp Glu Val Asp Glu Asp Thr Ile Leu Ser Lys Tyr Asn Ile Gly Ser
                595                 600                 605

Gly Asp Leu Arg Asn Met Val Thr Met Asp Trp Leu Thr Tyr Ser
610                 615                 620

Ala Tyr His Leu Ser Arg Glu Leu Lys Leu Asn Glu His Ala Asp Lys
625                 630                 635                 640

Leu Arg Ile Leu Asn Leu Arg Val Arg Asp Gly Ile Lys Glu Glu Leu
                645                 650                 655

Leu Glu Leu Val Gln Ile Ser Gly Val Gly Arg Lys Arg Ala Arg Leu
                660                 665                 670

Leu Tyr Asn Asn Gly Ile Lys Glu Leu Gly Asp Val Val Met Asn Pro
                675                 680                 685

Asp Lys Val Lys Asn Leu Leu Gly Gln Lys Leu Gly Glu Lys Val Val
690                 695                 700

Gln Glu Ala Ala Arg Leu Leu Asn Arg Phe His
705                 710                 715

<210> SEQ ID NO 26
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 26

Gln Met Ser Gly Arg Ala Gly Arg
1               5

<210> SEQ ID NO 27
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 27
```

Gln Met Ser Gly Arg Ala Gly Arg Pro
1               5

<210> SEQ ID NO 28
<211> LENGTH: 685
<212> TYPE: PRT
<213> ORGANISM: Methanogenium frigidum

<400> SEQUENCE: 28

Met Asp Leu Ser Leu Pro Lys Ala Phe Ile Gln Tyr Tyr Lys Asp Lys
1               5                   10                  15

Gly Ile Glu Ser Leu Tyr Pro Pro Gln Ser Glu Cys Ile Glu Asn Gly
            20                  25                  30

Leu Leu Asp Gly Ala Asp Leu Leu Val Ala Ile Pro Thr Ala Ser Gly
        35                  40                  45

Lys Thr Leu Ile Ala Glu Met Ala Met His Ala Ala Ile Ala Arg Gly
    50                  55                  60

Gly Met Cys Leu Tyr Ile Val Pro Leu Lys Ala Leu Ala Thr Glu Lys
65                  70                  75                  80

Ala Gln Glu Phe Lys Gly Lys Gly Ala Glu Ile Gly Val Ala Thr Gly
                85                  90                  95

Asp Tyr Asp Gln Lys Glu Lys Arg Leu Gly Ser Asn Asp Ile Val Ile
            100                 105                 110

Ala Thr Ser Glu Lys Val Asp Ser Leu Leu Arg Asn Gly Val Pro Trp
        115                 120                 125

Leu Ser Gln Val Thr Cys Leu Val Val Asp Glu Val His Leu Ile Asp
130                 135                 140

Asp Glu Ser Arg Gly Pro Thr Leu Glu Met Val Ile Thr Lys Leu Arg
145                 150                 155                 160

His Ala Ser Pro Asp Met Gln Val Ile Gly Leu Ser Ala Thr Ile Gly
                165                 170                 175

Asn Pro Lys Glu Leu Ala Gly Trp Leu Gly Ala Asp Leu Ile Thr Ser
            180                 185                 190

Asp Trp Arg Pro Val Asp Leu Arg Glu Gly Ile Cys Tyr His Asn Thr
        195                 200                 205

Ile Tyr Phe Asp Asn Glu Asp Lys Glu Ile Pro Ala Pro Ala Lys Thr
    210                 215                 220

Glu Asp Ile Asn Leu Leu Leu Asp Cys Val Ala Asp Gly Gly Gln Cys
225                 230                 235                 240

Leu Val Phe Val Ser Ser Arg Arg Asn Ala Glu Gly Tyr Ala Lys Arg
                245                 250                 255

Ala Ala Thr Ala Leu Lys Cys Ser His Ala Ala Leu Asp Ser Ile Ala
            260                 265                 270

Glu Lys Leu Glu Ala Ala Ala Glu Thr Asp Met Gly Arg Val Leu Ala
        275                 280                 285

Thr Cys Val Lys Lys Gly Ala Ala Phe His His Ala Gly Met Asn Arg
    290                 295                 300

Met Gln Arg Thr Leu Val Glu Gly Gly Phe Arg Asp Gly Phe Ile Lys
305                 310                 315                 320

Ser Ile Ser Ser Thr Pro Thr Leu Ala Ala Gly Leu Asn Leu Pro Ala
                325                 330                 335

Arg Arg Val Ile Ile Arg Asp Tyr Leu Arg Tyr Ser Gly Gly Glu Gly
            340                 345                 350

Met Arg Pro Ile Pro Val Arg Glu Tyr Arg Gln Met Ala Gly Arg Ala

-continued

```
                355                 360                 365
Gly Arg Pro His Leu Asp Pro Tyr Gly Glu Ala Ile Leu Ile Ala Lys
            370                 375                 380
Thr Glu Tyr Ala Val Asn Asp Leu His Glu Glu Tyr Val Glu Ala Pro
385                 390                 395                 400
Asp Glu Asp Val Thr Ser Arg Cys Gly Glu Lys Gly Val Leu Thr Ala
                405                 410                 415
His Ile Leu Ser Leu Ile Ala Thr Gly Tyr Ala Arg Ser Tyr Asp Glu
            420                 425                 430
Leu Met Ala Phe Leu Glu Lys Thr Leu Tyr Ala Tyr Gln His Thr Gly
        435                 440                 445
Lys Lys Ala Leu Thr Arg Thr Leu Asp Asp Ala Leu Gly Phe Leu Thr
    450                 455                 460
Glu Ala Glu Met Val Thr Asp Leu Ser Gly Met Leu His Ala Thr Glu
465                 470                 475                 480
Tyr Gly Asp Leu Thr Ser Arg Leu Tyr Ile Asp Pro His Ser Ala Glu
                485                 490                 495
Ile Ile Thr Thr Ala Leu Arg Glu Gly Glu Leu Thr Asp Leu Ala
            500                 505                 510
Leu Leu Gln Leu Leu Cys Met Thr Pro Asp Met Phe Thr Leu Tyr Val
        515                 520                 525
Lys Lys Asn Asp Leu Gly Thr Leu Glu Lys Phe Phe Glu His Glu
    530                 535                 540
Glu Glu Phe Arg Thr Glu Phe Ser Tyr Asp Glu Met Glu Asp Phe Phe
545                 550                 555                 560
Arg Ser Leu Lys Thr Ala Met Leu Leu Ser Asp Trp Thr Asp Glu Ile
                565                 570                 575
Gly Asp Asp Thr Ile Cys Thr Arg Phe Gly Val Gly Pro Gly Asp Ile
            580                 585                 590
Phe Asn Ala Val Gln Gly Ile Ser Trp Leu Leu His Ala Ser Gly Arg
        595                 600                 605
Leu Ala Arg Leu Val Ala Pro Glu His Arg Asp Ala Val Glu Glu Thr
    610                 615                 620
Thr Leu Arg Val Arg His Gly Ile Arg Arg Glu Leu Ile Pro Leu Val
625                 630                 635                 640
Arg Val Lys Gly Ile Gly Arg Val Arg Ala Arg Arg Leu Phe Asn Asn
                645                 650                 655
Gly Ile Thr Gly Pro Glu Leu Leu Ala Ala Asp Pro Ser Val Val
            660                 665                 670
Gly His Ile Val Gly Gly Lys Thr Ala Glu Ser Ile Ile
        675                 680                 685
```

<210> SEQ ID NO 29
<211> LENGTH: 775
<212> TYPE: PRT
<213> ORGANISM: Methanothermococcus okinawensis

<400> SEQUENCE: 29

```
Met Leu Met Leu Met Glu Val Leu Lys Glu Asn Gly Ile Ala Glu Leu
1               5                   10                  15
Arg Pro Pro Gln Lys Lys Val Val Glu Gly Gly Leu Leu Asn Lys Asn
                20                  25                  30
Lys Asn Phe Leu Ile Cys Ile Pro Thr Ala Ser Gly Lys Thr Leu Ile
            35                  40                  45
```

```
Gly Glu Met Ala Phe Ile Asn His Leu Leu Asp Asn Asn Lys Thr Pro
 50                  55                  60

Thr Asn Lys Lys Gly Leu Phe Ile Val Pro Leu Lys Ala Leu Ala Asn
 65                  70                  75                  80

Glu Lys Tyr Glu Glu Phe Lys Gly Lys Tyr Glu Lys Tyr Gly Leu Lys
                     85                  90                  95

Ile Ala Leu Ser Ile Gly Asp Phe Asp Glu Lys Glu Asp Leu Lys Gly
                100                 105                 110

Tyr Asp Leu Ile Ile Thr Thr Ala Glu Lys Leu Asp Ser Leu Ile Arg
                115                 120                 125

His Lys Val Glu Trp Ile Lys Asp Ile Ser Val Val Ile Asp Glu
130                 135                 140

Ile His Leu Ile Gly Asp Glu Ser Arg Gly Gly Thr Leu Glu Val Leu
145                 150                 155                 160

Leu Thr Lys Leu Lys Thr Lys Lys Thr Ile Gln Ile Ile Gly Leu Ser
                165                 170                 175

Ala Thr Ile Gly Asn Pro Glu Glu Leu Ala Lys Trp Leu Asn Ala Glu
                180                 185                 190

Leu Ile Val Asp Glu Trp Arg Pro Val Lys Leu Lys Lys Gly Ile Gly
                195                 200                 205

Tyr Gly Asn Lys Ile Met Phe Ile Asp Asp Asn Gly Asn Thr Ile Asn
210                 215                 220

Glu Val Ile Val Asp Glu Ile Ser Lys Asn Asn Met Phe Asn Leu Val
225                 230                 235                 240

Val Asp Ser Ile Leu Lys Asp Gly Ser Cys Ile Ile Phe Cys Asn Ser
                245                 250                 255

Lys Arg Gly Ala Val Gly Glu Ala Lys Lys Leu Asn Leu Lys Lys Tyr
                260                 265                 270

Leu Ser Pro Asp Glu Ile Ser Glu Leu Arg His Leu Lys Glu Glu Val
                275                 280                 285

Leu Ser Val Leu Asp Asn Pro Thr Lys Thr Cys Lys Asp Leu Ala Glu
                290                 295                 300

Cys Ile Glu Lys Gly Val Ala Phe His His Ala Gly Leu Thr Tyr Glu
305                 310                 315                 320

Gln Arg Lys Ile Val Glu Gly Phe Arg Lys Lys Leu Ile Lys Ala
                325                 330                 335

Ile Cys Cys Thr Pro Thr Leu Ser Ala Gly Ile Asn Met Pro Cys Arg
                340                 345                 350

Arg Ala Ile Ile Arg Asp Leu Lys Arg Phe Ser Ser Arg Gly Tyr Ile
                355                 360                 365

Pro Ile Pro Lys Met Glu Ile His Gln Cys Ile Gly Arg Ala Gly Arg
                370                 375                 380

Pro Asn Leu Asp Pro Tyr Gly Glu Gly Ile Ile Tyr Ile Asn Asn Thr
385                 390                 395                 400

Glu Asn Pro Glu Leu Ile Glu Asn Ala Lys Asn Tyr Leu Ile Gly Asn
                405                 410                 415

Val Glu Glu Ile Tyr Ser Lys Leu Ser Asn Gln Lys Val Leu Arg Thr
                420                 425                 430

His Met Leu Gly Leu Ile Thr Thr Gly Asp Ile Lys Asn Lys Asn Asp
                435                 440                 445

Leu Glu Glu Phe Ile Lys Asn Thr Phe Tyr Ala Tyr Gln Tyr Gln Asn
                450                 455                 460

Thr Lys Lys Ile Leu Glu Asn Ile Tyr Glu Ile Thr Asn Phe Leu Glu
```

```
                465                 470                 475                 480
Lys Asn Gly Phe Ile Glu Leu Asn Tyr Arg Arg Asp Glu Asn Lys Asp
                    485                 490                 495
Lys Ser Asn Asn Ser His Asn Asn Lys Lys Asn Ile Ser Asn Thr Asn
                500                 505                 510
Asn Ser Ile Lys Met Leu Val Leu Asp Asn Asn Ser Leu Thr Ile
            515                 520                 525
Lys Ser Arg His Glu Glu Asp Val Tyr Tyr Asn Ile Thr Pro Leu Gly
            530                 535                 540
Lys Lys Val Ser Glu Leu Tyr Ile Asp Pro Leu Ser Ala Glu Tyr Ile
545                 550                 555                 560
Ile Asp Gly Leu Lys Asn Leu His Lys Lys Thr Leu Ser Asn Pro Lys
                565                 570                 575
Asn Met Glu Cys Tyr Ile Leu His Ile Leu Tyr Ile Ile Ser Lys Thr
                580                 585                 590
Thr Glu Met Gln Pro Val Leu Arg Val Arg Arg Lys Glu Gly Asn Asp
                595                 600                 605
Leu Ile Asn Asp Met Ile Lys Leu Asp Ile Asp Val Asp Val Ile
            610                 615                 620
Tyr Gly Ile Ser Ser Glu Asn Leu Glu Tyr Phe Lys Asn Ala Lys Leu
625                 630                 635                 640
Phe Tyr Asp Trp Ile Asn Glu Ile Pro Glu Glu Leu Leu Leu Gly
                    645                 650                 655
Tyr Asn Ile Glu Pro Gly Ile Leu Arg Tyr Asn Val Glu Gln Ala Lys
                660                 665                 670
Trp Met Ile His Ser Ala Lys Glu Ile Phe Asn Leu Leu Asn Ile Asp
                675                 680                 685
Asn Lys Val Ile Lys Asp Cys Leu Asn Asp Leu Glu Ile Arg Met Glu
                690                 695                 700
Tyr Gly Ala Lys Gln Asp Ile Ile Glu Leu Leu Lys Ile Lys His Ile
705                 710                 715                 720
Gly Arg Ala Arg Ala Arg Ile Leu Tyr Asn Ala Gly Ile Lys Asn Ala
                    725                 730                 735
Asn Asp Ile Ile Asn Asn Gln Lys Asn Ile Ile Asn Leu Leu Gly Glu
                740                 745                 750
Lys Ile Ala Arg Lys Ile Leu Ser Glu Leu Gly Val Asp Thr Lys Phe
                755                 760                 765
Gly Gln Met Arg Leu Ser Ile
770                 775
```

<210> SEQ ID NO 30
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 30

Gln Cys Ile Gly Arg Ala Gly Arg
1               5

<210> SEQ ID NO 31
<211> LENGTH: 9
<212> TYPE: PRT
<213> ORGANISM: Artificial sequence
<220> FEATURE:
<223> OTHER INFORMATION: Exemplary extended Hel308 motif -continued

<400> SEQUENCE: 31

Gln Cys Ile Gly Arg Ala Gly Arg Pro
1               5

<210> SEQ ID NO 32
<211> LENGTH: 699
<212> TYPE: PRT
<213> ORGANISM: Methanotorris igneus

<400> SEQUENCE: 32

Met Gln Lys Tyr Ser His Val Phe Glu Val Leu Lys Glu Asn Gly Ile
1               5                   10                  15

Lys Glu Leu Arg Pro Pro Gln Lys Lys Val Ile Glu Lys Gly Leu Leu
                20                  25                  30

Asn Lys Glu Lys Asn Phe Leu Ile Cys Ile Pro Thr Ala Ser Gly Lys
            35                  40                  45

Thr Leu Ile Gly Glu Met Ala Leu Ile Asn His Leu Leu Asp Glu Asn
50                  55                  60

Lys Thr Pro Thr Asn Lys Lys Gly Leu Phe Ile Val Pro Leu Lys Ala
65                  70                  75                  80

Leu Ala Ser Glu Lys Tyr Glu Glu Phe Lys Arg Lys Tyr Glu Lys Tyr
                85                  90                  95

Gly Leu Lys Val Ala Leu Ser Ile Gly Asp Tyr Asp Glu Lys Glu Asp
            100                 105                 110

Leu Ser Ser Tyr Asn Ile Ile Ile Thr Thr Ala Glu Lys Leu Asp Ser
        115                 120                 125

Leu Met Arg His Glu Ile Asp Trp Leu Asn Tyr Val Ser Val Ala Ile
130                 135                 140

Val Asp Glu Ile His Met Ile Asn Asp Glu Lys Arg Gly Gly Thr Leu
145                 150                 155                 160

Glu Val Leu Leu Thr Lys Leu Lys Asn Leu Asp Val Gln Ile Ile Gly
                165                 170                 175

Leu Ser Ala Thr Ile Gly Asn Pro Glu Glu Leu Ala Glu Trp Leu Asn
            180                 185                 190

Ala Glu Leu Ile Ile Asp Asn Trp Arg Pro Val Lys Leu Arg Lys Gly
        195                 200                 205

Ile Phe Phe Gln Asn Lys Ile Met Tyr Leu Asn Gly Ala Cys Lys Glu
210                 215                 220

Leu Pro Asn Phe Ser Asn Asn Pro Met Leu Asn Leu Val Leu Asp Cys
225                 230                 235                 240

Val Lys Glu Gly Gly Cys Cys Leu Val Phe Cys Asn Ser Lys Asn Gly
                245                 250                 255

Ala Val Ser Glu Ala Lys Lys Leu Asn Leu Lys Lys Tyr Leu Ser Asn
            260                 265                 270

Ser Glu Lys Tyr Glu Leu Gln Lys Leu Lys Glu Glu Ile Leu Ser Ile
        275                 280                 285

Leu Asp Pro Pro Thr Glu Thr Cys Lys Thr Leu Ala Glu Cys Leu Glu
290                 295                 300

Lys Gly Val Ala Phe His His Ala Gly Leu Thr Tyr Glu His Arg Lys
305                 310                 315                 320

Ile Val Glu Glu Gly Phe Arg Asn Lys Leu Ile Lys Val Ile Cys Cys
                325                 330                 335

Thr Pro Thr Leu Ser Ala Gly Ile Asn Ile Pro Cys Arg Arg Ala Ile
            340                 345                 350

```
Val Arg Asp Leu Met Arg Phe Ser Asn Gly Arg Met Lys Pro Ile Pro
            355                 360                 365

Ile Met Glu Ile His Gln Cys Ile Gly Arg Ala Gly Arg Pro Gly Leu
        370                 375                 380

Asp Pro Tyr Gly Glu Gly Ile Ile Phe Val Lys Asn Glu Arg Asp Leu
385                 390                 395                 400

Glu Arg Ala Glu Gln Tyr Leu Glu Gly Lys Pro Glu Tyr Ile Tyr Ser
                405                 410                 415

Lys Leu Ser Asn Gln Ala Val Leu Arg Thr Gln Leu Leu Gly Met Ile
                420                 425                 430

Ala Thr Arg Glu Ile Glu Asn Glu Phe Asp Leu Ile Ser Phe Ile Lys
            435                 440                 445

Asn Thr Phe Tyr Ala His Gln Tyr Gly Asn Leu Gly Gly Val Leu Arg
        450                 455                 460

Asn Ile Lys Glu Val Ile Asn Phe Leu Glu Glu Asn Asp Phe Ile Ala
465                 470                 475                 480

Asp Tyr Phe Pro Thr Lys Leu Gly Lys Arg Val Ser Glu Leu Tyr Ile
                485                 490                 495

Asp Pro Leu Ser Ala Lys Ile Ile Asp Gly Leu Lys Glu Met Gly
                500                 505                 510

Asn Val Asp Asn Glu Glu Leu Tyr Tyr Leu Tyr Leu Ile Ser Lys Thr
            515                 520                 525

Leu Glu Met Met Pro Leu Leu Arg Val Asn Ser Phe Glu Glu Leu Asp
            530                 535                 540

Leu Ile Leu Glu Met Glu Ala Gly Ile Tyr Asp Arg Thr Tyr Asp
545                 550                 555                 560

Asp Leu Ala Ala Phe Lys Asn Ala Lys Met Leu Tyr Asp Trp Ile Asn
                565                 570                 575

Glu Val Pro Glu Asp Glu Ile Leu Lys Lys Tyr Lys Ile Glu Pro Gly
            580                 585                 590

Ile Leu Arg Tyr Lys Val Glu Gln Ala Lys Trp Met Ile Tyr Ser Thr
        595                 600                 605

Lys Glu Ile Ala Lys Leu Leu Asn Arg Asn Ile Asp Thr Leu Ser Lys
    610                 615                 620

Leu Glu Ile Arg Leu Glu Tyr Gly Ala Lys Glu Asp Ile Ile Glu Leu
625                 630                 635                 640

Leu Lys Ile Lys Tyr Val Gly Arg Ala Arg Ala Arg Lys Leu Tyr Asp
                645                 650                 655

Ala Gly Ile Arg Ser Val Glu Asp Ile Ile Asn Asn Pro Lys Lys Val
            660                 665                 670

Ala Ser Leu Leu Gly Lys Ile Ala Lys Lys Ile Leu Gly Glu Leu
            675                 680                 685

Gly Met Lys Phe Gly Gln Gln Thr Leu Gln Ile
    690                 695

<210> SEQ ID NO 33
<211> LENGTH: 720
<212> TYPE: PRT
<213> ORGANISM: Thermococcus gammatolerans

<400> SEQUENCE: 33

Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
```

```
                    20                  25                  30
Lys Ser Gly Ala Leu Glu Gly Arg Asn Leu Val Leu Ala Ile Pro Thr
            35                  40                  45
Ala Ser Gly Lys Thr Leu Val Ser Glu Ile Val Met Val Asn Lys Leu
    50                  55                  60
Ile Gln Glu Gly Gly Lys Ala Val Tyr Leu Val Pro Leu Lys Ala Leu
65                  70                  75                  80
Ala Glu Glu Lys Tyr Arg Glu Phe Lys Glu Trp Glu Lys Leu Gly Leu
                85                  90                  95
Lys Val Ala Ala Thr Gly Asp Tyr Asp Ser Thr Asp Asp Trp Leu
            100                 105                 110
Gly Arg Tyr Asp Ile Ile Val Ala Thr Ala Glu Lys Phe Asp Ser Leu
            115                 120                 125
Leu Arg His Gly Ala Arg Trp Ile Asn Asp Val Lys Leu Val Val Ala
            130                 135                 140
Asp Glu Val His Leu Ile Gly Ser Tyr Asp Arg Gly Ala Thr Leu Glu
145                 150                 155                 160
Met Ile Leu Thr His Met Leu Gly Arg Ala Gln Ile Leu Ala Leu Ser
                165                 170                 175
Ala Thr Val Gly Asn Ala Glu Glu Leu Ala Glu Trp Leu Asp Ala Ser
                180                 185                 190
Leu Val Val Ser Asp Trp Arg Pro Val Gln Leu Arg Arg Gly Val Phe
            195                 200                 205
His Leu Gly Thr Leu Ile Trp Glu Asp Gly Lys Val Glu Ser Tyr Pro
            210                 215                 220
Glu Asn Trp Tyr Ser Leu Val Val Asp Ala Val Lys Arg Gly Lys Gly
225                 230                 235                 240
Ala Leu Val Phe Val Asn Thr Arg Arg Ser Ala Glu Lys Glu Ala Leu
                245                 250                 255
Ala Leu Ser Lys Leu Val Ser Ser His Leu Thr Lys Pro Glu Lys Arg
            260                 265                 270
Ala Leu Glu Ser Leu Ala Ser Gln Leu Glu Asp Asn Pro Thr Ser Glu
            275                 280                 285
Lys Leu Lys Arg Ala Leu Arg Gly Gly Val Ala Phe His His Ala Gly
            290                 295                 300
Leu Ser Arg Val Glu Arg Thr Leu Ile Glu Asp Ala Phe Arg Glu Gly
305                 310                 315                 320
Leu Ile Lys Val Ile Thr Ala Thr Pro Thr Leu Ser Ala Gly Val Asn
                325                 330                 335
Leu Pro Ser Phe Arg Val Ile Ile Arg Asp Thr Lys Arg Tyr Ala Gly
                340                 345                 350
Phe Gly Trp Thr Asp Ile Pro Val Leu Glu Ile Gln Gln Met Met Gly
                355                 360                 365
Arg Ala Gly Arg Pro Arg Tyr Asp Lys Tyr Gly Glu Ala Ile Ile Val
            370                 375                 380
Ala Arg Thr Asp Glu Pro Gly Lys Leu Met Glu Arg Tyr Ile Arg Gly
385                 390                 395                 400
Lys Pro Glu Lys Leu Phe Ser Met Leu Ala Asn Glu Gln Ala Phe Arg
                405                 410                 415
Ser Gln Val Leu Ala Leu Ile Thr Asn Phe Gly Ile Arg Ser Phe Pro
            420                 425                 430
Glu Leu Val Arg Phe Leu Glu Arg Thr Phe Tyr Ala His Gln Arg Lys
            435                 440                 445
```

```
Asp Leu Ser Ser Leu Glu Tyr Lys Ala Lys Glu Val Val Tyr Phe Leu
            450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
                485                 490                 495

Ala Lys Lys Phe Lys Asp Ala Phe Pro Ala Ile Glu Arg Asn Pro Asn
            500                 505                 510

Pro Phe Gly Ile Phe Gln Leu Ile Ala Ser Thr Pro Asp Met Ala Thr
            515                 520                 525

Leu Thr Ala Arg Arg Glu Met Glu Asp Tyr Leu Asp Leu Ala Tyr
            530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
            580                 585                 590

Ile Asp Pro Gly Asp Leu Tyr Arg Leu Leu Glu Leu Ala Asp Trp Leu
            595                 600                 605

Met Tyr Ser Leu Ile Glu Leu Tyr Lys Leu Phe Glu Pro Lys Glu Glu
            610                 615                 620

Ile Leu Asn Tyr Leu Arg Asp Leu His Leu Arg Leu Arg His Gly Val
625                 630                 635                 640

Arg Glu Glu Leu Leu Glu Leu Val Arg Leu Pro Asn Ile Gly Arg Lys
                645                 650                 655

Arg Ala Arg Ala Leu Tyr Asn Ala Gly Phe Arg Ser Val Glu Ala Ile
            660                 665                 670

Ala Asn Ala Lys Pro Ala Glu Leu Leu Ala Val Glu Gly Ile Gly Ala
            675                 680                 685

Lys Ile Leu Asp Gly Ile Tyr Arg His Leu Gly Ile Glu Lys Arg Val
690                 695                 700

Thr Glu Glu Lys Pro Lys Arg Lys Gly Thr Leu Glu Asp Phe Leu Arg
705                 710                 715                 720

<210> SEQ ID NO 34
<211> LENGTH: 755
<212> TYPE: PRT
<213> ORGANISM: Thermococcus barophilus

<400> SEQUENCE: 34

Met Leu Ser Thr Lys Pro Lys Ala Tyr Lys Arg Phe Ser Pro Ile Gly
1               5                   10                  15

Tyr Ala Met Gln Val Asp Glu Leu Ser Lys Phe Gly Val Asp Glu Arg
            20                  25                  30

Ile Ile Arg Lys Ile Lys Glu Arg Gly Ile Ser Glu Phe Tyr Pro Pro
        35                  40                  45

Gln Ala Glu Ala Leu Arg Ser Gly Val Leu Asn Gly Glu Asn Leu Leu
    50                  55                  60

Leu Ala Ile Pro Thr Ala Ser Gly Lys Thr Leu Val Ala Glu Ile Val
65                  70                  75                  80

Met Leu His Lys Leu Phe Thr Gly Gly Gly Lys Ala Val Tyr Leu Val
                85                  90                  95

Pro Leu Lys Ala Leu Ala Glu Glu Lys Tyr Arg Glu Phe Lys Thr Trp
```

```
            100                 105                 110
Glu Asp Leu Gly Val Arg Val Ala Val Thr Thr Gly Asp Tyr Asp Ser
            115                 120                 125
Ser Glu Glu Trp Leu Gly Lys Tyr Asp Ile Ile Ile Ala Thr Ser Glu
            130                 135                 140
Lys Phe Asp Ser Leu Leu Arg His Lys Ser Arg Trp Ile Arg Asp Val
145                 150                 155                 160
Thr Leu Ile Val Ala Asp Glu Ile His Leu Leu Gly Ser Tyr Asp Arg
                165                 170                 175
Gly Ala Thr Leu Glu Met Ile Leu Ser His Met Leu Gly Lys Ala Gln
            180                 185                 190
Ile Leu Gly Leu Ser Ala Thr Val Gly Asn Ala Glu Glu Leu Ala Glu
            195                 200                 205
Trp Leu Asn Ala Lys Leu Val Val Ser Asp Trp Arg Pro Val Lys Leu
            210                 215                 220
Arg Lys Gly Val Phe Ala His Gly Gln Leu Ile Trp Glu Asp Gly Lys
225                 230                 235                 240
Val Asp Lys Phe Pro Pro Gln Trp Asp Ser Leu Val Ile Asp Ala Val
                245                 250                 255
Lys Lys Gly Lys Gln Ala Leu Val Phe Val Asn Thr Arg Arg Ser Ala
            260                 265                 270
Glu Lys Glu Ala Gly Met Leu Gly Lys Lys Val Arg Arg Leu Leu Thr
            275                 280                 285
Lys Pro Glu Ala Arg Arg Leu Lys Glu Leu Ala Glu Ser Leu Glu Ser
            290                 295                 300
Asn Pro Thr Asn Asp Lys Leu Lys Glu Val Leu Val Asn Gly Ala Ala
305                 310                 315                 320
Phe His His Ala Gly Leu Gly Arg Ala Glu Arg Thr Leu Ile Glu Asp
                325                 330                 335
Ala Phe Arg Glu Gly Leu Ile Lys Val Leu Thr Ala Thr Pro Thr Leu
            340                 345                 350
Ala Met Gly Val Asn Leu Pro Ser Phe Arg Val Ile Ile Arg Asp Thr
            355                 360                 365
Lys Arg Tyr Ser Thr Phe Gly Trp Ser Asp Ile Pro Val Leu Glu Ile
            370                 375                 380
Gln Gln Met Ile Gly Arg Ala Gly Arg Pro Lys Tyr Asp Lys Glu Gly
385                 390                 395                 400
Glu Ala Ile Ile Val Ala Lys Thr Glu Lys Pro Glu Glu Leu Met Glu
                405                 410                 415
Lys Tyr Ile Phe Gly Lys Pro Glu Lys Leu Phe Ser Met Leu Ser Asn
            420                 425                 430
Asp Ala Ala Phe Arg Ser Gln Val Leu Ala Leu Ile Thr Asn Phe Gly
            435                 440                 445
Val Glu Ser Phe Arg Glu Leu Ile Gly Phe Leu Glu Lys Thr Phe Tyr
            450                 455                 460
Tyr His Gln Arg Lys Asp Leu Glu Ile Leu Glu Gly Lys Ala Lys Ser
465                 470                 475                 480
Ile Val Tyr Phe Leu Leu Glu Asn Glu Phe Ile Asp Ile Asp Leu Asn
                485                 490                 495
Asp Ser Phe Ile Ala Leu Pro Phe Gly Ile Arg Thr Ser Gln Leu Tyr
            500                 505                 510
Leu Asp Pro Leu Thr Ala Lys Lys Phe Lys Asp Ala Leu Pro Gln Ile
            515                 520                 525
```

Glu Glu Asn Pro Asn Pro Leu Gly Ile Phe Gln Leu Leu Ala Ser Thr
            530                 535                 540

Pro Asp Met Gly Thr Leu Ser Ile Lys Arg Lys Glu Gln Glu Ser Tyr
545                 550                 555                 560

Leu Asp Tyr Ala Tyr Glu Met Glu Asp Tyr Leu Tyr Arg Ser Ile Pro
                565                 570                 575

Tyr Trp Glu Asp Tyr Glu Phe Gln Lys Phe Leu Ser Glu Val Lys Thr
            580                 585                 590

Ala Lys Leu Leu Leu Asp Trp Ile Asn Glu Val Ser Glu Ala Lys Leu
        595                 600                 605

Ile Glu Ala Tyr Gly Ile Asp Thr Gly Asp Leu Tyr Arg Ile Ile Glu
    610                 615                 620

Leu Ala Asp Trp Leu Met Tyr Ser Leu Ile Glu Leu Ala Lys Val Leu
625                 630                 635                 640

Asn Ala Gly Gly Glu Thr Ile Lys Tyr Leu Arg Arg Leu His Leu Arg
                645                 650                 655

Leu Lys His Gly Val Arg Glu Glu Leu Glu Leu Val Glu Leu Pro
            660                 665                 670

Met Ile Gly Arg Arg Arg Ala Arg Ala Leu Tyr Asn Ala Gly Phe Lys
        675                 680                 685

Asn Val Asn Asp Ile Val Lys Ala Lys Pro Ser Glu Leu Leu Ala Val
    690                 695                 700

Glu Gly Ile Gly Val Lys Val Leu Glu Arg Ile Tyr Arg His Phe Gly
705                 710                 715                 720

Val Glu Leu Pro Leu Leu Lys Asn Ile Lys Asp Pro Asp Lys Pro Glu
                725                 730                 735

Asp Lys Pro Lys Glu Lys Pro Lys Pro Lys Lys Gly Thr Leu Asp Tyr
            740                 745                 750

Phe Leu Lys
        755

<210> SEQ ID NO 35
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 35

Gln Met Ile Gly Arg Ala Gly Arg
1               5

<210> SEQ ID NO 36
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 36

Gln Met Ile Gly Arg Ala Gly Arg Pro
1               5

<210> SEQ ID NO 37
<211> LENGTH: 744
<212> TYPE: PRT
<213> ORGANISM: Thermococcus sibiricus

<400> SEQUENCE: 37

-continued

```
Met Lys Leu Asn Lys Leu Lys Ser Tyr Ile Asn Ala Phe Leu Leu Gly
1               5                   10                  15

Met Val Met Ser Met Lys Val Asp Glu Leu Lys Ser Leu Gly Val Asp
            20                  25                  30

Glu Arg Ile Leu Arg Leu Leu Arg Glu Arg Gly Ile Glu Glu Leu Tyr
            35                  40                  45

Pro Pro Gln Ala Asp Ala Leu Lys Thr Glu Val Leu Lys Gly Lys Asn
50                      55                  60

Leu Val Leu Ala Ile Pro Thr Ala Ser Gly Lys Thr Leu Val Ala Glu
65                  70                  75                  80

Ile Val Met Ile Asn Lys Ile Leu Arg Glu Gly Gly Lys Thr Val Tyr
                85                  90                  95

Leu Val Pro Leu Lys Ala Leu Ala Glu Glu Lys Tyr Lys Glu Phe Lys
                100                 105                 110

Phe Trp Glu Lys Leu Gly Ile Arg Ile Ala Met Thr Thr Gly Asp Tyr
            115                 120                 125

Asp Ser Thr Glu Glu Trp Leu Gly Lys Tyr Asp Ile Ile Ala Thr
        130                 135                 140

Ser Glu Lys Phe Asp Ser Leu Leu Arg His Lys Ser Pro Trp Ile Lys
145                 150                 155                 160

Asp Ile Asn Leu Val Ile Ala Asp Glu Ile His Leu Leu Gly Ser Tyr
                165                 170                 175

Asp Arg Gly Ala Thr Leu Glu Met Ile Leu Ala His Leu Asp Asp Lys
            180                 185                 190

Ala Gln Ile Leu Gly Leu Ser Ala Thr Val Gly Asn Ala Glu Glu Val
            195                 200                 205

Ala Glu Trp Leu Asn Ala Asp Leu Val Met Ser Glu Trp Arg Pro Val
            210                 215                 220

Ala Leu Arg Lys Gly Val Phe Tyr His Gly Glu Leu Phe Trp Glu Asp
225                 230                 235                 240

Gly Ser Ile Glu Arg Phe Pro Thr Gln Trp Asp Ser Leu Val Ile Asp
                245                 250                 255

Ala Leu Lys Lys Gly Lys Gln Ala Leu Val Phe Val Asn Thr Arg Arg
                260                 265                 270

Ser Ala Glu Lys Glu Ala Leu Leu Leu Ala Gly Lys Ile Gln Arg Phe
        275                 280                 285

Leu Thr Lys Pro Glu Glu Arg Lys Leu Lys Gln Leu Ala Asp Gly Leu
        290                 295                 300

Asp Thr Thr Pro Thr Asn Gln Lys Leu Lys Glu Ala Leu Thr Lys Gly
305                 310                 315                 320

Val Ala Phe His His Ala Gly Leu Gly Arg Thr Glu Arg Ser Ile Ile
                325                 330                 335

Glu Asp Ala Phe Arg Glu Gly Leu Ile Lys Val Ile Thr Ala Thr Pro
            340                 345                 350

Thr Leu Ser Ala Gly Val Asn Leu Pro Ala Tyr Arg Val Ile Ile Arg
            355                 360                 365

Asp Thr Lys Arg Tyr Ser Asn Phe Gly Trp Val Asp Ile Pro Val Leu
        370                 375                 380

Glu Ile Gln Gln Met Met Gly Arg Ala Gly Arg Pro Lys Tyr Asp Ile
385                 390                 395                 400

Glu Gly Gln Ala Ile Ile Ile Ala Lys Thr Glu Lys Pro Glu Asp Leu
                405                 410                 415
```

```
Met Lys Arg Tyr Val Leu Gly Lys Pro Glu Lys Leu Phe Ser Met Leu
                420                 425                 430

Ser Asn Glu Ala Ser Phe Arg Ser Gln Val Leu Ala Leu Ile Thr Asn
        435                 440                 445

Phe Gly Val Gly Asn Phe Lys Glu Leu Val Asn Phe Leu Glu Arg Thr
    450                 455                 460

Phe Tyr Tyr His Gln Arg Lys Asn Leu Glu Ala Leu Glu Gly Lys Ala
465                 470                 475                 480

Lys Ser Ile Val Tyr Phe Leu Phe Glu Asn Glu Phe Ile Asp Ile Asp
                485                 490                 495

Leu Asn Asp Gln Phe Met Pro Leu Pro Leu Gly Ile Arg Thr Ser Gln
            500                 505                 510

Leu Tyr Leu Asp Pro Val Thr Ala Lys Lys Phe Lys Asp Ala Phe Glu
        515                 520                 525

Lys Leu Glu Lys Asn Pro Asn Pro Leu Gly Ile Phe Gln Leu Leu Ala
    530                 535                 540

Ser Thr Pro Asp Met Ser Ser Leu Arg Val Lys Arg Lys Glu Gln Glu
545                 550                 555                 560

Asp Leu Leu Asp Tyr Ala Tyr Glu Met Glu Glu Tyr Leu Tyr Gln Asn
                565                 570                 575

Ile Pro Tyr Trp Glu Asp Tyr Lys Phe Glu Lys Phe Leu Gly Glu Thr
            580                 585                 590

Lys Thr Ala Lys Leu Leu Leu Asp Trp Ile Asn Glu Val Asn Asp Val
        595                 600                 605

Lys Ile Leu Glu Thr Tyr Glu Ile Asp Thr Gly Asp Leu Tyr Arg Ile
    610                 615                 620

Leu Glu Leu Val Asp Trp Leu Met Tyr Ser Leu Ile Glu Leu Tyr Lys
625                 630                 635                 640

Leu Phe Asp Pro Lys Pro Glu Val Leu Asp Phe Leu Lys Lys Leu His
                645                 650                 655

Ile Arg Val Lys His Gly Val Arg Glu Glu Leu Glu Leu Ile Thr
            660                 665                 670

Leu Pro Met Ile Gly Arg Lys Arg Ala Arg Ala Leu Tyr Asn Ala Gly
        675                 680                 685

Phe Lys Gly Ile Asp Asp Ile Val Arg Ala Lys Ala Ser Glu Leu Leu
690                 695                 700

Lys Val Glu Gly Ile Gly Ile Gly Val Ile Glu Lys Ile Tyr Gln His
705                 710                 715                 720

Phe Gly Val Glu Leu Pro Thr Asn Glu Lys Lys Lys Val Lys Lys
                725                 730                 735

Gly Thr Leu Asp Glu Phe Phe Lys
            740

<210> SEQ ID NO 38
<211> LENGTH: 729
<212> TYPE: PRT
<213> ORGANISM: Methanosarcina barkeri fusaro

<400> SEQUENCE: 38

Met Lys Ile Glu Ser Leu Asp Leu Pro Asp Glu Val Lys Gln Phe Tyr
1               5                   10                  15

Leu Asn Ser Gly Ile Met Glu Leu Tyr Pro Pro Gln Ala Glu Ala Val
            20                  25                  30

Glu Lys Gly Leu Leu Glu Gly Arg Asn Leu Leu Ala Ala Ile Pro Thr
        35                  40                  45
```

```
Ala Ser Gly Lys Thr Leu Leu Ala Glu Leu Ala Met Leu Lys Ser Ile
 50                  55                  60

Leu Ala Gly Gly Lys Ala Leu Tyr Ile Val Pro Leu Arg Ala Leu Ala
 65                  70                  75                  80

Ser Glu Lys Phe Arg Arg Phe Arg Glu Phe Ser Glu Leu Gly Ile Arg
                 85                  90                  95

Val Gly Ile Ser Thr Gly Asp Tyr Asp Leu Arg Asp Glu Gly Leu Gly
             100                 105                 110

Val Asn Asp Ile Ile Val Ala Thr Ser Glu Lys Thr Asp Ser Leu Leu
             115                 120                 125

Arg Asn Glu Thr Val Trp Met Gln Glu Ile Ser Val Val Val Ala Asp
             130                 135                 140

Glu Val His Leu Ile Asp Ser Pro Asp Arg Gly Pro Thr Leu Glu Val
145                 150                 155                 160

Thr Leu Ala Lys Leu Arg Lys Met Asn Pro Ser Cys Gln Ile Leu Ala
                165                 170                 175

Leu Ser Ala Thr Val Gly Asn Ala Asp Glu Leu Ala Val Trp Leu Glu
                180                 185                 190

Ala Glu Leu Val Val Ser Glu Trp Arg Pro Thr Glu Leu Leu Glu Gly
                195                 200                 205

Val Phe Phe Asn Gly Thr Phe Tyr Cys Lys Asp Arg Glu Lys Thr Val
            210                 215                 220

Glu Gln Ser Thr Lys Asp Glu Ala Val Asn Leu Ala Leu Asp Thr Leu
225                 230                 235                 240

Lys Lys Asp Gly Gln Cys Leu Val Phe Glu Ser Ser Arg Lys Asn Cys
                245                 250                 255

Met Ala Phe Ala Lys Lys Ala Ala Ser Thr Val Lys Lys Thr Leu Ser
                260                 265                 270

Ala Glu Asp Arg Asn Ala Leu Ala Gly Ile Ala Asp Glu Ile Leu Glu
                275                 280                 285

Asn Ser Glu Thr Asp Thr Ser Thr Asn Leu Ala Val Cys Ile Arg Ser
            290                 295                 300

Gly Thr Ala Phe His His Ala Gly Leu Thr Thr Pro Leu Arg Glu Leu
305                 310                 315                 320

Val Glu Asp Gly Phe Arg Ala Gly Arg Ile Lys Leu Ile Ser Ser Thr
                325                 330                 335

Pro Thr Leu Ala Ala Gly Leu Asn Leu Pro Ala Arg Arg Val Ile Ile
                340                 345                 350

Arg Asn Tyr Arg Arg Tyr Ser Ser Glu Asp Gly Met Gln Pro Ile Pro
            355                 360                 365

Val Leu Glu Tyr Lys Gln Met Ala Gly Arg Ala Gly Arg Pro Arg Leu
            370                 375                 380

Asp Pro Tyr Gly Glu Ala Val Leu Val Ala Lys Ser Tyr Lys Glu Phe
385                 390                 395                 400

Val Phe Leu Phe Glu Asn Tyr Ile Glu Ala Asn Ala Glu Asp Ile Trp
                405                 410                 415

Ser Lys Leu Gly Thr Glu Asn Ala Leu Arg Thr His Val Leu Ser Thr
            420                 425                 430

Ile Ser Asn Gly Phe Ala Arg Thr Tyr Asp Glu Leu Met Asp Phe Leu
            435                 440                 445

Glu Ala Thr Phe Phe Ala Phe Gln Tyr Ser Asn Phe Gly Leu Ser Thr
            450                 455                 460
```

-continued

Val Val Asn Glu Cys Leu Asn Phe Leu Arg Gln Glu Gly Met Leu Glu
465                 470                 475                 480

Lys Asp Asp Ala Leu Ile Pro Thr Ser Phe Gly Lys Leu Val Ser Arg
            485                 490                 495

Leu Tyr Ile Asp Pro Leu Ser Ala Ala Arg Ile Ala Lys Gly Leu Lys
            500                 505                 510

Gly Ala Lys Ser Leu Ser Glu Leu Thr Leu Leu His Leu Val Cys Ser
            515                 520                 525

Thr Pro Asp Met Arg Leu Leu Tyr Met Arg Ser His Asp Tyr Gln Asp
            530                 535                 540

Ile Asn Asp Tyr Val Met Ala His Ala Ser Glu Phe Val Lys Val Pro
545                 550                 555                 560

Ser Pro Phe Asp Thr Thr Glu Tyr Glu Trp Phe Leu Gly Val Lys
            565                 570                 575

Thr Ser Leu Leu Leu Leu Asp Trp Ile His Glu Lys Ser Glu Asn Glu
            580                 585                 590

Ile Cys Leu Lys Phe Gly Thr Gly Glu Gly Asp Ile His Ser Ile Ala
            595                 600                 605

Asp Ile Ala Glu Trp Ile Met His Val Thr Ser Gln Leu Ala Gly Leu
            610                 615                 620

Leu Asp Leu Lys Gly Ala Arg Glu Ala Ala Glu Leu Glu Lys Arg Ile
625                 630                 635                 640

His Tyr Gly Ala Ala Pro Glu Leu Ile Asp Leu Leu Asn Ile Arg Gly
            645                 650                 655

Ile Gly Arg Val Arg Ala Arg Lys Leu Tyr Glu Ala Gly Phe Lys Ser
            660                 665                 670

Ser Ala Glu Leu Ala Glu Val Asp Pro Glu Lys Val Ala Ala Leu Leu
            675                 680                 685

Gly Pro Lys Ile Ala Asp Arg Ile Phe Lys Gln Ile Arg Gly Arg Gly
            690                 695                 700

Thr Ser Ser Gly Ile Ile Ala Ser Glu Pro Pro Glu Lys Ser Pro Tyr
705                 710                 715                 720

Ser Gly Gln Lys Thr Ile Ser Asp Tyr
            725

<210> SEQ ID NO 39
<211> LENGTH: 730
<212> TYPE: PRT
<213> ORGANISM: Methanosarcina acetivorans

<400> SEQUENCE: 39

Met Lys Ile Glu Ser Leu Asp Leu Pro Asp Glu Val Lys Arg Phe Tyr
1               5                   10                  15

Glu Asn Ser Gly Ile Pro Glu Leu Tyr Pro Pro Gln Ala Glu Ala Val
            20                  25                  30

Glu Lys Gly Leu Leu Glu Gly Lys Asn Leu Leu Ala Ala Ile Pro Thr
        35                  40                  45

Ala Ser Gly Lys Thr Leu Leu Ala Glu Leu Ala Met Leu Lys Ser Val
    50                  55                  60

Leu Ala Gly Gly Lys Ala Leu Tyr Ile Val Pro Leu Arg Ala Leu Ala
65                  70                  75                  80

Ser Glu Lys Phe Arg Arg Phe Gln Asp Phe Ser Glu Leu Gly Ile Arg
                85                  90                  95

Val Gly Ile Ser Thr Gly Asp Tyr Asp Arg Arg Asp Glu Gly Leu Gly
            100                 105                 110

```
Ile Asn Asp Ile Ile Val Ala Thr Ser Glu Lys Thr Asp Ser Leu Leu
        115                 120                 125

Arg Asn Glu Thr Ala Trp Met Gln Glu Ile Ser Val Val Val Val Asp
130                 135                 140

Glu Val His Leu Ile Asp Ser Ala Asp Arg Gly Pro Thr Leu Glu Val
145                 150                 155                 160

Thr Leu Ala Lys Leu Arg Lys Met Asn Pro Phe Cys Gln Ile Leu Ala
                165                 170                 175

Leu Ser Ala Thr Val Gly Asn Ala Asp Glu Leu Ala Ala Trp Leu Asp
                180                 185                 190

Ala Glu Leu Val Leu Ser Glu Trp Arg Pro Thr Asp Leu Met Glu Gly
                195                 200                 205

Val Phe Phe Asp Gly Thr Phe Phe Cys Lys Asp Lys Glu Lys Leu Ile
        210                 215                 220

Glu Gln Pro Thr Lys Asp Glu Ala Ile Asn Leu Val Leu Asp Thr Leu
225                 230                 235                 240

Arg Glu Gly Gly Gln Cys Leu Val Phe Glu Ser Ser Arg Lys Asn Cys
                245                 250                 255

Met Gly Phe Ala Lys Lys Ala Thr Ser Ala Val Lys Lys Thr Leu Ser
                260                 265                 270

Ala Glu Asp Lys Glu Lys Leu Ala Gly Ile Ala Asp Glu Ile Leu Glu
                275                 280                 285

Asn Ser Glu Thr Asp Thr Ala Ser Val Leu Ala Ser Cys Val Arg Ala
                290                 295                 300

Gly Thr Ala Phe His His Ala Gly Leu Thr Ser Pro Leu Arg Glu Leu
305                 310                 315                 320

Val Glu Thr Gly Phe Arg Glu Gly Tyr Val Lys Leu Ile Ser Ser Thr
                325                 330                 335

Pro Thr Leu Ala Ala Gly Leu Asn Leu Pro Ala Arg Arg Val Ile Ile
                340                 345                 350

Arg Ser Tyr Arg Arg Tyr Ser Ser Asp Ser Gly Met Gln Pro Ile Pro
                355                 360                 365

Val Leu Glu Tyr Lys Gln Met Ala Gly Arg Ala Gly Arg Pro Arg Leu
                370                 375                 380

Asp Pro Tyr Gly Glu Ala Val Leu Leu Ala Lys Ser Tyr Glu Glu Leu
385                 390                 395                 400

Leu Phe Leu Phe Glu Lys Tyr Ile Glu Ala Gly Ala Glu Asp Ile Trp
                405                 410                 415

Ser Lys Leu Gly Thr Glu Asn Ala Leu Arg Thr His Val Leu Ser Thr
                420                 425                 430

Ile Ser Asn Gly Phe Ala Arg Thr Lys Glu Glu Leu Met Asp Phe Leu
                435                 440                 445

Glu Ala Thr Phe Phe Ala Tyr Gln Tyr Ser Asn Phe Gly Leu Ser Val
450                 455                 460

Val Val Asp Glu Cys Leu Asn Phe Leu Arg Gln Glu Gly Met Leu Glu
465                 470                 475                 480

Gln Asp Ser Asp Ala Leu Ile Ser Thr Met Phe Gly Lys Leu Val Ser
                485                 490                 495

Arg Leu Tyr Ile Asp Pro Leu Ser Ala Ala Leu Ile Ala Lys Gly Leu
                500                 505                 510

Arg Glu Ala Gly Thr Leu Thr Glu Leu Thr Leu Leu His Leu Val Cys
515                 520                 525
```

```
Ser Thr Pro Asp Met Arg Leu Met Tyr Met Arg Ser Gln Asp Tyr Gln
        530                 535                 540

Asp Ile Asn Asp Phe Val Met Ala His Ala Glu Glu Phe Ser Lys Val
545                 550                 555                 560

Pro Ser Pro Phe Asn Ile Val Glu Tyr Glu Trp Phe Leu Ser Glu Val
                565                 570                 575

Lys Thr Ser Leu Leu Met Asp Trp Ile His Glu Lys Pro Glu Asn
        580                 585                 590

Glu Ile Cys Leu Lys Phe Gly Thr Gly Glu Gly Asp Ile His Thr Thr
        595                 600                 605

Ala Asp Ile Ala Glu Trp Ile Met His Val Ala Thr Gln Leu Ala Arg
610                 615                 620

Leu Leu Asp Leu Lys Gly Ala Lys Glu Ala Ala Glu Leu Glu Lys Arg
625                 630                 635                 640

Ile His Tyr Gly Ala Gly Pro Glu Leu Met Asp Leu Leu Asp Ile Arg
                645                 650                 655

Gly Ile Gly Arg Val Arg Ala Arg Lys Leu Tyr Gly Ala Gly Phe Lys
                660                 665                 670

Ser Thr Ala Asp Leu Ala Gly Ala Thr Pro Glu Lys Val Ala Ala Leu
        675                 680                 685

Val Gly Pro Lys Ile Ala Glu Arg Ile Phe Arg Gln Ile Gly Arg Arg
        690                 695                 700

Glu Ala Val Ser Glu Ile Ser Asp Ser Glu Arg Leu Glu Lys Ser Ser
705                 710                 715                 720

Gln Asp Gly Gln Ser Thr Ile Ser Asp Phe
                725                 730

<210> SEQ ID NO 40
<211> LENGTH: 729
<212> TYPE: PRT
<213> ORGANISM: Methanohalophilus mahii

<400> SEQUENCE: 40

Met Lys Ile Glu Glu Leu Asp Leu Pro Ser Glu Ala Ile Glu Val Tyr
1               5                   10                  15

Leu Gln Ala Gly Ile Glu Glu Leu Tyr Pro Pro Gln Ala Asp Ala Val
                20                  25                  30

Glu Lys Gly Leu Leu Gln Gly Glu Asn Leu Leu Ala Ala Ile Pro Thr
        35                  40                  45

Ala Ser Gly Lys Thr Leu Leu Ala Glu Met Ala Met Leu Lys Ala Ile
50                  55                  60

Lys Lys Gly Gly Lys Ala Leu Tyr Ile Val Pro Leu Arg Ala Leu Ala
65                  70                  75                  80

Ser Glu Lys Phe Arg Asp Phe Lys Arg Phe Glu Ser Leu Gly Ile Lys
                85                  90                  95

Thr Ala Ile Ser Thr Gly Asp Phe Asp Ser Arg Asp Glu Trp Leu Gly
                100                 105                 110

Ser Asn Asp Ile Ile Val Ala Thr Ser Glu Lys Thr Asp Ser Leu Leu
        115                 120                 125

Arg Asn Ser Thr Pro Trp Met Lys Asp Ile Thr Ala Val Ile Val Asp
130                 135                 140

Glu Val His Leu Leu Asp Ser Ala Asn Arg Gly Pro Thr Leu Glu Val
145                 150                 155                 160

Thr Leu Ala Lys Leu Lys Arg Leu Asn Pro Gly Ala Gln Val Val Ala
                165                 170                 175
```

```
Leu Ser Ala Thr Val Gly Asn Ala Met Glu Ile Ala Gln Trp Leu Glu
            180                 185                 190

Ala Lys Leu Val Leu Ser Glu Trp Arg Pro Thr Tyr Leu His Glu Gly
        195                 200                 205

Ile Phe Tyr Gly Asp Ala Ile Asn Phe Asp Glu Asp Gln Thr Phe Ile
210                 215                 220

Glu Arg Arg His Lys Glu Asp Ser Val Asn Leu Val Ile Asp Thr Val
225                 230                 235                 240

Ile Gln Gly Gly Gln Cys Leu Val Phe Asp Ser Ser Arg Arg Asn Cys
                245                 250                 255

Val Gly Phe Ala Lys Lys Cys Ala Pro Ala Val Gly Glu Leu Leu Asp
            260                 265                 270

Arg Gln Asn Arg Asn Glu Leu Glu Glu Val Ala Lys Glu Val Leu Glu
        275                 280                 285

Asn Gly Glu Thr Lys Leu Thr Glu Thr Leu Ala Tyr Cys Ile Lys Lys
    290                 295                 300

Gly Val Ala Phe His His Ala Gly Leu Asn Ser Ala His Arg Arg Ile
305                 310                 315                 320

Val Glu Asp Ala Phe Arg Asn Asn Leu Ile Lys Met Ile Cys Ser Thr
                325                 330                 335

Pro Thr Leu Ala Ala Gly Leu Asn Leu Pro Ala Arg Arg Val Ile Ile
            340                 345                 350

Arg Ser Tyr Lys Arg Tyr Asp Pro Asn Ala Gly Met Gln Pro Ile Pro
        355                 360                 365

Val Leu Asp Tyr Lys Gln Met Ala Gly Arg Ala Gly Arg Pro His Leu
    370                 375                 380

Asp Pro Tyr Gly Glu Ala Val Val Ile Val Lys Thr Tyr Glu Glu Phe
385                 390                 395                 400

Thr Asp Val Leu Glu Arg Tyr Ile Ser Ala Ser Ala Glu Asp Ile Trp
                405                 410                 415

Ser Lys Leu Gly Thr Glu Asn Ala Leu Arg Thr His Ile Leu Ser Thr
            420                 425                 430

Ile Ala Ser Gly Phe Ala Asn Cys His Arg Glu Ile Leu Thr Phe Leu
        435                 440                 445

Gly Ser Thr Phe Phe Ala His Gln Gln Gln Ser Trp Asn Phe Glu Glu
    450                 455                 460

Leu Leu Glu Asp Cys Leu Ile Phe Leu Lys Asn Glu Gly Met Leu Glu
465                 470                 475                 480

Gln Asp Asn Glu Thr Ile Arg Ala Thr Glu Leu Gly Lys Met Ile Ser
                485                 490                 495

Ser Leu Tyr Ile Asp Pro Leu Ser Ala Ser Lys Ile Ile Arg Gly Leu
            500                 505                 510

Glu Lys Thr Thr His Val Thr Asp Met Thr Leu Leu Gln Leu Ile Cys
        515                 520                 525

Ser Thr Pro Asp Met Arg Leu Leu Tyr Leu Arg Asn Arg Asp Tyr Glu
    530                 535                 540

Ile Ile Asn Asp Tyr Val Met Asn His Thr Glu Glu Phe Ile Glu Val
545                 550                 555                 560

Pro Ser Pro Phe Lys Gln Ile Glu Tyr Glu Trp Phe Leu Ser Glu Val
                565                 570                 575

Lys Thr Ala Leu Leu Leu Leu Glu Trp Ile Asn Glu Lys Ser Leu Glu
            580                 585                 590
```

```
Lys Ile Val Glu Asn Tyr Gln Val Gly Gly Asp Ile Tyr Ala Ser
            595                 600                 605

Ser Asp Ile Ala Glu Trp Leu Met His Ala Thr Gln Arg Ile Ala Ser
610                 615                 620

Arg Ile Asn Pro Gln Leu Glu Thr Glu Cys Ala Lys Leu Glu Lys Arg
625                 630                 635                 640

Ile His Tyr Gly Ala Gly Ser Glu Leu Ile Glu Leu Val Glu Ile Pro
                645                 650                 655

Asn Val Gly Arg Ala Arg Ala Arg Lys Leu Phe Lys Lys Gly Tyr Arg
            660                 665                 670

Ser Arg Gln Lys Leu Ala Thr Ala Asp Glu Lys Gln Leu Ala Gly Ile
        675                 680                 685

Val Gly Pro Lys Ile Ala Gln Lys Ile Leu Ser Tyr Leu Gly Arg Glu
    690                 695                 700

Thr Asp Ser Asn Gly Tyr Val Glu Pro Glu Thr Leu Glu Asn Lys Lys
705                 710                 715                 720

Gln Gln Lys Thr Phe Gln Asp Phe Ile
                725

<210> SEQ ID NO 41
<211> LENGTH: 730
<212> TYPE: PRT
<213> ORGANISM: Methanosarcina mazei

<400> SEQUENCE: 41

Met Lys Ile Glu Ser Leu Asp Leu Pro Asp Glu Ile Lys Arg Phe Tyr
1               5                   10                  15

Glu Asn Ser Gly Ile Leu Glu Leu Tyr Pro Pro Gln Ala Glu Ala Val
                20                  25                  30

Glu Lys Gly Leu Leu Glu Gly Lys Asn Leu Leu Ala Ala Ile Pro Thr
            35                  40                  45

Ala Ser Gly Lys Thr Leu Leu Ala Glu Leu Ala Met Leu Lys Ser Val
        50                  55                  60

Leu Asn Gly Gly Lys Ala Leu Tyr Ile Val Pro Leu Arg Ala Leu Ala
65                  70                  75                  80

Ser Glu Lys Phe Arg Arg Phe Gln Glu Phe Ser Val Leu Gly Met Arg
                85                  90                  95

Val Gly Ile Ser Thr Gly Asp Tyr Asp Arg Arg Asp Glu Gly Leu Gly
                100                 105                 110

Ile Asn Asp Ile Ile Val Ala Thr Ser Glu Lys Thr Asp Ser Leu Leu
            115                 120                 125

Arg Asn Glu Thr Ala Trp Met Gln Glu Ile Ser Val Val Ala Asp
        130                 135                 140

Glu Val His Leu Ile Asp Ser Pro Asp Arg Gly Pro Thr Leu Glu Ile
145                 150                 155                 160

Thr Leu Ser Lys Leu Arg Arg Met Asn Pro Ser Cys Gln Val Leu Ala
                165                 170                 175

Leu Ser Ala Thr Val Gly Asn Ala Asp Glu Leu Ala Ala Trp Leu Asp
            180                 185                 190

Ala Glu Leu Val Leu Ser Glu Trp Arg Pro Thr Asp Leu Met Glu Gly
        195                 200                 205

Val Phe Tyr Asn Gly Ile Phe Tyr Cys Lys Asp Lys Glu Lys Pro Val
    210                 215                 220

Gly Gln Pro Thr Lys Asp Glu Ala Val Asn Leu Val Leu Asp Thr Ile
225                 230                 235                 240
```

-continued

```
Lys Glu Gly Gly Gln Cys Leu Val Phe Glu Ser Ser Arg Lys Asn Cys
                245                 250                 255
Met Gly Phe Ala Lys Lys Ala Val Ser Ala Val Lys Lys Thr Leu Ser
            260                 265                 270
Asn Glu Asp Arg Glu Thr Leu Ala Gly Ile Ala Asp Glu Ile Ile Glu
        275                 280                 285
Asn Ser Glu Thr Asp Val Ser Ser Val Leu Ala Thr Cys Val Arg Ser
    290                 295                 300
Gly Thr Ala Phe His His Ala Gly Leu Thr Thr Pro Leu Arg Glu Leu
305                 310                 315                 320
Val Glu Asn Gly Phe Arg Glu Gly Arg Ile Lys Ile Ile Ser Ser Thr
                325                 330                 335
Pro Thr Leu Ala Ala Gly Leu Asn Leu Pro Ala Arg Arg Val Ile Ile
            340                 345                 350
Arg Ser Tyr Arg Arg Tyr Ser Ser Asp Ser Gly Met Gln Pro Ile Pro
        355                 360                 365
Val Leu Glu Tyr Lys Gln Met Ala Gly Arg Ala Gly Arg Pro Arg Leu
    370                 375                 380
Asp Pro Tyr Gly Glu Ala Val Leu Leu Ala Lys Ser Tyr Glu Phe
385                 390                 395                 400
Val Phe Leu Phe Glu Lys Tyr Ile Glu Ala Gly Ala Glu Asp Ile Trp
                405                 410                 415
Ser Lys Leu Gly Thr Glu Asn Ala Leu Arg Thr His Ile Leu Ser Thr
            420                 425                 430
Ile Ser Asn Gly Phe Ala Arg Thr Arg Glu Glu Leu Met Asp Phe Leu
        435                 440                 445
Glu Ala Thr Phe Phe Ala Phe Gln Tyr Ser Asn Phe Gly Leu Ser Ala
    450                 455                 460
Val Val Asp Glu Cys Leu Asp Phe Leu Arg Arg Glu Gly Met Leu Glu
465                 470                 475                 480
Lys Asp Pro Asp Ala Leu Val Ser Thr Val Phe Gly Lys Leu Val Ser
                485                 490                 495
Arg Leu Tyr Ile Asp Pro Leu Ser Ala Ala Leu Ile Ala Lys Gly Leu
            500                 505                 510
Arg Glu Ala Gly Thr Leu Thr Glu Leu Thr Leu Leu His Leu Ile Cys
        515                 520                 525
Ser Thr Pro Asp Met Arg Leu Met Tyr Met Arg Ser Gln Asp Tyr Gln
    530                 535                 540
Glu Val Asn Asp Tyr Val Met Ala His Ala Gly Glu Phe Ser Lys Val
545                 550                 555                 560
Pro Asn Pro Phe Asn Ile Ala Glu Tyr Glu Trp Phe Leu Gly Glu Val
                565                 570                 575
Lys Thr Ser Leu Leu Leu Met Asp Trp Ile His Glu Lys Pro Glu Asn
            580                 585                 590
Glu Ile Cys Leu Lys Phe Gly Ile Gly Glu Gly Asp Ile His Ala Thr
        595                 600                 605
Ala Asp Ile Ala Glu Trp Ile Met His Val Thr Ala Gln Leu Ala Gly
    610                 615                 620
Leu Leu Asp Leu Lys Gly Ala Lys Glu Ala Ser Glu Leu Glu Lys Arg
625                 630                 635                 640
Ile Arg Tyr Gly Ala Ala Pro Glu Leu Met Asp Leu Leu Asp Ile Arg
                645                 650                 655
```

```
Ser Val Gly Arg Val Arg Ala Arg Lys Leu Tyr Glu Ala Gly Phe Lys
                660                 665                 670

Ser Thr Ala Glu Leu Ala Ala Ser Pro Glu His Ile Ala Val Leu
        675                 680                 685

Val Gly Pro Lys Ile Thr Glu Arg Ile Phe Lys Gln Ile Gly Arg Arg
690                 695                 700

Glu Ala Val Ser Glu Phe Ser Asp Ile Glu Pro Leu Glu Lys Gly Ser
705                 710                 715                 720

Ser Asp Gly Gln Arg Thr Ile Ser Asp Tyr
                725                 730

<210> SEQ ID NO 42
<211> LENGTH: 693
<212> TYPE: PRT
<213> ORGANISM: Methanosaeta thermophila

<400> SEQUENCE: 42

Met Leu Thr Ile Arg Asp Leu Ile Arg Trp Leu Pro Glu Ser Val Ile
1               5                   10                  15

Glu Leu Tyr Glu Ala Leu Gly Ile Asp Glu Leu Tyr Pro Pro Gln Ala
                20                  25                  30

Glu Ala Ile Glu Arg Gly Leu Leu Asp Gly Arg Asn Met Ile Ile Ser
            35                  40                  45

Val Pro Thr Ala Ala Gly Lys Thr Leu Leu Ala Glu Leu Ala Met Leu
50                  55                  60

Arg Gly Ala Leu Ser Gly Lys Arg Ser Leu Tyr Ile Val Pro Leu Arg
65                  70                  75                  80

Ala Leu Ala Ser Glu Lys Phe Glu Ser Phe Ser Arg Phe Ser Lys Leu
                85                  90                  95

Gly Leu Arg Val Gly Ile Ser Thr Gly Asp Phe Glu Lys Arg Asp Glu
            100                 105                 110

Arg Leu Gly Arg Asn Asp Ile Ile Ile Ala Thr Ser Glu Lys Ala Asp
            115                 120                 125

Ser Leu Ile Arg Asn Gly Ala Ser Trp Val Arg Arg Ile Gly Val Leu
        130                 135                 140

Val Val Asp Glu Ile His Leu Leu Asp Ser Ala Asn Arg Gly Pro Thr
145                 150                 155                 160

Leu Glu Met Thr Met Thr Lys Leu Met His Leu Asn Pro Glu Met Gln
                165                 170                 175

Val Ile Gly Leu Ser Ala Thr Ile Ala Asn Gly Arg Glu Ile Ala Asp
            180                 185                 190

Trp Ile Lys Gly Glu Ile Val Ser Ser Asp Trp Arg Pro Val Arg Leu
        195                 200                 205

Arg Glu Gly Val Leu Leu Glu Asp Arg Leu Val Phe Pro Asp Gly Glu
    210                 215                 220

Ile Gln Leu Glu Asn Arg Asn Arg Asp Pro Val Leu Asn Leu Val Leu
225                 230                 235                 240

Asp Thr Val Asp Gln Gly Gly Gln Met Leu Ile Phe Glu Ser Thr Arg
                245                 250                 255

Arg Asn Ala Glu Ser Met Ala Lys Lys Val Ser Gly Ala Leu Gln Glu
            260                 265                 270

Ser Gly Glu Thr Ile Glu Leu Ala Glu Arg Leu Ser Gly Glu Gly Lys
        275                 280                 285

Thr Ala Lys Lys Leu Ala Met Cys Leu Arg His Gly Ala Ala Phe His
    290                 295                 300
```

His Ala Gly Leu Leu Pro Glu Gln Arg Arg Leu Ile Glu Leu Gly Phe
305                 310                 315                 320

Arg Gln Asn Val Val Lys Val Ile Ala Cys Thr Pro Thr Leu Ala Ala
                325                 330                 335

Gly Leu Asn Leu Pro Ala Arg Arg Val Leu Ile Arg Ser Tyr Lys Arg
            340                 345                 350

Tyr Glu Ala Gly Leu Gly Thr Arg Pro Ile Pro Val Met Glu Tyr Arg
        355                 360                 365

Gln Met Ala Gly Arg Ala Gly Arg Pro Gly Leu Asp Pro Tyr Gly Glu
370                 375                 380

Ser Leu Ile Met Ala Arg Ser Glu Ser Glu Leu Gln Lys Leu Met Asp
385                 390                 395                 400

His Tyr Val Met Gly Glu Pro Glu Asp Ile Trp Ser Lys Leu Ala Ser
                405                 410                 415

Glu Arg Ala Leu Arg Thr His Val Leu Ala Thr Ile Ala Ser Arg Phe
            420                 425                 430

Ala Asp Ser Val Asp Ser Leu Ser Arg Leu Met Ala Ser Thr Phe Tyr
        435                 440                 445

Ala Arg Gln Gln Asp Pro Ser Tyr Leu Gly Glu Thr Ile Ala Ser Val
450                 455                 460

Leu Glu Phe Leu Val Arg Ser Asp Met Ile Asp Lys Asp Leu Thr Pro
465                 470                 475                 480

Thr Pro Leu Gly Ala Leu Val Ser Arg Leu Tyr Ile Asp Pro Leu Ser
                485                 490                 495

Ala Met Val Met Ile Gln Glu Ile Arg Gly Ile Arg Arg Pro Thr Val
            500                 505                 510

Leu Thr Leu Leu His Val Ile Thr Met Thr Pro Asp Met Glu Leu Leu
        515                 520                 525

Phe Val Gln Gln Ser Asp Asn Trp Leu Glu Asp Phe Ile Ser Glu His
530                 535                 540

Ser Ser Glu Leu Gly Asn Glu Lys Asn Phe Asp Trp Leu Leu Arg Glu
545                 550                 555                 560

Val Lys Thr Ala Ser Met Leu Met Asp Trp Ile Asn Glu Val His Glu
                565                 570                 575

Asp Arg Ile Glu Asp Arg Tyr Ser Ile Ser Pro Gly Asp Leu Val Arg
            580                 585                 590

Ile Ala Glu Thr Ala Glu Trp Leu Met Ser Ala Leu His Arg Ile Ser
        595                 600                 605

Lys His Met Asp Leu Gly Val Thr Tyr Leu Ala Glu Arg Leu Ala Leu
610                 615                 620

Arg Ile His Tyr Gly Ala Gly Asp Glu Leu Leu Gln Leu Leu Glu Leu
625                 630                 635                 640

Lys Gly Ile Gly Arg Val Arg Ala Arg Lys Leu Tyr Gln Ala Gly Tyr
                645                 650                 655

Arg Ser Leu Glu Asp Leu Lys Ala Ala Asp Lys Ser Thr Leu Ser Glu
            660                 665                 670

Ile Leu Gly Pro Lys Ile Ala Glu Gly Val Ile Ser Gln Leu Lys Glu
        675                 680                 685

Pro Gly Val Ser Ala
    690

<210> SEQ ID NO 43
<211> LENGTH: 739

<212> TYPE: PRT
<213> ORGANISM: Methanosalsum zhilinae

<400> SEQUENCE: 43

```
Met Asn Ile Asn Asn Leu Asn Leu Pro Glu Lys Val Lys Tyr Tyr
1               5                   10                  15

Thr Asp Thr Gly Ile Val Asp Leu Tyr Pro Pro Gln Arg Glu Ala Val
            20                  25                  30

Asp Lys Gly Leu Leu Asp Gly Glu Asn Ile Val Ala Ala Ile Pro Thr
        35                  40                  45

Ala Ser Gly Lys Thr Leu Leu Ala Glu Leu Cys Met Leu Lys Ser Ile
    50                  55                  60

Gly Met Gly Gly Lys Cys Leu Tyr Ile Val Pro Leu Lys Ala Leu Ala
65                  70                  75                  80

Ser Glu Lys Tyr Ser Arg Phe Arg Glu Phe Glu Ser Leu Gly Ile Lys
                85                  90                  95

Val Gly Ile Ala Thr Gly Asp Leu Asp Ser Arg Glu Glu Trp Leu Gly
            100                 105                 110

Lys Asn Asp Ile Ile Ile Ala Thr Ser Glu Lys Val Asp Ser Leu Leu
        115                 120                 125

Arg Asn Glu Ser Ser Trp Met Lys Glu Ile Asn Thr Val Val Ala Asp
    130                 135                 140

Glu Val His Leu Leu Asn Ser Val Asn Arg Gly Pro Thr Leu Glu Ile
145                 150                 155                 160

Thr Leu Ala Lys Leu Ile His Leu Asn Pro Gly Ser Gln Ile Ile Ala
                165                 170                 175

Leu Ser Ala Thr Ile Gly Asn Pro Glu Asp Ile Ala Gly Trp Leu Gly
            180                 185                 190

Ala Arg Leu Val Val Ser Glu Trp Arg Pro Thr Asp Leu Tyr Glu Gly
        195                 200                 205

Ile Leu Leu Asp Gly Leu Leu His Ile Gly Asn Ile Lys Lys Asp Ile
    210                 215                 220

Gln Asp Glu Ser Arg Asp Asp Ala Val Asn Leu Val Ile Asp Thr Val
225                 230                 235                 240

Lys Asp Lys Gly Gln Cys Leu Val Phe Glu Ser Ser Arg Arg Asn Cys
                245                 250                 255

Met Gly Phe Ala Lys Lys Ala Gly Lys Trp Val Ser Lys Ile Leu Asp
            260                 265                 270

Glu His Asp Thr Ile Gln Leu Lys Ser Leu Ser Gln Glu Ile Gly Glu
        275                 280                 285

Ala Gly Glu Thr Glu Ile Ala Asp Val Leu Ser Arg Cys Val Arg Gln
    290                 295                 300

Gly Val Ala Phe His His Ala Gly Leu Asn Ser Glu His Arg Arg Met
305                 310                 315                 320

Val Glu Glu Gly Phe Arg Lys Asn Leu Ile Lys Met Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Lys Arg Tyr Asp Pro Asn Phe Gly Met Lys Pro Ile Pro
        355                 360                 365

Val Leu Glu Tyr Lys Gln Met Ala Gly Arg Ala Gly Arg Pro His Leu
    370                 375                 380

Asp Pro Tyr Gly Glu Ser Val Leu Ile Ala Arg Ser Tyr Asp Glu Phe
385                 390                 395                 400
```

Met Asp Ile Met Glu Asn Tyr Val Asn Ala Asp Pro Glu Asp Ile Trp
                405                 410                 415

Ser Lys Leu Gly Thr Glu Asn Ala Leu Arg Thr His Val Leu Ser Thr
            420                 425                 430

Ile Val Asn Gly Phe Ala Tyr Thr Tyr Arg Gly Leu Met Asp Phe Val
        435                 440                 445

Lys Met Thr Phe Phe Ala Tyr Gln Lys Glu Ala Ser Asp Leu His Asp
    450                 455                 460

Val Ile Glu Glu Cys Val Arg Phe Leu Ile Asp Asn Glu Met Ile Ile
465                 470                 475                 480

Ser Asp Ser Asn Asp Ile Leu Pro Glu Ser Ala Phe Arg Ser Thr Ala
                485                 490                 495

Thr Gly Lys Leu Ile Ser Met Leu Tyr Ile Asp Pro Leu Ser Gly Ser
            500                 505                 510

Leu Ile Met Asp Gly Ile Arg Lys Ala Asp Tyr Phe Glu Asp Ile Thr
        515                 520                 525

Met Met His Leu Ile Cys Ser Thr Pro Asp Met Lys Asn Leu Tyr Met
    530                 535                 540

Arg Ser Ser Asp Tyr Glu Asn Val Asn Met Tyr Val Leu Gln Asn Lys
545                 550                 555                 560

Asp Lys Phe Ile Ser Met Pro Ser Pro Phe Lys Met Ile Glu Tyr Glu
                565                 570                 575

Trp Phe Leu Gly Glu Val Lys Thr Ala Leu Leu Leu Asp Trp Ile
            580                 585                 590

Asn Glu Val Pro Ala Asp Asp Ile Cys Lys Lys Tyr Gly Ile Gly Glu
        595                 600                 605

Gly Asp Ile Arg Met Phe Ser Glu Thr Ala Val Trp Leu Met His Ala
    610                 615                 620

Thr Ser Arg Leu Ser Gly Leu Leu Lys Val Ser Glu Ala Ser Glu Lys
625                 630                 635                 640

Ser Lys Glu Leu Glu Lys Arg Leu Ser Tyr Gly Ile Asn Ser Glu Leu
                645                 650                 655

Val Asn Ile Val Ala Leu Lys Gly Ile Gly Arg Val Arg Ala Arg Lys
            660                 665                 670

Ile Tyr Glu Asn Gly Tyr Arg Ser Ile Asp Asp Leu Lys Lys Ala Asp
        675                 680                 685

Pro Leu Lys Leu Ser Lys Ile Val Gly Ser Lys Ile Ser Gln Lys Ile
    690                 695                 700

Leu Lys Gln Leu Asp Ile Asp Val Asp Ile Ser Glu Ile Lys Glu Lys
705                 710                 715                 720

Asp Ser Asp Thr Val Pro Glu Pro Glu Ser Ser Gln Lys Thr Ile Ser
                725                 730                 735

Asp Phe Thr

<210> SEQ ID NO 44
<211> LENGTH: 733
<212> TYPE: PRT
<213> ORGANISM: Methanohalobium evestigatum

<400> SEQUENCE: 44

Met Glu Thr Gly Lys Leu Glu Leu Pro Glu Tyr Val Ile Gln Phe Tyr
1               5                   10                  15

Leu Asp Thr Gly Ile Glu Lys Leu Tyr Pro Pro Gln Ala Glu Ala Val
            20                  25                  30

```
Glu Lys Gly Leu Leu Asp Asn Lys Asn Leu Leu Ala Ala Ile Pro Thr
            35                  40                  45

Ala Ser Gly Lys Thr Leu Ile Ser Glu Leu Ala Met Leu Lys Ser Ile
 50                  55                  60

Ser Asn Gly Gly Lys Cys Leu Tyr Ile Val Pro Leu Arg Ala Leu Ala
 65                  70                  75                  80

Ser Glu Lys Phe Glu Arg Phe Lys Gln Phe Ser Ser Ile Gly Val Asn
                 85                  90                  95

Ile Gly Ile Ser Thr Gly Asp Phe Asp Ser Thr Asp Glu Trp Leu Gly
                100                 105                 110

Ser Asn Asp Ile Ile Val Ala Thr Ser Glu Lys Ala Asp Ser Leu Leu
            115                 120                 125

Arg Asn Glu Thr Ser Trp Met Lys Asp Ile Thr Thr Ile Val Val Asp
130                 135                 140

Glu Ile His Leu Leu Asp Ser Ala Asp Arg Gly Pro Thr Leu Glu Ile
145                 150                 155                 160

Thr Ile Ala Lys Leu Leu Arg Leu Asn Pro Asn Ser Gln Ile Ile Gly
                165                 170                 175

Leu Ser Ala Thr Ile Gly Asn Ala Glu Glu Ile Ala Gly Trp Leu Asp
            180                 185                 190

Ala Glu Leu Val Gln Ser Gln Trp Arg Pro Ile Glu Leu Tyr Glu Gly
            195                 200                 205

Val Phe Leu Glu Asp Asn Ile Asn Phe Lys Gln Ser Gln Lys Pro Ile
            210                 215                 220

Lys Asn Ile Val Lys Asp Thr Ala Val Asn Leu Val Leu Asp Thr Ile
225                 230                 235                 240

Asp Glu Asn Gly Gln Cys Leu Val Phe Glu Ser Ser Arg Arg Asn Cys
                245                 250                 255

Ala Gly Phe Ala Lys Lys Ala Lys Ser Lys Val Gly Lys Ser Leu Asp
            260                 265                 270

Lys Gly Leu Leu Ala Glu Leu Asn Asn Ile Ala Glu Glu Val Leu Glu
            275                 280                 285

Thr Ser Asp Thr Glu Thr Thr Lys Glu Leu Ala Ser Cys Ile Lys Arg
            290                 295                 300

Gly Thr Ala Phe His His Ala Gly Leu Asn Ser Ala Gln Arg Lys Ile
305                 310                 315                 320

Val Glu Asp Asn Phe Arg Asn Asn Lys Ile Lys Val Ile Ser Ser Thr
                325                 330                 335

Pro Thr Leu Ala Ala Gly Leu Asn Leu Pro Ala Arg Arg Val Ile Val
            340                 345                 350

Arg Asn Tyr Lys Arg Tyr Asp Pro Asn Phe Gly Met Gln Pro Ile Pro
            355                 360                 365

Val Leu Asp Tyr Lys Gln Met Ala Gly Arg Ala Gly Arg Pro Ser Leu
            370                 375                 380

Asp Pro Tyr Gly Glu Ser Val Leu Ile Ser His Thr Tyr Asn Glu Phe
385                 390                 395                 400

Thr Asp Leu Leu Asp Arg Tyr Ile Asp Ala Glu Pro Glu Asp Ile Leu
                405                 410                 415

Ser Lys Leu Gly Thr Glu Asn Ala Leu Arg Thr His Val Leu Ser Thr
            420                 425                 430

Ile Val Asn Gly Phe Ala Thr Thr Arg Gln Gly Met Val Asp Phe Met
            435                 440                 445
```

```
Gly Ser Ser Phe Phe Ala Tyr Gln Gln Gln Lys Trp Ser Leu Ile Asp
            450                 455                 460

Val Val Asp Asp Cys Ile Glu Phe Leu Gln Asp Asn Glu Met Ile Lys
465                 470                 475                 480

Asp Asp Gly Glu Arg Leu Tyr Ala Thr Arg Leu Gly Gln Val Ile Ser
                485                 490                 495

Thr Leu Tyr Ile Asp Pro Leu Ser Gly Ala Ile Ile Asp Lys Leu
            500                 505                 510

Lys Lys Ala Asp Lys Val Thr Asp Met Thr Met Leu His Ile Ile Cys
            515                 520                 525

Ser Thr Pro Asp Met Arg Gln Leu Tyr Leu Arg Ser Lys Glu Tyr Glu
530                 535                 540

Lys Ile Asn Glu Tyr Val Met Thr His Ser Asp Glu Phe Val Glu Val
545                 550                 555                 560

Pro Asn Pro Phe Lys Ser Ile Glu Tyr Glu Trp Phe Leu Gly Glu Val
                565                 570                 575

Lys Thr Ala Leu Leu Ile Asn Glu Trp Ile Asp Glu Lys Thr Leu Asp
            580                 585                 590

Asp Ile Thr Ala Glu Phe Gly Val Gly Glu Gly Asp Ile Asn Ala Leu
            595                 600                 605

Ser Asp Ile Ser Glu Trp Leu Met His Ser Ala Val Asn Leu Ala Asn
            610                 615                 620

Leu Thr Asp Leu Asp Ala Asp Lys Ala Gln Glu Leu Glu Lys Arg Ile
625                 630                 635                 640

His His Gly Val Asn Lys Asp Leu Ile Gln Leu Val Ser Ile Ser Asn
                645                 650                 655

Ile Gly Arg Val Arg Ala Arg Lys Leu Tyr Glu Ala Gly Ile Gln Ser
            660                 665                 670

Val Ser Asp Ile Lys Asn Thr Lys Leu His Ile Leu Ser Asn Tyr Leu
675                 680                 685

Gly Arg Lys Thr Ala Tyr Lys Val Leu Glu Gln Leu Gly Val Glu Pro
            690                 695                 700

Glu Asp Asn Gln Gln Ile Asp Glu Glu Pro Glu Ser Ile Lys Ser Tyr
705                 710                 715                 720

Ser Gly Asn Asp Gln Gly Gln Lys Thr Phe Asn Asp Phe
                725                 730

<210> SEQ ID NO 45
<211> LENGTH: 747
<212> TYPE: PRT
<213> ORGANISM: Methanococcus maripaludis

<400> SEQUENCE: 45

Met His Val Leu Asp Leu Leu Lys Glu Asn Lys Ile Thr Glu Leu Arg
1               5                   10                  15

Pro Pro Gln Lys Lys Val Ile Asp Glu Gly Leu Phe Asp Lys Thr Lys
                20                  25                  30

Asn Phe Leu Ile Cys Ile Pro Thr Ala Ser Gly Lys Thr Leu Ile Gly
            35                  40                  45

Glu Met Ala Leu Leu Asn His Ile Leu Asp Glu Asn Lys Asn Leu Thr
50                  55                  60

Gly Lys Lys Gly Leu Phe Ile Val Pro Leu Lys Ala Leu Ala Asn Glu
65                  70                  75                  80

Lys Phe Asp Glu Phe Arg Glu Lys Tyr Glu Lys Tyr Gly Ile Lys Val
                85                  90                  95
```

-continued

```
Gly Leu Ser Ile Gly Asp Phe Asp Thr Lys Glu Asn Leu Ser Lys Phe
            100                 105                 110
His Ile Ile Ile Thr Thr Ser Glu Lys Leu Asp Ser Leu Met Arg His
            115                 120                 125
Asn Val Glu Trp Ile Asn Asp Val Ser Leu Ala Val Ile Asp Glu Ile
130                 135                 140
His Leu Ile Gly Asp Asn Glu Arg Gly Gly Thr Leu Glu Val Ile Leu
145                 150                 155                 160
Thr Lys Leu Lys Asn Leu Asn Ala Gln Ile Val Gly Leu Ser Ala Thr
                165                 170                 175
Ile Gly Asn Pro Glu Glu Leu Ser Asn Trp Leu Asn Ala Lys Leu Ile
            180                 185                 190
Val Asp Gly Trp Arg Pro Val Glu Leu Lys Lys Gly Ile Tyr Phe Glu
            195                 200                 205
Asn Glu Leu Glu Phe Leu Lys Asn Pro Ala Lys Lys Ile Lys Gln Val
            210                 215                 220
Ser Arg Asn Asn Leu Thr Asp Leu Ile Val Asp Ser Val Glu Glu Lys
225                 230                 235                 240
Gly Ser Cys Leu Ile Phe Cys Asn Ser Lys Arg Asn Ala Val Gly Glu
                245                 250                 255
Ala Lys Lys His Asn Leu Ala Lys Tyr Leu Thr Arg Thr Glu Gln His
            260                 265                 270
Glu Leu Asn Lys Leu Ser Glu Glu Ile Leu Ser Ile Leu Asp Arg Pro
            275                 280                 285
Val Glu Thr Cys Lys Ala Leu Ser Lys Cys Ile Gln Asn Gly Val Ala
            290                 295                 300
Phe His His Ala Gly Leu Thr Tyr Lys His Arg Lys Ile Val Glu Asp
305                 310                 315                 320
Gly Phe Arg Asn Arg Leu Ile Lys Val Ile Cys Cys Thr Pro Thr Leu
                325                 330                 335
Ser Ala Gly Leu Asn Leu Pro Cys Arg Arg Ala Ile Val Arg Asp Ile
            340                 345                 350
Lys Arg Tyr Ser Gln Asn Gly Leu Val Asp Ile Pro Arg Met Glu Ile
            355                 360                 365
Gln Gln Cys Ile Gly Arg Ala Gly Arg Pro Gly Leu Asp Pro Tyr Gly
            370                 375                 380
Glu Gly Ile Ile Tyr Ile Lys Asn Glu Arg Asp Ala Glu Lys Ala Tyr
385                 390                 395                 400
Glu Ile Leu Thr Gly Ser Val Glu Asn Ile Tyr Ser Lys Leu Ala Asn
                405                 410                 415
Gln Lys Val Leu Arg Ile His Ile Leu Gly Leu Ile Ser Thr Gly Glu
            420                 425                 430
Ile Lys Asp Gly Gln Asn Leu Val Asn Phe Met Lys Asn Thr Phe Tyr
            435                 440                 445
Ala His Gln Phe Gly Asn Ile Gly Ala Val Leu Leu Asn Val Ser Glu
            450                 455                 460
Val Val Glu Phe Leu Glu Lys Asn Lys Phe Leu Glu Thr Thr Ile His
465                 470                 475                 480
Lys Lys Thr Glu Asn Lys Val Arg Glu Leu Ser Phe Asp Ser Ser Asn
                485                 490                 495
Asn Leu Val Leu Asp Ser Lys Glu Thr Ser Phe Asp Leu Thr Asn Pro
            500                 505                 510
```

Asn Ser Asn Ile Glu Phe Arg Ser Thr Lys Leu Gly Lys Arg Ile Ser
            515                 520                 525

Glu Leu Tyr Ile Asp Pro Met Ser Ser Glu Ile Ile Glu Glu Leu
530                 535                 540

His Glu Leu Lys Lys Cys Asp Gln Leu Asp Arg Ser Lys Ile Asp
545                 550                 555                 560

Gln Tyr Leu Phe Tyr Leu Ile Ser Lys Thr Asn Glu Met Arg Pro Leu
            565                 570                 575

Leu Arg Ile Arg Pro Asn Glu Glu Leu Asp Leu Ile Leu Glu Met Asp
            580                 585                 590

Lys Met Gly Leu Lys Asp Tyr Ser Ile Glu Asn Ile Glu Ala Phe Lys
            595                 600                 605

Asn Ser Lys Met Phe Cys Asp Trp Val Ser Glu Ile Pro Glu Glu Ile
            610                 615                 620

Ile Leu Glu Lys Tyr Gly Val Glu Pro Gly Ile Leu Arg Tyr Lys Val
625                 630                 635                 640

Glu Gln Ala Lys Trp Met Ile Tyr Ser Thr Lys Glu Ile Ala Lys Leu
            645                 650                 655

Ile His Leu Asp Asn Ser Glu Ile Tyr Lys Ser Leu Leu Lys Met Glu
            660                 665                 670

Val Arg Ile Glu Tyr Gly Ala Lys Glu Leu Ile Glu Leu Leu Asn
            675                 680                 685

Val Lys Asn Val Gly Arg Ile Arg Ser Arg Lys Leu Tyr Asp Ala Gly
            690                 695                 700

Ile Arg Ser Lys Ile Glu Ile Asn Lys Asn Pro Glu Lys Ile Leu Glu
705                 710                 715                 720

Leu Phe Gly Glu Lys Ile Gly Lys Lys Ile Leu Gly Glu His Gly Met
            725                 730                 735

Lys Tyr Gly Gln Gln Thr Leu Leu Asn Phe Asn
            740                 745

<210> SEQ ID NO 46
<211> LENGTH: 799
<212> TYPE: PRT
<213> ORGANISM: Natrialba magadii

<400> SEQUENCE: 46

Met Asn Val Glu Glu Leu Ser Gly Leu Pro Pro Gly Ala Arg Ser His
1               5                   10                  15

Phe Gln Glu Gln Gly Ile Glu Glu Leu Tyr Pro Pro Gln Ala Glu Ala
            20                  25                  30

Val Glu Ala Gly Ala Thr Glu Gly Glu Asn Leu Val Ala Ala Val Pro
        35                  40                  45

Thr Ala Ser Gly Lys Thr Met Ile Ala Ala Leu Ser Met Leu Ser Ala
    50                  55                  60

Val Gln Arg Gly Gly Lys Ala Leu Tyr Ile Val Pro Leu Arg Ala Leu
65                  70                  75                  80

Ala Ser Glu Lys Lys Ala Glu Phe Asp Ala Tyr Glu Glu Phe Gly Val
            85                  90                  95

Thr Thr Gly Val Ala Thr Gly Asn Tyr Glu Ser Thr Ser Glu Trp Leu
            100                 105                 110

Ala Thr Lys Asp Ile Ile Val Ala Thr Ser Glu Lys Val Asp Ser Leu
        115                 120                 125

Val Arg Asn Gly Ala Asp Trp Leu Ser Asp Leu Thr Cys Val Val Ser
    130                 135                 140

```
Asp Glu Val His Leu Ile Asp Asp Arg Asn Arg Gly Pro Thr Leu Glu
145                 150                 155                 160

Val Thr Leu Ala Lys Leu Arg Arg Leu Asn Pro Gln Leu Gln Val Val
            165                 170                 175

Ala Leu Ser Ala Thr Val Gly Asn Ala Asp Glu Leu Ala Asp Trp Leu
            180                 185                 190

Asp Ala Glu Leu Val Asp Thr Asp Trp Arg Pro Ile Asp Leu Gln Met
            195                 200                 205

Gly Val His Tyr Gly Asn Ala Leu Asn Phe Asp Asp Gly Glu Thr Arg
            210                 215                 220

Glu Val Pro Val Glu Ala Gly Glu Lys Gln Glu Ala Ala Leu Val Arg
225                 230                 235                 240

Asp Ile Leu Gln Glu Gly Gly Ser Ser Leu Val Phe Val Asn Ser Arg
            245                 250                 255

Arg Asn Ala Glu Ala Ala Ala Arg Arg Leu Gly Gln Val Ser Ser Arg
            260                 265                 270

Glu Leu Thr Ala Gly Glu Gln Asn Asp Leu Ala Ala Leu Ala Thr Glu
            275                 280                 285

Ile Arg Glu Asp Ser Asp Thr Glu Thr Ser Gln Asp Leu Ala Asp Cys
            290                 295                 300

Val Glu Arg Gly Ala Ala Phe His His Ala Gly Leu Ser Ser Thr Gln
305                 310                 315                 320

Arg Ser Leu Val Glu Asp Ala Phe Arg Asp Arg Leu Leu Lys Val Ile
            325                 330                 335

Ser Ala Thr Pro Thr Leu Ala Ala Gly Val Asn Thr Pro Ala Arg Arg
            340                 345                 350

Val Ile Val Arg Asp Trp Arg Arg Phe Asp Pro Ser Ala Gly Gly Met
            355                 360                 365

Ala Pro Leu Asp Val Leu Glu Val His Gln Met Met Gly Arg Ala Gly
            370                 375                 380

Arg Pro Gly Leu Asp Pro Tyr Gly Glu Ala Val Leu Leu Ala Lys Ser
385                 390                 395                 400

His Asp Glu Ser Gln Glu Leu Phe Asp Arg Tyr Val Trp Ala Asp Pro
            405                 410                 415

Glu Pro Val Arg Ser Lys Leu Ala Ala Glu Pro Ala Leu Arg Thr His
            420                 425                 430

Val Leu Ala Thr Ile Ala Ser Gly Phe Ala Arg Thr Arg Glu Gly Leu
            435                 440                 445

Leu Glu Phe Leu Glu Ala Thr Leu Tyr Ala Ser Gln Ser Ser Glu Gly
            450                 455                 460

Gly Arg Leu Glu Arg Val Thr Asp Asp Val Leu Ser Tyr Leu Glu Arg
465                 470                 475                 480

Asn Asp Phe Ile Glu Arg Ser Gly Gly Pro Glu Asp Thr Leu Asn Ser
            485                 490                 495

Glu Ala Asp Ala Ala Ser Ala Phe Thr Ser Ala Ala Asp Leu Ala Asp
            500                 505                 510

Ser Asp Gly Gly Asp Ser Gly Gly Thr Thr Gly Gln Glu Glu Asp Leu
            515                 520                 525

Glu Ala Thr Ser Leu Gly His Thr Val Ser Arg Leu Tyr Leu Asp Pro
            530                 535                 540

Met Ser Ala Ala Glu Ile Val His Gly Leu Glu Asp Ala Asp Glu Arg
545                 550                 555                 560
```

```
Pro Thr Ala Leu Gly Leu Tyr Gln Leu Val Ser Arg Thr Pro Asp Met
                565                 570                 575

Tyr Glu Leu Tyr Leu Arg Ser Gly Glu Asp Glu Lys Phe Gly Glu Leu
            580                 585                 590

Tyr Tyr Glu Arg Glu Arg Glu Leu Leu Gly Asp Ala Pro Ser Glu Phe
            595                 600                 605

Glu Glu Glu Arg Phe Glu Asp Trp Leu Ala Ala Leu Lys Thr Gly Lys
        610                 615                 620

Leu Leu Glu Asp Trp Ala Thr Glu Asp Asp Glu Gln Ile Thr Glu
625                 630                 635                 640

Arg Tyr Lys Ile Gly Pro Gly Asp Leu Arg Gly Lys Val Asp Thr Ala
                645                 650                 655

Glu Trp Leu Leu Gly Ala Ala Glu Ser Leu Ala Ser Glu Ile Asp Ser
            660                 665                 670

Glu Trp Ala Val Ala Val Arg Glu Ala Arg Ala Arg Val Glu His Gly
        675                 680                 685

Val Gly Glu Glu Leu Leu Glu Leu Val Ser Val Ser Gly Ile Gly Arg
        690                 695                 700

Lys Arg Ala Arg Arg Leu Tyr Ala Ala Gly Ile Glu Glu Pro Ala Ala
705                 710                 715                 720

Leu Arg Ser Ala Asp Lys Gly Val Ile Leu His Val Leu Lys Gly Glu
                725                 730                 735

Lys Thr Ala Glu Asn Ile Leu Glu Asn Ala Gly Arg Glu Glu Pro Ser
            740                 745                 750

Met Asp Gly Val Glu Pro Ile Pro Val Glu Gly Ser Gly Ser Gly
        755                 760                 765

Ser Ser Asn Ser Ser Gly Ser Ser Glu Pro Asn Ala Asp Ala Asn Ala
        770                 775                 780

Thr Glu Asp Asp Ala Asp Asp Asn Gln Ser Ser Leu Gly Asp Phe
785                 790                 795

<210> SEQ ID NO 47
<211> LENGTH: 723
<212> TYPE: PRT
<213> ORGANISM: Methanoregula boonei

<400> SEQUENCE: 47

Met Gln Ile Gln Asp Leu Ala Ile Pro Glu Pro Leu Arg Gln Gln Tyr
1               5                   10                  15

Leu Gly Leu Gly Ile Arg Glu Leu Tyr Pro Pro Gln Ala Ala Cys Val
            20                  25                  30

Glu Arg Gly Leu Leu Asp Gly Lys Asn Leu Leu Val Ala Ile Pro Thr
        35                  40                  45

Ala Ser Gly Lys Thr Leu Ile Ala Glu Met Ala Met His Arg His Ile
    50                  55                  60

Ala Asn Gly Gly Lys Cys Leu Tyr Ile Val Pro Leu Lys Ala Leu Ala
65                  70                  75                  80

Ser Glu Lys Tyr Glu Glu Phe Gly Asn Lys Gly Val Lys Val Gly Leu
                85                  90                  95

Ser Thr Gly Asp Leu Asp Arg Arg Asp Asp Ala Leu Gly Lys Asn Asp
            100                 105                 110

Ile Ile Val Ala Thr Ser Glu Lys Val Asp Ser Leu Leu Arg Asn Gly
        115                 120                 125

Ala Arg Trp Ile Pro Asp Ile Thr Leu Val Val Ile Asp Glu Ile His
    130                 135                 140
```

```
Leu Ile Asp Ser Pro Asp Arg Gly Pro Thr Leu Glu Met Val Ile Ala
145                 150                 155                 160

Lys Met Arg Ser Lys Asn Pro Gly Met Gln Leu Ile Gly Leu Ser Ala
            165                 170                 175

Thr Ile Gly Asn Pro Lys Val Leu Ala Gly Trp Leu Asp Ala Glu Leu
        180                 185                 190

Val Thr Ser Ser Trp Arg Pro Val Asp Leu Arg Gln Gly Val Phe Tyr
    195                 200                 205

Asp Asn Arg Ile Gln Phe Ala Glu Arg Met Arg Pro Val Lys Gln Val
210                 215                 220

Ser Lys Asn Tyr Asp Asp Leu Asn Leu Cys Leu Asp Thr Ile Ala Glu
225                 230                 235                 240

Gly Gly Gln Cys Leu Val Phe Val Ser Ser Arg Arg Asn Ala Glu Ala
                245                 250                 255

Phe Ala Lys Arg Ala Ala Gly Ala Ile Lys Ser Glu Asp Ala Ala Leu
            260                 265                 270

Ala Ala Cys Ala Glu Arg Leu Leu Glu Gly Thr Pro Thr Glu Met Val
        275                 280                 285

Lys Thr Leu Ala Ala Cys Val Ala Lys Gly Ala Ala Phe His His Ala
290                 295                 300

Gly Leu Ser Arg Lys Glu Arg Ser Ile Val Glu Glu Ala Phe Arg Lys
305                 310                 315                 320

Asn Leu Leu Lys Cys Ile Ser Ser Thr Pro Thr Leu Ala Ala Gly Leu
                325                 330                 335

Asn Leu Pro Ala Arg Arg Val Ile Ile Arg Asp Tyr Leu Arg Phe Ser
            340                 345                 350

Ala Gly Glu Gly Met Gln Pro Ile Pro Val Ser Glu Tyr Arg Gln Met
        355                 360                 365

Ala Gly Arg Ala Gly Arg Pro Arg Leu Asp Pro Tyr Gly Glu Ala Val
370                 375                 380

Leu Ile Ala Lys Glu Ala Glu Gln Val Pro Glu Leu Phe Glu Val Tyr
385                 390                 395                 400

Ile Glu Ala Glu Ala Glu Asp Val His Ser Arg Ile Ala Glu Pro Thr
                405                 410                 415

Ala Leu Tyr Thr His Val Leu Ser Leu Val Ala Ser Gly Phe Ala Gly
            420                 425                 430

Thr Arg Gly Glu Leu Thr Glu Phe Met Asn Arg Ser Phe Tyr Val His
        435                 440                 445

Glu His Lys Gln Gly Arg Leu Ile His Arg Ala Ile Asp Glu Ala Leu
450                 455                 460

Gln Phe Leu Ile Thr Ala Glu Met Val Glu Val Gly Glu His Ile
465                 470                 475                 480

Gly Ala Thr Glu Leu Gly Thr Leu Val Ser Arg Met Tyr Ile Asp Pro
                485                 490                 495

Arg Ser Ala Phe Ala Ile Val Thr Thr Leu Arg Glu Gln Glu Lys Tyr
            500                 505                 510

Ala Asp Leu Gly Leu Ile Gln Leu Ile Cys Thr Thr Pro Asp Met Pro
        515                 520                 525

Thr Leu Tyr Ala Lys Asn Ala Asp Leu Pro Ala Leu Ser Arg Met Leu
530                 535                 540

Glu Val Arg Gly Ala Asp Ile Trp Leu Pro Pro Pro Leu Asp Asp Asp
545                 550                 555                 560
```

```
Ala Ala Glu Thr Tyr Tyr Arg Ala Val Lys Thr Ala Met Leu Leu Ser
            565                 570                 575

Asp Trp Thr Asp Glu Leu Ser Glu Glu Lys Ile Cys Glu Arg Tyr Gly
            580                 585                 590

Val Gly Pro Gly Asp Val Phe Gly Met Val Glu Asn Ile Asn Trp Leu
            595                 600                 605

Leu His Ala Thr Ser Gln Leu Ala Arg Met Phe Val Pro Lys Phe Tyr
            610                 615                 620

Gly Gln Ile Ala Asp Cys Glu Ile Cys Met Lys Asn Gly Ile Arg Arg
625                 630                 635                 640

Glu Leu Leu Pro Leu Val Arg Leu Arg Gly Ile Gly Arg Val Arg Ala
            645                 650                 655

Arg Arg Leu Phe Asn Asn Gly Ile Thr Ser Pro Glu Glu Leu Ser Arg
            660                 665                 670

His Lys Lys Glu Asp Leu Val Lys Ile Leu Gly Ser Gly Ile Ala Glu
            675                 680                 685

Gln Val Leu Glu Gln Leu His Pro Ser Lys Asp Thr Gly Lys Lys Glu
            690                 695                 700

Pro Pro Ser Gly Asp Lys Asn Thr Asn Pro Gly Gln Ser Thr Leu Phe
705                 710                 715                 720

His Phe Gly

<210> SEQ ID NO 48
<211> LENGTH: 681
<212> TYPE: PRT
<213> ORGANISM: Ferroplasma acidarmanus

<400> SEQUENCE: 48

Met Lys Leu Ser Glu Ile Thr Pro Ser Glu Phe Leu Lys Val Thr Asp
1               5                   10                  15

Asn Asn Asp Phe Thr Leu Tyr Glu His Gln Glu Glu Ala Val Ala Lys
            20                  25                  30

Leu Arg Glu Asn Lys Asn Val Ile Val Ser Val Pro Thr Ala Ser Gly
        35                  40                  45

Lys Thr Leu Ile Gly Tyr Ile Ser Ile Tyr Asp Thr Tyr Leu Lys Gly
    50                  55                  60

Lys Lys Ser Met Tyr Ile Val Pro Leu Arg Ser Leu Ala Met Glu Lys
65              70                  75                  80

Phe Ser Glu Leu Leu Ser Leu Arg Asn Leu Gly Val Lys Val Thr Met
                85                  90                  95

Ser Ile Gly Asp Tyr Asp Val Pro Ser Phe Val Lys Asn Tyr Asp
            100                 105                 110

Val Ile Ile Ala Thr Ser Glu Arg Ala Asp Ser Met Leu His Arg Asp
        115                 120                 125

Pro Asp Ile Leu Asn Tyr Phe Gly Leu Val Ile Asp Glu Ile His
    130                 135                 140

Met Ile Ser Asp Pro Ser Arg Gly Pro Arg Leu Glu Thr Val Ile Ser
145                 150                 155                 160

Ser Leu Leu Tyr Leu Asn Pro Glu Ile Leu Leu Gly Leu Ser Ala
                165                 170                 175

Thr Val Ser Asn Ile Gln Glu Ile Ala Glu Trp Met Asn Ala Glu Thr
            180                 185                 190

Val Val Ser Asn Phe Arg Ala Val Pro Leu Glu Thr Gly Ile Ile Phe
        195                 200                 205
```

```
Lys Gly Asn Leu Ile Thr Asp Gly Glu Lys Lys His Leu Gly Arg Asp
210                 215                 220

Asp Glu Val Ser Leu Ile Lys Glu Ser Ile Glu Ser Gly Gly Gln Ala
225                 230                 235                 240

Leu Val Phe Arg Asn Ser Arg Arg Asn Ala Glu Lys Tyr Ala Gln Ser
                245                 250                 255

Met Val Asn Phe Phe Asp Phe Gln Asn Asp Phe Glu Lys Leu Glu Ile
                260                 265                 270

Pro Pro Asp Leu Phe Asn Glu Ala Gln Ala Asn Met Val Ala His Gly
            275                 280                 285

Val Met Phe His His Ala Gly Leu Ser Asn Asp Gln Arg Thr Met Ile
290                 295                 300

Glu Lys Leu Phe Lys Gln Gly Tyr Ile Lys Ile Leu Thr Ala Thr Pro
305                 310                 315                 320

Thr Leu Ala Ala Gly Val Asn Leu Pro Ala Arg Thr Val Ile Ile Arg
                325                 330                 335

Asp Ile Thr Arg Phe Ser Asp Gly Tyr Ser Lys Pro Ile Ser Gly Ile
                340                 345                 350

Glu Ile Gln Gln Met Ile Gly Arg Ala Gly Arg Pro Lys Tyr Asp Lys
            355                 360                 365

Lys Gly Tyr Gly Tyr Ile Tyr Ala Ala Ser Pro Gly Met Leu Arg Val
370                 375                 380

Ala Glu Gly Tyr Leu Thr Gly Glu Leu Glu Pro Val Ile Ser Arg Met
385                 390                 395                 400

Asp Ser Asn Ser Leu Ile Arg Phe Asn Val Leu Ala Leu Ile Ser Ser
                405                 410                 415

Gly Ile Ala Thr Asp Leu Lys Gly Ile Gln Asp Phe Tyr Gly Lys Thr
                420                 425                 430

Leu Leu Ala Ala Gln Asn Asp Ile Asp Gly Tyr Glu Leu Ala Phe Glu
            435                 440                 445

Ser Ala Leu Tyr Phe Leu Lys Asp Asn Asp Phe Ile Thr Glu Glu Asn
450                 455                 460

Asp Ile Tyr Ser Ala Thr Lys Phe Gly Arg Leu Thr Ser Asp Leu Tyr
465                 470                 475                 480

Ile Asp Pro Val Ser Ser Leu Ile Leu Lys Lys Cys Leu Asp Leu Glu
                485                 490                 495

Phe Ser Glu Glu Leu Tyr Leu Tyr Tyr Ile Ser Lys Thr Pro Asp Met
            500                 505                 510

Leu Thr Phe Asn Tyr Arg Ala Ser Asp Tyr Glu Tyr Leu Glu Glu Phe
            515                 520                 525

Leu Asp Arg His Asn Ile Ser Asp Phe Ser Glu Glu Ser Met Gly Ala
530                 535                 540

Ala Lys Thr Ala Ile Ile Leu Asn Glu Trp Ile Asn Glu Val Pro Ile
545                 550                 555                 560

Asn Thr Ile Ala Glu Thr Phe Gly Ile Gly Pro Gly Asp Ile Gln Ala
                565                 570                 575

Lys Ala Ser Ser Ala Asp Trp Ile Ser Tyr Ser Leu Tyr Arg Leu Gly
            580                 585                 590

Ser Met Phe Asp Lys Glu Asn Asn Leu Leu His Leu Asn Ile
            595                 600                 605

Arg Ile Lys Glu Gly Val Lys Glu Ile Ile Arg Ile Ile Glu Ile
610                 615                 620

Pro Gln Val Gly Arg Val Arg Gly Arg Arg Leu Tyr Asn Asn Gly Phe
```

```
                625                 630                 635                 640
Lys Ser Ile Asp Asp Ile Ala Asn Ala Arg Val Glu Asp Ile Ser Arg
                    645                 650                 655
Ile Phe Gly Phe Ser Thr Lys Leu Ala Lys Asp Ile Ile Glu Asn Ala
                660                 665                 670
Gly Lys Leu Asn Asn Arg Tyr Tyr Arg
                675                 680

<210> SEQ ID NO 49
<211> LENGTH: 696
<212> TYPE: PRT
<213> ORGANISM: Methanocaldococcus fervens

<400> SEQUENCE: 49

Met Pro Thr Asn Lys Ile Leu Glu Ile Leu Lys Asp Phe Gly Ile Glu
1               5                   10                  15

Glu Leu Arg Pro Pro Gln Lys Lys Ala Leu Glu Lys Gly Leu Leu Asp
                20                  25                  30

Lys Asn Lys Asn Phe Leu Ile Ser Ile Pro Thr Ala Ser Gly Lys Thr
            35                  40                  45

Leu Ile Gly Glu Met Ala Leu Ile Asn His Leu Asp Glu Asn Lys
    50                  55                  60

Asn Pro Thr Asn Lys Lys Gly Ile Phe Ile Val Pro Leu Lys Ala Leu
65                  70                  75                  80

Ala Ser Glu Lys Tyr Glu Glu Phe Lys Asn Lys Tyr Glu Arg Tyr Gly
                85                  90                  95

Leu Arg Val Ala Leu Ser Ile Gly Asp Tyr Asp Glu Asp Leu
                100                 105                 110

Ser Arg Tyr His Leu Ile Ile Thr Thr Ala Glu Lys Leu Asp Ser Leu
            115                 120                 125

Trp Arg His Lys Ile Asp Trp Ile Asp Asp Val Ser Val Val Val Val
    130                 135                 140

Asp Glu Ile His Leu Ile Asn Asp Glu Ser Arg Gly Gly Thr Leu Glu
145                 150                 155                 160

Ile Leu Leu Thr Lys Leu Lys Lys Phe Asn Ile Gln Ile Ile Gly Leu
                165                 170                 175

Ser Ala Thr Ile Gly Asn Pro Glu Glu Leu Ala Asn Trp Leu Asn Ala
            180                 185                 190

Glu Leu Ile Val Asp Asp Trp Arg Pro Val Glu Leu Lys Lys Gly Ile
    195                 200                 205

Tyr Lys Asn Gly Ile Ile Glu Phe Ile Asn Gly Glu Asn Arg Glu Ile
                210                 215                 220

Lys Ala Ile Asn Asn Asn Asp Ile Tyr Asn Leu Val Val Asp Cys Val
225                 230                 235                 240

Lys Asp Gly Gly Cys Cys Ile Val Phe Cys Asn Thr Lys Arg Gly Ala
                245                 250                 255

Val Asn Glu Ala Lys Lys Leu Asn Leu Lys Lys Phe Leu Thr Asn Glu
            260                 265                 270

Glu Lys Arg Lys Leu Lys Glu Val Ala Glu Glu Ile Leu Ser Ile Leu
    275                 280                 285

Glu Pro Pro Thr Glu Met Cys Lys Thr Leu Ala Glu Cys Ile Leu Asn
                290                 295                 300

Gly Ser Ala Phe His His Ala Gly Leu Thr Tyr Gln His Arg Lys Ile
305                 310                 315                 320
```

| | | | | | | | | | | | |
|---|---|---|---|---|---|---|---|---|---|---|---|
|Val|Glu|Asp|Ala|Phe|Arg|Asn|Lys|Leu|Ile|Lys|Val|Ile|Cys|Cys|Thr|
| | | | |325| | | |330| | | |  |  |335|  |
|Pro|Thr|Leu|Ser|Val|Gly|Leu|Asn|Leu|Pro|Cys|Arg|Arg|Ala|Ile|Val|
| | | |340| | | | |345| | | |350|  |  |  |
|Lys|Asp|Leu|Thr|Arg|Tyr|Thr|Asn|Arg|Gly|Met|Arg|Tyr|Ile|Pro|Ile|
| | |355| | | | |360| | | | |365|  |  |  |

Val Glu Asp Ala Phe Arg Asn Lys Leu Ile Lys Val Ile Cys Cys Thr
                325                 330                 335
Pro Thr Leu Ser Val Gly Leu Asn Leu Pro Cys Arg Arg Ala Ile Val
            340                 345                 350
Lys Asp Leu Thr Arg Tyr Thr Asn Arg Gly Met Arg Tyr Ile Pro Ile
        355                 360                 365
Met Glu Ile Gln Gln Cys Ile Gly Arg Ala Gly Arg Leu Gly Leu Asp
    370                 375                 380
Pro Tyr Gly Glu Gly Ile Ile Val Ala Lys Asn Asp Arg Asp Tyr Leu
385                 390                 395                 400
Arg Ser Tyr Gln Val Leu Thr Gln Lys Pro Glu Pro Ile Tyr Ser Lys
                405                 410                 415
Leu Ser Asn Gln Ala Val Leu Arg Thr Gln Leu Leu Gly Leu Ile Ala
            420                 425                 430
Thr Ile Glu Ile Arg Asp Glu Tyr Asp Leu Glu Trp Phe Ile Arg Asn
        435                 440                 445
Thr Phe Tyr Ala Tyr Gln Tyr Gly Asn Leu Arg Glu Val Ala Lys Asn
    450                 455                 460
Ile Asn Glu Val Ile Arg Phe Leu Glu Glu Lys Glu Phe Met Ile Asp
465                 470                 475                 480
Phe Ile Pro Thr Glu Leu Gly Lys Arg Val Ala Glu Leu Tyr Ile Asp
                485                 490                 495
Pro Leu Ser Ala Lys Tyr Met Ile Asp Gly Leu Asn Glu Met Glu Asn
            500                 505                 510
Glu Asp Asp Ile Tyr Tyr Leu Tyr Leu Ile Ser Lys Thr Leu Glu Met
        515                 520                 525
Met Pro Asn Leu Arg Val Tyr Lys Ser Glu Glu Leu Asn Leu Ile Asp
    530                 535                 540
Glu Met Glu Asn Leu Gly Ile Lys Ser Phe Glu Ile Glu Asp Leu Glu
545                 550                 555                 560
Ala Phe Lys Thr Ala Lys Met Leu Tyr Asp Trp Ile Ser Glu Val Pro
                565                 570                 575
Glu Asp Glu Ile Leu Lys Lys Tyr Lys Ile Glu Pro Gly Ile Leu Arg
            580                 585                 590
Tyr Lys Val Glu Asn Ala Val Trp Leu Met His Ala Leu Lys Glu Met
        595                 600                 605
Ala Lys Ile Ile Gly Lys Asn Ser Glu Ile Pro Glu Lys Leu Glu Ile
    610                 615                 620
Arg Leu Glu Tyr Gly Ala Lys Glu Asp Ile Ile Glu Leu Leu Asn Val
625                 630                 635                 640
Lys Tyr Ile Gly Arg Val Arg Ala Arg Lys Leu Tyr Asn Ala Gly Ile
                645                 650                 655
Arg Asn Val Glu Asp Ile Ile Asn Asn Pro Ser Lys Val Ala Ser Ile
            660                 665                 670
Ile Gly Glu Lys Ile Thr Lys Lys Ile Leu Glu Asp Leu Gly Ile Lys
        675                 680                 685
Phe Gly Gln Gln Lys Leu Ile Phe
    690                 695

<210> SEQ ID NO 50
<211> LENGTH: 729
<212> TYPE: PRT
<213> ORGANISM: Methanocaldococcus jannaschii

<400> SEQUENCE: 50

```
Met Asp Lys Ile Leu Glu Ile Leu Lys Asp Phe Gly Ile Val Glu Leu
1               5                   10                  15

Arg Pro Pro Gln Lys Lys Ala Leu Glu Arg Gly Leu Leu Asp Lys Asn
            20                  25                  30

Lys Asn Phe Leu Ile Ser Ile Pro Thr Ala Ser Gly Lys Thr Leu Ile
        35                  40                  45

Gly Glu Met Ala Leu Ile Asn His Leu Leu Asp Gly Asn Lys Asn Pro
50                  55                  60

Thr Asn Lys Lys Gly Ile Phe Ile Val Pro Leu Lys Ala Leu Ala Ser
65                  70                  75                  80

Glu Lys Tyr Glu Glu Phe Lys Ser Lys Tyr Glu Arg Tyr Gly Leu Arg
                85                  90                  95

Ile Ala Leu Ser Ile Gly Asp Tyr Asp Glu Asp Glu Asp Leu Ser Lys
            100                 105                 110

Tyr His Leu Ile Ile Thr Thr Ala Glu Lys Leu Asp Ser Leu Trp Arg
        115                 120                 125

His Lys Ile Asp Trp Ile Asn Asp Val Ser Val Val Val Asp Glu
    130                 135                 140

Ile His Leu Ile Asn Asp Glu Thr Arg Gly Gly Thr Leu Glu Ile Leu
145                 150                 155                 160

Leu Thr Lys Leu Lys Glu Phe Asn Val Gln Ile Ile Gly Leu Ser Ala
            165                 170                 175

Thr Ile Gly Asn Pro Asp Glu Leu Ala Glu Trp Leu Asn Ala Glu Leu
            180                 185                 190

Ile Val Asp Asp Trp Arg Pro Val Glu Leu Lys Lys Gly Ile Tyr Lys
            195                 200                 205

Asn Glu Ala Ile Glu Phe Ile Asn Gly Glu Ile Arg Glu Ile Lys Ala
210                 215                 220

Val Asp Asn Asn Asp Ile Tyr Asn Leu Val Val Asp Cys Val Lys Glu
225                 230                 235                 240

Gly Gly Cys Cys Leu Val Phe Cys Asn Thr Lys Arg Asn Ala Val Asn
            245                 250                 255

Glu Ala Lys Lys Leu Asn Leu Lys Lys Phe Leu Thr Glu Glu Glu Lys
            260                 265                 270

Ile Arg Leu Lys Glu Ile Ala Glu Glu Ile Leu Ser Ile Leu Glu Pro
            275                 280                 285

Pro Thr Glu Met Cys Lys Thr Leu Ala Glu Cys Ile Leu Asn Gly Ser
290                 295                 300

Ala Phe His His Ala Gly Leu Thr Tyr Gln His Arg Lys Ile Val Glu
305                 310                 315                 320

Asp Ala Phe Arg Lys Arg Leu Ile Lys Val Ile Cys Cys Thr Pro Thr
            325                 330                 335

Leu Ser Ala Gly Leu Asn Leu Pro Cys Arg Arg Ala Ile Val Lys Asp
            340                 345                 350

Leu Thr Arg Phe Thr Asn Lys Gly Met Arg Tyr Ile Pro Ile Met Glu
            355                 360                 365

Ile Gln Gln Cys Ile Gly Arg Ala Gly Arg Pro Gly Leu Asp Pro Tyr
370                 375                 380

Gly Glu Gly Ile Ile Val Ala Lys Asn Asp Arg Asp Tyr Leu Arg Ala
385                 390                 395                 400

Tyr Gln Ala Leu Thr Gln Lys Pro Glu Pro Ile Tyr Ser Lys Leu Ser
                405                 410                 415
```

```
Asn Gln Ala Val Leu Arg Thr Gln Leu Gly Leu Ile Ala Thr Gly
                420                 425                 430

Glu Ile Arg Asp Glu Tyr Asp Leu Glu Trp Phe Ile Arg Asn Thr Phe
            435                 440                 445

Tyr Ala His Gln Tyr Gly Asn Leu Arg Glu Val Ala Lys Asn Ile Asn
450                 455                 460

Glu Val Ile Arg Phe Leu Glu Glu Asn Glu Phe Ile Asp Phe Met
465                 470                 475                 480

Pro Thr Glu Leu Gly Lys Arg Val Ser Glu Leu Tyr Ile Asp Pro Leu
                485                 490                 495

Ser Ala Lys Phe Ile Ile Asp Gly Leu Glu Glu Met Glu Asn Glu Glu
                500                 505                 510

Glu Ile Tyr Tyr Leu Tyr Leu Ile Ser Lys Thr Leu Glu Met Met Pro
            515                 520                 525

Asn Leu Arg Val Tyr Asn Ser Glu Glu Leu Asn Leu Ile Asp Glu Met
530                 535                 540

Asp Ser Leu Gly Ile Lys Ser Phe Glu Ile Glu Asp Leu Glu Ala Phe
545                 550                 555                 560

Lys Thr Ala Lys Met Leu Tyr Asp Trp Ile Asn Glu Val Pro Glu Asp
                565                 570                 575

Glu Ile Leu Lys Arg Tyr Lys Ile Glu Pro Gly Ile Leu Arg Tyr Lys
                580                 585                 590

Val Glu Asn Ala Val Trp Ile Met His Ala Leu Lys Glu Ile Ala Lys
                595                 600                 605

Leu Ile Gly Lys Ser Ser Asp Ile Pro Glu Lys Leu Glu Ile Arg Leu
                610                 615                 620

Glu Tyr Gly Ala Lys Glu Asp Ile Ile Glu Leu Leu Ser Ile Lys Tyr
625                 630                 635                 640

Ile Gly Arg Val Arg Ala Arg Lys Leu Tyr Asn Ala Gly Ile Arg Ser
                645                 650                 655

Ile Glu Asp Ile Ile Asn Asn Pro Ser Lys Val Ala Ser Ile Ile Gly
                660                 665                 670

Glu Lys Ile Ala Lys Lys Ile Leu Asp Glu Leu Gly Val Lys Phe Gly
                675                 680                 685

Gln Gln Lys Leu Ser Phe Ser Gly Gly Ser Ala Trp Ser His Pro Gln
                690                 695                 700

Phe Glu Lys Gly Gly Gly Ser Gly Gly Gly Ser Gly Gly Ser Ala Trp
705                 710                 715                 720

Ser His Pro Gln Phe Glu Lys Lys Leu
                725

<210> SEQ ID NO 51
<211> LENGTH: 670
<212> TYPE: PRT
<213> ORGANISM: Methanocaldococcus infernus

<400> SEQUENCE: 51

Met Asp Glu Ile Leu Lys Phe Leu Gly Ile Lys Glu Leu Arg Pro Pro
1               5                   10                  15

Gln Lys Lys Ala Leu Glu Leu Gly Ile Leu Asp Lys Lys Asn Phe
                20                  25                  30

Leu Ile Ser Ile Pro Thr Gly Ala Gly Lys Thr Val Ile Ala Glu Met
            35                  40                  45

Ala Leu Ile Asn His Leu Leu Leu Asp Lys Gly Lys Lys Gly Val Tyr
        50                  55                  60
```

```
Ile Val Pro Leu Lys Ala Leu Ala Ser Glu Lys Tyr Glu Glu Phe Lys
 65                  70                  75                  80

Lys Lys Tyr Glu Lys Phe Gly Val Arg Val Ala Leu Ser Ile Gly Asp
                 85                  90                  95

Tyr Asp Glu Asp Glu Asp Leu Glu Asn Tyr Asp Leu Ile Ile Thr Thr
                100                 105                 110

Ala Glu Lys Phe Asp Ser Leu Trp Arg His Gly Ile Lys Leu Ser Asp
                115                 120                 125

Ile Ser Val Val Val Asp Glu Ile His Val Ile Gly Asp Ser Glu
    130                 135                 140

Arg Gly Gly Thr Leu Glu Val Leu Leu Thr Lys Leu Lys Glu Leu Asp
145                 150                 155                 160

Val Gln Ile Ile Gly Leu Ser Ala Thr Ile Gly Asn Pro Glu Glu Leu
                165                 170                 175

Ser Glu Trp Leu Asn Ala Glu Leu Leu Leu Asp Asn Trp Arg Pro Val
                180                 185                 190

Glu Leu Arg Lys Gly Ile Tyr Arg Glu Gly Val Ile Glu Tyr Leu Asp
                195                 200                 205

Gly Glu Val Lys Glu Cys Gln Asp Ile Val Lys Glu Val Val Lys Asp
                210                 215                 220

Asn Gly Ser Val Ile Ile Phe Cys Pro Thr Lys Lys Ala Glu Asn
225                 230                 235                 240

Arg Ala Leu Ser Leu Asp Leu Ser Asp Leu Leu Lys Ser Glu Lys
                245                 250                 255

Arg Lys Leu Glu Glu Ile Ser Glu Glu Leu Leu Ser Leu Phe Asp Pro
                260                 265                 270

Pro Thr Glu Leu Cys Lys Lys Leu Ala Ser Cys Val Arg Lys Gly Ile
                275                 280                 285

Ala Phe His His Ser Gly Leu Thr Tyr Glu His Arg Lys Ile Ile Glu
                290                 295                 300

Lys Ala Phe Arg Glu Arg Ile Leu Lys Val Ile Cys Ser Thr Thr Thr
305                 310                 315                 320

Leu Ala Phe Gly Leu Asn Leu Pro Cys Arg Arg Val Ile Ile Ser Glu
                325                 330                 335

Leu Lys Arg Tyr Thr Arg Arg Gly Leu Thr Tyr Ile Pro Ile Met Glu
                340                 345                 350

Val Gln Gln Cys Ile Gly Arg Ala Gly Arg Pro Gly Leu Asp Glu Tyr
                355                 360                 365

Gly Glu Gly Ile Leu Val Ala Lys Asp Glu Arg Asp Tyr Leu Arg Ala
                370                 375                 380

Leu Gln Cys Leu Thr Gln Lys Pro Glu Pro Ile Tyr Ser Lys Leu Ser
385                 390                 395                 400

Asn Asp Ser Val Leu Arg Thr Gln Ile Leu Gly Leu Ile Ala Thr Arg
                405                 410                 415

Tyr Val Leu Asp Glu Tyr Asp Leu Glu Glu Phe Ile Lys Asn Thr Phe
                420                 425                 430

Tyr Ala Tyr Gln Tyr Lys Asn Leu Asp Glu Ile Lys Lys Lys Ile Lys
                435                 440                 445

Glu Ile Ile Glu Phe Leu Glu Asp Cys Asn Phe Ile Lys Asn Phe Glu
                450                 455                 460

Val Thr Pro Leu Gly Lys Lys Val Ser Asn Leu Tyr Leu Asp Pro Leu
465                 470                 475                 480
```

-continued

Ser Ala Lys Ile Met Ile Asp Asn Ile Glu Val Lys Asp Asp Leu His
            485             490             495

Leu Leu Tyr Ile Leu Cys Lys Cys Ile Glu Met Lys Pro Leu Leu Arg
            500             505             510

Val Tyr Arg Lys Glu Glu Glu Leu Ala Glu Glu Leu Leu Asn Tyr
            515             520             525

Glu Ile Phe Ile Ser Tyr Glu Asn Leu Glu Glu Phe Lys Thr Ala Lys
            530             535             540

Met Leu Tyr Asp Trp Ile Asn Glu Val Pro Glu Asp Glu Ile Leu Lys
545             550             555             560

Thr Tyr Lys Val Glu Pro Gly Ile Leu Arg Tyr Lys Val Glu Val Ala
            565             570             575

Lys Trp Leu Ser Tyr Ser Leu Lys Glu Ile Ala Lys Ile Leu Asn Lys
            580             585             590

Glu Val Pro Asn Leu Glu Leu Arg Leu Glu Tyr Gly Ala Lys Glu Glu
            595             600             605

Leu Leu Glu Leu Leu Lys Ile Lys Tyr Ile Gly Arg Val Arg Ala Arg
            610             615             620

Lys Leu Tyr Ser Ala Gly Ile Arg Asn Arg Glu Asp Ile Ile Lys Asn
625             630             635             640

Pro Lys Lys Val Ala Asn Ile Leu Gly Glu Lys Ile Ser Lys Lys Ile
            645             650             655

Phe Glu Glu Leu Gly Val Arg Tyr Gly Gln Gln Arg Leu Ile
            660             665             670

<210> SEQ ID NO 52
<211> LENGTH: 799
<212> TYPE: PRT
<213> ORGANISM: Methanospirillum hungatei

<400> SEQUENCE: 52

Met Glu Ile Ala Ser Leu Pro Leu Pro Asp Ser Phe Ile Arg Ala Cys
1               5               10              15

His Ala Lys Gly Ile Arg Ser Leu Tyr Pro Pro Gln Ala Glu Cys Ile
            20              25              30

Glu Lys Gly Leu Leu Glu Gly Lys Asn Leu Leu Ile Ser Ile Pro Thr
            35              40              45

Ala Ser Gly Lys Thr Leu Leu Ala Glu Met Ala Met Trp Ser Arg Ile
50              55              60

Ala Ala Gly Gly Lys Cys Leu Tyr Ile Val Pro Leu Arg Ala Leu Ala
65              70              75              80

Ser Glu Lys Tyr Asp Glu Phe Ser Lys Lys Gly Val Ile Arg Val Gly
            85              90              95

Ile Ala Thr Gly Asp Leu Asp Arg Thr Asp Ala Tyr Leu Gly Glu Asn
            100             105             110

Asp Ile Ile Val Ala Thr Ser Glu Lys Thr Asp Ser Leu Leu Arg Asn
            115             120             125

Arg Thr Pro Trp Leu Ser Gln Ile Thr Cys Ile Val Leu Asp Glu Val
            130             135             140

His Leu Ile Gly Ser Glu Asn Arg Gly Ala Thr Leu Glu Met Val Ile
145             150             155             160

Thr Lys Leu Arg Tyr Thr Asn Pro Val Met Gln Ile Ile Gly Leu Ser
            165             170             175

Ala Thr Ile Gly Asn Pro Ala Gln Leu Ala Glu Trp Leu Asp Ala Thr
            180             185             190

```
Leu Ile Thr Ser Thr Trp Arg Pro Val Asp Leu Arg Gln Gly Val Tyr
        195                 200                 205

Tyr Asn Gly Lys Ile Arg Phe Ser Asp Ser Glu Arg Pro Ile Gln Gly
    210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Arg Arg Asn Ala Glu Gly
                245                 250                 255

Phe Ala Lys Lys Ala Ala Gly Ala Leu Lys Ala Gly Ser Pro Asp Ser
                260                 265                 270

Lys Ala Leu Ala Gln Glu Leu Arg Arg Leu Arg Asp Asp Glu Gly
                275                 280                 285

Asn Val Leu Ala Asp Cys Val Glu Arg Gly Ala Ala Phe His His Ala
                290                 295                 300

Gly Leu Ile Arg Gln Glu Arg Thr Ile Ile Glu Glu Gly Phe Arg Asn
305                 310                 315                 320

Gly Tyr Ile Glu Val Ile Ala Ala Thr Pro Thr Leu Ala Ala Gly Leu
                325                 330                 335

Asn Leu Pro Ala Arg Arg Val Ile Ile Arg Asp Tyr Asn Arg Phe Ala
                340                 345                 350

Ser Gly Leu Gly Met Val Pro Ile Pro Val Gly Glu Tyr His Gln Met
                355                 360                 365

Ala Gly Arg Ala Gly Arg Pro His Leu Asp Pro Tyr Gly Glu Ala Val
                370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
                405                 410                 415

Ser Leu Cys Ala His Ile Leu Ser Leu Ile Ala Thr Gly Phe Ala His
                420                 425                 430

Asp Gln Glu Ala Leu Ser Ser Phe Met Glu Arg Thr Phe Tyr Phe Phe
                435                 440                 445

Gln His Pro Lys Thr Arg Ser Leu Pro Arg Leu Val Ala Asp Ala Ile
                450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
                485                 490                 495

Cys Thr Ala Arg Leu Ile Leu Asp Ser Leu Lys Ser Cys Lys Thr Pro
                500                 505                 510

Thr Leu Ile Gly Leu Leu His Val Ile Cys Val Ser Pro Asp Met Gln
                515                 520                 525

Arg Leu Tyr Leu Lys Ala Ala Asp Thr Gln Leu Leu Arg Thr Phe Leu
                530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr
                565                 570                 575

Asp Trp Ala Asp Glu Phe Ser Glu Gly Met Ile Glu Glu Arg Tyr Gly
                580                 585                 590

Ile Gly Ala Gly Asp Leu Tyr Asn Ile Val Asp Ser Gly Lys Trp Leu
                595                 600                 605
```

```
Leu His Gly Thr Glu Arg Leu Val Ser Val Glu Met Pro Glu Met Ser
    610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
            660                 665                 670

Ala Gly Leu Ser Thr Ile Ala Arg Ile Ile Gly Glu Gly Ile Ala Arg
            675                 680                 685

Gln Val Ile Asp Glu Ile Thr Gly Val Lys Arg Ser Gly Ile His Ser
            690                 695                 700

Ser Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
                725                 730                 735

Ile Thr Val Ser Asp Leu Leu Thr Ala Asp Glu Val Leu Leu Ser Asp
            740                 745                 750

Val Leu Gly Ala Ala Arg Ala Arg Lys Val Leu Ala Phe Leu Ser Asn
            755                 760                 765

Ser Glu Lys Glu Asn Ser Ser Ser Asp Lys Thr Glu Glu Ile Pro Asp
770                 775                 780

Thr Gln Lys Ile Arg Gly Gln Ser Ser Trp Glu Asp Phe Gly Cys
785                 790                 795

<210> SEQ ID NO 53
<211> LENGTH: 702
<212> TYPE: PRT
<213> ORGANISM: Archaeoglobus fulgidus

<400> SEQUENCE: 53

Met Lys Val Glu Glu Leu Ala Glu Ser Ile Ser Ser Tyr Ala Val Gly
1               5                   10                  15

Ile Leu Lys Glu Glu Gly Ile Glu Glu Leu Phe Pro Pro Gln Ala Glu
                20                  25                  30

Ala Val Glu Lys Val Phe Ser Gly Lys Asn Leu Leu Leu Ala Met Pro
            35                  40                  45

Thr Ala Ala Gly Lys Thr Leu Leu Ala Glu Met Ala Met Val Arg Glu
        50                  55                  60

Ala Ile Lys Gly Gly Lys Ser Leu Tyr Val Val Pro Leu Arg Ala Leu
65              70                  75                  80

Ala Gly Glu Lys Tyr Glu Ser Phe Lys Lys Trp Lys Ile Gly Leu
                85                  90                  95

Arg Ile Gly Ile Ser Thr Gly Asp Tyr Glu Ser Arg Asp Glu His Leu
                100                 105                 110

Gly Asp Cys Asp Ile Ile Val Thr Thr Ser Glu Lys Ala Asp Ser Leu
            115                 120                 125

Ile Arg Asn Arg Ala Ser Trp Ile Lys Ala Val Ser Cys Leu Val Val
        130                 135                 140

Asp Glu Ile His Leu Leu Asp Ser Glu Lys Arg Gly Ala Thr Leu Glu
145                 150                 155                 160

Ile Leu Val Thr Lys Met Arg Arg Met Asn Lys Ala Leu Arg Val Ile
                165                 170                 175

Gly Leu Ser Ala Thr Ala Pro Asn Val Thr Glu Ile Ala Glu Trp Leu
            180                 185                 190
```

-continued

```
Asp Ala Asp Tyr Tyr Val Ser Asp Trp Arg Pro Val Pro Leu Val Glu
        195                 200                 205
Gly Val Leu Cys Glu Gly Thr Leu Glu Leu Phe Asp Gly Ala Phe Ser
    210                 215                 220
Thr Ser Arg Arg Val Lys Phe Glu Glu Leu Val Glu Glu Cys Val Ala
225                 230                 235                 240
Glu Asn Gly Gly Val Leu Val Phe Glu Ser Thr Arg Arg Gly Ala Glu
                245                 250                 255
Lys Thr Ala Val Lys Leu Ser Ala Ile Thr Ala Lys Tyr Val Glu Asn
            260                 265                 270
Glu Gly Leu Glu Lys Ala Ile Leu Glu Glu Asn Glu Gly Glu Met Ser
        275                 280                 285
Arg Lys Leu Ala Glu Cys Val Arg Lys Gly Ala Ala Phe His His Ala
    290                 295                 300
Gly Leu Leu Asn Gly Gln Arg Val Val Glu Asp Ala Phe Arg Arg
305                 310                 315                 320
Gly Asn Ile Lys Val Val Ala Thr Pro Thr Leu Ala Ala Gly Val
                325                 330                 335
Asn Leu Pro Ala Arg Arg Val Ile Val Arg Ser Leu Tyr Arg Phe Asp
            340                 345                 350
Gly Tyr Ser Lys Arg Ile Lys Val Ser Glu Tyr Lys Gln Met Ala Gly
        355                 360                 365
Arg Ala Gly Arg Pro Gly Met Asp Glu Arg Gly Glu Ala Ile Ile Ile
    370                 375                 380
Val Gly Lys Arg Asp Arg Glu Ile Ala Val Lys Arg Tyr Ile Phe Gly
385                 390                 395                 400
Glu Pro Glu Arg Ile Thr Ser Lys Leu Gly Val Glu Thr His Leu Arg
                405                 410                 415
Phe His Ser Leu Ser Ile Ile Cys Asp Gly Tyr Ala Lys Thr Leu Glu
            420                 425                 430
Glu Leu Glu Asp Phe Phe Ala Asp Thr Phe Phe Lys Gln Asn Glu
        435                 440                 445
Ile Ser Leu Ser Tyr Glu Leu Glu Arg Val Val Arg Gln Leu Glu Asn
    450                 455                 460
Trp Gly Met Val Val Glu Asp His His Leu Ala Pro Thr Lys Leu Gly
465                 470                 475                 480
Ser Leu Val Ser Arg Leu Tyr Ile Asp Pro Leu Thr Gly Phe Ile Phe
                485                 490                 495
His Asp Val Leu Ser Arg Met Glu Leu Ser Asp Ile Gly Ala Leu His
            500                 505                 510
Leu Ile Cys Arg Thr Pro Asp Met Glu Arg Leu Thr Val Arg Lys Thr
        515                 520                 525
Asp Ser Trp Val Glu Glu Glu Ala Phe Arg Leu Arg Lys Glu Leu Ser
    530                 535                 540
Tyr Tyr Pro Ser Asp Phe Ser Val Glu Tyr Asp Trp Phe Leu Ser Glu
545                 550                 555                 560
Val Lys Thr Ala Leu Cys Leu Lys Asp Trp Ile Glu Lys Asp Glu
                565                 570                 575
Asp Glu Ile Cys Ala Lys Tyr Gly Ile Ala Pro Gly Asp Leu Arg Arg
            580                 585                 590
Ile Val Glu Thr Ala Glu Trp Leu Ser Asn Ala Met Asn Arg Ile Ala
        595                 600                 605
```

```
Glu Glu Val Gly Asn Thr Ser Val Ser Gly Leu Thr Glu Arg Ile Lys
    610                 615                 620

His Gly Val Lys Glu Glu Leu Glu Leu Val Arg Ile Arg His Ile
625                 630                 635                 640

Gly Arg Val Arg Ala Arg Lys Leu Tyr Asn Ala Gly Ile Arg Asn Ala
                645                 650                 655

Glu Asp Ile Val Arg His Arg Glu Lys Val Ala Ser Leu Ile Gly Arg
            660                 665                 670

Gly Ile Ala Glu Arg Val Val Glu Gly Ile Ser Val Lys Ser Leu Asn
        675                 680                 685

Pro Glu Ser Ala Ala Leu Glu His His His His His His
    690                 695                 700

<210> SEQ ID NO 54
<211> LENGTH: 791
<212> TYPE: PRT
<213> ORGANISM: Haloterrigena turkmenica

<400> SEQUENCE: 54

Met Asn Leu Glu Glu Leu Thr Gly Leu Pro Pro Gly Ala Thr Asp His
1               5                   10                  15

Phe Arg Gly Glu Gly Ile Glu Leu Tyr Pro Pro Gln Ala Asp Ala
            20                  25                  30

Val Glu Ala Gly Ala Thr Asp Gly Glu Asn Leu Val Ala Ala Val Pro
        35                  40                  45

Thr Ala Ser Gly Lys Thr Met Ile Ala Ala Leu Ser Met Leu Ser Ala
    50                  55                  60

Val Gln Arg Gly Gly Lys Ala Leu Tyr Ile Val Pro Leu Arg Ala Leu
65                  70                  75                  80

Ala Ser Glu Lys Lys Glu Glu Phe Glu Ala Tyr Glu Glu Phe Gly Val
                85                  90                  95

Thr Thr Gly Val Thr Thr Gly Asn Tyr Glu Ser Thr Asp Asp Trp Leu
            100                 105                 110

Ala Thr Lys Asp Ile Ile Val Ala Thr Ser Glu Lys Val Asp Ser Leu
        115                 120                 125

Val Arg Asn Gly Ala Asp Trp Leu Ser Glu Leu Thr Cys Val Val Ser
    130                 135                 140

Asp Glu Val His Leu Ile Asp Asp Arg Asn Arg Gly Pro Thr Leu Glu
145                 150                 155                 160

Val Thr Leu Ala Lys Leu Arg Arg Leu Asn Pro Gly Met Gln Val Val
                165                 170                 175

Ala Leu Ser Ala Thr Val Gly Asn Ala Asp Glu Ile Ala Asp Trp Leu
            180                 185                 190

Asp Ala Ser Leu Val Asp Thr Asp Trp Arg Pro Ile Asp Leu Gln Met
        195                 200                 205

Gly Val His Tyr Gly Asn Ala Leu Asn Phe Asp Asp Gly Ser Thr Arg
    210                 215                 220

Glu Val Pro Val Glu Gly Ser Glu Lys Gln Glu Ala Ala Leu Val Arg
225                 230                 235                 240

Asp Ile Leu Arg Glu Gly Gly Ser Ser Leu Val Phe Val Asn Ser Arg
                245                 250                 255

Arg Asn Ala Glu Gly Ala Ala Lys Arg Leu Gly Gln Val Ser Ser Arg
            260                 265                 270

Glu Ile Thr Glu Asp Glu Arg Ala Glu Leu Ala Glu Leu Ala Asp Asp
        275                 280                 285
```

-continued

```
Ile Arg Asp Asp Ser Asp Thr Glu Thr Ser Ala Asp Leu Ala Asp Cys
    290                 295                 300

Val Glu Arg Gly Ala Ala Phe His His Ala Gly Leu Ser Ser Thr Gln
305                 310                 315                 320

Arg Ser Leu Val Glu Asp Ala Phe Arg Asp Arg Leu Leu Lys Val Ile
                325                 330                 335

Ser Ala Thr Pro Thr Leu Ala Ala Gly Val Asn Thr Pro Ala Arg Arg
            340                 345                 350

Val Ile Val Arg Asp Trp Arg Arg Phe Asp Pro Ser Ala Gly Gly Met
        355                 360                 365

Ala Pro Leu Asp Val Leu Glu Val His Gln Met Met Gly Arg Ala Gly
370                 375                 380

Arg Pro Gly Leu Asp Pro Tyr Gly Glu Ala Val Leu Leu Ala Lys Ser
385                 390                 395                 400

His Asp Glu Ser Glu Glu Leu Phe Asp Arg Tyr Ile Trp Ala Asp Pro
                405                 410                 415

Glu Pro Val Arg Ser Lys Leu Ala Ala Glu Pro Ala Leu Arg Thr His
            420                 425                 430

Val Leu Ala Thr Ile Ala Ser Gly Phe Ala Arg Thr Arg Gly Gly Leu
        435                 440                 445

Leu Glu Phe Leu Glu Ala Thr Leu Tyr Ala Ser Gln Ser Ser Glu Ala
450                 455                 460

Gly Arg Leu Glu Ser Val Thr Asp Asp Val Leu Asp Tyr Leu Glu Arg
465                 470                 475                 480

Asn Asp Phe Ile Glu Arg Ser Arg Asp Glu Ala Glu Asp Ser Gly
                485                 490                 495

Glu Asp Asp Gly Pro Phe Thr Ser Ala Ala Asp Leu Ala Glu Gln Gln
            500                 505                 510

Ala Ala Lys Arg Glu Glu Thr Leu Glu Ala Thr Ser Leu Gly His Thr
        515                 520                 525

Val Ser Arg Leu Tyr Leu Asp Pro Met Ser Ala Ala Glu Ile Val His
530                 535                 540

Gly Leu Glu Arg Ala Asp Glu Arg Pro Thr Ala Leu Gly Leu Tyr Gln
545                 550                 555                 560

Leu Val Ser Arg Thr Pro Asp Met Tyr Glu Leu Tyr Leu Arg Ser Gly
                565                 570                 575

Glu Asp Glu Lys Phe Gly Glu Leu Phe Tyr Glu Arg Glu Thr Glu Leu
            580                 585                 590

Leu Gly Asp Ala Pro Ser Glu Tyr Glu Glu Asp Arg Phe Glu Asp Trp
        595                 600                 605

Leu Ala Ala Leu Lys Thr Gly Lys Leu Leu Glu Asp Trp Ala Asp Glu
610                 615                 620

Thr Asp Glu Glu Thr Ile Thr Asp Arg Tyr Lys Ile Gly Pro Gly Asp
625                 630                 635                 640

Leu Arg Gly Lys Val Asp Thr Ala Glu Trp Leu Leu Gly Ala Ala Glu
                645                 650                 655

Ser Leu Ala Ala Glu Ile Asp Ser Glu Trp Thr Val Ala Val Arg Glu
            660                 665                 670

Ala Arg Ala Arg Val Glu His Gly Val Gly Glu Leu Leu Glu Leu
        675                 680                 685

Val Ser Val Gly Gly Val Gly Arg Lys Arg Ala Arg Arg Leu Tyr Asp
690                 695                 700
```

```
Ala Gly Ile Glu Glu Pro Ala Asp Leu Arg Ser Ala Asp Lys Gly Ile
705                 710                 715                 720

Val Leu Ser Val Leu Lys Gly Glu Lys Thr Ala Glu Asn Ile Leu Glu
                725                 730                 735

Asn Ala Gly Arg Glu Asp Pro Ser Met Asp Gly Val Glu Pro Ala Asp
            740                 745                 750

Gly Gly Pro Ala Val Gly Ala Ala Thr Asn Gly Ser Ser Gly Gly Ser
        755                 760                 765

Glu Thr Asp Glu Thr Gly Arg Ala Asp Ala Ala Glu Ser Asp Asp Ser
    770                 775                 780

Gln Ser Ser Leu Gly Asp Phe
785                 790

<210> SEQ ID NO 55
<211> LENGTH: 752
<212> TYPE: PRT
<213> ORGANISM: Haladaptatus paucihalophilus

<400> SEQUENCE: 55

Met Asn Val Ala Asp Leu Thr Gly Leu Pro Asp Gly Val Pro Glu His
1               5                   10                  15

Phe His Ala Gln Gly Ile Glu Glu Leu Tyr Pro Pro Gln Ala Glu Ala
                20                  25                  30

Val Glu Ala Gly Ile Thr Glu Gly Glu Ser Val Val Ala Ser Ile Pro
            35                  40                  45

Thr Ala Ser Gly Lys Thr Phe Ile Ala Glu Leu Ala Met Leu Ser Ser
    50                  55                  60

Val Ala Arg Gly Gly Lys Ala Leu Tyr Ile Val Pro Leu Arg Ala Leu
65                  70                  75                  80

Ala Ser Glu Lys Lys Glu Glu Phe Glu Glu Phe Glu Gln Tyr Gly Val
                85                  90                  95

Ser Ile Gly Val Ser Thr Gly Asn Tyr Glu Ser Asp Gly Asp Trp Leu
                100                 105                 110

Ala Ser Arg Asp Ile Ile Val Ala Thr Ser Glu Lys Val Asp Ser Leu
            115                 120                 125

Val Arg Asn Gly Ala Lys Trp Ile Asp Asp Leu Ser Cys Val Val Ala
130                 135                 140

Asp Glu Val His Leu Val Asn Asp Ala His Arg Gly Pro Thr Leu Glu
145                 150                 155                 160

Val Thr Leu Ala Lys Leu Arg Arg Val Asn Pro Asp Leu Gln Thr Val
                165                 170                 175

Ala Leu Ser Ala Thr Val Gly Asn Ala Gly Glu Met Ala Asp Trp Leu
            180                 185                 190

Asp Ala Thr Leu Val Asp Ser Thr Trp Arg Pro Ile Asp Leu Arg Lys
        195                 200                 205

Gly Val Leu Tyr Gly Gln Ala Leu His Phe Asp Asp Gly Thr Gln Gln
    210                 215                 220

Glu Leu Ala Arg Gly Asn Glu Lys Glu Thr Ala Ala Leu Val Arg Asp
225                 230                 235                 240

Thr Leu Glu Asp Gly Gly Ser Ser Leu Val Phe Val Asn Ser Arg Arg
                245                 250                 255

Asn Ala Glu Ala Ala Ala Lys Arg Leu Ala Asp Val Thr Lys Thr His
            260                 265                 270

Leu Thr Asp Asp Glu Arg Arg Asp Leu Leu Asp Ile Ala Asp Gln Ile
        275                 280                 285
```

```
Arg Asp Val Ser Asp Thr Glu Thr Ser Asp Asp Leu Ala Thr Ala Ile
    290                 295                 300

Glu Lys Gly Ala Ala Phe His His Ala Gly Leu Ala Ser Asp His Arg
305                 310                 315                 320

Ser Leu Val Glu Asp Ala Phe Arg Asp Lys Leu Ile Lys Val Ile Ser
                325                 330                 335

Ala Thr Pro Thr Leu Ala Ala Gly Val Asn Thr Pro Ser Arg Arg Val
            340                 345                 350

Ile Val Arg Asp Trp Arg Arg Tyr Asp Gly Asp Ile Gly Gly Met Gln
        355                 360                 365

Pro Leu Asp Val Leu Glu Val His Gln Met Phe Gly Arg Ala Gly Arg
    370                 375                 380

Pro Gly Leu Asp Pro His Gly Glu Ala Val Leu Ile Ala Lys Ser His
385                 390                 395                 400

Asp Glu Leu Gln Glu Leu Phe Asp Gln Tyr Val Trp Ala Asp Pro Glu
                405                 410                 415

Pro Val His Ser Lys Leu Ala Ala Glu Pro Ala Leu Arg Thr His Ile
            420                 425                 430

Leu Ala Thr Val Ala Ser Gly Phe Ala Gly Thr Glu Glu Leu Leu
        435                 440                 445

Asp Phe Leu Glu Arg Thr Leu Tyr Ala Thr Gln Thr Asp Glu Thr Gly
    450                 455                 460

Arg Leu Glu Thr Val Thr Gln His Val Leu Asp Tyr Leu Asp Arg Asn
465                 470                 475                 480

Gly Phe Leu Glu Arg Asp Asp Arg Leu Arg Ala Thr Gly Leu Gly His
                485                 490                 495

Arg Val Ser Gln Leu Tyr Leu Asp Pro Met Ser Ala Ala Glu Ile Ile
            500                 505                 510

Asp Gly Leu Arg Asp Ala Asp Gly Lys Pro Thr Ala Leu Gly Leu Tyr
        515                 520                 525

His Leu Val Ser Arg Thr Pro Asp Met Tyr Gln Leu Tyr Leu Arg Ser
    530                 535                 540

Gly Asp Arg Glu Arg Tyr Thr Glu Ile Ala Tyr Glu Arg Glu Pro Glu
545                 550                 555                 560

Phe Leu Gly His Met Pro Ser Glu Phe Glu Asp Asn Ala Phe Glu Asp
                565                 570                 575

Trp Leu Ser Ala Leu Lys Thr Ala Arg Leu Leu Glu Asp Trp Ala Ser
            580                 585                 590

Glu Leu Asp Glu Asp Arg Ile Thr Glu Arg Tyr Ala Ile Gly Pro Gly
        595                 600                 605

Asp Ile Arg Gly Lys Val Glu Thr Ala Gln Trp Leu Leu Asn Ala Ala
    610                 615                 620

Glu Arg Leu Ala Ala Glu Leu Gln Arg Asp Asp Ala Glu Gly Ile Pro
625                 630                 635                 640

Ser Ala Thr Thr Thr Ala Val Arg Glu Ala Arg Lys Arg Val Glu Tyr
                645                 650                 655

Gly Val Glu Glu Glu Leu Leu Asp Leu Ala Gly Val Arg Asn Val Gly
            660                 665                 670

Arg Lys Arg Ala Arg Arg Leu Tyr Glu Ala Gly Ile Glu Ser Arg Ala
        675                 680                 685

Asp Leu Arg Glu Ala Asp Lys Ser Val Val Leu Gly Ala Leu Arg Gly
    690                 695                 700
```

```
Arg Lys Lys Thr Ala Glu Asn Ile Leu Glu Asn Val Gly Arg Gln Asp
705                 710                 715                 720

Pro Ser Leu Asp Asp Val Glu Asp Ala Glu Thr Ala Ala Thr Ser
                725                 730                 735

Ala Arg Ala Thr Asn Asp Gly Gly Gln Gln Ser Leu Gly Asp Phe Glu
            740                 745                 750
```

<210> SEQ ID NO 56
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 56

```
Gln Met Phe Gly Arg Ala Gly Arg
1               5
```

<210> SEQ ID NO 57
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 57

```
Gln Met Phe Gly Arg Ala Gly Arg Pro
1               5
```

<210> SEQ ID NO 58
<211> LENGTH: 783
<212> TYPE: PRT
<213> ORGANISM: Halobacterium sp. NRC-1

<400> SEQUENCE: 58

```
Met Arg Val Ala Asp Val Pro Gly Leu Pro Gly Gly Val Ala Asp His
1               5                   10                  15

Phe Glu Gly Glu Gly Val Glu Glu Leu Tyr Pro Pro Gln Ala Glu Ala
                20                  25                  30

Val Glu Arg Gly Val Thr Glu Gly Ala Asn Leu Val Ala Ser Val Pro
            35                  40                  45

Thr Ala Ser Gly Lys Thr Leu Ile Ala Gln Leu Ala Met Leu Ser Ala
        50                  55                  60

Ile Ala Glu Gly Gly Asp Ser Pro Thr Phe Ser Gly Asp Gly Thr Ala
65                  70                  75                  80

Leu Tyr Ile Val Pro Leu Arg Ala Leu Ala Gly Glu Lys Ala Gln Glu
                85                  90                  95

Phe Glu Ala Phe Glu Arg Phe Gly Leu Ser Val Gly Val Ser Thr Gly
                100                 105                 110

Asn Tyr Glu Arg Asp Gly Ala Arg Leu Ala Asp Asn Asp Ile Val Val
            115                 120                 125

Ala Thr Ser Glu Lys Val Asp Ser Leu Val Arg Asn Gly Ala Gly Trp
        130                 135                 140

Ile Asp Asp Leu Ser Cys Val Val Ala Asp Glu Val His Leu Val Asp
145                 150                 155                 160

Asp Asp His Arg Gly Pro Thr Leu Glu Val Thr Leu Ala Lys Leu Arg
                165                 170                 175

Gln Gln Val Ala Asp Leu Gln Val Val Ala Leu Ser Ala Thr Val Gly
            180                 185                 190
```

-continued

```
Asn Ala Gly Glu Leu Ala Ala Trp Leu Asp Ala Glu Leu Val Asp Ser
            195                 200                 205
Asp Trp Arg Pro Ile Glu Leu Arg Thr Gly Val His Tyr Gly Gln Ser
210                 215                 220
Leu His Tyr Asp Asp Gly Thr Gln Ala Glu Leu Ser Val Gly Ser Gly
225                 230                 235                 240
Ser Gln Thr Ala Ala Val Val Ala Asp Thr Leu Ala Asp Asp Gly Ser
                245                 250                 255
Thr Leu Val Phe Val Asn Ser Arg Arg Asn Ala Glu Ala Ser Ala Arg
                260                 265                 270
Arg Leu Ala Asp Val Thr Gly Asn Ala Leu Ser Ser Ala Glu Arg Glu
            275                 280                 285
Arg Leu Ala Asp Ile Ala Ala Glu Ile Arg Gly Val Ser Asp Thr Glu
            290                 295                 300
Thr Ser Asp Glu Leu Ala Asp Ala Val Ala Ser Gly Ala Ala Phe His
305                 310                 315                 320
His Ala Gly Leu Ala Arg Glu His Arg Glu Leu Val Glu Glu Ala Phe
                325                 330                 335
Arg Asp Arg Leu Val Lys Ala Val Ser Ala Thr Pro Thr Leu Ala Ala
            340                 345                 350
Gly Val Asn Thr Pro Ala Arg Arg Val Val Arg Asp Trp Gln Arg
            355                 360                 365
Tyr Asp Gly Thr Ala Gly Gly Met Gln Pro Leu Asp Val Leu Glu Val
370                 375                 380
His Gln Met Phe Gly Arg Ala Gly Arg Pro Gly Leu Asp Pro Tyr Gly
385                 390                 395                 400
Glu Ala Val Leu Leu Ala Asn Ser His Asp Glu Leu Glu Glu Leu Phe
                405                 410                 415
Asp Arg Tyr Val Tyr Ala Asp Pro Glu Pro Val Arg Ser Lys Leu Ala
            420                 425                 430
Ala Glu Pro Ala Leu Arg Thr His Val Leu Ala Ala Ile Ala Thr Gly
            435                 440                 445
Phe Thr Thr Thr Glu Asp Gly Leu His Glu Phe Leu Gly Gly Thr Leu
450                 455                 460
Tyr Ala Thr Gln Thr Asp Asp Thr Gly Arg Leu Arg Ser Val Thr Gly
465                 470                 475                 480
Asp Val Leu Arg Tyr Leu Asp Arg Asn Gly Phe Val Glu Arg Asp Gly
                485                 490                 495
Ala Ala Leu Arg Ala Thr Ala Thr Gly Gln Leu Val Ser Arg Leu Tyr
            500                 505                 510
Val Asp Pro Met Ser Ala Ala Thr Ile Ile Asp Gly Leu Arg Asp Ala
            515                 520                 525
Ala Arg Asp Ala Thr Glu Thr Asp Asp Glu Gly Ala Phe Arg Pro Ala
530                 535                 540
Ser Glu Leu Gly Asp Asp Ala Ala Leu Pro Ala Asp Ala Ser Val Glu
545                 550                 555                 560
Pro Thr Pro Leu Gly Leu Tyr His Leu Val Ser Arg Thr Pro Asp Met
                565                 570                 575
Tyr Glu Leu Tyr Leu Arg Ser Gly Asp Arg Glu Gln Tyr Thr Glu Val
            580                 585                 590
Ala Tyr Glu His Glu Asp Glu Leu Leu Gly Ala Thr Pro Arg Glu Glu
            595                 600                 605
Gln Ala Glu Phe Glu Asp Trp Leu Ser Ala Leu Lys Thr Ala Arg Leu
```

```
                610               615               620
Met Ala Asp Trp Ala Ser Glu Leu Asp Glu Glu Arg Ile Ala Glu Arg
625                 630                 635                 640

Tyr Asp Val Gly Pro Gly Asp Ile Arg Gly Lys Val Glu Thr Ala Glu
                645                 650                 655

Trp Leu Leu Asn Ala Ala Glu Arg Leu Ala Gly Glu Leu Asp Val Glu
                660                 665                 670

Cys Gly Pro Ala Val Arg Glu Ala Lys Arg Val Gln Tyr Gly Val
                675                 680                 685

Arg Glu Glu Leu Leu Gly Leu Ala Gly Val Arg Asn Val Gly Arg Lys
                690                 695                 700

Arg Ala Arg Arg Leu Tyr Asn Ala Gly Val Glu Ser Arg Ala Asp Leu
705                 710                 715                 720

Arg Asn Ala Asp Lys Gly Val Val Leu Gly Ala Val Arg Gly Arg Ala
                725                 730                 735

Ala Thr Ala Glu Arg Ile Leu Glu Thr Val Gly His Pro Asp Pro Gly
                740                 745                 750

Met Asp Gly Val Ala Ala Asp Thr Asp Ala Ala Pro Glu Ser Gly Gly
                755                 760                 765

Glu Ala Gly Gly Asp Glu Gly Gln Ala Ser Leu Gly Asp Phe Ser
                770                 775                 780

<210> SEQ ID NO 59
<211> LENGTH: 450
<212> TYPE: DNA
<213> ORGANISM: Artificial sequence
<220> FEATURE:
<223> OTHER INFORMATION: Sequence used in the Examples

<400> SEQUENCE: 59
tttttttttt tttttttttt tttttttttt tttttttttt tttttttttt ggttgtttct      60
gttggtgctg atattgcttt tgatgccgac cctaaatttt ttgcctgttt ggttcgcttt     120
gagtcttctt cggttccgac taccctcccg actgcctatg atgtttatcc tttgaatggt     180
cgccatgatg gtggttatta taccgtcaag gactgtgtga ctattgacgt ccttccccgt     240
acgccgggca ataacgttta tgttggtttc atggtttggt ctaactttac cgctactaaa     300
tgccgcggat ggtttcgct gaatcaggtt attaaagaga ttatttgtct ccagccactt     360
aagtgaggtg atttatgttt ggtgctattg ctggcggtat tgcttctgct cttgctggtg     420
gcgccatgtc taaattgttt ggaggcggtc                                      450

<210> SEQ ID NO 60
<211> LENGTH: 57
<212> TYPE: DNA
<213> ORGANISM: Artificial sequence
<220> FEATURE:
<223> OTHER INFORMATION: Sequence used in the Examples

<400> SEQUENCE: 60
gcaatatcag caccaacaga aacaaccttt ttttttttt tttttttttt tttttt           57

<210> SEQ ID NO 61
<211> LENGTH: 80
<212> TYPE: DNA
<213> ORGANISM: Artificial sequence
<220> FEATURE:
<223> OTHER INFORMATION: Sequence used in the Examples

<400> SEQUENCE: 61
```

```
ctattctgtt tatgtttctt gtttgttagc cctattctgt cccccccccc acccccccc       60 acccccccc accccccccc                                                  80
```

<210> SEQ ID NO 62
<211> LENGTH: 40
<212> TYPE: DNA
<213> ORGANISM: Artificial sequence
<220> FEATURE:
<223> OTHER INFORMATION: Sequence used in the Examples

<400> SEQUENCE: 62

```
acagaatagg gctaacaaac aagaaacata aacagaatag                           40
```

<210> SEQ ID NO 63
<211> LENGTH: 60
<212> TYPE: DNA
<213> ORGANISM: Artificial sequence
<220> FEATURE:
<223> OTHER INFORMATION: Sequence used in the Examples

<400> SEQUENCE: 63

```
ctattctgtt tatgtttctt gtttgttagc cctattctgt cccccccccc acccccccc      60
```

<210> SEQ ID NO 64
<211> LENGTH: 40
<212> TYPE: DNA
<213> ORGANISM: Artificial sequence
<220> FEATURE:
<223> OTHER INFORMATION: Sequence used in the Examples

<400> SEQUENCE: 64

```
ctattctgtt tatgtttctt gtttgttagc cctattctgt                           40
```

<210> SEQ ID NO 65
<211> LENGTH: 20
<212> TYPE: DNA
<213> ORGANISM: Artificial sequence
<220> FEATURE:
<223> OTHER INFORMATION: Sequence used in the Examples

<400> SEQUENCE: 65

```
cccccccccc acccccccc                                                  20
```

<210> SEQ ID NO 66
<211> LENGTH: 40
<212> TYPE: DNA
<213> ORGANISM: Artificial sequence
<220> FEATURE:
<223> OTHER INFORMATION: Sequence used in the Examples

<400> SEQUENCE: 66

```
ctattctgtt tatgtttctt gtttgttagc cctattctgt                           40
```

<210> SEQ ID NO 67
<211> LENGTH: 974
<212> TYPE: DNA
<213> ORGANISM: Artificial sequence
<220> FEATURE:
<223> OTHER INFORMATION: Sequence used in the Examples

<400> SEQUENCE: 67

```
tttttttttt tttttttttt tttttttttt tttttttttt tttttttttt ggttgtttct    60
gttggtgctg atattgctgt gttctatgtc ttattctgtg tatgtatctt gtctgttagc   120
```

| | |
|---|---|
| cccgattgtt accggataat tcgagctcgg tacccacccc ggttgataat cagaaaagcc | 180 |
| ccaaaaacag gaagattgta taagcaaata tttaaattgt aaacgttaat attttgttaa | 240 |
| aattcgcgtt aaattttgt taaatcagct cattttttaa ccaataggcc gaaatcggca | 300 |
| aaatcccta taaatcaaaa gaatagaccg atagggtt gagtgttgtt ccagtttgga | 360 |
| acaagagtcc agtattaaag aacgtggact ccaacgtcaa agggcgaaaa accgtctatc | 420 |
| agggcgatgg cccactacgt gaaccatcac cctaatcaag ttttttgggg tcgaggtgcc | 480 |
| gtaaagcact aaatcggaac cctaaaggga tgccccgatt tagagcttga cggggaaagc | 540 |
| cggcgaacgt ggcgagaaag gaagggaaga agcgaaagg agcgggcgct agggcgctgg | 600 |
| caagtgtagc ggtcacgctg cgcgtaacca ccacacccgc cgcgcttaat gcgccgctac | 660 |
| agggcgcgtg gggatcctct agagtcgacc tgcaggcatg caagctatcc cgcaagaggc | 720 |
| ccggcagtac cggcataacc aagcctatgc ctacagcatc cagggtgacg gtgccgagga | 780 |
| tgacgatgag cgcattgtta gatttcatac acggtgcctg actgcgttag caatttaact | 840 |
| gtgataaact accgcattaa agctagctta tcgatgataa gctgtcaaac atgagaattc | 900 |
| ttgaagacga aagggcctcg tgatacgcct atttttatag gttaatgtca tgataataat | 960 |
| ggtttcttag acgt | 974 |

<210> SEQ ID NO 68
<211> LENGTH: 893
<212> TYPE: DNA
<213> ORGANISM: Artificial sequence
<220> FEATURE:
<223> OTHER INFORMATION: Sequence used in the Examples

<400> SEQUENCE: 68

| | |
|---|---|
| ctaagaaacc attattatca tgacattaac ctataaaaat aggcgtatca cgaggcccttt | 60 |
| tcgtcttcaa gaattctcat gtttgacagc ttatcatcga taagctagct ttaatgcggt | 120 |
| agtttatcac agttaaattg ctaacgcagt caggcaccgt gtatgaaatc taacaatgcg | 180 |
| ctcatcgtca tcctcggcac cgtcaccctg gatgctgtag gcataggctt ggttatgccg | 240 |
| gtactgccgg gcctcttgcg ggatagcttg catgcctgca ggtcgactct agaggatccc | 300 |
| cacgcgccct gtagcggcgc attaagcgcg gcgggtgtgg tggttacgcg cagcgtgacc | 360 |
| gctacacttg ccagcgccct agcgcccgct cctttcgctt tcttcccttc ctttctcgcc | 420 |
| acgttcgccg gctttccccg tcaagctcta aatcggggca tccctttagg gttccgattt | 480 |
| agtgctttac ggcacctcga ccccaaaaaa cttgattagg gtgatggttc acgtagtggg | 540 |
| ccatcgccct gatagacggt ttttcgccct ttgacgttgg agtccacgtt ctttaatact | 600 |
| ggactcttgt tccaaactgg aacaacactc aaccctatct cggtctattc ttttgattta | 660 |
| taagggattt tgccgatttc ggcctattgg ttaaaaaatg agctgattta acaaaaattt | 720 |
| aacgcgaatt ttaacaaaat attaacgttt acaatttaaa tatttgctta tacaatcttc | 780 |
| ctgttttgg ggcttttctg attatcaacc ggggtgggta ccgagctcga attatccggt | 840 |
| aacaatcggg gctaacagac aagatacata cacagaataa gacatagaac aca | 893 |

<210> SEQ ID NO 69
<211> LENGTH: 28
<212> TYPE: DNA
<213> ORGANISM: Artificial sequence
<220> FEATURE:
<223> OTHER INFORMATION: Sequence used in the Examples

<400> SEQUENCE: 69
gcaatatcag caccaacaga aacaacct                                           28

<210> SEQ ID NO 70
<211> LENGTH: 117
<212> TYPE: DNA
<213> ORGANISM: Artificial sequence
<220> FEATURE:
<223> OTHER INFORMATION: Sequence used in the Examples

<400> SEQUENCE: 70
tcgctgctcc acaggtctca gcttgagcag cgaaaataag aacattatga tcagtaggag    60
cactacgacc tttgttctgg tgctcgtccg ggcgcccaaa gtggagcgag tgccccc      117

<210> SEQ ID NO 71
<211> LENGTH: 80
<212> TYPE: DNA
<213> ORGANISM: Artificial sequence
<220> FEATURE:
<223> OTHER INFORMATION: Sequence used in the Examples

<400> SEQUENCE: 71
gcactcgctc cactttgggc gcccggacga gcaccagaac aaaggtcgta gtgctcctac    60
tgatcataat gttcttattt                                                80

<210> SEQ ID NO 72
<211> LENGTH: 33
<212> TYPE: DNA
<213> ORGANISM: Artificial sequence
<220> FEATURE:
<223> OTHER INFORMATION: Sequence used in the Examples

<400> SEQUENCE: 72
tcgctgctca agctgagacc tgtggagcag cga                                 33

<210> SEQ ID NO 73
<211> LENGTH: 113
<212> TYPE: DNA
<213> ORGANISM: Artificial sequence
<220> FEATURE:
<223> OTHER INFORMATION: Sequence used in the Examples

<400> SEQUENCE: 73
tcgctgctcc acaggtctca gcttgagcag cgaaaataag aacattatga tcagtaggag    60
cactacgacc tttgttctgg tgctcgtccg ggcgcccaaa gtggagcgag tgc          113

<210> SEQ ID NO 74
<211> LENGTH: 28
<212> TYPE: DNA
<213> ORGANISM: Artificial sequence
<220> FEATURE:
<223> OTHER INFORMATION: Sequence used in the Examples

<400> SEQUENCE: 74
tcgctgctcc acaggtctca gcttcccc                                       28

<210> SEQ ID NO 75
<211> LENGTH: 966
<212> TYPE: PRT
<213> ORGANISM: Desulfonatronospira thiodismutans

<400> SEQUENCE: 75

Met Pro Gly Val Asp Glu Leu Leu Gln Gln Met Gly Gln Gly Asp Leu
1               5                   10                  15

```
Gln Gly Leu Ser Thr Val Ala Val Lys Glu Ile Pro Ala Arg Glu Ala
         20                  25                  30

Glu Phe Ser Gly Ile Glu Gly Leu Pro Pro Leu Lys Gln Ala Leu
         35                  40                  45

Thr Glu Ser Gly Ile Glu Asn Phe Tyr Thr His Gln Ala Arg Ala Val
 50                  55                  60

Asn Leu Val Arg Lys Gly Arg Ser Val Val Thr Ala Thr Pro Thr Ala
 65                  70                  75                  80

Ser Gly Lys Ser Leu Ile Tyr Asn Ile Pro Val Leu Glu Ser Ile Ile
                 85                  90                  95

Asn Asp Pro Ala Ser Arg Ala Leu Tyr Leu Phe Pro Leu Lys Ala Leu
             100                 105                 110

Thr Arg Asp Gln Leu Thr Ser Leu Glu Glu Phe Ala Arg Leu Leu Ala
         115                 120                 125

Gly Lys Val His Val Asp Ser Ala Val Tyr Asp Gly Asp Thr Asp Pro
 130                 135                 140

Gln Ala Arg Ala Arg Ile Arg Ser Lys Pro Pro Asn Ile Leu Leu Thr
145                 150                 155                 160

Asn Pro Asp Met Leu His Arg Ser Phe Leu Pro Tyr His Arg Ser Trp
                 165                 170                 175

Gln Lys Phe Phe Ser Ala Leu Lys Tyr Ile Val Val Asp Glu Val His
             180                 185                 190

Thr Tyr Arg Gly Val Met Gly Ser Asn Met Ala Trp Val Phe Arg Arg
         195                 200                 205

Leu Arg Arg Ile Cys Ala Gln Tyr Gly Arg Glu Pro Val Phe Ile Phe
 210                 215                 220

Ser Ser Ala Thr Ile Ala Asn Pro Gly Gln Leu Cys Ser Ala Leu Thr
225                 230                 235                 240

Gly His Glu Pro Glu Val Ile Gln Lys Gly Ala Pro Ala Gly Lys
                 245                 250                 255

Lys His Phe Leu Leu Leu Asp Pro Glu Met Gln Gly Ala Ala Gln Ser
             260                 265                 270

Ala Ile Arg Val Leu Gln Lys Ala Leu Glu Leu Gly Leu Arg Thr Ile
         275                 280                 285

Val Tyr Thr Gln Ser Arg Lys Met Thr Glu Leu Ile Ala Met Trp Ala
 290                 295                 300

Ser Gln Arg Ala Gly Arg Leu Lys Lys Tyr Ile Ser Ala Tyr Arg Ala
305                 310                 315                 320

Gly Phe Leu Pro Glu Gln Arg Arg Glu Ile Glu Gln Lys Leu Ala Ser
                 325                 330                 335

Gly Glu Leu Leu Ala Val Val Ser Thr Ser Ala Leu Glu Leu Gly Ile
             340                 345                 350

Asp Ile Gly His Leu Asp Leu Cys Leu Leu Val Gly Tyr Pro Gly Ser
         355                 360                 365

Val Met Ala Thr Met Gln Arg Gly Gly Arg Val Gly Arg Ser Gly Arg
 370                 375                 380

Asp Ser Ala Ile Met Leu Ile Gly His Glu Asp Ala Leu Asp Gln Tyr
385                 390                 395                 400

Leu Leu Arg Asn Pro Arg Glu Phe Phe Ser Leu Glu Pro Glu Ser Ala
                 405                 410                 415

Val Ile Asn Pro Asp Asn Pro Ser Ile Met Arg Arg His Leu Val Cys
             420                 425                 430
```

```
Ala Ala Ala Glu Lys Pro Ile Ala Leu Gln Glu Met Met Leu Asp Asn
            435                 440                 445
Glu Ala Gly Lys Cys Ile Lys Ser Leu Glu Lys Asp Gly Glu Leu Leu
        450                 455                 460
Ala Ser Arg Asp Arg Ser Phe Tyr Tyr Thr Arg Ala Arg Tyr Pro His
465                 470                 475                 480
Lys Asp Val Asp Leu Arg Gly Thr Gly Gln Thr Tyr Asn Ile Phe Glu
                485                 490                 495
His Ser Thr Gly Glu Tyr Leu Gly Glu Val Asp Gly Val Arg Ala Phe
            500                 505                 510
Lys Glu Thr His Pro Gly Ala Val Tyr Leu His Met Gly Glu Thr Tyr
        515                 520                 525
Val Val Gln Asp Leu Asp Leu Glu Thr Phe Ala Val Tyr Ala Ala Lys
530                 535                 540
Ser Glu Ala Asn Tyr Tyr Thr Arg Pro Ile Thr Glu Lys Tyr Thr Glu
545                 550                 555                 560
Ile Val Glu Val Gln Ala Thr Arg Ala Thr Ala Gly Glu Leu Cys
                565                 570                 575
Leu Gly Arg Leu Lys Val Thr Glu His Val Ser Ala Tyr Glu Lys Arg
            580                 585                 590
Leu Val Arg Gly Gln Ala Arg Ile Gly Leu Ile Pro Leu Asp Leu Pro
        595                 600                 605
Pro Leu Val Phe Glu Thr Gln Gly Met Trp Phe Thr Leu Asp Ser Gln
        610                 615                 620
Val Arg Arg Asp Val Glu Asp Arg Arg Leu His Phe Met Gly Gly Leu
625                 630                 635                 640
His Ala Leu Glu His Gly Leu Ile Gly Cys Met Pro Leu Ile Ile Leu
                645                 650                 655
Thr Asp Arg Asn Asp Leu Gly Gly Ile Ala Ser Pro Val His Glu Gln
            660                 665                 670
Leu His Lys Gly Ala Val Phe Ile Tyr Asp Gly Thr Pro Gly Gly Ile
        675                 680                 685
Gly Leu Cys Arg Gln Ala Phe Glu Leu Gly Asp Arg Leu Val Ala Arg
        690                 695                 700
Ala Met Gly Ile Leu Ser Ser Cys Thr Cys Glu Asn Gly Cys Pro Gly
705                 710                 715                 720
Cys Ile His Ser Pro Lys Cys Gly Ser Gly Asn Arg Pro Leu Asp Lys
                725                 730                 735
Glu Ala Ala Met His Met Leu Ala Val Leu Ala Gly Glu Arg Cys Gly
            740                 745                 750
Glu Ala Lys Arg Lys Asp Val Ser Cys Arg Ile Glu Thr Asp Glu Gly
        755                 760                 765
Ser Met Glu Ile Asp Ser Gly Tyr Thr Lys Ser Asp Gln Ala Glu Leu
        770                 775                 780
Pro Tyr Ala Val Leu Asp Ile Glu Thr Arg Tyr Ser Ala Gln Glu Val
785                 790                 795                 800
Gly Gly Trp Gly Asn Cys His Arg Met Gly Val Ser Phe Ala Val Val
                805                 810                 815
Phe Asp Ser Arg Asn Gln Glu Phe Val Thr Phe Asp Gln Glu Gln Ala
            820                 825                 830
Ala Asp Leu Gly Ser Phe Leu Glu Asp Phe Ser Leu Val Val Gly Phe
        835                 840                 845
Asn Leu Leu Lys Phe Asp Tyr Arg Val Leu Gln Gly Leu Ser Asp Tyr
```

```
                    850                 855                 860
Asp Phe Ser Ser Leu Pro Thr Leu Asp Met Leu Arg Glu Ile Glu Ala
865                 870                 875                 880

Arg Leu Gly His Arg Leu Ser Leu Asp His Leu Ala Arg His Thr Leu
                    885                 890                 895

Gly Thr Asn Lys Ser Ala Asn Gly Leu Met Ala Leu Lys Trp Trp Lys
                900                 905                 910

Glu Gly Glu Leu Asp Lys Ile Val Glu Tyr Cys Arg Gln Asp Val Ser
                915                 920                 925

Val Thr Arg Asp Leu Tyr Leu Phe Gly Arg Asp Lys Gly Tyr Leu Leu
            930                 935                 940

Phe Lys Asn Lys Ala Gly Lys Lys Val Arg Ile Pro Val Ser Trp Gln
945                 950                 955                 960

Asp Thr Ala Phe Gln Val
                965

<210> SEQ ID NO 76
<211> LENGTH: 799
<212> TYPE: PRT
<213> ORGANISM: Haloarcula marismortui

<400> SEQUENCE: 76

Met Asp Val Ala Asp Leu Pro Gly Val Pro Glu Trp Leu Pro Asp His
1               5                   10                  15

Leu Arg Asp Asp Gly Ile Glu Glu Leu Tyr Pro Pro Gln Ala Glu Ala
                20                  25                  30

Val Glu Ala Gly Val Thr Glu Gly Glu Asn Leu Val Ala Ser Ile Pro
            35                  40                  45

Thr Ala Ser Gly Lys Thr Leu Ile Ala Glu Leu Ala Met Leu Ser Ser
        50                  55                  60

Val Ala Arg Gly Gly Lys Ala Leu Tyr Ile Val Pro Leu Arg Ala Leu
65                  70                  75                  80

Ala Ser Glu Lys Gln Ala Asp Phe Glu Glu Phe Gln Tyr Gly Leu
                85                  90                  95

Asp Ile Gly Val Ser Thr Gly Asn Tyr Glu Ser Glu Gly Gly Trp Leu
            100                 105                 110

Ala Asp Lys Asp Ile Val Val Ala Thr Ser Glu Lys Val Asp Ser Leu
        115                 120                 125

Val Arg Asn Asp Ala Pro Trp Ile Glu Asp Leu Thr Cys Val Val Thr
130                 135                 140

Asp Glu Val His Leu Val Asp Asp Gly Glu Arg Gly Pro Thr Leu Glu
145                 150                 155                 160

Val Thr Leu Ala Lys Leu Arg Arg Leu Asn Pro Asp Leu Gln Thr Val
                165                 170                 175

Ala Leu Ser Ala Thr Ile Gly Asn Ala Glu Ala Leu Ala Thr Trp Leu
            180                 185                 190

Asp Ala Gly Leu Val Asp Ser Asp Trp Arg Pro Ile Asp Leu Gln Lys
        195                 200                 205

Gly Val His Tyr Gly Gln Ala Leu His Leu Glu Asp Gly Ser Gln Gln
    210                 215                 220

Arg Leu Ser Val Gln Asn Asn Glu Lys Gln Thr Ala Ala Ile Val Arg
225                 230                 235                 240

Asp Thr Leu Glu Asp Gly Ser Thr Leu Val Phe Val Asn Ser Arg
                245                 250                 255
```

Arg Asn Ala Glu Ala Ala Gly Arg Leu Ala Asn Thr Val Arg Pro
            260                 265                 270

His Leu Ser Thr Glu Glu Arg Asp Gln Leu Ala Asp Ile Ala Glu Glu
        275                 280                 285

Ile Arg Asp Val Ser Asp Thr Glu Thr Ser Asp Asp Leu Ala Asp Ala
    290                 295                 300

Val Ala Asp Gly Ala Ala Phe His His Ala Gly Leu Ser Arg Gly His
305                 310                 315                 320

Arg Glu Leu Val Glu Asp Ala Phe Arg Asp Arg Leu Val Lys Val Val
                325                 330                 335

Cys Ala Thr Pro Thr Leu Ala Ala Gly Val Asn Thr Pro Ser Arg Arg
            340                 345                 350

Val Val Val Arg Asp Trp Arg Arg Tyr Asp Gly Ser Ala Gly Gly Met
        355                 360                 365

Ala Pro Leu Ser Val Leu Glu Val His Gln Met Met Gly Arg Ala Gly
    370                 375                 380

Arg Pro Gly Leu Asp Pro Tyr Gly Glu Ala Val Leu Ile Ala Ser Ser
385                 390                 395                 400

His Asp Glu Val Asp Glu Leu Phe Glu Arg Tyr Val Trp Ala Asp Pro
                405                 410                 415

Glu Pro Val Arg Ser Lys Leu Ala Ala Glu Pro Ala Leu Arg Thr His
            420                 425                 430

Ile Leu Ala Thr Val Ala Ser Gly Phe Ala Arg Ser Arg Lys Gly Leu
        435                 440                 445

Leu Glu Phe Leu Glu Gln Thr Leu Tyr Ala Ser Gln Thr Asp Asp Ser
    450                 455                 460

Gly Gln Leu Glu Arg Val Val Asp Asp Val Leu Thr Tyr Leu Gln Arg
465                 470                 475                 480

Asn Asp Phe Leu Glu Ile Glu Ala Gly Glu Leu Asp Ala Thr Ser Leu
                485                 490                 495

Gly His Thr Val Ser Arg Leu Tyr Leu Asp Pro Met Ser Ala Ala Glu
            500                 505                 510

Ile Val Asp Gly Leu Arg Asp Trp Glu Arg Gly Ala Ser Asp Ser Thr
        515                 520                 525

Ser Ala Ser Gly Ser Pro Ala Asp Ala Gln Ala Glu Pro Pro Ala Asn
    530                 535                 540

Ser Gly Phe Thr Thr Ala Ser Glu Leu Ala Glu Asp Ala Asp Glu Ser
545                 550                 555                 560

Asp Ala Asp Arg Asp Pro Asp Asp Ile Ser Ala Leu Gly Leu Tyr His
                565                 570                 575

Leu Val Ser Arg Thr Pro Asp Met Tyr Gln Leu Tyr Leu Arg Ser Gly
            580                 585                 590

Asp Arg Glu Glu Tyr Glu Met Glu Leu Phe Glu Arg Glu Glu Glu Leu
        595                 600                 605

Leu Gly Pro Thr Pro Ser Glu Phe Glu Glu Gly Arg Phe Glu Asp Trp
    610                 615                 620

Leu Ser Ala Leu Lys Thr Ala Arg Leu Leu Glu Asp Trp Ala Thr Glu
625                 630                 635                 640

Val Asp Glu Ala Thr Ile Thr Asp Arg Tyr Gly Val Gly Pro Gly Asp
                645                 650                 655

Ile Arg Gly Lys Val Glu Thr Ala Gln Trp Leu Leu Gly Ala Ala Glu
            660                 665                 670

Ser Leu Ala Ser Glu Val Asp Leu Asp Ala Ala Arg Ala Ile Ser Glu

```
                675                 680                 685
Ala Arg Ile Arg Val Glu His Gly Val Arg Glu Leu Val Asp Leu
    690                 695                 700
Ala Gly Val Arg Gly Val Gly Arg Lys Arg Ala Arg Arg Leu Phe Gln
705                 710                 715                 720
Ala Gly Ile Thr Asp Arg Ala Gln Leu Arg Asp Ala Asp Lys Ala Val
                725                 730                 735
Val Leu Ala Ala Leu Arg Gly Arg Arg Lys Thr Ala Glu Asn Val Leu
                740                 745                 750
Glu Asn Ala Gly His Arg Asp Pro Ser Met Glu Gly Val Glu Pro Ala
                755                 760                 765
Pro Asp Val Ser Val Asp Leu Asn Asp Gly Ala Asp Gly Asp Ala Ser
770                 775                 780
Ala Glu Ser Thr Ala Asn Asp Asp Gln Ala Ser Leu Gly Asp Phe
785                 790                 795

<210> SEQ ID NO 77
<211> LENGTH: 711
<212> TYPE: PRT
<213> ORGANISM: Natranaerobius thermophilus

<400> SEQUENCE: 77

Met Ser Glu Thr Phe Tyr Leu Leu Ser Glu Arg Met Gln Lys Lys Ile
1               5                   10                  15

Trp Glu Met Gly Trp Asp Glu Phe Thr Pro Val Gln Asp Lys Thr Ile
                20                  25                  30

Pro Ile Val Met Asn Thr Asn Lys Asp Val Val Ser Ser Gly Thr
                35                  40                  45

Ala Ser Gly Lys Thr Glu Ala Val Phe Leu Pro Ile Leu Ser Gln Ile
50                  55                  60

Glu Lys Asp Ala Thr Lys Asp Leu Lys Ile Leu Tyr Ile Ser Pro Leu
65                  70                  75                  80

Lys Ala Leu Ile Asn Asp Gln Phe Glu Arg Ile Ile Lys Leu Cys Glu
                85                  90                  95

Lys Ser Tyr Ile Pro Ile His Arg Trp His Gly Asp Val Asn Gln Asn
                100                 105                 110

Lys Lys Lys Gln Leu Thr Lys Asn Pro Ala Gly Ile Leu Gln Ile Thr
            115                 120                 125

Pro Glu Ser Ile Glu Ser Leu Phe Ile Asn Arg Thr Asn Glu Leu Asn
130                 135                 140

Tyr Ile Leu Ser Asp Ile Glu Phe Ile Ile Ile Asp Glu Leu His Ala
145                 150                 155                 160

Phe Leu Asp Asn Glu Arg Gly Val His Leu Arg Ser Leu Leu Ser Arg
                165                 170                 175

Leu Glu Asn Tyr Ile Lys Glu Lys Pro Arg Tyr Phe Ala Leu Ser Ala
                180                 185                 190

Thr Leu Asn Asn Phe Lys Leu Ile Leu Lys Glu Trp Ile Asn Tyr Asn Asp
                195                 200                 205

Ile Lys Asn Val Glu Ile Ile Asp Ser Asn Glu Asp Asp Lys Asp Leu
                210                 215                 220

Leu Leu Ser Leu Met His Phe Asp Lys Gly Lys Asp Tyr Lys Pro
225                 230                 235                 240

Ile Asp Leu Tyr Gln Asp Leu Arg Glu Leu Thr Lys Asn Val His Ser
                245                 250                 255
```

-continued

```
Leu Ile Phe Cys Asn Ser Arg Ala Glu Val Glu Thr Thr Leu Tyr
                260                 265                 270

Leu Asn Arg Leu Ala Asn Arg Glu Val Asn Thr Glu Leu Tyr Leu Ala
            275                 280                 285

His His Ser Ser Ile Asp Lys Lys Glu Arg Glu Tyr Val Glu Lys Thr
        290                 295                 300

Met Ala Asn Ser Lys Ser Pro Lys Ser Val Val Thr Thr Ser Ser Leu
305                 310                 315                 320

Glu Leu Gly Ile Asp Ile Gly Ala Ile Asp Tyr Val Val Gln Ile Asp
                325                 330                 335

Asp Thr His Thr Val Ser Ser Leu Lys Gln Arg Leu Gly Arg Ser Gly
            340                 345                 350

Arg Lys Leu Gly Thr Asn Gln Val Leu Gln Val Tyr Ser Thr Thr Asn
        355                 360                 365

Asp Ser Leu Val Gln Ser Leu Ala Val Ile Asp Leu Leu Leu Glu Lys
370                 375                 380

Trp Ile Glu Pro Ala Thr Glu Tyr Pro Leu Pro Leu Asp Ile Leu Phe
385                 390                 395                 400

His Gln Ile Ile Ser Ile Cys His Glu Ala Asn Gly Val Arg Leu Asp
                405                 410                 415

Pro Leu Ile Asp Asn Ile Lys Ala Asn Ala Ala Phe Tyr Lys Leu Lys
            420                 425                 430

Glu Glu Asp Ile Asn His Val Ile Asn Tyr Met Ile Glu Asn Asp Phe
        435                 440                 445

Leu Gln Leu Ile Arg Asn Ser Ala Glu Leu Ile Val Gly Leu Glu Gly
450                 455                 460

Glu Arg Leu Leu Arg Gly Lys Glu Phe Tyr Ala Val Phe Met Thr Gln
465                 470                 475                 480

Glu Glu Phe Glu Val Arg Glu Gly Ile Arg Lys Ile Gly Ser Ile Asp
                485                 490                 495

Lys Ser Leu Met Val Ser Glu Gly Asp Asn Ile Ile Leu Ala Gly Gln
            500                 505                 510

Leu Trp Thr Ile Lys Asn Ile Asp Ile Glu Arg Asp Ile Ile Tyr Val
        515                 520                 525

Ala Lys Ala Val Asp Gly Lys Pro Lys Tyr Ser Gly Gly Gly Phe
530                 535                 540

Ile Leu Asn Pro Lys Ile Pro Glu Arg Met His Lys Ile Leu Cys Glu
545                 550                 555                 560

Arg Lys Asn Phe Glu Phe Ile Asp Asn Met Ala Gln Asn His Leu Glu
                565                 570                 575

Glu Gln Arg Lys Pro Phe Glu Leu Tyr Asn Ile Lys Pro Asn Glu Arg
            580                 585                 590

Val Ile Trp Asn Asn Gly Asp Glu Ile Leu Phe Glu Thr Tyr Thr Gly
        595                 600                 605

Thr Lys Ile Phe Gln Thr Leu Ala Trp Ile Leu Arg Ser Tyr Asn Val
        610                 615                 620

Asn Ile Lys Glu Ile Asp Gly Ile Gly Arg Ile Asn Ile Glu Gly Gly
625                 630                 635                 640

Ile Asp Leu Pro Gly Val Leu Gln Asp Ile Lys Glu Thr Asp Trp Arg
                645                 650                 655

Pro Glu Tyr Leu Leu Asp Phe Thr Leu Glu Gln Glu Lys Phe Lys Ser
            660                 665                 670

Lys Phe Ser Pro Tyr Leu Pro Lys Asp Leu Gln Asp Lys Met His Ile
```

```
                    675                 680                 685
Ala His Leu Val Asp Ile Glu Gly Val Lys Thr Phe Leu Glu Asn Lys
            690                 695                 700

Lys Ile Lys Glu Ile Lys Leu
705             710

<210> SEQ ID NO 78
<211> LENGTH: 491
<212> TYPE: PRT
<213> ORGANISM: Artificial sequence
<220> FEATURE:
<223> OTHER INFORMATION: Consensus sequence from alignment of Hel308
      sequences

<400> SEQUENCE: 78

Leu Pro Val Leu Glu Gly Ile Glu Leu Tyr Pro Pro Gln Ala Glu Ala
1               5                   10                  15

Val Glu Gly Leu Leu Asp Gly Lys Asn Leu Leu Ile Ala Ile Pro Thr
            20                  25                  30

Ala Ser Gly Lys Thr Leu Ile Ala Glu Leu Ala Met Leu Ile Leu Gly
        35                  40                  45

Gly Lys Ala Leu Tyr Ile Val Pro Leu Arg Ala Leu Ala Ser Glu Lys
    50                  55                  60

Tyr Glu Phe Lys Phe Glu Gly Val Arg Val Gly Ile Ser Thr Gly Asp
65                  70                  75                  80

Tyr Asp Asp Glu Trp Leu Gly Asp Ile Ile Val Ala Thr Ser Glu Lys
                85                  90                  95

Val Asp Ser Leu Leu Arg Asn Trp Ile Asp Ile Thr Val Val Val Val
            100                 105                 110

Asp Glu Ile His Leu Ile Asp Arg Gly Pro Thr Leu Glu Val Leu Leu
        115                 120                 125

Ala Lys Leu Arg Leu Asn Pro Leu Gln Ile Ile Ala Leu Ser Ala Thr
    130                 135                 140

Ile Gly Asn Ala Glu Glu Leu Ala Glu Trp Leu Ala Glu Leu Val Val
145                 150                 155                 160

Ser Asp Trp Arg Pro Val Asp Leu Arg Gly Val Phe Tyr Leu Phe Asp
                165                 170                 175

Ile Leu Val Leu Asp Thr Val Glu Gly Gly Gln Leu Val Phe Asn Ser
            180                 185                 190

Arg Arg Asn Ala Glu Ala Lys Lys Leu Ala Val Lys Leu Thr Glu Leu
        195                 200                 205

Leu Ala Glu Glu Ile Glu Thr Glu Thr Ser Leu Ala Cys Val Lys Gly
    210                 215                 220

Ala Phe His His Ala Gly Leu Arg Leu Val Glu Asp Ala Phe Arg Leu
225                 230                 235                 240

Ile Lys Val Ile Ala Thr Pro Thr Leu Ala Ala Gly Leu Asn Leu Pro
                245                 250                 255

Ala Arg Arg Val Ile Ile Arg Asp Tyr Lys Arg Tyr Gly Met Pro Ile
            260                 265                 270

Pro Val Leu Glu Ile Gln Met Gly Arg Ala Gly Arg Pro Leu Asp Pro
        275                 280                 285

Tyr Gly Glu Ala Val Leu Ile Ala Lys Ser Asp Glu Leu Glu Tyr Ile
    290                 295                 300

Ala Asp Pro Glu Ile Trp Ser Lys Leu Ala Glu Ala Leu Arg Thr His
305                 310                 315                 320
```

-continued

```
Val Leu Ala Leu Ile Ala Ser Gly Phe Ala Thr Glu Leu Leu Asp Phe
                325                 330                 335

Leu Thr Phe Tyr Ala Tyr Gln Leu Ile Glu Val Leu Phe Leu Asn Ile
            340                 345             350

Leu Ala Thr Leu Gly Val Ser Leu Tyr Ile Asp Pro Leu Ser Ala Ile
        355                 360                 365

Ile Asp Gly Leu Leu Gly Leu Leu His Leu Ile Ser Thr Pro Asp Met
    370                 375                 380

Leu Tyr Leu Arg Asp Glu Leu Glu Ile Glu Glu Phe Phe Glu Phe Leu
385                 390                 395                 400

Val Lys Thr Ala Leu Leu Asp Trp Ile Glu Val Glu Asp Ile Glu Arg
            405                 410                 415

Tyr Gly Ile Gly Pro Gly Asp Leu Val Glu Ala Glu Trp Leu Met His
            420                 425                 430

Ala Leu Ala Lys Leu Leu Leu Glu Leu Ile Arg Ile Tyr Gly Val Lys
            435                 440                 445

Glu Glu Leu Leu Glu Leu Val Ile Arg Ile Gly Arg Val Arg Ala Arg
    450                 455                 460

Lys Leu Tyr Ala Gly Ile Arg Ser Asp Leu Ala Leu Ile Leu Gly Lys
465                 470                 475                 480

Ile Ala Glu Lys Ile Leu Leu Gly Thr Leu Phe
                485                 490
```